(12) United States Patent
Miyazaki et al.

(10) Patent No.: US 10,807,986 B2
(45) Date of Patent: Oct. 20, 2020

(54) FUSED PYRIMIDINE COMPOUND OR SALT THEREOF

(71) Applicant: TAIHO PHARMACEUTICAL CO., LTD., Tokyo (JP)

(72) Inventors: Isao Miyazaki, Tsukuba (JP); Tadashi Shimamura, Tsukuba (JP); Masanori Kato, Tsukuba (JP); Hidenori Fujita, Tsukuba (JP); Satoru Iguchi, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/177,844

(22) Filed: Nov. 1, 2018

(65) Prior Publication Data

US 2019/0330214 A1 Oct. 31, 2019

Related U.S. Application Data

(60) Division of application No. 15/708,917, filed on Sep. 19, 2017, now Pat. No. 10,155,768, which is a continuation of application No. PCT/JP2017/006672, filed on Feb. 22, 2017.

(30) Foreign Application Priority Data

Feb. 23, 2016 (JP) .................................. 2016-031919
Jul. 15, 2016 (JP) .................................. 2016-140801

(51) Int. Cl.
*A61K 31/519* (2006.01)
*C07D 487/04* (2006.01)
*A61P 35/00* (2006.01)

(52) U.S. Cl.
CPC .......... *C07D 487/04* (2013.01); *A61K 31/519* (2013.01); *A61P 35/00* (2018.01)

(58) Field of Classification Search
CPC ............................. A61K 31/519; C07D 487/04
USPC .................... 514/262.1, 265.1; 544/262, 280
See application file for complete search history.

(56) References Cited

U.S. PATENT DOCUMENTS

| | | | |
|---|---|---|---|
| 5,665,721 A | 9/1997 | Bhagwat et al. | |
| 10,155,768 B2 * | 12/2018 | Miyazaki | C07D 487/04 |
| 2006/0211678 A1 | 9/2006 | Ahmed et al. | |
| 2007/0135387 A1 | 6/2007 | Michaelides et al. | |
| 2014/0108453 A1 | 4/2014 | Venkataraman et al. | |
| 2016/0115168 A1 | 4/2016 | Iguchi et al. | |
| 2017/0217970 A1 | 8/2017 | Kawai et al. | |
| 2018/0009817 A1 | 1/2018 | Miyazaki et al. | |

FOREIGN PATENT DOCUMENTS

| | | |
|---|---|---|
| JP | 2007-521334 A | 8/2007 |
| JP | 2008-508358 A | 3/2008 |
| JP | 2009-518434 A | 5/2009 |
| JP | 2015505555 A | 2/2015 |
| WO | 96/40686 A1 | 12/1996 |
| WO | 2004056830 A1 | 7/2004 |
| WO | 2005047289 A1 | 5/2005 |
| WO | 2005062795 A2 | 7/2005 |
| WO | 2006017443 A2 | 2/2006 |
| WO | 2007067781 A2 | 6/2007 |
| WO | 2011018894 A1 | 2/2011 |
| WO | 2013059740 A1 | 4/2013 |
| WO | 2013114113 A1 | 8/2013 |
| WO | 2014130975 A1 | 8/2014 |
| WO | 2014184069 A1 | 11/2014 |
| WO | 2015022926 A1 | 2/2015 |
| WO | 2015078417 A1 | 6/2015 |
| WO | 2017038838 A1 | 3/2017 |
| WO | 2017043550 A1 | 3/2017 |

OTHER PUBLICATIONS

Mulligan, "RET revisited: expanding the oncogenic portfolio", Nature Reviews, 14(3):pp. 173-186, (2014).
Ibanez, "Structure and Physiology of the RET Receptor Tyrosine Kinase", Cold Spring Harbor Perspectives in Biology, 5(2) a009134:pp. 1-10, (2013).
Kohno et al., "KIF5B-RET fusions in lung adenocarcinoma", Nature Medicine, 18(3) :pp. 375-377, (2012).

(Continued)

*Primary Examiner* — Jeffrey H Murray
(74) *Attorney, Agent, or Firm* — Rothwell, Figg, Ernst & Manbeck, P.C.

(57) ABSTRACT

The problem to be solved by the present invention is to provide a novel compound having RET inhibitory activity. The present invention also provides a pharmaceutical preparation that is useful for the prevention and/or treatment of RET-related diseases, particularly cancer, based on RET inhibitory activity. The present invention provides a compound represented by Formula (I):

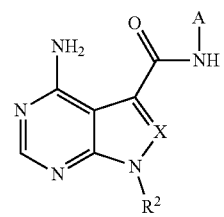

wherein A, $R^2$, and X are as defined in the specification; or a salt thereof.

7 Claims, 2 Drawing Sheets

(56) References Cited

OTHER PUBLICATIONS

Santoro et al, "RET/PTC activation in papillary thyroid carcinoma: European Journal of Endocrinology Prize Lecture", European Journal of Endocrinology, 155:pp. 645-653, (2006).
Yeganeh et al, "RET Proto Oncogene Mutation Detection and Medullary Thyroid Carcinoma Prevention", Asian Pacific Journal of Cancer Prevention, 16(6):pp. 2107-2117, (2015).
Gattelli et al.,"RET inhibition decreases growth and metastatic potential of estrogen receptor positive breast cancer cells", EMBO Molecular Medicine, 5:pp. 1335-1350, (2013).
Ito et al., "Expression of glial cell line-derived neurotrophic factor family members and their receptors in pancreatic cancers", Surgery, 138(4):pp. 788-794, (2005).
Dawson et al.,"Altered Expression of RET Proto-oncogene Product in Prostatic Intraepithelial Neoplasia and Prostate Cancer", Journal of the National Cancer Institute, 90(7):pp. 519-523, (1998).
Cai et al., "KIF5B-RET Fusions in Chinese Patients With Non-Small Cell Lung Cancer", Cancer, 119:pp. 1486-1494, (2013).
Elisei et al., "Prognostic Significance of Somatic RET Oncogene Mutations in Sporadic Medullary Thyroid Cancer: A 10-Year Follow-Up Study", The Journal of Clinical Endocrinology & Metabolism, 93(3):pp. 682-687, (2008).
Zeng et al., "The Relationship between Over-expression of Glial Cell-derived Neurotrophic Factor and Its RET Receptor with Progression and Prognosis of Human Pancreatic Cancer", The Journal of International Medical Research, 36:pp. 656-664, (2008).
Carlomagno et al, "The Kinase Inhibitor PP1 Blocks Tumorigenesis Induced by RET Oncogenes1" Cancer Research, 62(4):pp. 1077-1082, (2002).
Waltenberger et al, "A Dual Inhibitor of Platelet-Derived Growth Factor b-Receptor and Src Kinase Activity Potently Interferes With Motogenic and Mitogenic Responses to PDGF in Vascular Smooth Muscle Cells A Novel Candidate for Prevention of Vascular Remodeling", Circulation Research, 85(1):pp. 12-22, (1999).
Tatton et al., "The Src-selective Kinase Inhibitor PP1 Also Inhibits Kit and Bcr-Abl Tyrosine Kinases*", The Journal of Biological Chemistry, 278(7):pp. 4847-4853, (2003).
Warmuth et al., "Dual-specific Src and Abl kinase inhibitors, PP1 and CGP76030, inhibit growth and survival of cells expressing imatinib mesylate-resistant Bcr-Abl kinases", Blood, 101(2):pp. 664-672, (2003).
Lowe et al., "Osteopetrosis in Src-deficient mice is due to an autonomous defect of osteoclasts", Proceedings of the National Academy of Sciences of the United States of America, 90(10):pp. 4485-4489, (1993).
Molina et al., "Profound block in thymocyte development in mice lacking p56", Nature, 357(6374):pp. 161-164, (1992).
Mcclellan et al., "Discovery of potent and selective thienopyrimidine inhibitors of Aurora kinases". Bioorganic & Medicinal Chemistry Letters 21, 2011, pp. 5620-5624.
Bavetsias et al., "Aurora Kinase Inhibitors: Current Status and Outlook", Frontiers in Oncology, 2015, vol. 5, Art.278.
Keefe et al., "Tumor control versus adverse events with targeted anticancer therapies" Nature Reviews Clinical Oncology, 2012, vol. 9, No. 2, pp. 98-109.
International Search Report cited in PCT/JP2017/006672 dated Apr. 25, 2017, 2 pages.
U.S. Appl. No. 15/700,800, filed Sep. 11, 2017.
F. Hidenori et al., "4784 / 13—TAS0286/HM05, A Novel Highly Selective RET Inhibitor, Prominently Inhibits Various Ret Defective Tumor Growth", AACR Annual Meeting 2018 Online Proceedings and Itinerary Planner Home, Abstract Apr. 17, 2018, 1 page.
F. Hidenori et al., "TAS0286/HMO5, A Novel Highly Selective RET Inhibitor, Prominently Inhibits Various RET Defective Tumor Growth", 4784 Abstract, Mar. 14, 2018, 1 page.
Extended European Search Report dated Jan. 12, 2018, cited in the related European application No. 17756554.6, 6 pages.
Dyson G, "Chemistry of Synthetic Medical Substances", M.: Mir, 1964, pp. 12-19.
Belikov, Pharmaceutical Chemistry in Two Parts, "Pharmaceutical Chemistry", 1993, pp. 43-47.
Mashkovsky, "MD Medicines", 1993, Part 1—S.1,8.
Patani et al., "Bioisosterism: A Rational Approach in Drug Design", Chemical Reviews, 1996, vol. 96, No. 8, pp. 3147-3176.
Office Action for the related RU patent application No. 2018112252, dated Dec. 14, 2018, 20 pages.
Office Action for the related TW patent application No. 105128898, dated Jan. 3, 2019, 8 pages.
Vaughan et al., "Cytoplasmic Dynein Binds Dynactin through a Direct Interaction between the Intermediate Chains and p150 Glued" The Journal of Cell Biology, 1995, Vo. 131, No. 6, pp. 1507-1516.
Wang et al., Fusion of dynactin 1 to anaplastic lymphoma kinase in inflammatory myofibroblastic tumor, Human Pathology, 2012, vol. 43, pp. 2047-2052.
Chen et al., "Increasing Incidence of Differentiated Thyroid Cancer in the United States, 1988-2005", Cancer, 2009, vol. 115, No. 16, pp. 3801-3807.
Yoh et al., Vandetanib in patients with previously treated RET-rearranged advanced non-small-cell lung cancer (LURET): an open-label, multicentre phase 2 trial, Lancet Respiratory Medicine, 2017, vol. 5, pp. 42-50.
Soares et al., "BRAF mutations and RET/PTC rearrangements are alternative events in the etiopathogenesis of PTC" Oncogene, 2003, vol. 22, No. 29, pp. 4578-4580.
"Integrated Genomic Characterization of Papillary Thyroid Carcinoma", Cell, 2014, vol. 159, No. 3, pp. 676-690.
Drilon et al., "Response to Cabozantinib in Patients with RET Fusion-Positive Lung Adenocarcinomas", Cancer Discovery, 2013, vol. 3, No. 6, pp. 630-635.
"Comprehensive molecular profiling of lung adenocarcinoma", Nature, 2014, vol. 511, No. 7511, pp. 543-550.

* cited by examiner

FUSED PYRIMIDINE COMPOUND OR SALT THEREOF

CROSS-REFERENCE TO RELATED PATENT APPLICATIONS

The present application is a divisional of U.S. Ser. No. 15/708,917, filed Sep. 19, 2017, which is a continuation of PCT/JP2017/006672, filed Feb. 22, 2017, which claims claims priority to Japanese Patent Application No. 2016-031919 filed on Feb. 23, 2016 and Japanese Patent Application No. 2016-140801 filed on Jul. 15, 2016, which are incorporated herein by reference in their entirety.

TECHNICAL FIELD

The present invention relates to a novel fused pyrimidine compound having RET inhibitory activity or a salt thereof, and to a pharmaceutical composition containing the compound or salt.

BACKGROUND ART

Various protein kinases are present in vivo, and are known to be involved in a wide range of functional regulations. RET is a receptor tyrosine kinase identified as one of the proto-oncogenes. RET binds to the glial cell line-derived neurotrophic factor (GDNF) and GDNF receptor to form a complex, which enables RET to perform physiological functions through intracellular phosphorylation signaling (Non-patent Literature 1). A study reports that in normal tissues, RET contributes to kidney development and neurogenesis during fetal life (Non-patent Literature 2). Some studies indicate that in cancers, such as lung cancer, thyroid cancer, breast cancer, pancreas cancer, and prostate cancer, the translocation, mutation, and overexpression of RET enhances its activation to thereby contribute to cell growth, tumor formation, or tissue infiltration (Non-patent Literature 3, 4, 5, 6, 7, and 8). In addition, RET is known to be a poor prognostic factor of cancer, as indicated in some reports that the translocation of RET and its enhanced activation level are also inversely correlated with prognosis in cancer (Non-patent Literature 9, 10, 11, and 12).

Therefore, an inhibitor capable of inhibiting RET activity is thought to be useful as a therapeutic agent for diseases associated with abnormally enhanced RET signaling pathways.

It is expected, for example, that in cancers involving translocated, mutated, and overexpressed RET, the administration of a medicament capable of specifically inhibiting RET will selectively and intensively suppress the proliferation of cancer cells and contribute to the treatment, life prolongation, and improvement in quality of life of cancer patients.

As such compounds having RET inhibitory activity, PP1 is known (Non-patent Literature 13). In PP1, a p-tolyl group is bonded to a fused ring pyrimidine skeleton. PP1 is known to exhibit high inhibitory activity against not only RET but also Src (Non-patent Literature 14), c-Kit, Bcr-Abl (Non-patent Literature 15 and 16), and others. For example, as side effects, the inhibition of Src may lead to abnormally enhanced bone formation, and the inhibition of Lck may suppress T cells (Non-patent Literature 17 and 18). Since multikinase inhibitors inhibit not only RET but also various signaling pathways to inhibit cell growth and other functions, the inhibitors raise concerns about possible various side effects, which may require dose reduction and/or drug holidays, thus leading to insufficient RET inhibitory activity. From the standpoint of side-effect reduction, RET inhibitors that have high inhibitory activity against RET with low inhibitory activity against other kinases have been desired.

Non-patent Literature 19 and Patent Literature 1 disclose a substance with a fused pyrimidine skeleton to which a ring structure is attached through an amide bond. This compound is described as having Aurora kinase inhibitory activity.

Patent Literature 2 discloses a pyrrolopyrimidine derivative that selectively inhibits Tie-2, TrkA, and its family member TrkB.

Patent Literature 3 discloses a pyrrolopyrimidine derivative that selectively inhibits Tie-2 and its family members.

Patent Literature 4 discloses a pyrrolopyrimidine derivative that is a potassium channel modulator.

Patent Literature 5 discloses a pyrrolopyrimidine derivative that has a therapeutic effect on diabetes.

Patent Literature 6 and 7 disclose a heterocyclic substituted cyclopentane compound that inhibits adenosine kinase.

Patent Literature 8 discloses a pyrrolopyrimidine derivative that has a vinyl group or an ethynyl group.

Patent Literature 9 discloses a fused pyrimidine derivative that has a BTK inhibitory activity.

However, none of Patent Literature above specifically discloses or even suggests an RET inhibitory compound with a fused pyrimidine skeleton that contains an amino group at the 4-position and a ring attached through an amide bond.

CITATION LIST

Patent Literature

Patent Literature 1: WO2007/067781 Pamphlet
Patent Literature 2: WO2004056830A1 Pamphlet
Patent Literature 3: WO2005047289A1 Pamphlet
Patent Literature 4: WO2011018894A1 Pamphlet
Patent Literature 5: WO2015078417A1 Pamphlet
Patent Literature 6: U.S. Pat. No. 5,665,721
Patent Literature 7: WO9640686A1 Pamphlet
Patent Literature 8: WO2014184069A1 Pamphlet
Patent Literature 9: WO2015022926A1 Pamphlet

Non-Patent Literature

Non-patent Literature 1: Lois M. Mulligan, Nature Rev., 14(3): pp. 173-186, (2014)
Non-patent Literature 2: Carlos F. Ibanez, Cold Spring Harb Perspect Biol., 5(2): pp. 1-10, (2013)
Non-patent Literature 3: Takashi Kohno, Nature Med., 18(3): pp. 375-377, (2012)
Non-patent Literature 4: Massimo Santoro, Eur J Endocrinol., 155: pp. 645-653, (2006)
Non-patent Literature 5: Marjan Zarif Yeganeh, Asian Pac J Cancer Prev., 16(6): pp. 2107-2117, (2015)
Non-patent Literature 6: Albana Gattelli, EMBO Mol Med., 5: pp. 1335-1350, (2013)
Non-patent Literature 7: Yoshinori Ito, Surgery, 138: pp. 788-794, (2005)
Non-patent Literature 8: Dawn M. Dawson, J Natl Cancer Inst., 90: pp. 519-523, (1998)
Non-patent Literature 9: Weijing Cai, Cancer, 119: pp. 1486-1494, (2013)
Non-patent Literature 10: Rossella Elisei, J Clin Endocrinol Metab., 93(3): pp. 682-687, (2008)
Non-patent Literature 11: Albana Gattelli, EMBO Mol Med., 5: pp. 1335-1350, (2013)

Non-patent Literature 12: Q Zeng, J. Int. Med. Res., 36: pp. 656-664, (2008)

Non-patent Literature 13: Francesca Carlomagno, Cancer Res., 62(4): pp. 1077-1082, (2002)

Non-patent Literature 14: Johannes Waltenberger, Circ Res., 85(1): pp. 12-22, (1999)

Non-patent Literature 15: Louise Tatton, J Biol Chem., 278(7): pp. 4847-4853, (2003)

Non-patent Literature 16: Markus Warmuth, Blood. 101(2): pp. 664-672, (2003)

Non-patent Literature 17: Carolyn Lowe, Proc Natl Acad Sci USA, 90(10): pp. 4485-9, (1993)

Non-patent Literature 18: Thierry Molina, Nature, 357 (6374): pp. 161-4, (1992)

Non-patent Literature 19: McClellan W J, Bioorganic & Medicinal Chemistry Letters 21: pp. 5620-5624 (2011)

Non-patent Literature 20: Front Oncol. 2015 Dec. 21; 5:278

Non-patent Literature 21: Nature Reviews Clinical Oncology, vol. 9, no. 2, pp. 98-109, 2012

SUMMARY OF INVENTION

Technical Problem

An object of the present invention is to provide a novel compound or a salt thereof that selectively and potently inhibit RET, and a pharmaceutical composition comprising the same.

Solution to Problem

The present inventors conducted extensive research to achieve the above object, and consequently found that a compound group represented by Formulas (I) and (I') below showed excellent inhibitory activity against RET and kinase selectivity, and was useful as a pharmaceutical preparation for treating RET-related diseases, such as malignant tumors. Thus, the present invention has been completed.

Specifically, the present invention provides a compound represented by Formula (I) below or a salt thereof:

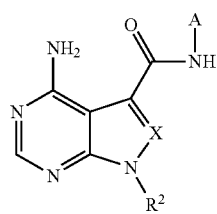
(I)

wherein in Formula (I), A is

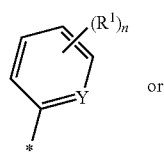 or
A1

A2 wherein $R^1$ is
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen, oxygen, and sulfur,
Y is N or CH, and
n is an integer of 0 to 2,
wherein when n is 2, the two $R^1$ may be identical or different from each other;
in Formula A2, the group:

forms, together with phenyl or pyridinyl to which this group is bonded, polycyclic C8-C14 aromatic hydrocarbon or an 8- to 14-membered polycyclic unsaturated heterocyclic group containing 1 to 3 identical or different heteroatoms selected from nitrogen, oxygen, and sulfur;
$R^2$ is
substituted or unsubstituted C3-C10 alkyl,
substituted or unsubstituted C3-C7 cycloalkyl,
substituted or unsubstituted C4-C12 bridged cycloalkyl,
substituted or unsubstituted C2-C6 alkenyl,
substituted or unsubstituted C3-C7 cycloalkenyl, or
a substituted or unsubstituted 4- to 10-membered monocyclic or polycyclic saturated heterocyclic group containing 1 to 3 identical or different heteroatoms selected from nitrogen, oxygen, and sulfur,
provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and
X is
N or
$CR^3$, wherein $R^3$ is
hydrogen,
halogen,
cyano,
nitro,
substituted or unsubstituted C1-C6 alkyl,
substituted or unsubstituted C1-C6 alkoxy,
substituted or unsubstituted C1-C6 alkylthio,
substituted or unsubstituted C3-C7 cycloalkyl,
substituted or unsubstituted C2-C6 alkenyl, substituted or unsubstituted C2-C6 alkynyl,
substituted or unsubstituted amino,
substituted or unsubstituted carbamoyl,
substituted or unsubstituted C6-C14 aromatic hydrocarbon, or
a substituted or unsubstituted 4- to 10-membered monocyclic or polycyclic saturated or unsaturated heterocyclic group containing 1 to 3 identical or different heteroatoms selected from nitrogen, oxygen, and sulfur.

The present invention also provides a compound represented by Formula (I') below or a salt thereof:

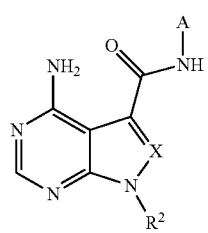
(I')

wherein in Formula (I'), A is

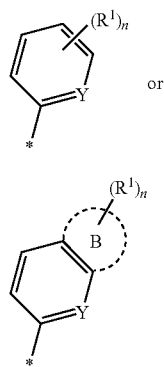

A1 or

A2 wherein R¹ is
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen, oxygen, and sulfur,
Y is N or CH, and
n is an integer of 0 to 2,
wherein when n is 2, the two R¹ may be identical or different from each other;
in Formula A2, the group:

forms, together with phenyl or pyridinyl to which this group is bonded, polycyclic C8-C14 aromatic hydrocarbon or an 8- to 14-membered polycyclic unsaturated heterocyclic group containing 1 to 3 identical or different heteroatoms selected from nitrogen, oxygen, and sulfur;
$R^2$ is
substituted or unsubstituted C3-C10 alkyl,
substituted or unsubstituted C3-C4 cycloalkyl,
substituted or unsubstituted C4-C12 bridged cycloalkyl,
substituted or unsubstituted C2-C6 alkenyl,
substituted or unsubstituted C3-C4 cycloalkenyl, or
a substituted or unsubstituted 4- to 10-membered monocyclic or polycyclic saturated heterocyclic group containing 1 to 3 identical or different heteroatoms selected from nitrogen, oxygen, and sulfur,
provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and
X is
N or
$CR^3$, wherein $R^3$ is
hydrogen,
halogen,
cyano,
nitro,
substituted or unsubstituted C1-C6 alkyl,
substituted or unsubstituted C1-C6 alkoxy,
substituted or unsubstituted C1-C6 alkylthio,
substituted or unsubstituted C3-C7 cycloalkyl,
substituted or unsubstituted C2-C6 alkenyl,
substituted or unsubstituted C2-C6 alkynyl,
substituted or unsubstituted amino,
substituted or unsubstituted carbamoyl,
substituted or unsubstituted C6-C14 aromatic hydrocarbon, or
a substituted or unsubstituted 4- to 10-membered monocyclic or polycyclic saturated or unsaturated heterocyclic group containing 1 to 3 identical or different heteroatoms selected from nitrogen, oxygen, and sulfur.

The present invention also provides medicinal use, such as a RET inhibitor, a pharmaceutical composition, and an antitumor agent, all of which comprise a compound represented by Formula (I) or (I') above or a salt thereof.

Advantageous Effects of Invention

The present invention provides a novel compound represented by Formula (I) or (I') above or a salt thereof, both of which are useful as RET inhibitors.

It was revealed that the compounds or salts thereof of the present invention show excellent inhibitory activity against RET and kinase selectivity. Therefore, the compounds or salts thereof of the present invention do not lead to side effects that may be caused by inhibiting, for example, Src, Lck, Aurora B, EGFR, and like kinases other than RET, and is useful as an agent for preventing and/or treating RET-related diseases (e.g., cancer).

DESCRIPTION OF EMBODIMENTS

Figure 1:
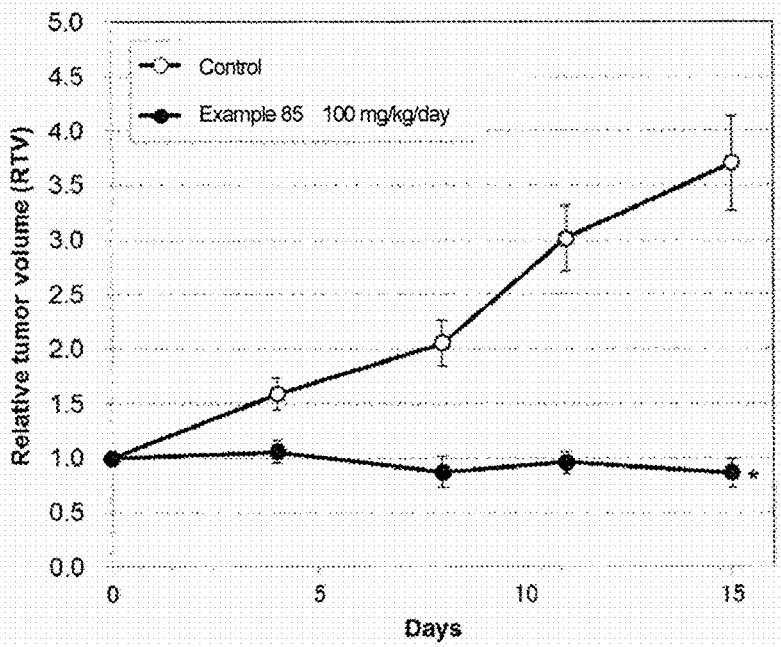
FIG. 1 illustrates relative tumor volume changes observed over time in Test Example 10.

The compounds of the present invention represented by Formulas (I) and (I') above are compounds having a fused pyrimidine skeleton having an amino group at position 4 thereof, with a benzene ring, a pyridine ring, or a fused ring containing a benzene ring or a pyridine ring, via an amide bond, and are novel compounds that are not disclosed in any of the above prior art documents.

In the present specification, * represents a bonding position, unless otherwise specified. For example, when A in Formula (I) or (I') is A1 below:

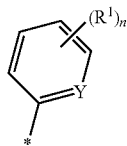

A1

A1 is supposed to be bonded to the carbamoyl group in Formula (I) or (I') in the position shown by *.

In the present specification, the above-mentioned group:

is also simply referred to as the group B or the B moiety.

In the present specification, the following portion:

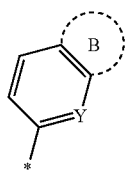

wherein the group B and Y are as defined above;
of Formula A2 below:

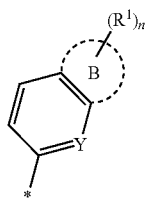

A2 wherein the group B, Y, and $R^1$ are as defined above;
is polycyclic C8-C14 aromatic hydrocarbon containing a benzene ring (Y is CH) or a pyridine ring (Y is N) represented by the following formula:

or an 8- to 14-membered polycyclic unsaturated heterocyclic group containing 1 to 3 identical or different heteroatoms selected from nitrogen, oxygen, and sulfur. In other words, in A2, the following group:

indicates a ring having 0 to 2 nitrogen atoms, oxygen atoms, or sulfur atoms as heteroatoms. The group B forms, together with phenyl or pyridinyl, polycyclic C8-C14 aromatic hydrocarbon, or an 8- to 14-membered polycyclic unsaturated heterocyclic group containing 1 to 3 identical or different heteroatoms selected from nitrogen, oxygen, and sulfur.

In the present specification, unless otherwise specified, examples of the "substituent" include deuterium, halogen, hydroxy, cyano, nitro, alkyl, halogenoalkyl, hydroxyalkyl, alkoxy, alkoxyalkyl, cycloalkyl, cycloalkyl-alkyl, bridged cycloalkyl, aralkyl, alkenyl, cycloalkenyl, alkynyl, halogenoalkoxy, cycloalkoxy, cycloalkyl-alkoxy, aralkyloxy, alkylthio, cycloalkyl-alkylthio, amino, mono- or dialkylamino, cycloalkylamino, cycloalkyl-alkylamino, aralkylamino, aromatic hydrocarbon amino, acylamino, alkoxycarbonylamino, aralkyloxycarbonylamino, acyl, acyloxy, alkylsilyloxy, oxo, carboxyl, alkoxycarbonyl, aralkyloxycarbonyl, carbamoyl, saturated or unsaturated heterocyclic group, aromatic hydrocarbon, saturated heterocyclic oxy, unsaturated heterocyclic oxy, etc. When a substituent listed above is present, the number thereof is typically one, two, or three.

In the present specification, examples of the "halogen" include fluorine, chlorine, bromine, and iodine.

In the present specification, the "alkyl" refers to linear or branched saturated hydrocarbon. Examples include methyl, ethyl, n-propyl, isopropyl, n-butyl, sec-butyl, isobutyl, tert-butyl, 1-methylpropyl, n-pentyl, isopentyl, tert-pentyl, pentan-3-yl, n-hexyl, 1,1-dimethylpropyl, 1,1,2,2-tetramethylethyl, n-heptyl, 1,1,2,2-tetramethylpropyl, n-octyl, n-nonyl, n-decyl, etc.; and specifically include C1-C10 alkyl, C3-C10 alkyl, C1-C6 alkyl, C1-C4 alkyl, C3-C8 alkyl, C3-C6 alkyl, etc.

In the present specification, the "halogenoalkyl" refers to alkyl mentioned above having one or more (e.g., 1 to 10, 1 to 7, or 1 to 5) halogen atoms mentioned above. Examples include fluoromethyl, difluoromethyl, trifluoromethyl, trichloromethyl, fluoroethyl, 1,1,1-trifluoroethyl, monofluoro-n-propyl, perfluoro-n-propyl, perfluoroisopropyl, monofluoro-n-butyl, monofluoro-n-pentyl, monofluoro-n-hexyl, etc.; and specifically include halogeno C1-C6 alkyl, halogeno C1-C4 alkyl, etc.

In the present specification, the "hydroxyalkyl" refers to alkyl mentioned above having one or more (e.g., 1 to 5, 1 to 3, or 1) hydroxy groups. Examples include hydroxymethyl, hydroxyethyl (1-hydroxyethyl or 2-hydroxyethyl), hydroxypropyl, hydroxybutyl, hydroxypentyl, hydroxyhexyl, etc.; and specifically include hydroxy C1-C6 alkyl, hydroxy C1-C4 alkyl, etc.

In the present specification, the "alkoxy" refers to oxy to which alkyl mentioned above is bonded. Examples include methoxy, ethoxy, n-propoxy, isopropoxy, n-butoxy, isobutoxy, tert-butoxy, n-pentyloxy, isopentyloxy, n-hexyloxy, etc.; and specifically include C1-C6 alkoxy, C1-C4 alkoxy, etc.

In the present specification, the "alkoxyalkyl" refers to alkyl mentioned above having one or more (e.g., 1 to 5, preferably 1 to 3, and more preferably 1) alkoxy groups mentioned above. Examples include methoxymethyl, ethoxymethyl, n-propoxymethyl, n-butoxymethyl, 2-methoxyethyl, 1-methoxy-n-propyl, 3-methoxy-n-propyl, 2-ethoxy-n-butyl, 4-methoxy-n-butyl, 5-methoxy-n-pentyl, 6-methoxy-n-hexyl, etc.; and specifically include C1-C4 alkoxy C1-C6 alkyl, C1-C4 alkoxy C1-C4 alkyl, etc.

In the present specification, the "cycloalkyl" refers to monocyclic or polycyclic (e.g., bicyclic or tricyclic) saturated hydrocarbon. Examples include monocyclic cycloalkyl, such as cyclopropyl, cyclobutyl, cyclopentyl, cyclohexyl, and cycloheptyl; polycyclic cycloalkyl, such as spiro[3.3]heptyl, spiro[3.4]octyl, and dispiro[5.1.7$^8$.2$^6$]heptadecanyl; and specifically include C3-C7 cycloalkyl, C3-C5 cycloalkyl, etc. In the present invention, the "cycloalkyl" should be specified independently from "bridged cycloalkyl," described later. Therefore, in the present invention, the "bridged cycloalkyl" is excluded from the "cycloalkyl."

In the present specification, the "cycloalkyl-alkyl" refers to alkyl mentioned above having one or more (e.g., 1 to 3, and preferably 1) cycloalkyl groups mentioned above. Examples include cyclopropylmethyl, cyclobutylmethyl, cyclopentylmethyl, cyclohexylmethyl, cycloheptylmethyl, etc.; and specifically include C3-C7 cycloalkyl-substituted C1-C10 alkyl, C3-C7 cycloalkyl-substituted C1-C6 alkyl, etc.

In the present specification, the "bridged cycloalkyl" refers to polycyclic (e.g., bicyclic or tricyclic) saturated hydrocarbon in which at least two (e.g., two or three) saturated hydrocarbon rings have at least two carbon atoms shared with the adjacent ring. Examples include bicyclo[1.1.0]butyl (bicyclo[1.1.0]butan-1-yl or bicyclo[1.1.0]butan-2-yl), bicyclo[1.1.1]pentyl (bicyclo[1.1.1]pentan-1-yl or bicyclo[1.1.1]pentan-2-yl), bicyclo[3.1.0]hexyl (bicyclo[3.1.0]hexan-1-yl, bicyclo[3.1.0]hexan-2-yl, bicyclo[3.1.0]hexan-3-yl, or bicyclo[3.1.0]hexan-6-yl), bicyclo[2.2.1]heptyl (bicyclo[2.2.1]heptan-1-yl, bicyclo[2.2.1]heptan-2-yl, or bicyclo[2.2.1]heptan-7-yl), bicyclo[3.1.1]heptyl (bicyclo[3.1.1]heptan-1-yl, bicyclo[3.1.1]heptan-2-yl, bicyclo[3.1.1]heptan-3-yl, or bicyclo[3.1.1]heptan-6-yl), bicyclo[4.4.0]decyl (bicyclo[4.4.0]decan-2-yl, bicyclo[4.4.0]decan-3-yl, etc.), adamanthyl (adamantan-1-yl or adamantan-2-yl), etc.; and specifically include C4-C12 bridged cycloalkyl, C5-C10 bridged cycloalkyl, etc.

In the present specification, the "aromatic hydrocarbon" refers to a monocyclic or polycyclic (e.g., bicyclic or tricyclic) ring substituent comprising carbon and hydrogen having an unsaturated bond, and containing 4e+2 number of electrons (e is an integer of 1 or more) in the cyclic n electron system. Examples include phenyl, naphthyl, anthracenyl, phenanthryl, fluorenyl, tetrahydronaphthyl, etc.; and specifically include C6-C14, C6-C10, and C8-C14 aromatic hydrocarbons.

In the present specification, the "aralkyl" refers to alkyl mentioned above having one or more (e.g., 1 to 3, and preferably 1) aromatic hydrocarbon groups mentioned above. Examples include benzyl, phenethyl, diphenylmethyl (benzhydryl), triphenylmethyl (trityl), naphthylmethyl, fluorenylmethyl, etc.; and specifically include C7-C14 aralkyl, C6-C14 aromatic hydrocarbon-substituted C1-C6 alkyl (C1-C6 alkyl having one or more C6-C14 aromatic hydrocarbons), etc.

In the present specification, the "alkenyl" refers to linear or branched unsaturated hydrocarbon having at least one (e.g., 1 or 2, or 1) double bond. Examples include vinyl, allyl, 1-propenyl, 2-methyl-2-propenyl, isopropenyl, 1-, 2- or 3-butenyl, 2-, 3-, or 4-pentenyl, 2-methyl-2-butenyl, 3-methyl-2-butenyl, 5-hexenyl, 3-methyl-3-butenyl, etc.; and specifically include C2-C6 alkenyl, C2-C4 alkenyl, etc.

In the present specification, the "cycloalkenyl" refers to monocyclic or polycyclic (e.g., bicyclic or tricyclic) unsaturated hydrocarbon having at least one (e.g., 1 or 2, or 1) double bond. Examples include cyclopropenyl (e.g., 2-cyclopropen-1-yl), cyclobutenyl (e.g., 2-cyclobuten-1-yl), cyclopentenyl (e.g., 2-cyclopenten-1-yl and 3-cyclopenten-1-yl), cyclopentadienyl (e.g., 2,4-cyclopentadien-1-yl), cyclohexenyl (e.g., 3-cyclohexen-1-yl), cycloheptenyl (e.g., 3-cyclohepten-1-yl), etc.; and specifically include C3-C7 cycloalkenyl, etc.

In the present specification, the "alkynyl" refers to linear or branched unsaturated hydrocarbon having at least one (e.g., 1 or 2, or 1) triple bond. Examples include ethynyl, 1- or 2-propynyl, 1-, 2-, or 3-butynyl, 1-methyl-2-propynyl, etc.; and specifically include C2-C6 alkynyl, C2-C4 alkynyl, etc.

In the present specification, the "halogenoalkoxy" refers to alkoxy mentioned above having one or more (e.g., 1 to 10, 1 to 7, or 1 to 5) halogen atoms. Examples include fluoromethoxy, difluoromethoxy, trifluoromethoxy, trichloromethoxy, fluoroethoxy, 1,1,1-trifluoroethoxy, monofluoro-n-propoxy, perfluoro-n-propoxy, perfluoro-isopropoxy, etc.; and specifically include halogeno C1-C6 alkoxy, halogeno C1-C4 alkoxy, etc.

In the present specification, the "cycloalkoxy" refers to oxy to which cycloalkyl mentioned above is bonded. Examples include cyclopropoxy, cyclobutoxy, cyclopenthyloxy, cyclohexyloxy, cycloheptyloxy, etc.; and specifically include C3-C7 cycloalkoxy.

In the present specification, the "cycloalkyl-alkoxy" refers to alkoxy mentioned above having one or more (e.g., 1 to 3, and preferably 1) cycloalkyl groups mentioned above. Examples include cyclopropylmethoxy, cyclobutylmethoxy, cyclopentylmethoxy, cyclohexylmethoxy, cycloheptylmethoxy, etc.; and specifically include C3-C7 cycloalkyl-substituted C1-C4 alkoxy (C1-C4 alkoxy having one or more (e.g., 1 to 3, and preferably 1) C3-C7 cycloalkyl groups).

In the present specification, the "aralkyloxy" refers to alkoxy mentioned above having one or more (e.g., 1 to 3, and preferably 1) aromatic hydrocarbon groups mentioned above. Examples include benzyloxy, phenethyloxy, naphthylmethyloxy, fluorenylmethyloxy, etc.; and specifically include C7-C14 aralkyloxy.

In the present specification, the "alkylthio" refers to mercapto in which the hydrogen is replaced by alkyl mentioned above. Examples include methylthio, ethylthio, n-propylthio, isopropylthio, n-butylthio, isobutylthio, tert-butylthio, n-pentylthio, isopentylthio, hexylthio, etc.; and specifically include C1-C6 alkylthio, C1-C4 alkylthio, etc.

In the present specification, the "cycloalkyl-alkylthio" refers to alkylthio mentioned above having one or more (e.g., 1 to 3, and preferably 1) cycloalkyl groups mentioned above. Examples include cyclopropylmethylthio, cyclobutylmethylthio, cyclopentylmethylthio, cyclohexylmethylthio, cycloheptylmethylthio, etc.; and specifically include C3-C7 cycloalkyl-substituted C1-C4 alkylthio (C1-C4 alkylthio having one or more (e.g., 1 to 3, and preferably 1) C3-C7 cycloalkyl groups).

In the present specification, the "monoalkylamino" refers to amino having one alkyl group mentioned above. Examples include methylamino, ethylamino, n-propylamino, isopropylamino, n-butylamino, isobutylamino, tert-butylamino, n-pentylamino, isopentylamino, hexylamino, etc.; and specifically include mono(C1-C6 alkyl)amino.

In the present specification, the "dialkylamino" refers to amino having two alkyl groups mentioned above. Examples include dimethylamino, ethylmethylamino, diethylamino, di(n-propyl)amino, diisopropylamino, di(n-butyl)amino, diisobutylamino, di(tert-butyl)amino, di(n-pentyl)amino, diisopentylamino, dihexylamino, etc.; and specifically include di(C1-C6 alkyl)amino.

In the present specification, "alkylamino" alone includes both monoalkylamino and dialkylamino.

In the present specification, the "cycloalkylamino" refers to amino having one or two cycloalkyl groups mentioned above. Examples include cyclopropylamino, cyclobutylamino, cyclopentylamino, cyclohexylamino, cycloheptylamino, dicyclobutylamino, etc.; and specifically include C3-C7 cycloalkyl-substituted amino (amino having one or two C3-C7 cycloalkyl groups).

In the present specification, the "cycloalkyl-alkylamino" refers to amino having one or two cycloalkyl-alkyl groups mentioned above. Examples include N-cyclopropylmethylamino, N-cyclobutylmethylamino, N-cyclopentylmethylamino, N-cyclohexylmethylamino, N-cycloheptylmethylamino, etc.; and specifically include N—C3-C7 cycloalkyl-substituted C1-C4 alkylamino (amino having one or two "C1-C4 alkyl groups having one or more (e.g., 1 to 3, and preferably 1) C3-C7 cycloalkyl groups").

In the present specification, the "aralkylamino" refers to amino having one or two aralkyl groups mentioned above. Examples include benzylamino, phenethylamino, naphthylmethylamino, fluorenylmethylamino, etc.; and specifically include C7-C14 aralkyl-substituted amino.

In the present specification, the "aromatic hydrocarbon amino" refers to amino having one or two aromatic hydrocarbon groups mentioned above. Examples include phenylamino, naphthylamino, anthracenylamino, phenanthrylamino, fluorenylamino, tetrahydronaphthylamino, etc.; and specifically include C6-C14 aromatic hydrocarbon-substituted amino.

In the present specification, the "acyl" refers to formyl, alkylcarbonyl, cycloalkylcarbonyl, aralkylcarbonyl, or aromatic hydrocarbon carbonyl.

In the present specification, the "alkylcarbonyl" refers to carbonyl having alkyl mentioned above. Examples include methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, hexylcarbonyl, etc.; and specifically include (C1-C6 alkyl)carbonyl (carbonyl having C1-C6 alkyl).

In the present specification, the "cycloalkylcarbonyl" refers to carbonyl having cycloalkyl mentioned above. Examples include cyclopropylcarbonyl, cyclobutylcarbonyl, cyclopentylcarbonyl, cyclohexylcarbonyl, cycloheptylcarbonyl, etc.; and specifically include (C3-C7 cycloalkyl) carbonyl (carbonyl having C3-C7 cycloalkyl).

In the present specification, the "aralkylcarbonyl" refers to carbonyl having aralkyl mentioned above. Examples include benzylcarbonyl, phenethylcarbonyl, naphthylmethylcarbonyl, fluorenylmethylcarbonyl, etc.; and specifically include (C7-C14 aralkyl)carbonyl (carbonyl having C7-C14 aralkyl).

In the present specification, the "aromatic hydrocarbon carbonyl" include carbonyl having aromatic hydrocarbon mentioned above. Examples include phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, phenanthrylcarbonyl, etc.; and specifically include (C6-C14 aromatic hydrocarbon)carbonyl.

In the present specification, the "acylamino" refers to amino having one or two acyl groups mentioned above. Examples include N-formylamino, N-methylcarbonylamino, N-ethylcarbonylamino, N-n-propylcarbonylamino, N-isopropylcarbonylamino, N-n-butylcarbonylamino, N-isobutylcarbonylamino, N-tert-butylcarbonylamino, N-n-pentylcarbonylamino, N-isopentylcarbonylamino, N-hexylcarbonylamino, N,N-dimethylcarbonylamino, N-cyclopropylcarbonylamino, N-cyclobutylcarbonylamino, N-cyclopentylcarbonylamino, N-cyclohexylcarbonylamino, N-cycloheptylcarbonylamino, N-benzylcarbonylamino, N-phenethylcarbonylamino, N-naphthylmethylcarbonylamino, N-fluorenylmethylcarbonylamino, etc.; and specifically include N-formylamino, N—(C1-C6 alkyl)carbonyl-substituted amino (amino having one or two (C1-C6 alkyl)carbonyl groups), N—(C3-C7 cycloalkyl)carbonyl-substituted amino (amino having one or two (C3-C7 cycloalkyl)carbonyl groups), (C7-C14 aralkyl)carbonyl-substituted amino (amino having one or two (C7-C14 aralkyl)carbonyl groups), etc.

In the present specification, the "acyloxy" refers to formyloxy, alkylcarbonyloxy, cycloalkylcarbonyloxy, aralkylcarbonyloxy, or aromatic hydrocarbon carbonyloxy.

In the present specification, the "alkylcarbonyloxy" refers to oxy having alkylcarbonyl mentioned above. Examples include methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, n-hexylcarbonyloxy, etc.; and specifically include (C1-C6 alkyl)carbonyloxy.

In the present specification, the "cycloalkylcarbonyloxy" refers to oxy having cycloalkylcarbonyl mentioned above. Examples include cyclopropylcarbonyloxy, cyclobutylcarbonyloxy, cyclopentylcarbonyloxy, cyclohexylcarbonyloxy, cycloheptylcarbonyloxy, etc.; and specifically include C3-C7 cycloalkyl-substituted carbonyloxy (carbonyloxy having C3-C7 cycloalkyl).

In the present specification, the "aralkylcarbonyloxy" refers to oxy having cycloalkylcarbonyl mentioned above. Examples include benzylcarbonyloxy, 1-phenethylcarbonyloxy, 2-phenethylcarbonyloxy, naphthylmethylcarbonyloxy, fluorenylmethylcarbonyloxy, etc.; and specifically include (C7-C14 aralkyl)carbonyloxy (carbonyloxy having C7-C14 aralkyl).

In the present specification, the "aromatic hydrocarbon carbonyloxy" refers to oxy having aromatic hydrocarbon carbonyl mentioned above. Examples include phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, phenanthrylcarbonyloxy, etc.; and specifically include (C6-C14 aromatic hydrocarbon)carbonyloxy.

In the present specification, the "alkylsilyloxy" refers to silyloxy having alkyl mentioned above and optionally having phenyl. Examples include oxy to which tert-butyldiphenylsilyl, trimethylsilyl, triethylsilyl, tert-butyldimethylsilyl, triisopropylsilyl, tert-butyldiphenylsilyl, or the like is bonded; and specifically include mono-C1-C6 alkylsilyloxy (silyloxy substituted with one C1-C6 alkyl group), di-C1-C6 alkylsilyloxy (silyloxy substituted with two C1-C6 alkyl groups), and tri-C1-C6 alkylsilyloxy (silyloxy substituted with three C1-C6 alkyl groups). In the present specification, "C1-C6 alkylsilyloxy" alone includes all of mono-C1-C6 alkylsilyloxy, di-C1-C6 alkylsilyloxy, and tri-C1-C6 alkylsilyloxy.

In the present specification, the "alkoxycarbonyl" refers to carbonyl having alkoxy mentioned above. Examples include methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl, isopentyloxycarbonyl, n-hexyloxycarbonyl, etc.; and specifically include (C1-C6 alkoxy)carbonyl.

In the present specification, the "alkoxycarbonylamino" refers to amino having one or two alkoxycarbonyl groups mentioned above. Examples include methoxycarbonylamino, ethoxycarbonylamino, n-propoxycarbonylamino, isopropoxycarbonylamino, n-butoxycarbonylamino, isobutoxycarbonylamino, tert-butoxycarbonylamino, n-pentyloxycarbonylamino, isopentyloxycarbonylamino, n-hexyloxycarbonylamino, di(methoxycarbonyl)amino, etc.; and specifically include (C1-C6 alkoxy)carbonyl-substituted amino (amino having one or two (C1-C6 alkoxy)carbonyl groups).

In the present specification, the "aralkyloxycarbonyl" refers to carbonyl having aralkyloxy mentioned above. Examples include benzyloxycarbonyl, 1-phenethyloxycarbonyl, 2-phenethyloxycarbonyl, naphthlmethyloxycarbonyl, fluorenylmethyloxycarbonyl, etc.; and specifically include (C7-C14 aralkyl)oxycarbonyl.

In the present specification, the "aralkyloxycarbonylamino" refers to amino having one or two aralkyloxycarbonyl groups mentioned above. Examples include benzyloxycarbonylamino, 1-phenethyloxycarbonylamino, 2-phenethyloxycarbonylamino, naphtylmethyloxycarbonylamino, fluorenylmethyloxycarbonylamino, etc.; and specifically include (C7-C14 aralkyl)oxycarbonyl-substituted amino (amino having one or two (C7-C14 aralkyl)oxycarbonyl groups).

In the present specification, the "saturated heterocyclic group" refers to a monocyclic or polycyclic (e.g., bicyclic or tricyclic) saturated heterocyclic group having one or more (e.g., 1 to 3) identical or different heteroatoms selected from nitrogen, oxygen, and sulfur. Examples include morpholino, 1-pyrrolidinyl, piperidino, piperazinyl, 4-methyl-1-piperazinyl, tetrahydrofuranyl, tetrahydropyranyl, tetrahydrothiophenyl, thiazolidinyl, oxazolidinyl, 7-azabicyclo[2.2.1]hept-2-yl, 2,6-dioxabicyclo[3.2.1]oct-7-yl, 7-oxabicyclo[2.2.1]heptane, etc.; and specifically include 4- to 10-membered, 8- to 14-membered, 8- to 10-membered, and 4- to 6-membered saturated heterocyclic groups.

In the present specification, the "unsaturated heterocyclic group" refers to a monocyclic or polycyclic (e.g., bicyclic or tricyclic), completely or partially unsaturated heterocyclic group having one or more (e.g., 1 to 3) identical or different heteroatoms selected from nitrogen, oxygen, and sulfur. Examples include imidazolyl, thienyl, furyl, pyrrolyl, oxazolyl, isoxazolyl, thiazolyl, isothiazolyl, thiadiazolyl, pyrazolyl, triazolyl, tetrazolyl, pyridinyl, pyrazyl, pyrimidinyl, pyridazinyl, indolyl, isoindolyl, indazolyl, triazolopyridinyl, benzoimidazolyl, benzoxazolyl, benzothiazolyl, benzothienyl, benzofuranyl, purinyl, quinolyl, isoquinolyl, quinazolinyl, quinoxalinyl, methylenedioxyphenyl, ethylenedioxyphenyl, dihydrobenzofuranyl, dihydrothiazolyl, benzothiophenyl, etc.; and specifically include 4- to 10-membered, 8- to 14-membered, 8- to 10-membered, and 4- to 6-membered unsaturated heterocyclic groups.

In the present specification, the "saturated heterocyclic oxy" refers to oxy having a saturated heterocyclic ring mentioned above. Examples include morpholinyloxy, 1-pyrrolidinyloxy, piperidinooxy, piperazinyloxy, 4-methyl-1-piperazinyloxy, tetrahydrofuranyloxy, tetrahydropyranyloxy, tetrahydrothiophenyloxy, thiazolidinyloxy, and oxazolidinyloxy; and specifically include 4- to 10-membered, 8- to 14-membered, 8- to 10-membered, and 4- to 6-membered saturated heterocyclic oxy.

In the present specification, the "unsaturated heterocyclic oxy" refers to oxy having an unsaturated heterocyclic ring mentioned above. Examples include imidazolyloxy, thienyloxy, furyloxy, pyrrolyloxy, oxazolyloxy, isoxazolyloxy, thiazolyloxy, isothiazolyloxy, thiadiazolyloxy, pyrazolyloxy, triazolyloxy, tetrazolyloxy, pyridinyloxy, pyrazyloxy, pyrimidinyloxy, pyridazinyloxy, indolyloxy, isoindolyloxy, indazolyloxy, triazolopyridinyloxy, benzoimidazolyloxy, benzoxazolyloxy, benzothiazolyloxy, benzothienyloxy, benzofuranyloxy, purinyloxy, quinolyloxy, isoquinolyloxy, quinazolinyloxy, quinoxalinyloxy, methylenedioxyphenyloxy, ethylenedioxyphenyloxy, dihydrobenzofuranyloxy, dihydrothiazolyloxy, benzothiophenyloxy, etc.; and specifically include 4- to 10-membered, 8- to 14-membered, 8- to 10-membered, and 4- to 6-membered unsaturated heterocyclic oxy.

The term "Ca-Cb" in the description regarding the substituent in the present specification indicates that the substituent has a- to b-number of carbon atoms. For example, "C1-C6 alkyl" refers to alkyl having 1 to 6 carbon atoms, and "C6-C14 aromatic hydrocarbon oxy" refers to oxy to which aromatic hydrocarbon having 6 to 14 carbon atoms is bonded. Further, the term "a- to b-membered" indicates that the number of atoms (number of ring members) that constitute the ring is a to b. For example, a "4- to 10-membered saturated heterocyclic group" refers to a saturated heterocyclic group with a 4- to 10-membered ring. Moreover, the following formula:

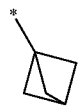 [SMILES: *C12CC(C1)C2]

is "C05 bridged cycloalkyl."

In the present specification, when there are several options for the substituents possessed by each group defined in Formulas (I) and (I'), each group may have the same or different types of substituents, unless otherwise specified. For example, "C1-C6 alkyl that is substituted with halogen or hydroxy" includes not only C1-C6 alkyl that is substituted with halogen alone and C1-C6 alkyl that is substituted with hydroxy alone, but also C1-C6 alkyl that is substituted with both halogen and hydroxy, unless otherwise specified. Moreover, "C1-C6 alkyl that is substituted with halogen or hydroxy" includes, for example, C1-C6 alkyl that is substituted with two or more kinds of halogen atoms (e.g., fluorine and chlorine).

A1 is preferably

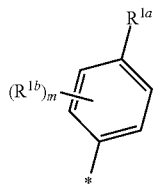

more preferably

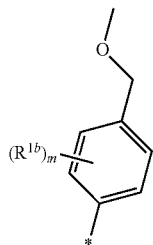

and even more preferably

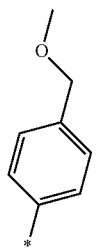 [SMILES: *c1ccc(COC)cc1]

A2 is preferably

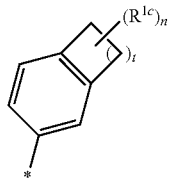

The substituents, such as $R^1$, $R^2$, $R^3$, $R^4$, $R^5$, $R^6$, and $R^7$, in the formulas representing the compounds of the present invention are explained in detail below. In the explanation of the substituents, the substituents, such as $R^1$, $R^2$, $R^3$, $R^4$, $R^5$, $R^6$, and $R^7$, refer to the respective substituents in Formula (I) or (I'), unless otherwise specified.

$R^1$, $R^{1a}$, $R^{1b}$, and $R^{1c}$ are each
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen, oxygen, and sulfur.

Examples of the "substituent" when the groups represented by $R^1$, $R^{1a}$, $R^{1b}$, and $R^{1c}$ each have a substituent include those mentioned above, and the number thereof is typically one, two, or three.

Examples of the "halogen" represented by $R^1$, $R^{1a}$, $R^{1b}$, and $R^{1c}$ include those mentioned above; preferably fluorine, chlorine, and bromine; more preferably fluorine and chlorine; and even more preferably fluorine.

Examples of the "C1-C6 alkyl" in the "substituted or unsubstituted C1-C6 alkyl" represented by $R^1$, $R^{1a}$, $R^{1b}$, and $R^{1c}$ include those mentioned above, preferably C1-C4 alkyl, more preferably methyl or n-propyl, and even more preferably methyl.

Examples of the "substituent" in the "substituted or unsubstituted C1-C6 alkyl" represented by $R^1$, $R^{1a}$, $R^{1b}$, and $R^{1c}$ include those mentioned above;

preferably hydroxy, C1-C6 alkoxy wherein hydrogen contained in the alkoxy may be replaced by 1 or more deuterium atoms, C1-C6 alkylthio, or C6-C14 aromatic hydrocarbon;

more preferably C1-C6 alkoxy wherein hydrogen contained in the alkoxy may be replaced by 1 or more deuterium atoms, or C1-C6 alkylthio;

even more preferably C1-C4 alkoxy wherein hydrogen contained in the alkoxy may be replaced by 1 or more deuterium atoms; and still more preferably methoxy.

The number of substituents is not particularly limited, but is preferably 0 to 3, and more preferably 1.

The "substituted or unsubstituted C1-C6 alkyl" represent by $R^1$, $R^{1a}$, $R^{1b}$, and $R^{1c}$ is preferably C1-C6 alkyl that may be substituted with "hydroxy, C1-C6 alkoxy wherein hydrogen contained in the alkoxy may be replaced by 1 or more deuterium atoms, C1-C6 alkylthio, or C6-C14 aromatic hydrocarbon";

more preferably C1-C6 alkyl that may be substituted with "C1-C6 alkoxy wherein hydrogen contained in the alkoxy may be replaced by 1 or more deuterium atoms, or C1-C6 alkylthio";

even more preferably C1-C6 alkyl that is substituted with "C1-C6 alkoxy wherein hydrogen contained in the alkoxy may be replaced by 1 or more deuterium atoms, or C1-C6 alkylthio";

still more preferably C1-C4 alkyl that is substituted with one "C1-C4 alkoxy wherein hydrogen contained in the alkoxy may be replaced by 1 or more deuterium atoms";

further still more preferably C1-C4 alkyl that is substituted with one C1-C4 alkoxy; and further still more preferably methoxymethyl.

The "C1-C6 alkoxy" in the "substituted or unsubstituted C1-C6 alkoxy" represented by $R^1$, $R^{1a}$, $R^{1b}$, and $R^{1c}$ include those mentioned above, preferably C1-C4 alkoxy, and more preferably methoxy.

Examples of the "substituent" in the "substituted or unsubstituted C1-C6 alkoxy" represented by $R^1$, $R^{1a}$, $R^{1b}$, and $R^{1c}$ include those mentioned above, preferably halogen, and more preferably fluorine.

When the substituent in the "substituted or unsubstituted C1-C6 alkoxy" represented by $R^1$, $R^{1a}$, $R^{1b}$, and $R^{1c}$ is halogen, the number thereof is not particularly limited, but is preferably 1 to 3, and more preferably 3.

The "substituted or unsubstituted C1-C6 alkoxy" represented by $R^1$, $R^{1a}$, $R^{1b}$, and $R^{1c}$ is preferably C1-C6 alkoxy that may be substituted with halogen, more preferably C1-C6 alkoxy, even more preferably C1-C4 alkoxy, and still more preferably methoxy.

Examples of the "C2-C6 alkenyl" in the "substituted or unsubstituted C2-C6 alkenyl" represented by $R^1$, $R^{1a}$, $R^{1b}$, and $R^{1c}$ include those mentioned above, preferably C2-C4 alkenyl, and more preferably vinyl and 1-propenyl.

Examples of the "substituent" in the "substituted or unsubstituted C2-C6 alkenyl" represented by $R^1$, $R^{1a}$, $R^{1b}$, and $R^{1c}$ include those mentioned above.

The "substituted or unsubstituted C2-C6 alkenyl" represented by $R^1$, $R^{1a}$, $R^{1b}$, and $R^{1c}$ is preferably C2-C6 alkenyl, more preferably C2-C4 alkenyl, even more preferably vinyl and 1-propenyl, and most preferably 1-propenyl.

The "C2-C6 alkynyl" in the "substituted or unsubstituted C2-C6 alkynyl" represented by $R^1$, $R^{1a}$, $R^{1b}$, and $R^{1c}$ include those mentioned above, preferably C2-C4 alkynyl, and more preferably ethynyl.

Examples of the "substituent" in the "substituted or unsubstituted C2-C6 alkynyl" represented by $R^1$, $R^{1a}$, $R^{1b}$, and $R^{1c}$ include those mentioned above.

The "substituted or unsubstituted C2-C6 alkynyl" represented by $R^1$, $R^{1a}$, $R^{1b}$, and $R^{1c}$ is preferably C2-C6 alkynyl, more preferably C2-C4 alkynyl, and even more preferably ethynyl.

Examples of the "substituent" in the "substituted or unsubstituted amino" represented by $R^1$, $R^{1a}$, $R^{1b}$, and $R^{1c}$ include those mentioned above;

preferably a 4- to 10-membered monocyclic or polycyclic unsaturated heterocyclic group containing 1 to 3 identical or different heteroatoms selected from nitrogen, oxygen, and sulfur, or C6-C14 aromatic hydrocarbon;

more preferably a 4- to 6-membered monocyclic or polycyclic unsaturated heterocyclic group containing 1 to 3 identical or different heteroatoms selected from nitrogen, oxygen, and sulfur, or C6-C10 aromatic hydrocarbon;

even more preferably a 4- to 6-membered monocyclic unsaturated heterocyclic group containing one nitrogen atom, or C6-C10 aromatic hydrocarbon; and still more preferably phenyl or pyridinyl.

The number of substituents is not particularly limited, but is preferably 1.

The "substituted or unsubstituted amino" represented by $R^1$, $R^{1a}$, $R^{1b}$, and $R^{1c}$ is preferably amino that may be substituted with "one or more 4- to 10-membered monocyclic or polycyclic unsaturated heterocyclic groups containing 1 to 3 identical or different heteroatoms selected from nitrogen, oxygen, and sulfur; or C6-C14 aromatic hydrocarbon";

more preferably amino that may be substituted with "one or more 4- to 6-membered monocyclic or polycyclic unsaturated heterocyclic groups containing 1 to 3 identical or different heteroatoms selected from nitrogen, oxygen, and sulfur, or C6-C10 aromatic hydrocarbon";

even more preferably amino that is substituted with one "4- to 6-membered monocyclic unsaturated heterocyclic group containing one nitrogen atom, or C6-C10 aromatic hydrocarbon"; and still more preferably amino that is substituted with one "phenyl or pyridinyl group"

Examples of the "4- to 10-membered monocyclic or polycyclic unsaturated heterocyclic group containing 1 to 3 identical or different heteroatoms selected from nitrogen, oxygen, and sulfur" in the "substituted or unsubstituted 4- to 10-membered monocyclic or polycyclic unsaturated heterocyclic group containing 1 to 3 identical or different heteroatoms selected from nitrogen, oxygen, and sulfur" represented by $R^1$, $R^{1a}$, $R^{1b}$, and $R^{1c}$ include those mentioned above. The "4- to 10-membered monocyclic or polycyclic unsaturated heterocyclic group containing 1 to 3 identical or different heteroatoms selected from nitrogen, oxygen, and sulfur" is preferably a 4- to 6-membered monocyclic unsaturated heterocyclic group containing 1 to 3 identical or different heteroatoms selected from nitrogen, oxygen, and sulfur. Specific examples include pyrazolyl, furyl, oxazolyl, etc. The "4- to 10-membered monocyclic or polycyclic unsaturated heterocyclic group containing 1 to 3 identical or different heteroatoms selected from nitrogen, oxygen, and sulfur" is more preferably a 4- to 6-membered monocyclic unsaturated heterocyclic group containing one oxygen atom; even more preferably furyl; and still more preferably furan-2-yl.

Examples of the "substituent" in the "substituted or unsubstituted 4- to 10-membered monocyclic or polycyclic unsaturated heterocyclic group containing 1 to 3 identical or different heteroatoms selected from nitrogen, oxygen, and sulfur" represented by $R^1$, $R^{1a}$, $R^{1b}$, and $R^{1c}$ include those mentioned above.

The "substituted or unsubstituted 4- to 10-membered monocyclic or polycyclic unsaturated heterocyclic group containing 1 to 3 identical or different heteroatoms selected from nitrogen, oxygen, and sulfur" represented by $R^1$, $R^{1a}$, $R^{1b}$, and $R^{1c}$ is preferably a 4- to 6-membered monocyclic unsaturated heterocyclic group containing 1 to 3 identical or different heteroatoms selected from nitrogen, oxygen, and sulfur; more preferably a 4- to 6-membered monocyclic unsaturated heterocyclic group containing one oxygen atom; even more preferably furyl; and still more preferably furan-2-yl.

$R^1$ is preferably
halogen,
cyano,
nitro,
C1-C6 alkyl that may be substituted with "hydroxy, C1-C6 alkoxy wherein hydrogen contained in the alkoxy may be replaced by 1 or more deuterium atoms, C1-C6 alkylthio, or C6-C14 aromatic hydrocarbon,"
C1-C6 alkoxy that may be substituted with halogen,
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur.

$R^1$ is more preferably
halogen,
cyano,
nitro,
C1-C6 alkyl that may be substituted with "C1-C6 alkoxy wherein hydrogen contained in the alkoxy may be replaced by 1 or more deuterium atoms, or C1-C6 alkylthio,"
C1-C6 alkoxy that may be substituted with halogen,
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or a 4- to 10-membered monocyclic or polycyclic unsaturated heterocyclic group containing 1 to 3 identical or different heteroatoms selected from nitrogen, oxygen, and sulfur.

$R^1$ is even more preferably halogen,

C1-C6 alkyl that may be substituted with "C1-C6 alkoxy wherein hydrogen contained in the alkoxy may be replaced by 1 or more deuterium atoms, or C1-C6 alkylthio,"

C1-C6 alkoxy,

C2-C6 alkenyl,

C2-C6 alkynyl, amino that may be substituted with "one or more 4- to 6-membered monocyclic unsaturated heterocyclic groups containing 1 to 3 identical or different heteroatoms selected from nitrogen, oxygen, and sulfur, or C6-C10 aromatic hydrocarbon," or a 4- to 6-membered monocyclic unsaturated heterocyclic group containing 1 to 3 identical or different heteroatoms selected from nitrogen, oxygen, and sulfur.

$R^1$ is even more preferably halogen,

C1-C6 alkyl that is substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, or a 4- to 6-membered monocyclic unsaturated heterocyclic group containing 1 to 3 identical or different heteroatoms selected from nitrogen, oxygen, and sulfur.

$R^1$ is still more preferably halogen,

C1-C4 alkyl that is substituted with one C1-C4 alkoxy wherein hydrogen contained in the alkoxy may be replaced by 1 or more deuterium atoms, C2-C6 alkenyl, C2-C6 alkynyl, or a 4- to 6-membered monocyclic unsaturated heterocyclic group containing one oxygen atom."

$R^1$ is further still more preferably C1-C4 alkyl that is substituted with one C1-C4 alkoxy.

$R^1$ is further still more preferably halogen or methoxymethyl.

$R^{1a}$ is preferably cyano, nitro,

C1-C6 alkyl that may be substituted with "hydroxy, C1-C6 alkoxy wherein hydrogen contained in the alkoxy may be replaced by 1 or more deuterium atoms, or C1-C6 alkylthio," C1-C6 alkoxy that may be substituted with halogen, C2-C6 alkenyl, C2-C6 alkynyl, amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or a 4- to 10-membered monocyclic or polycyclic unsaturated heterocyclic group containing 1 to 3 identical or different heteroatoms selected from nitrogen, oxygen, and sulfur.

$R^{1a}$ is more preferably

C1-C6 alkyl that may be substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or a 4- to 10-membered monocyclic or polycyclic unsaturated heterocyclic group containing 1 to 3 identical or different heteroatoms selected from nitrogen, oxygen, and sulfur.

$R^{1a}$ is even more preferably

C1-C6 alkyl that may be substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, amino that may be substituted with "one or more 4- to 6-membered monocyclic unsaturated heterocyclic groups containing 1 to 3 identical or different heteroatoms selected from nitrogen, oxygen, and sulfur, or C6-C10 aromatic hydrocarbon," or a 4- to 6-membered monocyclic unsaturated heterocyclic group containing 1 to 3 identical or different heteroatoms selected from nitrogen, oxygen, and sulfur.

$R^{1a}$ is still more preferably

C1-C6 alkyl that is substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, or a 4- to 6-membered monocyclic unsaturated heterocyclic group containing 1 to 3 identical or different heteroatoms selected from nitrogen, oxygen, and sulfur.

$R^{1c}$ is further still more preferably

C1-C4 alkyl that is substituted with one C1-C4 alkoxy wherein hydrogen contained in the alkoxy may be replaced by 1 or more deuterium atoms, C2-C6 alkenyl, C2-C6 alkynyl, or a 4- to 6-membered monocyclic unsaturated heterocyclic group containing one oxygen atom.

$R^{1a}$ is further still more preferably C1-C4 alkyl that is substituted with one C1-C4 alkoxy.

$R^{1a}$ is further still more preferably methoxymethyl.

$R^{1b}$ is preferably halogen, C1-C6 alkyl, or C1-C6 alkoxy, more preferably halogen, and even more preferably fluorine.

$R^{1c}$ is preferably C1-C6 alkoxy, more preferably C1-C4 alkoxy, and even more preferably methoxy.

Examples of the "substituent" when each group represented by $R^2$ has a substituent include those mentioned above, and the number of substituents is typically one, two, or three. However, in the present invention, the substituent possessed by each group represented by $R^2$ must not be a "substituted or unsubstituted saturated heterocyclic group that may have at least one identical or different heteroatom selected from oxygen and sulfur, and has at least one nitrogen atom." When each group represented by $R^2$ has a substituent, examples of the substituent that can be possessed by the saturated heterocyclic group in the "substituted or unsubstituted saturated heterocyclic group that may have at least one identical or different heteroatom selected from oxygen and sulfur, and has at least one nitrogen atom" excluded from the "substituent" include those mentioned above; however, the substituent that can be possessed by the saturated heterocyclic group includes at least alkyl. Therefore, when each group represented by $R^2$ has a substituent, this "substituent" excludes, for example, the following:

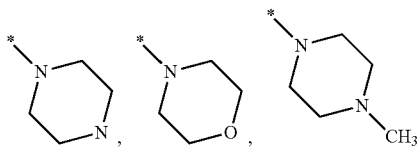

Examples of the "C3-C10 alkyl" in the "substituted or unsubstituted C3-C10 alkyl" represented by $R^2$ include those mentioned above, preferably branched C3-C8 alkyl, more preferably branched C3-C6 alkyl, and even more preferably tert-butyl.

Examples of the "substituent" in the "substituted or unsubstituted C3-C10 alkyl" represented by $R^2$ include those mentioned above. However, the "substituent" is preferably halogen, C1-C6 alkoxy, C3-C7 cycloalkyl, or a "4- to 10-membered monocyclic or polycyclic unsaturated heterocyclic group containing 1 to 3 identical or different heteroatoms selected from nitrogen, oxygen, and sulfur";

more preferably halogen, C3-C7 cycloalkyl, or a "4- to 10-membered monocyclic or polycyclic unsaturated heterocyclic group containing 1 to 3 identical or different heteroatoms selected from nitrogen, oxygen, and sulfur";

even more preferably halogen or C3-C7 cycloalkyl;

still more preferably halogen; and further still more preferably fluorine.

The number of substituents is not particularly limited, but is preferably 0 to 3, and more preferably 0 or 1.

The "substituted or unsubstituted C3-C10 alkyl" represented by $R^2$ is preferably C3-C10 alkyl that may be substituted with "halogen, C1-C6 alkoxy, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur";

more preferably C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur";

even more preferably branched C3-C8 alkyl that may be substituted with "halogen or C3-C7 cycloalkyl";

still more preferably branched C3-C6 alkyl that may be substituted with halogen;

further still more preferably branched C3-C6 alkyl that may be substituted with one halogen atom; and further still more preferably tert-butyl that may be substituted with fluorine.

In Formula (I), examples of the "C3-C7 cycloalkyl" in the "substituted or unsubstituted C3-C7 cycloalkyl" represented by $R^2$ include those mentioned above, preferably C3-C5 cycloalkyl, more preferably C3-C4 cycloalkyl, and even more preferably cyclopropyl.

In Formula (I'), examples of the "C3-C4 cycloalkyl" in the "substituted or unsubstituted C3-C4 cycloalkyl" represented by $R^2$ include those mentioned above, and preferably cyclopropyl.

In Formulas (I) and (I'), examples of the "substituent" in the "substituted or unsubstituted C3-C7 cycloalkyl" and the "substituted or unsubstituted C3-C4 cycloalkyl" represented by $R^2$ include those mentioned above;

preferably halogen, C1-C6 alkyl, C3-C7 cycloalkyl, or halogeno C1-C6 alkyl;

more preferably C1-C6 alkyl, C3-C7 cycloalkyl, or halogeno C1-C6 alkyl;

even more preferably C1-C4 alkyl or C3-C5 cycloalkyl;

still more preferably methyl or cyclopropyl; and further still more preferably methyl.

The number of substituents is not particularly limited, but is preferably 0 to 3, more preferably 0 to 2, and even more preferably 1.

The "substituted or unsubstituted C3-C7 cycloalkyl" represented by $R^2$ in Formula (I) is preferably C3-C7 cycloalkyl that may be substituted with "halogen, C1-C6 alkyl, C3-C7 cycloalkyl, or halogeno C1-C6 alkyl";

more preferably C3-C7 cycloalkyl that may be substituted with "C1-C6 alkyl, C3-C7 cycloalkyl, or halogeno C1-C6 alkyl";

even more preferably C3-C7 cycloalkyl that may be substituted with "C1-C4 alkyl or C3-C5 cycloalkyl";

still more preferably C3-C5 cycloalkyl that may be substituted with one "C1-C4 alkyl or C3-C5 cycloalkyl";

further still more preferably C3-C4 cycloalkyl that may be substituted with one "C1-C4 alkyl or C3-C5 cycloalkyl";

further still more preferably cyclopropyl that may be substituted with one "methyl or cyclopropyl"; and further still more preferably

The "substituted or unsubstituted C3-C4 cycloalkyl" represented by $R^2$ in Formula (I') is preferably C3-C4 cycloalkyl that may be substituted with "halogen, C1-C6 alkyl, C3-C7 cycloalkyl, or halogeno C1-C6 alkyl";

more preferably C3-C4 cycloalkyl that may be substituted with "C1-C6 alkyl, C3-C7 cycloalkyl, or halogeno C1-C6 alkyl";

even more preferably C3-C4 cycloalkyl that may be substituted with "C1-C4 alkyl or C3-C5 cycloalkyl";

still more preferably C3-C4 cycloalkyl that may be substituted with one "C1-C4 alkyl or C3-C5 cycloalkyl";

further still more preferably cycloalkyl that may be substituted with one "methyl or cyclopropyl"; and further still more preferably

Examples of the "C4-C12 bridged cycloalkyl" in the "substituted or unsubstituted C4-C12 bridged cycloalkyl" represented by $R^2$ include those mentioned above, preferably C5-C10 bridged cycloalkyl, and more preferably

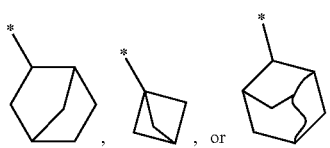

Examples of the "substituent" in the "substituted or unsubstituted C4-C12 bridged cycloalkyl" represented by $R^2$ include those mentioned above.

The "substituted or unsubstituted C4-C12 bridged cycloalkyl" represented by $R^2$ is preferably C4-C12 bridged cycloalkyl, more preferably C5-C10 bridged cycloalkyl, and more preferably

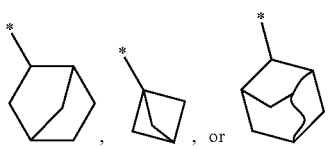
, or

Examples of the "C2-C6 alkenyl" in the "substituted or unsubstituted C2-C6 alkenyl" represented by R² include those mentioned above, preferably C2-C4 alkenyl, and more preferably isopropenyl.

Examples of the "substituent" in the "substituted or unsubstituted C2-C6 alkenyl" represented by R² include those mentioned above, preferably halogen, and more preferably fluorine.

The number of substituents is not particularly limited, but is preferably 1.

The "substituted or unsubstituted C2-C6 alkenyl" represented by R² is preferably C2-C6 alkenyl that may be substituted with halogen, more preferably C2-C4 alkenyl that may be substituted with fluorine, and even more preferably fluoroisopropenyl.

In Formula (I), examples of the "C3-C7 cycloalkenyl" in the "substituted or unsubstituted C3-C7 cycloalkenyl" represented by R² include those mentioned above, and preferably cyclopentenyl.

In Formula (I'), examples of the "C3-C4 cycloalkenyl" in the "substituted or unsubstituted C3-C4 cycloalkenyl" represented by R² include those mentioned above.

In Formulas (I) and (I'), examples of the "substituent" in the "substituted or unsubstituted C3-C7 cycloalkenyl" and the "substituted or unsubstituted C3-C4 cycloalkenyl" represented by R² include those mentioned above.

In Formula (I), the "substituted or unsubstituted C3-C7 cycloalkenyl" represented by R² is preferably C3-C7 cycloalkenyl, and more preferably cyclopentenyl.

In Formula (I'), the "substituted or unsubstituted C3-C4 cycloalkenyl" represented by R² is preferably C3-C4 cycloalkenyl.

Examples of the "4- to 10-membered monocyclic or polycyclic saturated heterocyclic group containing 1 to 3 identical or different heteroatoms selected from nitrogen, oxygen, and sulfur" in the "substituted or unsubstituted 4- to 10-membered monocyclic or polycyclic saturated heterocyclic group containing 1 to 3 identical or different heteroatoms selected from nitrogen, oxygen, and sulfur" represented by R² include those mentioned above.

The "substituent" in the "substituted or unsubstituted 4- to 10-membered monocyclic or polycyclic saturated heterocyclic group containing 1 to 3 identical or different heteroatoms selected from nitrogen, oxygen, and sulfur" represented by R² include those mentioned above.

R² in Formula (I) is preferably substituted or unsubstituted C3-C10 alkyl, substituted or unsubstituted C3-C7 cycloalkyl, substituted or unsubstituted C4-C12 bridged cycloalkyl, substituted or unsubstituted C2-C6 alkenyl, or substituted or unsubstituted C3-C7 cycloalkenyl, provided that when each group represented by R² has a substituent, the substituent must not be a "substituted or unsubstituted saturated heterocyclic group that may have at least one identical or different heteroatom selected from oxygen and sulfur, and has at least one nitrogen atom."

R² is more preferably
C3-C10 alkyl that may be substituted with "halogen, C1-C6 alkoxy, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "halogen, C1-C6 alkyl, C3-C7 cycloalkyl, or halogeno C1-C6 alkyl,"
C4-C12 bridged cycloalkyl,
C2-C6 alkenyl that may be substituted with halogen, or
C3-C7 cycloalkenyl.

R² is even more preferably
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "C1-C6 alkyl,
C3-C7 cycloalkyl, or halogeno C1-C6 alkyl,"
C4-C12 bridged cycloalkyl, or
C3-C7 cycloalkenyl.

R² is still more preferably
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "C1-C6 alkyl,
C3-C7 cycloalkyl, or halogeno C1-C6 alkyl," or
C4-C12 bridged cycloalkyl.

R² is further still more preferably
branched C3-C8 alkyl that may be substituted with "halogen or C3-C7 cycloalkyl,"
C3-C7 cycloalkyl that may be substituted with "C1-C4 alkyl or
C3-C5 cycloalkyl," or
C4-C12 bridged cycloalkyl.

R² is further still more preferably
branched C3-C6 alkyl that may be substituted with halogen, or C3-C7 cycloalkyl that may be substituted with "C1-C4 alkyl or C3-C5 cycloalkyl."

R² is further still more preferably
branched C3-C6 alkyl that may be substituted with halogen, or C3-C5 cycloalkyl that may be substituted with "C1-C4 alkyl or C3-C5 cycloalkyl."

R² is further still more preferably C3-C5 cycloalkyl that may be substituted with one C1-C4 alkyl.

R² is further still more preferably

Moreover, R² in Formula (I') is preferably
substituted or unsubstituted C3-C10 alkyl,
substituted or unsubstituted C3-C4 cycloalkyl,
substituted or unsubstituted C4-C12 bridged cycloalkyl,
substituted or unsubstituted C2-C6 alkenyl, or
substituted or unsubstituted C3-C4 cycloalkenyl,
provided that when each group represented by R² has a substituent, the substituent must not be a "substituted or unsubstituted saturated heterocyclic group that may have at least one identical or different heteroatom selected from oxygen and sulfur, and has at least one nitrogen atom."

R² is more preferably
C3-C10 alkyl that may be substituted with "halogen, C1-C6 alkoxy, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "halogen, C1-C6 alkyl, C3-C7 cycloalkyl, or halogeno C1-C6 alkyl,"
C4-C12 bridged cycloalkyl,
C2-C6 alkenyl that may be substituted with halogen, or
C3-C4 cycloalkenyl.

$R^2$ is even more preferably
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "C1-C6 alkyl,
C3-C7 cycloalkyl, or halogeno C1-C6 alkyl,"
C4-C12 bridged cycloalkyl, or
C3-C4 cycloalkenyl.

$R^2$ is still more preferably
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "C1-C6 alkyl,
C3-C7 cycloalkyl, or halogeno C1-C6 alkyl," or
C4-C12 bridged cycloalkyl.

$R^2$ is further still more preferably
branched C3-C8 alkyl that may be substituted with "halogen or C3-C7 cycloalkyl,"
C3-C4 cycloalkyl that may be substituted with "C1-C4 alkyl or
C3-C5 cycloalkyl," or
C4-C12 bridged cycloalkyl.

$R^2$ is further still more preferably
branched C3-C6 alkyl that may be substituted with halogen, or C3-C4 cycloalkyl that may be substituted with "C1-C4 alkyl or C3-C5 cycloalkyl."

$R^2$ is further still more preferably C3-C4 cycloalkyl that may be substituted with one C1-C4 alkyl.

$R^2$ is further still more preferably

It is preferable that $R^2$ is bonded to the nitrogen atom contained in the pyrrolopyrimidine or pyrazolopyrimidine skeleton in Formulas (I) and (I') via the carbon atom among the atoms contained in $R^2$, and that the number of hydrogen atoms possessed by the carbon atom is 0 or 1. That is, it is preferable that in the following portion of Formulas (I) and (I'):

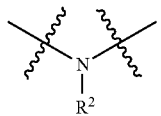

the carbon atom contained in $R^2$ and the above nitrogen atom are bonded together, and that the carbon atom has 0 or 1 hydrogen atom. In $R^2$, the number of hydrogen atoms possessed by the carbon atom is more preferably 0.

Examples of the "substituent" when each group represented by $R^3$ has a substituent include those mentioned above, and the number thereof is typically one, two, or three.

Examples of the "halogen" represented by $R^3$ include those mentioned above; and preferably fluorine, chlorine, and bromine.

Examples of the "C1-C6 alkyl" in the "substituted or unsubstituted C1-C6 alkyl" represented by $R^3$ include those mentioned above, preferably C1-C4 alkyl, more preferably methyl or ethyl, and even more preferably methyl.

Examples of the "substituent" in the "substituted or unsubstituted C1-C6 alkyl" represented by $R^3$ include those mentioned above, and preferably hydroxy or oxo.

The number of substituents is not particularly limited, but is preferably 0 or 1, and more preferably 0.

The "substituted or unsubstituted C1-C6 alkyl" represented by $R^3$ is preferably C1-C6 alkyl that may be substituted with hydroxy or oxo, more preferably C1-C4 alkyl that may be substituted with hydroxy or oxo, even more preferably C1-C4 alkyl, and still more preferably methyl.

The "C1-C6 alkoxy" in the "substituted or unsubstituted C1-C6 alkoxy" represented by $R^3$ include those mentioned above, preferably C1-C4 alkoxy, and more preferably methoxy or ethoxy.

Examples of the "substituent" in the "substituted or unsubstituted C1-C6 alkoxy" represented by $R^3$ include those mentioned above;
preferably halogen, C1-C6 alkoxy, C3-C7 cycloalkyl, or a 4- to 10-membered monocyclic saturated heterocyclic group that may be substituted with oxy and contains 1 to 3 identical or different heteroatoms selected from nitrogen, oxygen, and sulfur;
more preferably halogen, C1-C4 alkoxy, C3-C7 cycloalkyl, or a 4- to 6-membered monocyclic saturated heterocyclic group containing 1 to 3 identical or different heteroatoms selected from nitrogen, oxygen, and sulfur;
even more preferably C1-C4 alkoxy, C3-C7 cycloalkyl, or a 4- to 6-membered monocyclic saturated heterocyclic group containing one oxygen atom; and
still more preferably tetrahydrofuranyl.

The number of substituents is not particularly limited, but is preferably 0 or 1, and more preferably 1.

The "substituted or unsubstituted C1-C6 alkoxy" represented by $R^3$ is preferably C1-C6 alkoxy that may be substituted with "halogen, C1-C6 alkoxy, C3-C7 cycloalkyl, or one or more 4- to 10-membered monocyclic saturated heterocyclic groups that may be substituted with oxo and contain 1 to 3 identical or different heteroatoms selected from nitrogen, oxygen, and sulfur";
more preferably C1-C4 alkoxy that may be substituted with "halogen, C1-C4 alkoxy, C3-C7 cycloalkyl, or one or more 4- to 6-membered monocyclic saturated heterocyclic groups containing 1 to 3 identical or different heteroatoms selected from nitrogen, oxygen, and sulfur";
even more preferably C1-C4 alkoxy that may be substituted with "C1-C4 alkoxy, C3-C7 cycloalkyl, or one or more 4- to 6-membered monocyclic saturated heterocyclic groups containing one oxygen atom";
still more preferably C1-C4 alkoxy that may be substituted with "one or more 4- to 6-membered monocyclic saturated heterocyclic groups containing one oxygen atom"; and
further still more preferably ethoxy or tetrahydrofuranylmethoxy.

The "C1-C6 alkylthio" in the "substituted or unsubstituted C1-C6 alkylthio" represented by $R^3$ include those mentioned above, preferably C1-C4 alkylthio, and more preferably methylthio.

Examples of the "substituent" in the "substituted or unsubstituted C1-C6 alkylthio" represented by $R^3$ include those mentioned above.

The number of substituents is not particularly limited, but is preferably 0 or 1, and more preferably 0.

The "substituted or unsubstituted C1-C6 alkylthio" represented by $R^3$ is preferably C1-C6 alkylthio, more preferably C1-C4 alkylthio, and even more preferably methylthio.

The "C3-C7 cycloalkyl" in the "substituted or unsubstituted C3-C7 cycloalkyl" represented by $R^3$ include those mentioned above, and preferably cyclopropyl.

Examples of the "substituent" in the "substituted or unsubstituted C3-C7 cycloalkyl" represented by $R^3$ include those mentioned above.

The "substituted or unsubstituted C3-C7 cycloalkyl" represented by $R^3$ is preferably C3-C7 cycloalkyl, more preferably C3-C5 cycloalkyl, and even more preferably cyclopropyl.

Examples of the "C2-C6 alkenyl" in the "substituted or unsubstituted C2-C6 alkenyl" represented by $R^3$ include those mentioned above, preferably C2-C4 alkenyl, and even more preferably vinyl.

Examples of the "substituent" in the "substituted or unsubstituted C2-C6 alkenyl" represented by $R^3$ include those mentioned above, and preferably hydroxy.

The number of substituents is not particularly limited, but is preferably 0 or 1, and more preferably 0.

The "substituted or unsubstituted C2-C6 alkenyl" represented by $R^3$ is preferably C2-C6 alkenyl that may be substituted with "hydroxy";

more preferably C2-C4 alkenyl that may be substituted with "hydroxy";

even more preferably C2-C4 alkenyl; and still more preferably vinyl.

Examples of the "C2-C6 alkynyl" in the "substituted or unsubstituted C2-C6 alkynyl" represented by $R^3$ include those mentioned above, preferably C2-C4 alkynyl, and more preferably ethynyl or propynyl.

The number of triple bonds in the "C2-C6 alkynyl" is preferably 1, and the position of the triple bond is preferably disposed between the carbon atom bonded to the 7H-pyrrolo[2,3-d]pyrimidine skeleton and a carbon atom adjacent to the carbon atom.

Examples of the "substituent" in the "substituted or unsubstituted C2-C6 alkynyl" represented by $R^3$ include those mentioned above, and preferably hydroxy,
C1-C6 alkoxy,
amino that may be substituted with $R^4$,
C1-C6 alkylsilyloxy,
C3-C7 cycloalkyl that may be substituted with "hydroxy or oxo,"
C6-C14 aromatic hydrocarbon that may be substituted with $R^5$,
one or more 4- to 10-membered monocyclic saturated heterocyclic groups that may be substituted with $R^6$ and contain 1 to 3 identical or different heteroatoms selected from nitrogen, oxygen, and sulfur,
one or more 4- to 10-membered monocyclic or polycyclic unsaturated heterocyclic groups that may be substituted with $R^7$ and contain 1 to 3 identical or different heteroatoms selected from nitrogen, oxygen, and sulfur, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur.

The "C1-C6 alkoxy" mentioned above as an example of the substituent in the "substituted or unsubstituted C2-C6 alkynyl" represented by $R^3$ is preferably C1-C4 alkoxy, and more preferably methoxy.

$R^4$ in the "amino that may be substituted with $R^4$" mentioned above as an example of the substituent in the "substituted or unsubstituted C2-C6 alkynyl" represented by $R^3$ is preferably C1-C6 alkyl, C1-C4 alkoxy C1-C6 alkyl, or carbamoyl that may be substituted with C3-C7 cycloalkyl.

The "amino that may be substituted with $R^4$" mentioned above as an example of the substituent in the "substituted or unsubstituted C2-C6 alkynyl" represented by $R^3$ is preferably amino that may be substituted with $R^4$, wherein $R^4$ is C1-C4 alkyl or C1-C4 alkoxy C1-C4 alkyl; and more preferably amino that may be substituted with $R^4$, wherein $R^4$ is methyl or methoxyethyl.

The "C1-C6 alkylsilyloxy" mentioned above as an example of the substituent in the "substituted or unsubstituted C2-C6 alkynyl" represented by $R^3$ is preferably tri-C1-C6 alkylsilyloxy, and more preferably tert-butyldimethylsilyloxy.

The C3-C7 cycloalkyl that may be substituted with "hydroxy or oxo" mentioned above as an example of the substituent in the "substituted or unsubstituted C2-C6 alkynyl" represented by $R^3$ is preferably C3-C7 cycloalkyl that may be substituted with "hydroxy."

$R^5$ in the "C6-C14 aromatic hydrocarbon that may be substituted with $R^5$" mentioned above as an example of the substituent in the "substituted or unsubstituted C2-C6 alkynyl" represented by $R^3$ is preferably halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy.

The "C6-C14 aromatic hydrocarbon that may be substituted with $R^5$" mentioned above as an example of the substituent in the "substituted or unsubstituted C2-C6 alkynyl" represented by $R^3$ is preferably phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy; and more preferably phenyl that may be substituted with $R^5$, wherein $R^5$ is halogen.

$R^6$ in the "one or more 4- to 10-membered monocyclic saturated heterocyclic groups that may be substituted with $R^6$ and contain 1 to 3 identical or different heteroatoms selected from nitrogen, oxygen, and sulfur" mentioned above as an example of the substituent in the "substituted or unsubstituted C2-C6 alkynyl" represented by $R^3$ is preferably hydroxy, C1-C6 alkyl, C1-C6 alkoxy, or oxo.

The "one or more 4- to 10-membered monocyclic saturated heterocyclic groups that may be substituted with $R^6$ and contain 1 to 3 identical or different heteroatoms selected from nitrogen, oxygen, and sulfur" mentioned above as an example of the substituent in the "substituted or unsubstituted C2-C6 alkynyl" represented by $R^3$ are preferably "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo;

more preferably "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo;

even more preferably "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy or methyl; and still more preferably morpholino, tetrahydropyranyl, pyrrolidinyl, piperidinyl, or oxetanyl that may be substituted with $R^6$, wherein $R^6$ is hydroxy or methyl.

$R^7$ in the "one or more 4- to 10-membered monocyclic or polycyclic unsaturated heterocyclic groups that may be substituted with $R^7$ and contain 1 to 3 identical or different heteroatoms selected from nitrogen, oxygen, and sulfur" mentioned above as an example of the substituent in the "substituted or unsubstituted C2-C6 alkynyl" represented by $R^3$ is halogen, cyano, C1-C6 alkyl, C1-C6 alkoxy, or amino.

The "one or more 4- to 10-membered monocyclic or polycyclic unsaturated heterocyclic groups that may be substituted with $R^7$ and contain 1 to 3 identical or different heteroatoms selected from nitrogen, oxygen, and sulfur" are preferably "one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino;

more preferably "one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is C1-C4 alkyl or amino; and even more preferably pyrazolyl, imidazo[1,2-b]pyridazinyl, imidazolyl, pyridinyl, thiazolyl, or furo[3,2-b]pyridinyl that may be substituted with $R^7$, wherein $R^7$ is C1-C4 alkyl or amino.

The "unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur" mentioned above as an example of the substituent in the "substituted or unsubstituted C2-C6 alkynyl" represented by $R^3$ is preferably "unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur," and more preferably "pyridinyloxy that may be substituted with halogen."

The number of substituents in the "C2-C6 alkynyl" in the "substituted or unsubstituted C2-C6 alkynyl" represented by $R^3$ is not particularly limited, but is preferably 1.

The "substituted or unsubstituted C2-C6 alkynyl" represented by $R^3$ is preferably C2-C6 alkynyl that may be substituted with "hydroxy,
C1-C6 alkoxy,
amino that may be substituted with $R^4$, wherein $R^4$ is C1-C6 alkyl, C1-C4 alkoxy C1-C6 alkyl, or carbamoyl that may be substituted with C3-C7 cycloalkyl,
C1-C6 alkylsilyloxy,
C3-C7 cycloalkyl that may be substituted with "hydroxy or oxo,"
C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom;

more preferably C2-C6 alkynyl that may be substituted with

"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom;

even more preferably C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo,
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom;
still more preferably C2-C6 alkynyl that may be substituted with
"hydroxy,
amino that may be substituted with $R^4$, wherein $R^4$ is C1-C4 alkyl or C1-C4 alkoxy C1-C4 alkyl,
C3-C7 cycloalkyl that may be substituted with hydroxy,
phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo, or
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino,"
provided that the position of the triple bond of the C2-C6 alkynyl is disposed between the carbon atom bonded to the 7H-pyrrolo[2,3-d]pyrimidine skeleton and a carbon atom adjacent to the carbon atom; and
further still more preferably C2-C6 alkynyl that may be substituted with
"hydroxy,
amino that may be substituted with $R^4$, wherein $R^4$ is methyl or methoxyethyl,
C3-C7 cycloalkyl that may be substituted with hydroxy,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy or methyl, or
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is C1-C4 alkyl or amino,"
provided that the position of the triple bond of the C2-C6 alkynyl is disposed between the carbon atom bonded to the 7H-pyrrolo[2,3-d]pyrimidine skeleton and a carbon atom adjacent to the carbon atom.

Preferable specific examples include

Examples of the "substituent" in the "substituted or unsubstituted amino" represented by $R^3$ include those mentioned above.

Examples of the "substituent" in the "substituted or unsubstituted carbamoyl" represented by $R^3$ include those mentioned above.

Examples of the "C6-C14 aromatic hydrocarbon" in the "substituted or unsubstituted C6-C14 aromatic hydrocarbon" represented by $R^3$ include those mentioned above, and preferably phenyl.

Examples of the "substituent" in the "substituted or unsubstituted C6-C14 aromatic hydrocarbon" represented by $R^3$ include those mentioned above;

preferably
hydroxy,
C1-C6 alkyl that may be substituted with hydroxy, formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur;
more preferably
hydroxy,
C1-C4 alkyl that may be substituted with hydroxy, formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur;
even more preferably
hydroxy,
C1-C4 alkyl that may be substituted with hydroxy, or formyl; and
still more preferably
hydroxy, or
C1-C4 alkyl that may be substituted with hydroxy.

The number of substituents is not particularly limited, but is preferably 0 or 1, and more preferably 1.

The "substituted or unsubstituted C6-C14 aromatic hydrocarbon" represented by $R^3$ is preferably C6-C14 aromatic hydrocarbon that may be substituted with "hydroxy, C1-C6 alkyl that may be substituted with hydroxy, formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur";
more preferably phenyl that may be substituted with "hydroxy,
C1-C4 alkyl that may be substituted with hydroxy, formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur";
even more preferably phenyl that may be substituted with "hydroxy,
C1-C4 alkyl that may be substituted with hydroxy, or formyl"; and
still more preferably phenyl that may be substituted with "hydroxy, or
C1-C4 alkyl that may be substituted with hydroxy."

Examples of the "4- to 10-membered monocyclic or polycyclic saturated heterocyclic group containing 1 to 3 identical or different heteroatoms selected from nitrogen, oxygen, and sulfur" in the "substituted or unsubstituted 4- to 10-membered monocyclic or polycyclic saturated heterocyclic group containing 1 to 3 identical or different heteroatoms selected from nitrogen, oxygen, and sulfur" represented by $R^3$ include those mentioned above.

Examples of the "substituent" in the "substituted or unsubstituted 4- to 10-membered monocyclic or polycyclic saturated heterocyclic group containing 1 to 3 identical or different heteroatoms selected from nitrogen, oxygen, and sulfur" represented by $R^3$ include those mentioned above.

The "4- to 10-membered monocyclic or polycyclic unsaturated heterocyclic group containing 1 to 3 identical or different heteroatoms selected from nitrogen, oxygen, and sulfur" in the "substituted or unsubstituted 4- to 10-membered monocyclic or polycyclic unsaturated heterocyclic group containing 1 to 3 identical or different heteroatoms selected from nitrogen, oxygen, and sulfur" represented by $R^3$ include those mentioned above; preferably a 4- to 6-membered monocyclic or polycyclic unsaturated heterocyclic group containing 1 to 3 identical or different heteroatoms selected from nitrogen, oxygen, and sulfur; more preferably a 4- to 6-membered monocyclic unsaturated heterocyclic group containing one or two nitrogen atoms; and even more preferably pyrazolyl.

Examples of the "substituent" in the "substituted or unsubstituted 4- to 10-membered monocyclic or polycyclic unsaturated heterocyclic group containing 1 to 3 identical or different heteroatoms selected from nitrogen, oxygen, and sulfur" represented by $R^3$ include those mentioned above;
preferably halogen, C1-C6 alkyl that may be substituted with hydroxy, or amino that may be substituted with C1-C6 alkyl(carbonyl);
more preferably halogen, C1-C4 alkyl that may be substituted with hydroxy, or amino that may be substituted with C1-C4 alkyl(carbonyl); and
even more preferably fluorine, methyl that may be substituted with hydroxy, or acetylamino.

The number of substituents is not particularly limited, but is preferably 0 or 1, and more preferably 1.

The "substituted or unsubstituted 4- to 10-membered monocyclic or polycyclic unsaturated heterocyclic group containing 1 to 3 identical or different heteroatoms selected from nitrogen, oxygen, and sulfur" represented by $R^3$ is preferably a 4- to 6-membered monocyclic unsaturated heterocyclic group that may be substituted with "halogen, C1-C6 alkyl that may be substituted with hydroxy, or amino that may be substituted with C1-C6 alkyl(carbonyl)" and contains 1 to 3 identical or different heteroatoms selected from nitrogen, oxygen, and sulfur;
more preferably a 4- to 6-membered monocyclic unsaturated heterocyclic group that may be substituted with "halogen, C1-C4 alkyl that may be substituted with hydroxy, or amino that may be substituted with C1-C4 alkyl(carbonyl)" and contains 1 to 3 identical or different heteroatoms selected from nitrogen, oxygen, and sulfur;
even more preferably a 4- to 6-membered monocyclic unsaturated heterocyclic group containing 1 to 3 identical or different heteroatoms selected from nitrogen, oxygen, and sulfur;
still more preferably a 4- to 6-membered monocyclic unsaturated heterocyclic group containing one or two nitrogen atoms; and
further still more preferably pyrazolyl.

$R^3$ is preferably
hydrogen,
halogen,
cyano,
substituted or unsubstituted C1-C6 alkyl,
substituted or unsubstituted C1-C6 alkoxy,
substituted or unsubstituted C1-C6 alkylthio,
substituted or unsubstituted C3-C7 cycloalkyl,
substituted or unsubstituted C2-C6 alkenyl,
substituted or unsubstituted C2-C6 alkynyl, provided that the position of the triple bond of the C2-C6 alkynyl is disposed between the carbon atom bonded to the 7H-pyrrolo[2,3-d]pyrimidine skeleton and a carbon atom adjacent to the carbon atom,
substituted or unsubstituted C6-C14 aromatic hydrocarbon, or a substituted or unsubstituted 4- to 10-membered monocyclic unsaturated heterocyclic group containing 1 to 3 identical or different heteroatoms selected from nitrogen, oxygen, and sulfur.

$R^3$ is more preferably
hydrogen,
halogen,
cyano,
C1-C6 alkyl that may be substituted with hydroxy or oxo,
C1-C6 alkoxy that may be substituted with
  "halogen,
  C1-C6 alkoxy,
  C3-C7 cycloalkyl, or
  one or more 4- to 10-membered monocyclic saturated heterocyclic groups that may be substituted with oxo and contain 1 to 3 identical or different heteroatoms selected from nitrogen, oxygen, and sulfur,"
C1-C6 alkylthio,
C3-C7 cycloalkyl,
C2-C6 alkenyl that may be substituted with "hydroxy,"
C2-C6 alkynyl that may be substituted with
  "hydroxy,
  C1-C6 alkoxy,
  amino that may be substituted with $R^4$, wherein $R^4$ is C1-C6 alkyl, C1-C4 alkoxy C1-C6 alkyl, or carbamoyl that may be substituted with C3-C7 cycloalkyl,
  C1-C6 alkylsilyloxy,
  C3-C7 cycloalkyl that may be substituted with "hydroxy or oxo,"
  C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
  one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
  one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
  unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
  provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
  "hydroxy,
  C1-C6 alkyl that may be substituted with hydroxy,
  formyl, or
  one or more 4- to 10-membered monocyclic saturated heterocyclic groups that may be substituted with C1-C6 alkyl and contain 1 to 3 identical or different heteroatoms selected from nitrogen, oxygen, and sulfur," or
a 4- to 6-membered monocyclic unsaturated heterocyclic group that may be substituted with
  "halogen,
  C1-C6 alkyl that may be substituted with hydroxy, or
  amino that may be substituted with C1-C6 alkyl(carbonyl),"
and contains 1 to 3 identical or different heteroatoms selected from nitrogen, oxygen, and sulfur.

$R^3$ is even more preferably
hydrogen,
halogen,
cyano,
C1-C4 alkyl that may be substituted with hydroxy or oxo,
C1-C6 alkoxy that may be substituted with
  "halogen,
  C1-C6 alkoxy,
  C3-C7 cycloalkyl, or
  one or more 4- to 10-membered monocyclic saturated heterocyclic groups that may be substituted with oxo and contain 1 to 3 identical or different heteroatoms selected from nitrogen, oxygen, and sulfur,
C1-C4 alkylthio,
C3-C5 cycloalkyl,
C2-C6 alkenyl that may be substituted with "hydroxy,"
C2-C6 alkynyl that may be substituted with
  "hydroxy,
  C1-C6 alkoxy,
  amino that may be substituted with $R^4$, wherein $R^4$ is C1-C6 alkyl, C1-C4 alkoxy C1-C6 alkyl, or carbamoyl that may be substituted with C3-C7 cycloalkyl,
  C1-C6 alkylsilyloxy,
  C3-C7 cycloalkyl that may be substituted with "hydroxy or oxo,"
  C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
  one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
  one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
  unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
  provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
  "hydroxy,
  C1-C6 alkyl that may be substituted with hydroxy,
  formyl, or
  one or more 4- to 10-membered monocyclic saturated heterocyclic groups that may be substituted with C1-C6 alkyl and contain 1 to 3 identical or different heteroatoms selected from nitrogen, oxygen, and sulfur," or
a 4- to 6-membered monocyclic unsaturated heterocyclic group that may be substituted with
  "halogen,
  C1-C6 alkyl that may be substituted with hydroxy, or
  amino that may be substituted with C1-C6 alkyl(carbonyl),"
and contains 1 to 3 identical or different heteroatoms selected from nitrogen, oxygen, and sulfur.

$R^3$ is still more preferably
hydrogen, halogen,
cyano,
C1-C4 alkyl,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C4 alkenyl that may be substituted with "hydroxy,"
C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom, phenyl that may be substituted with
"hydroxy,
C1-C4 alkyl that may be substituted with hydroxy,
formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur," or a 4- to 6-membered monocyclic unsaturated heterocyclic group that may be substituted with
"halogen,
C1-C4 alkyl that may be substituted with hydroxy, or
amino that may be substituted with C1-C4 alkyl(carbonyl),"
and contains 1 to 3 identical or different heteroatoms selected from nitrogen, oxygen, and sulfur.
$R^3$ is further still more preferably
hydrogen,
halogen,
C1-C4 alkyl,
C1-C4 alkoxy that may be substituted with
"halogen,
C1-C4 alkoxy,
C3-C7 cycloalkyl, or
one or more 4- to 6-membered monocyclic saturated heterocyclic groups containing 1 to 3 identical or different heteroatoms selected from nitrogen, oxygen, and sulfur,"
C1-C4 alkylthio,
C2-C4 alkenyl,
C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo,
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy, or
formyl," or
a 4- to 6-membered monocyclic unsaturated heterocyclic group containing 1 to 3 identical or different heteroatoms selected from nitrogen, oxygen, and sulfur.
$R^3$ is further still more preferably
hydrogen,
halogen,
C1-C4 alkoxy that may be substituted with
"C1-C4 alkoxy,
C3-C7 cycloalkyl, or
one or more 4- to 6-membered monocyclic saturated heterocyclic groups containing one oxygen atom,"
C1-C4 alkylthio,
C2-C4 alkenyl,
C2-C6 alkynyl that may be substituted with
"hydroxy,
amino that may be substituted with $R^4$, wherein $R^4$ is C1-C4 alkyl or C1-C4 alkoxy C1-C4 alkyl,
C3-C7 cycloalkyl that may be substituted with "hydroxy or oxo,"
phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo, or
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy or
C1-C4 alkyl that may be substituted with hydroxy," or
a 4- to 6-membered monocyclic unsaturated heterocyclic group containing 1 or 2 nitrogen atoms.
$R^3$ is further still more preferably
C1-C4 alkoxy that may be substituted with "one or more 4- to 6-membered monocyclic saturated heterocyclic groups containing one oxygen atom," or
C2-C6 alkynyl that may be substituted with
"hydroxy,
amino that may be substituted with $R^4$, wherein $R^4$ is methyl or methoxyethyl,
C3-C7 cycloalkyl that may be substituted with hydroxy,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy or methyl, or
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is C1-C4 alkyl or amino,"
provided that the position of the triple bond of the C2-C6 alkynyl is disposed between the carbon atom bonded to the 7H-pyrrolo[2,3-d]pyrimidine skeleton and a carbon atom adjacent to the carbon atom.
X is preferably $CR^3$ when A is A1, and X is preferably N when A is A2.
Y is preferably CH when A is A1 or A2.
When A is A1, n is preferably 1 or 2, and more preferably 1. When A is A2, n is preferably 0 or 1, and more preferably 1.
m is an integer of 0 or 1, and preferably 0.
l is an integer of 1 to 3, and preferably 2.
When A is A1, and n is 2, the bonding positions of $R^1$ preferably include one para-position and one ortho- or meta-position, and more preferably one meta-position and one para-position. When A is A1, and n is 1, the bonding position of $R^1$ is preferably the para- or meta-position, and most preferably the para-position. In the present specification, unless otherwise specified, the bonding position (ortho-, meta-, or para-position) of $R^1$ refers to the position of the carbon atom bonded to the carbamoyl group in Formulas (I) and (I'), among the carbon atoms contained in A1 (more specifically, the carbon atom indicated by the following arrow:

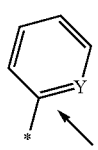

Even when A is

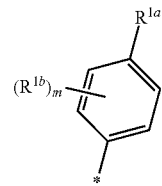

and m is 1, the bonding position of $R^{1b}$ is preferably the meta position.
A1 is preferably
[1]

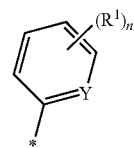

wherein $R^1$ is
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen, oxygen, and sulfur;
Y is N or CH; and
n is an integer of 1 or 2.
A1 is more preferably

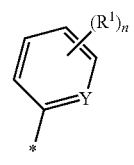

wherein $R^1$ is
halogen,
cyano,
nitro,
C1-C6 alkyl that may be substituted with "hydroxy, C1-C6 alkoxy wherein hydrogen contained in the alkoxy may be replaced by 1 or more deuterium atoms, C1-C6 alkylthio, or C6-C14 aromatic hydrocarbon,"
C1-C6 alkoxy that may be substituted with halogen,
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur;

Y is N or CH; and n is an integer of 1 or 2.

[2]

A1 is even more preferably

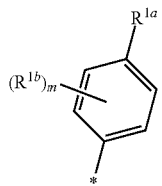

wherein $R^{1a}$ is

C1-C6 alkyl that may be substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or a 4- to 10-membered monocyclic or polycyclic unsaturated heterocyclic group containing 1 to 3 identical or different heteroatoms selected from nitrogen, oxygen, and sulfur;

$R^{1b}$ is halogen, C1-C6 alkyl, or C1-C6 alkoxy; and m is an integer of 0 or 1.

[3]

A1 is still more preferably

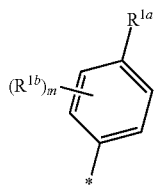

wherein $R^{1a}$ is

C1-C6 alkyl that may be substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, amino that may be substituted with "one or more 4- to 6-membered monocyclic unsaturated heterocyclic groups containing 1 to 3 identical or different heteroatoms selected from nitrogen, oxygen, and sulfur, or C6-C10 aromatic hydrocarbon," or a 4- to 6-membered monocyclic unsaturated heterocyclic group containing 1 to 3 identical or different heteroatoms selected from nitrogen, oxygen, and sulfur;

$R^{1b}$ is halogen, C1-C6 alkyl, or C1-C6 alkoxy; and m is an integer of 0 or 1.

[4]

A1 is further still more preferably

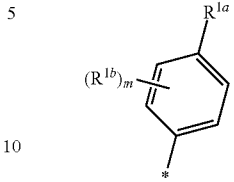

wherein $R^{1a}$ is

C1-C6 alkyl that is substituted with "C1-C6 alkoxy wherein hydrogen contained in the alkoxy may be replaced by 1 or more deuterium atoms, or C1-C6 alkylthio,"

C2-C6 alkenyl,

C2-C6 alkynyl, or a 4- to 6-membered monocyclic unsaturated heterocyclic group containing 1 to 3 identical or different heteroatoms selected from nitrogen, oxygen, and sulfur;

$R^{1b}$ is halogen; and m is an integer of 0 or 1.

[5]

A1 is further still more preferably

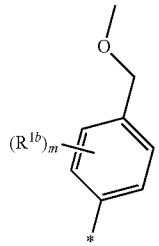

wherein $R^{1b}$ is halogen; and m is an integer of 0 or 1.

[6]

A1 is further still more preferably

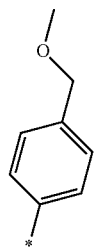 [SMILES: *c1ccc(COC)cc1]

When A is A2, and the following portion:

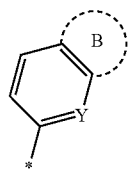

wherein the group B and Y are as defined above;
is polycyclic C8-C14 aromatic hydrocarbon, examples of the polycyclic C8-C14 aromatic hydrocarbon include those mentioned above; preferably bicyclic C8-C10 aromatic hydrocarbon; more preferably

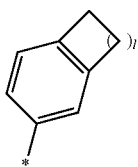

wherein l is as defined above;
and even more preferably

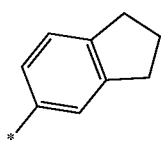 [SMILES: *c1ccc2c(c1)CCC2]

When A is A2, and the following portion:

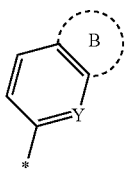

wherein the group B and Y are as defined above;
is an 8- to 14-membered polycyclic unsaturated heterocyclic group containing 1 to 3 identical or different heteroatoms selected from nitrogen, oxygen, and sulfur, examples of the 8- to 14-membered polycyclic unsaturated heterocyclic group containing 1 to 3 identical or different heteroatoms selected from nitrogen, oxygen, and sulfur include those mentioned above; preferably an 8- to 10-membered bicyclic unsaturated heterocyclic group containing 1 to 3 identical or different heteroatoms selected from nitrogen, oxygen, and sulfur; more preferably an 8- to 10-membered bicyclic unsaturated heterocyclic group containing one heteroatom selected from nitrogen, oxygen, and sulfur; and even more preferably

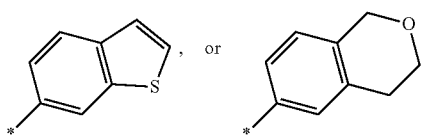 [SMILES: *c1ccc2ccsc2c1 ; *c1ccc2c(c1)CCOC2]

A2 is preferably

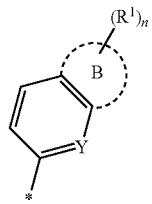

wherein $R^1$ is substituted or unsubstituted C1-C6 alkoxy; Y is CH; and
n is an integer of 0 or 1.
A2 is more preferably

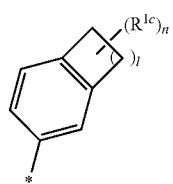

wherein $R^{1c}$ is C1-C6 alkoxy; l is an integer of 1 to 3; and n is an integer of 0 or 1; or
an 8- to 10-membered bicyclic unsaturated heterocyclic group containing 1 to 3 identical or different heteroatoms selected from nitrogen, oxygen, and sulfur.
A2 is even more preferably

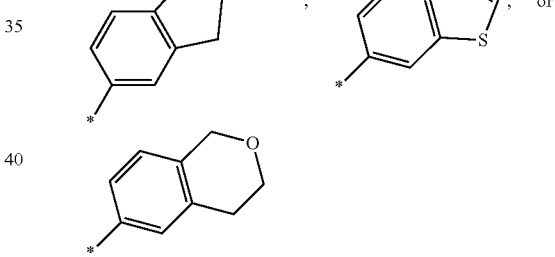

A2 is still more preferably

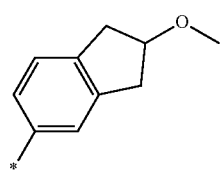 [SMILES: *c1ccc2c(c1)CC(OC)C2]

A is more preferably A1 rather than A2.
Preferred embodiments of the present invention are described in the following [1] to [6].
[1] More preferred is a compound represented by Formula (I) or a salt thereof, wherein
when A is A1,
$R^1$ is
halogen,
cyano,
nitro,
substituted or unsubstituted C1-C6 alkyl,
substituted or unsubstituted C1-C6 alkoxy, substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen,
oxygen, and sulfur;
Y is N or CH;
n is an integer of 1 or 2;
$R^2$ is
substituted or unsubstituted C3-C10 alkyl,
substituted or unsubstituted C3-C7 cycloalkyl,
substituted or unsubstituted C4-C12 bridged cycloalkyl,
substituted or unsubstituted C2-C6 alkenyl, or
substituted or unsubstituted C3-C7 cycloalkenyl,
provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and
X is
N or
$CR^3$, wherein $R^3$ is
  hydrogen,
  halogen,
  cyano,
  substituted or unsubstituted C1-C6 alkyl,
  substituted or unsubstituted C1-C6 alkoxy,
  substituted or unsubstituted C1-C6 alkylthio,
  substituted or unsubstituted C3-C7 cycloalkyl,
  substituted or unsubstituted C2-C6 alkenyl,
  substituted or unsubstituted C2-C6 alkynyl, provided that the position of the triple bond of the C2-C6 alkynyl is disposed between the carbon atom bonded to the 7H-pyrrolo[2,3-d]pyrimidine skeleton and a carbon atom adjacent to the carbon atom,
  substituted or unsubstituted C6-C14 aromatic hydrocarbon, or
    a substituted or unsubstituted 4- to 10-membered monocyclic unsaturated heterocyclic group containing 1 to 3 identical or different heteroatoms selected from nitrogen, oxygen, and sulfur; and
when A is A2,
$R^1$ is substituted or unsubstituted C1-C6 alkoxy;
Y is CH;
n is an integer of 0 or 1;
$R^2$ is substituted or unsubstituted C3-C7 cycloalkyl; and
X is N.
[1-2] More preferred is a compound represented by Formula (I) or a salt thereof, wherein
when A is A1,
$R^1$ is
halogen,
cyano,
nitro,
C1-C6 alkyl that may be substituted with "hydroxy, C1-C6 alkoxy wherein hydrogen contained in the alkoxy may be replaced by 1 or more deuterium atoms, C1-C6 alkylthio, or C6-C14 aromatic hydrocarbon,"
C1-C6 alkoxy that may be substituted with halogen,
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur;
Y is N or CH;
n is an integer of 1 or 2;
$R^2$ is
C3-C10 alkyl that may be substituted with "halogen, C1-C6 alkoxy, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "halogen, C1-C6 alkyl, C3-C7 cycloalkyl, or halogeno C1-C6 alkyl,"
C4-C12 bridged cycloalkyl,
C2-C6 alkenyl that may be substituted with halogen, or
C3-C7 cycloalkenyl; and
X is
N or
$CR^3$, wherein $R^3$ is
  hydrogen,
  halogen,
  cyano,
  C1-C6 alkyl that may be substituted with hydroxy or oxo,
  C1-C6 alkoxy that may be substituted with
  "halogen,
  C1-C6 alkoxy,
  C3-C7 cycloalkyl, or
  one or more 4- to 10-membered monocyclic saturated heterocyclic groups that may be substituted with oxo and contain 1 to 3 identical or different heteroatoms selected from nitrogen, oxygen, and sulfur,"
  C1-C6 alkylthio,
  C3-C7 cycloalkyl,
  C2-C6 alkenyl that may be substituted with "hydroxy,"
  C2-C6 alkynyl that may be substituted with
  "hydroxy,
  C1-C6 alkoxy,
  amino that may be substituted with $R^4$, wherein $R^4$ is C1-C6 alkyl, C1-C4 alkoxy C1-C6 alkyl, or carbamoyl that may be substituted with C3-C7 cycloalkyl,
  C1-C6 alkylsilyloxy,
  C3-C7 cycloalkyl that may be substituted with "hydroxy or oxo,"
  C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
  one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
  one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
  unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
"hydroxy,
C1-C6 alkyl that may be substituted with hydroxy, formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur," or
a 4- to 6-membered monocyclic unsaturated heterocyclic group that may be substituted with
"halogen,
C1-C6 alkyl that may be substituted with hydroxy, or
amino that may be substituted with C1-C6 alkyl(carbonyl),"
and contains 1 to 3 identical or different heteroatoms selected from nitrogen, oxygen, and sulfur; and
when A is A2,
$R^1$ is substituted or unsubstituted C1-C6 alkoxy;
Y is CH;
n is an integer of 0 or 1;
$R^2$ is substituted or unsubstituted C3-C7 cycloalkyl; and
X is N.

[2] More preferred is a compound represented by Formula (I) or a salt thereof, wherein
when A is A1,
A1 is

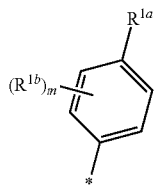

wherein $R^{1a}$ is
C1-C6 alkyl that may be substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur;
$R^{1b}$ is halogen, C1-C6 alkyl, or C1-C6 alkoxy;
m is an integer of 0 or 1;
$R^2$ is
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "C1-C6 alkyl,
C3-C7 cycloalkyl, or halogeno C1-C6 alkyl,"
C4-C12 bridged cycloalkyl, or
C3-C7 cycloalkenyl; and
X is
N or
$CR^3$, wherein $R^3$ is
hydrogen,
halogen,
cyano,
C1-C4 alkyl that may be substituted with hydroxy or oxo,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C6 alkenyl that may be substituted with "hydroxy,"
C2-C6 alkynyl that may be substituted with
"hydroxy,
C1-C6 alkoxy,
amino that may be substituted with $R^4$, wherein $R^4$ is C1-C6 alkyl, C1-C4 alkoxy C1-C6 alkyl, or carbamoyl that may be substituted with C3-C7 cycloalkyl,
C1-C6 alkylsilyloxy,
C3-C7 cycloalkyl that may be substituted with "hydroxy or oxo,"
C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
"hydroxy,
C1-C6 alkyl that may be substituted with hydroxy, formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur, or
a 4- to 6-membered monocyclic unsaturated heterocyclic group that may be substituted with
"halogen,
C1-C6 alkyl that may be substituted with hydroxy, or
amino that may be substituted with C1-C6 alkyl(carbonyl),"
and contains 1 to 3 identical or different heteroatoms selected from nitrogen, oxygen, and sulfur; and
when A is A2,
A2 is

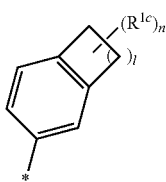

wherein $R^{1c}$ is C1-C6 alkoxy; l is an integer of 1 to 3; and n is an integer of 0 or 1;
$R^2$ is C3-C7 cycloalkyl; and
X is N.

[3] Even more preferred is a compound represented by Formula (I) or a salt thereof, wherein
A is

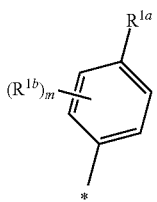

wherein $R^{1a}$ is
C1-C6 alkyl that may be substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl,
amino that may be substituted with "one or more 4- to 6-membered monocyclic unsaturated heterocyclic groups containing 1 to 3 identical or different heteroatoms selected from nitrogen, oxygen, and sulfur, or C6-C10 aromatic hydrocarbon," or
a 4- to 6-membered monocyclic unsaturated heterocyclic group containing 1 to 3 identical or different heteroatoms selected from nitrogen, oxygen, and sulfur;
$R^{1b}$ is halogen, C1-C6 alkyl, or C1-C6 alkoxy;
m is an integer of 0 or 1;
$R^2$ is
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C7 cycloalkyl that may be substituted with "C1-C6 alkyl, C3-C7 cycloalkyl, or halogeno C1-C6 alkyl," or
C4-C12 bridged cycloalkyl; and X is
N or
$CR^3$, wherein $R^3$ is
hydrogen,
halogen,
cyano,
C1-C4 alkyl,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C4 alkenyl that may be substituted with "hydroxy,"
C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy,
formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur," or
a 4- to 6-membered monocyclic unsaturated heterocyclic group that may be substituted with
"halogen,
C1-C4 alkyl that may be substituted with hydroxy, or
amino that may be substituted with C1-C4 alkyl(carbonyl),"

and contains 1 to 3 identical or different heteroatoms selected from nitrogen, oxygen, and sulfur.

[4] Still more preferred is a compound represented by Formula (I) or a salt thereof, wherein
A is

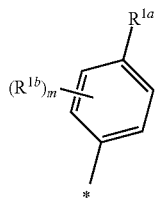

wherein $R^{1a}$ is
C1-C6 alkyl that is substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl, or
a 4- to 6-membered monocyclic unsaturated heterocyclic group containing 1 to 3 identical or different heteroatoms selected from nitrogen, oxygen, and sulfur;
$R^{1b}$ is halogen;
m is an integer of 0 or 1;
$R^2$ is
branched C3-C8 alkyl that may be substituted with "halogen or C3-C7 cycloalkyl,"
C3-C7 cycloalkyl that may be substituted with "C1-C4 alkyl or C3-C5 cycloalkyl," or
C4-C12 bridged cycloalkyl; and
X is
N or
$CR^3$, wherein $R^3$ is
  hydrogen,
  halogen,
  C1-C4 alkyl,
  C1-C4 alkoxy that may be substituted with
  "halogen,
  C1-C4 alkoxy,
  C3-C7 cycloalkyl, or
  one or more 4- to 6-membered monocyclic saturated heterocyclic groups containing 1 to 3 identical or different heteroatoms selected from nitrogen, oxygen, and sulfur,"
  C1-C4 alkylthio,
  C2-C4 alkenyl,
  C2-C6 alkynyl that may be substituted with
  "hydroxy,
  C1-C4 alkoxy,
  amino that may be substituted with $R^4$, wherein $R^4$ is C1-C4 alkyl, C1-C4 alkoxy C1-C4 alkyl, or carbamoyl that may be substituted with C3-C5 cycloalkyl,
  tri-C1-C6 alkylsilyloxy,
  C3-C7 cycloalkyl that may be substituted with "hydroxy or oxo,"
  phenyl that may be substituted with $R^5$, wherein $R^5$ is halogen,
  "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo,
  "one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino, or
  unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
  provided that the position of the triple bond of the C2-C6 alkynyl is disposed between the carbon atom bonded to the 7H-pyrrolo[2,3-d]pyrimidine skeleton and a carbon atom adjacent to the carbon atom,
  phenyl that may be substituted with
  "hydroxy,
  C1-C4 alkyl that may be substituted with hydroxy, or formyl," or
  a 4- to 6-membered monocyclic unsaturated heterocyclic group containing 1 to 3 identical or different heteroatoms selected from nitrogen, oxygen, and sulfur.

[5] Further still more preferred is a compound represented by Formula (I) or a salt thereof, wherein
A is

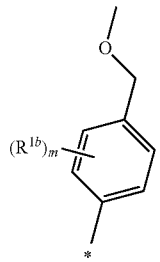

wherein $R^{1b}$ is halogen;
m is an integer of 0 or 1;
$R^2$ is
branched C3-C6 alkyl that may be substituted with halogen, or C3-C7 cycloalkyl that may be substituted with "C1-C4 alkyl or C3-C5 cycloalkyl";
X is $CR^3$, wherein $R^3$ is
  hydrogen,
  halogen,
  C1-C4 alkoxy that may be substituted with
  "C1-C4 alkoxy,
  C3-C7 cycloalkyl, or
  one or more 4- to 6-membered monocyclic saturated heterocyclic groups containing one oxygen atom,"
  C1-C4 alkylthio,
  C2-C4 alkenyl,
  C2-C6 alkynyl that may be substituted with
  "hydroxy,
  amino that may be substituted with $R^4$, wherein $R^4$ is C1-C4 alkyl or C1-C4 alkoxy C1-C4 alkyl,
  C3-C7 cycloalkyl that may be substituted with hydroxy,
  phenyl that may be substituted with $R^5$, wherein $R^5$ is halogen,
  "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo, or one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino,"

provided that the position of the triple bond of the C2-C6 alkynyl is disposed between the carbon atom bonded to the 7H-pyrrolo[2,3-d]pyrimidine skeleton and a carbon atom adjacent to the carbon atom, phenyl that may be substituted with "hydroxy, or C1-C4 alkyl that may be substituted with hydroxy," or a 4- to 6-membered monocyclic unsaturated heterocyclic group containing 1 or 2 nitrogen atoms.

[6] Further still more preferred is a compound represented by Formula (I) or a salt thereof, wherein A is

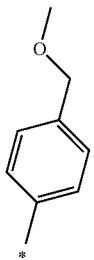

$R^2$ is

C3-C5 cycloalkyl that may be substituted with one C1-C4 alkyl; and

X is $CR^3$, wherein $R^3$ is

C1-C4 alkoxy that may be substituted with "one or more 4- to 6-membered monocyclic saturated heterocyclic groups containing one oxygen atom," or C2-C6 alkynyl that may be substituted with "hydroxy, amino that may be substituted with $R^4$, wherein $R^4$ is methyl or methoxyethyl, C3-C7 cycloalkyl that may be substituted with hydroxy, "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy or methyl, or one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is C1-C4 alkyl or amino,"

provided that the position of the triple bond of the C2-C6 alkynyl is disposed between the carbon atom bonded to the 7H-pyrrolo[2,3-d]pyrimidine skeleton and a carbon atom adjacent to the carbon atom.

Another preferred embodiment of the present invention is described below.

Preferred is a compound represented by Formula (I) or a salt thereof, wherein A is

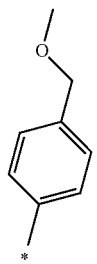

$R^2$ is

C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"

C3-C7 cycloalkyl that may be substituted with "C1-C6 alkyl,

C3-C7 cycloalkyl, or halogeno C1-C6 alkyl," or

C4-C12 bridged cycloalkyl; and

X is

N or $CR^3$, wherein $R^3$ is hydrogen, halogen, cyano,

C1-C4 alkyl,

C1-C6 alkoxy that may be substituted with

"halogen,

C1-C6 alkoxy,

C3-C7 cycloalkyl, or one or more 4- to 10-membered monocyclic saturated heterocyclic groups that may be substituted with oxo and contain 1 to 3 identical or different heteroatoms selected from nitrogen, oxygen, and sulfur,"

C1-C4 alkylthio,

C3-C5 cycloalkyl,

C2-C4 alkenyl that may be substituted with "hydroxy,"

C2-C6 alkynyl that may be substituted with

"hydroxy,

C1-C4 alkoxy, amino that may be substituted with $R^4$, wherein $R^4$ is C1-C4 alkyl, C1-C4 alkoxy C1-C4 alkyl, or carbamoyl that may be substituted with C3-C5 cycloalkyl, tri-C1-C6 alkylsilyloxy, C3-C7 cycloalkyl that may be substituted with "hydroxy or oxo,"

phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy, one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo, one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy, formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur, or
a 4- to 6-membered monocyclic unsaturated heterocyclic group that may be substituted with
"halogen,
C1-C4 alkyl that may be substituted with hydroxy, or
amino that may be substituted with C1-C4 alkyl(carbonyl),"
and contains 1 to 3 identical or different heteroatoms selected from nitrogen, oxygen, and sulfur.

More preferred is a compound represented by Formula (I) or a salt thereof, wherein A is

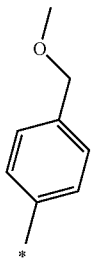

$R^2$ is
branched C3-C8 alkyl that may be substituted with "halogen or C3-C7 cycloalkyl,"
C3-C7 cycloalkyl that may be substituted with "C1-C4 alkyl or C3-C5 cycloalkyl," or
C4-C12 bridged cycloalkyl; and
X is
N or
$CR^3$, wherein $R^3$ is
hydrogen,
halogen,
C1-C4 alkyl,
C1-C4 alkoxy that may be substituted with
"halogen,
C1-C4 alkoxy,
C3-C7 cycloalkyl, or
one or more 4- to 6-membered monocyclic saturated heterocyclic groups containing 1 to 3 identical or different heteroatoms selected from nitrogen, oxygen, and sulfur,"
C1-C4 alkylthio,
C2-C4 alkenyl,
C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo,
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy, or
formyl," or
a 4- to 6-membered monocyclic unsaturated heterocyclic group containing 1 to 3 identical or different heteroatoms selected from nitrogen, oxygen, and sulfur.

Another preferred embodiment of the present invention is described below.

[1] Preferred is a compound represented by Formula (I') or a salt thereof, wherein
when A is A1,
$R^1$ is
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, or
a substituted or unsubstituted 4- to 10-membered monocyclic or polycyclic unsaturated heterocyclic group containing 1 to 3 identical or different heteroatoms selected from nitrogen, oxygen, and sulfur;
Y is N or CH;
n is an integer of 1 or 2;
$R^2$ is
substituted or unsubstituted C3-C10 alkyl,
substituted or unsubstituted C3-C4 cycloalkyl,
substituted or unsubstituted C4-C12 bridged cycloalkyl,
substituted or unsubstituted C2-C6 alkenyl, or
substituted or unsubstituted C3-C4 cycloalkenyl,
provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and
X is N or
CR³, wherein R³ is
hydrogen,
halogen,
cyano,
substituted or unsubstituted C1-C6 alkyl,
substituted or unsubstituted C1-C6 alkoxy,
substituted or unsubstituted C1-C6 alkylthio,
substituted or unsubstituted C3-C7 cycloalkyl,
substituted or unsubstituted C2-C6 alkenyl,
substituted or unsubstituted C2-C6 alkynyl, provided that the position of the triple bond of the C2-C6 alkynyl is disposed between the carbon atom bonded to the 7H-pyrrolo[2,3-d]pyrimidine skeleton and a carbon atom adjacent to the carbon atom,
substituted or unsubstituted C6-C14 aromatic hydrocarbon, or
a substituted or unsubstituted 4- to 10-membered monocyclic unsaturated heterocyclic group containing 1 to 3 identical or different heteroatoms selected from nitrogen, oxygen, and sulfur; and
when A is A2,
R¹ is substituted or unsubstituted C1-C6 alkoxy;
Y is CH;
n is an integer of 0 or 1;
R² is substituted or unsubstituted C3-C7 cycloalkyl; and
X is N.

[1-2] More preferred is a compound represented by Formula (I') or a salt thereof, wherein
when A is A1,
R¹ is
halogen,
cyano,
nitro,
C1-C6 alkyl that may be substituted with "hydroxy, C1-C6 alkoxy wherein hydrogen contained in the alkoxy may be replaced by 1 or more deuterium atoms, C1-C6 alkylthio, or C6-C14 aromatic hydrocarbon,"
C1-C6 alkoxy that may be substituted with halogen,
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur;
Y is N or CH;
n is an integer of 1 or 2;
R² is
C3-C10 alkyl that may be substituted with "halogen, C1-C6 alkoxy, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "halogen, C1-C6 alkyl, C3-C7 cycloalkyl, or halogeno C1-C6 alkyl,"
C4-C12 bridged cycloalkyl,
C2-C6 alkenyl that may be substituted with halogen, or
C3-C4 cycloalkenyl; and
X is
N or
CR³, wherein R³ is
hydrogen,
halogen,
cyano,
C1-C6 alkyl that may be substituted with hydroxy or oxo,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C6 alkylthio,
C3-C7 cycloalkyl,
C2-C6 alkenyl that may be substituted with "hydroxy,"
C2-C6 alkynyl that may be substituted with
"hydroxy,
C1-C6 alkoxy,
amino that may be substituted with R⁴, wherein R⁴ is C1-C6 alkyl, C1-C4 alkoxy C1-C6 alkyl, or carbamoyl that may be substituted with C3-C7 cycloalkyl,
C1-C6 alkylsilyloxy,
C3-C7 cycloalkyl that may be substituted with "hydroxy or oxo,"
C6-C14 aromatic hydrocarbon that may be substituted with R⁵, wherein R⁵ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
one or more 4- to 10-membered monocyclic saturated heterocyclic groups that may be substituted with R⁶ and contain 1 to 3 identical or different heteroatoms selected from nitrogen, oxygen, and sulfur, wherein R⁶ is hydroxy, C1-C6 alkyl, C1-C6 alkoxy, or oxo,
one or more 4- to 10-membered monocyclic or polycyclic unsaturated heterocyclic groups that may be substituted with R⁷ and contain 1 to 3 identical or different heteroatoms selected from nitrogen, oxygen, and sulfur, wherein R⁷ is halogen, cyano, C1-C6 alkyl, C1-C6 alkoxy, or amino, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
"hydroxy,
C1-C6 alkyl that may be substituted with hydroxy,
formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur," or
a 4- to 6-membered monocyclic unsaturated heterocyclic group that may be substituted with
"halogen,
C1-C6 alkyl that may be substituted with hydroxy, or
amino that may be substituted with C1-C6 alkyl(carbonyl),"
and contains 1 to 3 identical or different heteroatoms selected from nitrogen, oxygen, and sulfur; and
when A is A2, $R^1$ is substituted or unsubstituted C1-C6 alkoxy;
Y is CH;
n is an integer of 0 or 1;
$R^2$ is substituted or unsubstituted C3-C7 cycloalkyl; and
X is N.

[2] Even more preferred is a compound represented by Formula (I') or a salt thereof, wherein
when A is A1,
A1 is

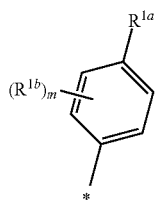

wherein $R^{1a}$ is
C1-C6 alkyl that may be substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl,
amino that may be substituted with "one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon," or
a 4- to 10-membered monocyclic or polycyclic unsaturated heterocyclic group containing 1 to 3 identical or different heteroatoms selected from nitrogen, oxygen, and sulfur;
$R^{1b}$ is halogen, C1-C6 alkyl, or C1-C6 alkoxy;
m is an integer of 0 or 1;
$R^2$ is
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "C1-C6 alkyl,
C3-C7 cycloalkyl, or halogeno C1-C6 alkyl,"
C4-C12 bridged cycloalkyl, or
C3-C4 cycloalkenyl; and
X is
N or
$CR^3$, wherein $R^3$ is
hydrogen,
halogen,
cyano,
C1-C4 alkyl that may be substituted with hydroxy or oxo,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C6 alkenyl that may be substituted with "hydroxy,"
C2-C6 alkynyl that may be substituted with "hydroxy,
C1-C6 alkoxy,
amino that may be substituted with $R^4$, wherein $R^4$ is C1-C6 alkyl, C1-C4 alkoxy C1-C6 alkyl, or carbamoyl that may be substituted with C3-C7 cycloalkyl,
C1-C6 alkylsilyloxy,
C3-C7 cycloalkyl that may be substituted with "hydroxy or oxo,"
C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
C6-C14 aromatic hydrocarbon that may be substituted with
"hydroxy,
C1-C6 alkyl that may be substituted with hydroxy,
formyl, or
one or more 4- to 10-membered monocyclic saturated heterocyclic groups that may be substituted with C1-C6 alkyl and contain 1 to 3 identical or different heteroatoms selected from nitrogen, oxygen, and sulfur, or
a 4- to 6-membered monocyclic unsaturated heterocyclic group that may be substituted with
"halogen,
C1-C6 alkyl that may be substituted with hydroxy, or
amino that may be substituted with C1-C6 alkyl(carbonyl),"
and contains 1 to 3 identical or different heteroatoms selected from nitrogen, oxygen, and sulfur; and
when A is A2,
A2 is

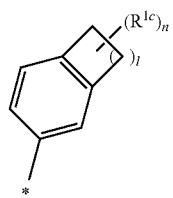

wherein $R^{1c}$ is C1-C6 alkoxy; l is an integer of 1 to 3; and n is an integer of 0 or 1;

$R^2$ is C3-C7 cycloalkyl; and
X is N.

[3] Still more preferred is a compound represented by Formula (I') or a salt thereof, wherein
A is

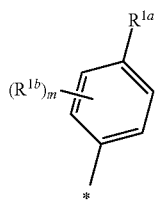

wherein $R^{1a}$ is
C1-C6 alkyl that may be substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl,
amino that may be substituted with "one or more 4- to 6-membered monocyclic unsaturated heterocyclic groups containing 1 to 3 identical or different heteroatoms selected from nitrogen, oxygen, and sulfur, or C6-C10 aromatic hydrocarbon," or
a 4- to 6-membered monocyclic unsaturated heterocyclic group containing 1 to 3 identical or different heteroatoms selected from nitrogen, oxygen, and sulfur;
$R^{1b}$ is halogen, C1-C6 alkyl, or C1-C6 alkoxy;
m is an integer of 0 or 1;
$R^2$ is
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "C1-C6 alkyl, C3-C7 cycloalkyl, or halogeno C1-C6 alkyl," or
C4-C12 bridged cycloalkyl; and
X is
N or
$CR^3$, wherein $R^3$ is
hydrogen,
halogen,
cyano,
C1-C4 alkyl,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C4 alkenyl that may be substituted with "hydroxy,"
C2-C6 alkynyl that may be substituted with
"hydroxy,
C1-C4 alkoxy,
amino that may be substituted with $R^4$, wherein $R^4$ is
C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy,
formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur," or
a 4- to 6-membered monocyclic unsaturated heterocyclic group that may be substituted with
"halogen,
C1-C4 alkyl that may be substituted with hydroxy, or
amino that may be substituted with C1-C4 alkyl(carbonyl),"
and contains 1 to 3 identical or different heteroatoms selected from nitrogen, oxygen, and sulfur.

[4] Further still more preferred is a compound represented by Formula (I') or a salt thereof, wherein
A is

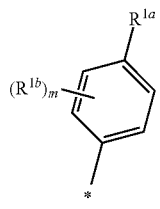

wherein $R^{1a}$ is
C1-C6 alkyl that is substituted with "C1-C6 alkoxy wherein hydrogen contained in the alkoxy may be replaced by 1 or more deuterium atoms, or C1-C6 alkylthio,"
C2-C6 alkenyl,
C2-C6 alkynyl, or a 4- to 6-membered monocyclic unsaturated heterocyclic group containing 1 to 3 identical or different heteroatoms selected from nitrogen, oxygen, and sulfur;
$R^{1b}$ is halogen;
m is an integer of 0 or 1;
$R^2$ is
branched C3-C8 alkyl that may be substituted with "halogen or C3-C7 cycloalkyl,"
C3-C4 cycloalkyl that may be substituted with "C1-C4 alkyl or C3-C5 cycloalkyl," or
C4-C12 bridged cycloalkyl; and
X is
N or
$CR^3$, wherein $R^3$ is
  hydrogen,
  halogen,
  C1-C4 alkyl,
  C1-C4 alkoxy that may be substituted with
  "halogen,
  C1-C4 alkoxy,
  C3-C7 cycloalkyl, or
  one or more 4- to 6-membered monocyclic saturated heterocyclic groups containing 1 to 3 identical or different heteroatoms selected from nitrogen, oxygen, and sulfur,"
  C1-C4 alkylthio,
  C2-C4 alkenyl,
  C2-C6 alkynyl that may be substituted with
  "hydroxy,
  C1-C4 alkoxy,
  amino that may be substituted with $R^4$, wherein $R^4$ is C1-C4 alkyl, C1-C4 alkoxy C1-C4 alkyl, or carbamoyl that may be substituted with C3-C5 cycloalkyl,
  tri-C1-C6 alkylsilyloxy,
  C3-C7 cycloalkyl that may be substituted with "hydroxy or oxo,"
  phenyl that may be substituted with $R^5$, wherein $R^5$ is halogen,
  "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, C1-C4 alkoxy, or oxo,
  "one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino, or
  unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
  provided that the position of the triple bond of the C2-C6 alkynyl is disposed between the carbon atom bonded to the 7H-pyrrolo[2,3-d]pyrimidine skeleton and a carbon atom adjacent to the carbon atom,
  phenyl that may be substituted with
  "hydroxy,
  C1-C4 alkyl that may be substituted with hydroxy, or formyl," or
  a 4- to 6-membered monocyclic unsaturated heterocyclic group containing 1 to 3 identical or different heteroatoms selected from nitrogen, oxygen, and sulfur.

[5] Further still more preferred is a compound represented by Formula (I') or a salt thereof, wherein A is

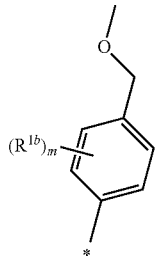

wherein $R^{1b}$ is halogen;
m is an integer of 0 or 1;
$R^2$ is
branched C3-C6 alkyl that may be substituted with halogen, or
C3-C4 cycloalkyl that may be substituted with "C1-C4 alkyl or C3-C5 cycloalkyl";
X is $CR^3$, wherein $R^3$ is
  hydrogen,
  halogen,
  C1-C4 alkoxy that may be substituted with
  "C1-C4 alkoxy,
  C3-C7 cycloalkyl, or
  one or more 4- to 6-membered monocyclic saturated heterocyclic groups containing one oxygen atom,"
  C1-C4 alkylthio,
  C2-C4 alkenyl,
  C2-C6 alkynyl that may be substituted with
  "hydroxy,
  amino that may be substituted with $R^4$, wherein $R^4$ is C1-C4 alkyl or C1-C4 alkoxy C1-C4 alkyl,
  C3-C7 cycloalkyl that may be substituted with hydroxy,
  phenyl that may be substituted with $R^5$, wherein $R^5$ is halogen,
  "one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo, or
  one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino,"
  provided that the position of the triple bond of the C2-C6 alkynyl is disposed between the carbon atom bonded to the 7H-pyrrolo[2,3-d]pyrimidine skeleton and a carbon atom adjacent to the carbon atom,
  phenyl that may be substituted with
  "hydroxy, or
  C1-C4 alkyl that may be substituted with hydroxy," or
  a 4- to 6-membered monocyclic unsaturated heterocyclic group containing 1 or 2 nitrogen atoms.

[6] Further still more preferred is a compound represented by Formula (I') or a salt thereof, wherein A is

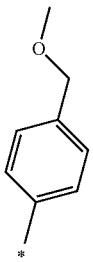

$R^2$ is
C3-C4 cycloalkyl that may be substituted with one C1-C4 alkyl; and
X is $CR^3$, wherein $R^3$ is
C1-C4 alkoxy that may be substituted with "one or more 4- to 6-membered monocyclic saturated heterocyclic groups containing one oxygen atom," or
C2-C6 alkynyl that may be substituted with
"hydroxy,
amino that may be substituted with $R^4$, wherein $R^4$ is methyl or methoxyethyl,
C3-C7 cycloalkyl that may be substituted with hydroxy,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy or methyl, or
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is C1-C4 alkyl or amino,"
provided that the position of the triple bond of the C2-C6 alkynyl is disposed between the carbon atom bonded to the 7H-pyrrolo[2,3-d]pyrimidine skeleton and a carbon atom adjacent to the carbon atom.

Another preferred embodiment of the present invention is described below.

Preferred is a compound represented by Formula (I') or a salt thereof, wherein
A is

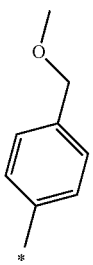

$R^2$ is
C3-C10 alkyl that may be substituted with "halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,"
C3-C4 cycloalkyl that may be substituted with "C1-C6 alkyl,
C3-C7 cycloalkyl, or halogeno C1-C6 alkyl," or
C4-C12 bridged cycloalkyl; and
X is
N or
$CR^3$, wherein $R^3$ is
hydrogen,
halogen,
cyano,
C1-C4 alkyl,
C1-C6 alkoxy that may be substituted with
"halogen,
C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur,"
C1-C4 alkylthio,
C3-C5 cycloalkyl,
C2-C4 alkenyl that may be substituted with "hydroxy,"
C2-C6 alkynyl that may be substituted with
"hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with "hydroxy or oxo,"
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, or
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
provided that the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with
"hydroxy,
C1-C4 alkyl that may be substituted with hydroxy, formyl, or
one or more 4- to 6-membered monocyclic saturated heterocyclic groups that may be substituted with C1-C4 alkyl and contain 1 to 3 identical or different heteroatoms selected from nitrogen, oxygen, and sulfur, or
a 4- to 6-membered monocyclic unsaturated heterocyclic group that may be substituted with
"halogen,
C1-C4 alkyl that may be substituted with hydroxy, or amino that may be substituted with C1-C4 alkyl(carbonyl)," and contains 1 to 3 identical or different heteroatoms selected from nitrogen, oxygen, and sulfur.

More preferred is a compound represented by Formula (I') or a salt thereof, wherein
A is

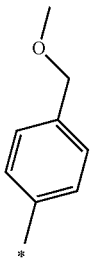

R² is
branched C3-C8 alkyl that may be substituted with "halogen or C3-C7 cycloalkyl,"
C3-C4 cycloalkyl that may be substituted with "C1-C4 alkyl or
C3-C5 cycloalkyl," or
C4-C12 bridged cycloalkyl; and
X is
N or
CR³, wherein R³ is
 hydrogen,
 halogen,
 C1-C4 alkyl,
 C1-C4 alkoxy that may be substituted with
  "halogen,
  C1-C4 alkoxy,
  C3-C7 cycloalkyl, or
  one or more 4- to 6-membered monocyclic saturated heterocyclic groups containing 1 to 3 identical or different heteroatoms selected from nitrogen, oxygen, and sulfur,"
 C1-C4 alkylthio,
 C2-C4 alkenyl,
 C2-C6 alkynyl that may be substituted with
  "hydroxy,
  C1-C4 alkoxy,
  amino that may be substituted with R⁴, wherein R⁴ is C1-C4 alkyl, C1-C4 alkoxy C1-C4 alkyl, or carbamoyl that may be substituted with C3-C5 cycloalkyl,
  tri-C1-C6 alkylsilyloxy,
  C3-C7 cycloalkyl that may be substituted with "hydroxy or oxo,"
  phenyl that may be substituted with R⁵, wherein R⁵ is halogen,
  "one or more 4- to 6-membered monocyclic saturated heterocyclic groups that may be substituted with R⁶ and contain 1 to 3 identical or different heteroatoms selected from nitrogen, oxygen, and sulfur," wherein R⁶ is hydroxy, C1-C4 alkyl, C1-C4 alkoxy, or oxo,
  "one or more 4- to 10-membered monocyclic or bicyclic unsaturated heterocyclic groups that may be substituted with R⁷ and contain 1 to 3 identical or different heteroatoms selected from nitrogen, oxygen, and sulfur," wherein R⁷ is halogen, cyano, C1-C4 alkyl, C1-C4 alkoxy, or amino, or
  unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,"
 provided that the position of the triple bond of the C2-C6 alkynyl is disposed between the carbon atom bonded to the 7H-pyrrolo[2,3-d]pyrimidine skeleton and a carbon atom adjacent to the carbon atom,
 phenyl that may be substituted with
  "hydroxy,
  C1-C4 alkyl that may be substituted with hydroxy, or
  formyl," or
 a 4- to 6-membered monocyclic unsaturated heterocyclic group containing 1 to 3 identical or different heteroatoms selected from nitrogen, oxygen, and sulfur.

Still another preferred embodiment of the present invention is described below.

Preferred are compounds represented by Formulas (I) and (I') or salts thereof, wherein
A is

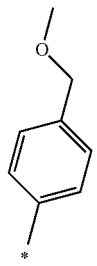

R² is

X is CR³, wherein R³ is preferably
 hydrogen,
 halogen,
 cyano,
 substituted or unsubstituted C1-C6 alkyl,
 substituted or unsubstituted C1-C6 alkoxy,
 substituted or unsubstituted C1-C6 alkylthio,
 substituted or unsubstituted C3-C7 cycloalkyl,
 substituted or unsubstituted C2-C6 alkenyl,
 substituted or unsubstituted C2-C6 alkynyl, provided that the position of the triple bond of the C2-C6 alkynyl is disposed between the carbon atom bonded to the 7H-pyrrolo[2,3-d]pyrimidine skeleton and a carbon atom adjacent to the carbon atom,
 substituted or unsubstituted C6-C14 aromatic hydrocarbon, or a substituted or unsubstituted 4- to 10-membered monocyclic unsaturated heterocyclic group containing 1 to 3 identical or different heteroatoms selected from nitrogen, oxygen, and sulfur;
 more preferably
 hydrogen,
 halogen,
 substituted or unsubstituted C1-C6 alkoxy, or substituted or unsubstituted C2-C6 alkynyl, provided that the position of the triple bond of the C2-C6 alkynyl is disposed between the carbon atom bonded to the 7H-pyrrolo [2,3-d]pyrimidine skeleton and a carbon atom adjacent to the carbon atom;
even more preferably
hydrogen,
halogen,
substituted or unsubstituted methoxy,
substituted or unsubstituted ethoxy,
substituted or unsubstituted ethynyl, or
substituted or unsubstituted propynyl, provided that the position of the triple bond is disposed between the carbon atom bonded to the 7H-pyrrolo[2,3-d]pyrimidine skeleton and a carbon atom adjacent to the carbon atom;
still more preferably
methoxy or ethoxy that may be substituted with
"C1-C6 alkoxy,
C3-C7 cycloalkyl, or
one or more 4- to 10-membered monocyclic saturated heterocyclic groups that may be substituted with oxo and contain 1 to 3 identical or different heteroatoms selected from nitrogen, oxygen, and sulfur," or
ethynyl or propynyl that may be substituted with
"hydroxy,
C1-C6 alkoxy,
amino that may be substituted with $R^4$, wherein $R^4$ is C1-C6 alkyl, C1-C4 alkoxy C1-C6 alkyl, or carbamoyl that may be substituted with C3-C7 cycloalkyl,
C1-C6 alkylsilyloxy,
C3-C7 cycloalkyl that may be substituted with "hydroxy or oxo,"
C6-C14 aromatic hydrocarbon that may be substituted with $R^5$, wherein $R^5$ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
one or more 4- to 10-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C6 alkyl, C1-C6 alkoxy, or oxo,
one or more 4- to 10-membered monocyclic or polycyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C6 alkyl, C1-C6 alkoxy, or amino, or
unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,"
provided that the position of the triple bond is disposed between the carbon atom bonded to the 7H-pyrrolo[2,3-d] pyrimidine skeleton and a carbon atom adjacent to the carbon atom; and
further still more preferably
ethynyl or propynyl that may be substituted with
"hydroxy,
amino that may be substituted with $R^4$, wherein $R^4$ is C1-C4 alkyl or C1-C4 alkoxy C1-C4 alkyl,
C3-C7 cycloalkyl that may be substituted with hydroxy, phenyl that may be substituted with $R^5$, wherein $R^5$ is halogen,
"one or more 4- to 6-membered monocyclic saturated heterocyclic groups that may be substituted with $R^6$ and contain 1 to 3 identical or different heteroatoms selected from nitrogen, oxygen, and sulfur," wherein $R^6$ is hydroxy, C1-C4 alkyl, or oxo, or
"one or more 4- to 10-membered monocyclic or bicyclic unsaturated heterocyclic groups that may be substituted with $R^7$ and contain 1 to 3 identical or different heteroatoms selected from nitrogen, oxygen, and sulfur," wherein $R^7$ is halogen, cyano, C1-C4 alkyl, C1-C4 alkoxy, or amino,"
provided that the position of the triple bond is disposed between the carbon atom bonded to the 7H-pyrrolo[2,3-d] pyrimidine skeleton and a carbon atom adjacent to the carbon atom.

Specific examples of the compounds of the present invention include, but are not limited to, compounds produced in the Examples described later.

Preferred examples of the compounds of the present invention are as follows:

(1) 4-amino-7-(tert-butyl)-N-(4-(methoxymethyl)phenyl)-7H-pyrrolo[2,3-d]pyrimidine-5-carboxamide;
(2) 4-amino-7-(1-fluoro-2-methylpropan-2-yl)-N-(4-(methoxymethyl)phenyl)-7H-pyrrolo[2,3-d]pyrimidine-5-carboxamide;
(3) 4-amino-N-(4-(methoxymethyl)phenyl)-7-(1-methylcyclopropyl)-7H-pyrrolo[2,3-d]pyrimidine-5-carboxamide;
(4) 4-amino-6-bromo-N-[4-(methoxymethyl)phenyl]-7-(1-methylcyclopropyl)-7H-pyrrolo[2,3-d]pyrimidine-5-carboxamide;
(5) 4-amino-6-chloro-N-[4-(methoxymethyl)phenyl]-7-(1-methylcyclopropyl)-7H-pyrrolo[2,3-d]pyrimidine-5-carboxamide;
(6) 4-amino-N-(4-(methoxymethyl)phenyl)-7-(1-methylcyclopropyl)-6-vinyl-7H-pyrrolo[2,3-d]pyrimidine-5-carboxamide;
(7) 4-amino-6-fluoro-N-(4-(methoxymethyl)phenyl)-7-(1-methylcyclopropyl)-7H-pyrrolo[2,3-d]pyrimidine-5-carboxamide;
(8) 4-amino-N-[4-(methoxymethyl)phenyl]-7-(1-methylcyclopropyl)-6-(3-morpholinoprop-1-yn-1-yl)-7H-pyrrolo[2,3-d]pyrimidine-5-carboxamide;
(9) 4-amino-6-(4-hydroxy-4-methylpent-1-yn-1-yl)-N-[4-(methoxymethyl)phenyl]-7-(1-methylcyclopropyl)-7H-pyrrolo[2,3-d]pyrimidine-5-carboxamide;
(10) 4-amino-N-[4-(methoxymethyl)phenyl]-7-(1-methylcyclopropyl)-6-((tetrahydro-2H-pyran-4-yl)ethynyl)-7H-pyrrolo[2,3-d]pyrimidine-5-carboxamide;
(11) 4-amino-N-[4-(methoxymethyl)phenyl]-7-(1-methylcyclopropyl)-6-(3-(pyrrolidin-1-yl)prop-1-yn-1-yl)-7H-pyrrolo[2,3-d]pyrimidine-5-carboxamide;
(12) (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide;
(13) 4-amino-N-[4-(methoxymethyl)phenyl]-6-((1-methyl-1H-pyrazol-4-yl) ethynyl)-7-(1-methylcyclopropyl)-7H-pyrrolo[2,3-d]pyrimidine-5-carboxamide;
(14) 4-amino-6-(imidazo[1,2-b]pyridazin-3-ylethynyl)-N-[4-(methoxymethyl)phenyl]-7-(1-methylcyclopropyl)-7H-pyrrolo[2,3-d]pyrimidine-5-carboxamide;
(15) 4-amino-N-(4-(methoxymethyl)phenyl)-6-((1-methyl-1H-pyrazol-3-yl)ethynyl)-7-(1-methylcyclopropyl)-7H-pyrrolo[2,3-d]pyrimidine-5-carboxamide;
(16) 4-amino-N-(4-(methoxymethyl)phenyl)-6-((1-methyl-1H-imidazol-5-yl)ethynyl)-7-(1-methylcyclopropyl)-7H-pyrrolo[2,3-d]pyrimidine-5-carboxamide;
(17) 4-amino-N-[4-(methoxymethyl)phenyl]-7-(1-methylcyclopropyl)-6-(pyridin-3-ylethynyl)-7H-pyrrolo[2,3-d] pyrimidine-5-carboxamide;

(18) 4-amino-N-(4-(methoxymethyl)phenyl)-7-(1-methyl-cyclopropyl)-6-(prop-1-yn-1-yl)-7H-pyrrolo[2,3-d]pyrimidine-5-carboxamide;
(19) 4-amino-N-[4-(methoxymethyl)phenyl]-7-(1-methylcyclopropyl)-6-(3-(piperidin-1-yl)prop-1-yn-1-yl)-7H-pyrrolo[2,3-d]pyrimidine-5-carboxamide;
(20) 4-amino-6-ethoxy-N-(4-(methoxymethyl)phenyl)-7-(1-methylcyclopropyl)-7H-pyrrolo[2,3-d]pyrimidine-5-carboxamide;
(21) 4-amino-6-((1-hydroxycyclopentyl)ethynyl)-N-(4-(methoxymethyl)phenyl)-7-(1-methylcyclopropyl)-7H-pyrrolo[2,3-d]pyrimidine-5-carboxamide;
(22) 4-amino-N-(4-(methoxymethyl)phenyl)-7-(1-methyl-cyclopropyl)-6-(3-thiomorpholinoprop-1-yn-1-yl)-7H-pyrrolo[2,3-d]pyrimidine-5-carboxamide;
(23) 4-amino-N-(4-(methoxymethyl)phenyl)-7-(1-methyl-cyclopropyl)-6-(3-(tetrahydro-2H-pyran-4-yl)prop-1-yn-1-yl)-7H-pyrrolo[2,3-d]pyrimidine-5-carboxamide;
(24) 4-amino-6-((6-aminopyridin-3-yl)ethynyl)-N-(4-(methoxymethyl)phenyl)-7-(1-methylcyclopropyl)-7H-pyrrolo[2,3-d]pyrimidine-5-carboxamide;
(25) 4-amino-6-((1,3-dimethyl-1H-pyrazol-4-yl)ethynyl)-N-(4-(methoxymethyl)phenyl)-7-(1-methylcyclopropyl)-7H-pyrrolo[2,3-d]pyrimidine-5-carboxamide;
(26) 4-amino-N-(4-(methoxymethyl)phenyl)-7-(1-methyl-cyclopropyl)-6-((1-methylpiperidin-4-yl)ethynyl)-7H-pyrrolo[2,3-d]pyrimidine-5-carboxamide;
(27) 4-amino-6-(3-(dimethylamino)prop-1-yn-1-yl)-N-(4-(methoxymethyl)phenyl)-7-(1-methylcyclopropyl)-7H-pyrrolo[2,3-d]pyrimidine-5-carboxamide;
(28) 4-amino-N-(3-fluoro-4-(methoxymethyl)phenyl)-7-(1-methylcyclopropyl)-6-((tetrahydro-2H-pyran-4-yl)ethynyl)-7H-pyrrolo[2,3-d]pyrimidine-5-carboxamide; and
(29) 4-amino-N-(3-fluoro-4-(methoxymethyl)phenyl)-7-(1-methylcyclopropyl)-6-(3-morpholinoprop-1-yn-1-yl)-7H-pyrrolo[2,3-d]pyrimidine-5-carboxamide.

More preferred examples of the compounds of the present invention are as follows:
(8) 4-amino-N-[4-(methoxymethyl)phenyl]-7-(1-methylcyclopropyl)-6-(3-morpholinoprop-1-yn-1-yl)-7H-pyrrolo[2,3-d]pyrimidine-5-carboxamide;
(10) 4-amino-N-[4-(methoxymethyl)phenyl]-7-(1-methyl-cyclopropyl)-6-((tetrahydro-2H-pyran-4-yl)ethynyl)-7H-pyrrolo[2,3-d]pyrimidine-5-carboxamide;
(12) (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide; and
(13) 4-amino-N-[4-(methoxymethyl)phenyl]-6-((1-methyl-1H-pyrazol-4-yl)ethynyl)-7-(1-methylcyclopropyl)-7H-pyrrolo[2,3-d]pyrimidine-5-carboxamide.

The present invention also provides a RET inhibitor comprising the compound or a salt thereof of the present invention, for example, the compound or a salt thereof according to any one of [1] to [6] above, as an active ingredient.

The present invention also provides a pharmaceutical composition comprising the compound or a salt thereof of the present invention, for example, the compound or a salt thereof according to any one of [1] to [6] above.

The present invention also provides a pharmaceutical composition for preventing or treating a disease that can be treated by RET inhibition, the pharmaceutical composition comprising the compound or a salt thereof of the present invention, for example, the compound or a salt thereof according to any one of [1] to [6] above.

The present invention also provides an antitumor agent comprising the compound or a salt thereof of the present invention, for example, the compound or a salt thereof according to any one of [1] to [6] above.

The present invention also provides an antitumor agent for treating a malignant tumor with enhanced activation of RET, the antitumor agent comprising the compound or a salt thereof of the present invention, for example, the compound or a salt thereof according to any one of [1] to [6] above.

The present invention also provides the compound or a salt thereof of the present invention, for example, the compound or a salt thereof according to any one of [1] to [6] above, for use in prevention or treatment of a malignant tumor.

The present invention also provides the compound or a salt thereof of the present invention, for example, the compound or a salt thereof according to any one of [1] to [6] above, for use in prevention or treatment of a malignant tumor with enhanced activation of RET.

The present invention also provides use of the compound or a salt thereof of the present invention, for example, the compound or a salt thereof according to any one of [1] to [6] above, for producing an antitumor agent.

The present invention also provides use of the compound or a salt thereof of the present invention, for example, the compound or a salt thereof according to any one of [1] to [6] above, for producing an antitumor agent for treating a malignant tumor with enhanced activation of RET.

The present invention also provides use of the compound or a salt thereof of the present invention, for example, the compound or a salt thereof according to any one of [1] to [6] above, for producing a RET inhibitor.

The present invention also provides use of the compound or a salt thereof of the present invention, for example, the compound or a salt thereof according to any one of [1] to [6] above, for preventing or treating a malignant tumor.

The present invention also provides use of the compound or a salt thereof of the present invention, for example, the compound or a salt thereof according to any one of [1] to [6] above, for preventing or treating a malignant tumor with enhanced activation of RET.

The present invention also provides a method for preventing or treating a malignant tumor, comprising administering the compound or a salt thereof of the present invention, for example, the compound or a salt thereof according to any one of [1] to [6] above, to a mammal.

The present invention also provides a method for preventing or treating a malignant tumor, comprising administering the compound or a salt thereof of the present invention, for example, the compound or a salt thereof according to any one of [1] to [6] above, to a mammal, wherein the malignant tumor is a malignant tumor with enhanced activation of RET.

The present invention also provides a method for inhibiting RET, comprising administering the compound or a salt thereof of the present invention, for example, the compound or a salt thereof according to any one of [1] to [6] above, to a mammal.

Next, the methods for producing the compounds of the present invention are described.

Compounds (I) and (I') of the present invention may be produced, for example, through the production methods below or the methods described in the Examples. However, the methods for producing Compounds (I) and (I') of the present invention are not limited to these reaction examples.

Production Method 1

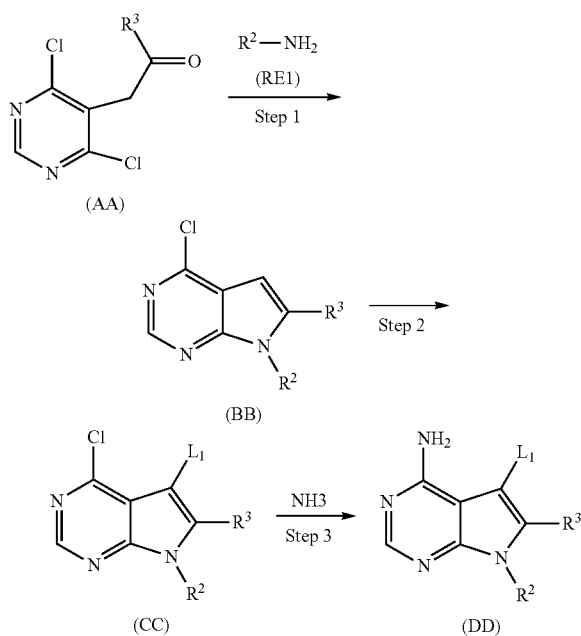

wherein L₁ is a leaving group, and $R^2$ and $R^3$ are as defined above.

Step 1

This step synthesizes a compound represented by Formula (BB) from a compound represented by Formula (AA). The compound represented by Formula (AA) can be obtained from commercial suppliers, or can be produced through a known method.

Step 1 is performed using an amino compound represented by Formula (RE1) or a salt thereof in an amount of generally 0.5 to 5 moles, preferably 0.9 to 1.5 moles, per mole of the compound represented by Formula (AA).

A base may be added in this step as necessary. Examples of bases include inorganic bases, such as sodium hydrogen carbonate, sodium carbonate, potassium carbonate, cesium carbonate, cesium hydroxide, sodium hydride, and potassium hydride; organic amines, such as trimethylamine, triethylamine, tripropylamine, diisopropylethylamine, N-methylmorpholine, pyridine, 4-(N,N-dimethylamino) pyridine, lutidine, and collidine; and the like. The amount of the base used is generally 1 to 100 moles, preferably 1 to 10 moles, per mole of the compound represented by Formula (AA). The amino compound can be obtained from commercial suppliers, or can be produced through a known method. Moreover, the reaction can be promoted by adding an acid during the reaction, if necessary. Examples of acids include formic acid, acetic acid, hydrochloric acid, phosphoric acid, and the like. The amount of the acid used is generally 1 to 100 moles, preferably 1 to 20 moles, per mole of the compound represented by Formula (AA)

The reaction solvent is not particularly limited, and any solvent that does not adversely affect the reaction can be used. Examples of the solvent include alcohols (e.g., methanol and ethanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., 1,2-dimethoxyethane and tetrahydrofuran), aprotic polar solvents (e.g., N,N-dimethylformamide, dimethylsulfoxide, and hexamethylphosphoramide), water, and mixtures thereof.

The reaction time generally ranges from 0.1 to 100 hours, preferably 0.5 to 24 hours. The reaction temperature generally ranges from 0 to 120° C., preferably 50 to 120° C.

The thus-obtained compound represented by Formula (BB) can be subjected to the subsequent step after, or without, isolation and purification from the reaction mixture by known separation and purification methods, such as concentration, vacuum concentration, crystallization, solvent extraction, reprecipitation, and chromatography.

Step 2

This step synthesizes a compound represented by Formula (CC) from the compound represented by Formula (BB).

Step 2 is generally performed using a halogenating reagent in an amount of 1 to 10 moles, preferably 1 to 5 moles, per mole of the compound represented by Formula (BB).

Examples of halogenating reagents include N-iodosuccinimide, N-bromosuccinimide, N-chlorosuccinimide, iodine, bromine, and the like. The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

Examples of the leaving group represented by L₁ include chlorine, bromine, iodine, and the like.

The reaction temperature generally ranges from −78 to 200° C., preferably 0 to 50° C. The reaction time generally ranges from 5 minutes to 6 days, preferably 10 minutes to 3 days.

The thus-obtained compound represented by Formula (CC) can be subjected to the subsequent step after, or without, isolation and purification from the reaction mixture by known separation and purification methods, such as concentration, vacuum concentration, crystallization, solvent extraction, reprecipitation, and chromatography.

Step 3

This step produces a compound represented by Formula (DD) by reacting the compound represented by Formula (CC) with ammonia or a salt thereof.

The amount of ammonia or a salt thereof used in this step is generally an equimolar to excessive molar amount per mole of the compound represented by Formula (CC).

The reaction solvent is not particularly limited, and any solvent that does not adversely affect the reaction can be used. Examples of the solvent include water, methanol, ethanol, isopropanol, tert-butyl alcohol, tetrahydrofuran, 1,4-dioxane, dimethylformamide, N-methylpyrrolidone, 1,2-dimethoxyethane, dimethylsulfoxide, and mixtures thereof.

The reaction temperature generally ranges from 0 to 200° C., preferably room temperature to 150° C. The reaction time generally ranges from 5 minutes to 7 days, preferably 30 minutes to 4 days.

The thus-obtained compound represented by Formula (DD) can be subjected to the subsequent step after, or without, isolation and purification from the reaction mixture by known separation and purification means, such as concentration, vacuum concentration, crystallization, solvent extraction, reprecipitation, and chromatography.

Production Method 2

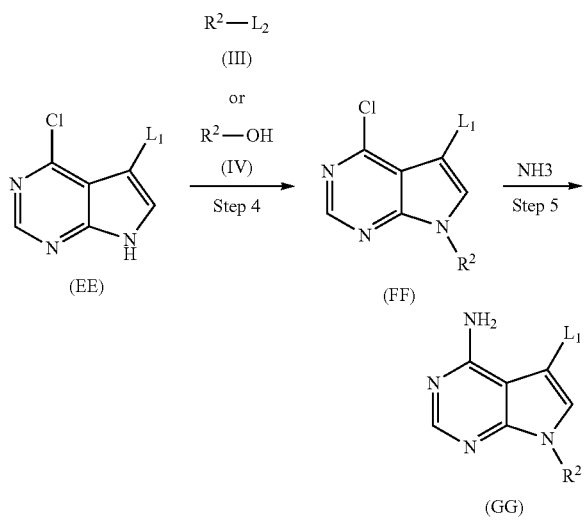

wherein L₁ and L₂ are each a leaving group, and R² is as defined above.

Step 4

This step produces a compound represented by Formula (FF) using a compound represented by Formula (EE) and a compound represented by Formula (III) or (IV). The compound represented by Formula (EE) can be obtained from commercial suppliers, or can be produced through a known method.

When the compound represented by Formula (III) is used as an alkylating reagent, the compound represented by Formula (FF) can be produced in the presence of a base. In Formula (III), L₂ is a leaving group such as chlorine, bromine, iodine, methanesulfonic acid ester, or p-toluenesulfonic acid ester. The compound represented by Formula (III) can be obtained from commercial suppliers, or can be produced through a known method. The amount of the compound represented by Formula (III) used is generally 1 to 10 moles, preferably 1 to 5 moles, per mole of the compound represented by Formula (EE).

Examples of bases include inorganic bases, such as sodium hydrogen carbonate, sodium carbonate, potassium carbonate, cesium carbonate, cesium hydroxide, sodium hydride, and potassium hydride; organic amines, such as trimethylamine, triethylamine, tripropylamine, diisopropylethylamine, N-methylmorpholine, pyridine, 4-(N,N-dimethylamino)pyridine, lutidine, and collidine; and the like. The amount of the base used is generally 1 to 100 moles, preferably 1 to 10 moles, per mole of the compound represented by Formula (EE).

The reaction solvent is not particularly limited, and any solvent that does not adversely affect the reaction can be used. Examples of the solvent include N,N-dimethylformamide, N,N-dimethylacetamide, dimethylsulfoxide, tetrahydrofuran, 1,4-dioxane, N-methylpyrrolidin-2-one, acetonitrile, and the like. These solvents may be used alone or in a mixture.

The reaction time generally ranges from 0.1 to 100 hours, preferably 0.5 to 24 hours. The reaction temperature ranges from 0° C. to the boiling temperature of the reaction solvent, preferably 0 to 100° C.

When the compound of Formula (IV) is used as an alkylating reagent, the compound represented by Formula (FF) can be produced through a Mitsunobu reaction. This step can generally be performed by a known method, for example, the method disclosed in Chemical Reviews, Vol. 109, p. 2551 (2009) For example, this step can be performed in the presence of a Mitsunobu reagent and a phosphine reagent in a solvent that does not adversely affect the reaction. This step is generally performed using the compound represented by Formula (IV) in an amount of 1 to 10 moles, preferably 1 to 5 moles, per mole of the compound represented by Formula (EE).

Examples of Mitsunobu reagents include diethyl azodicarboxylate, diisopropyl azodicarboxylate, and the like. The amount of the Mitsunobu reagent used is generally 1 to 10 moles, preferably 1 to 5 moles, per mole of the compound represented by Formula (EE).

Examples of phosphine reagents include triphenylphosphine and tributylphosphine. The amount of the phosphine reagent used is generally 1 to 10 moles, preferably 1 to 5 moles, per mole of the compound represented by Formula (EE).

The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

The reaction temperature generally ranges from −78 to 200° C., preferably 0 to 50° C. The reaction time generally ranges from 5 minutes to 3 days, preferably 10 minutes to 48 hours.

The thus-obtained compound represented by Formula (FF) can be subjected to the subsequent step after, or without, isolation and purification from the reaction mixture by known separation and purification methods, such as concentration, vacuum concentration, crystallization, solvent extraction, reprecipitation, and chromatography.

Step 5

This step produces a compound represented by Formula (GG) by reacting the compound represented by Formula (FF) with ammonia or a salt thereof.

The amount of ammonia or a salt thereof used in this step is generally an equimolar to excessive molar amount per mole of the compound represented by Formula (FF).

The reaction solvent is not particularly limited, and any solvent that does not adversely affect the reaction can be used. Examples of the solvent include water, methanol, ethanol, isopropanol, tert-butyl alcohol, tetrahydrofuran, 1,4-dioxane, dimethylformamide, 1,2-dimethoxyethane, N-methylpyrrolidone, dimethylsulfoxide, and mixtures thereof.

The reaction temperature generally ranges from 0 to 200° C., preferably room temperature to 150° C. The reaction time generally ranges from 5 minutes to 7 days, preferably 30 minutes to 4 days.

The thus-obtained compound represented by Formula (GG) can be subjected to the subsequent step after, or without, isolation and purification from the reaction mixture by known separation and purification methods, such as concentration, vacuum concentration, crystallization, solvent extraction, reprecipitation, and chromatography.

Production Method 3

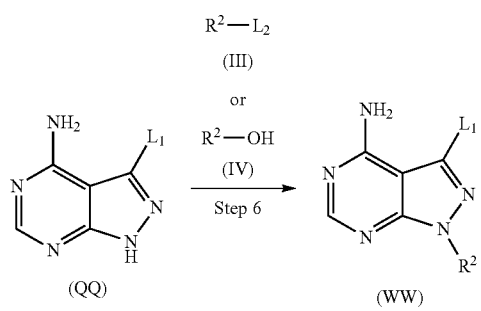

wherein $L_1$ and $L_2$ are each a leaving group, and $R^2$ is as defined above.

Step 6

This step produces a compound represented by Formula (WW) using a compound represented by Formula (QQ) and a compound represented by Formula (III) or (IV). The compound represented by Formula (QQ) can be obtained from commercial suppliers, or can be produced through a known method. When the compound represented by Formula (III) is used as an alkylating reagent, the compound represented by Formula (WW) can be produced in the presence of a base. In Formula (III), $L_2$ is a leaving group such as chlorine, bromine, iodine, methanesulfonic acid ester, or p-toluenesulfonic acid ester; and can be obtained from commercial suppliers, or can be produced through a known method. The amount of the compound represented by Formula (III) used is generally 1 to 10 moles, preferably 1 to 5 moles, per mole of the compound represented by Formula (QQ)

Examples of bases include inorganic bases, such as sodium hydrogen carbonate, sodium carbonate, potassium carbonate, cesium carbonate, cesium hydroxide, sodium hydride, and potassium hydride; organic amines, such as trimethylamine, triethylamine, tripropylamine, diisopropylethylamine, N-methylmorpholine, pyridine, 4-(N,N-dimethylamino)pyridine, lutidine, and collidine; and the like. The amount of the base used is generally 1 to 100 moles, preferably 2 to 10 moles, per mole of the compound represented by Formula (QQ). Examples of the reaction solvent include N,N-dimethylformamide, N,N-dimethylacetamide, dimethylsulfoxide, tetrahydrofuran, 1,4-dioxane, N-methylpyrrolidin-2-one, acetonitrile, and the like. These solvents may be used alone or in a mixture.

The reaction time generally ranges from 0.1 to 100 hours, preferably 0.5 to 24 hours. The reaction temperature ranges from 0° C. to the boiling temperature of the solvent, preferably 0 to 100° C.

When the compound of Formula (IV) is used as an alkylating reagent, the compound represented by Formula (WW) can be produced through a Mitsunobu reaction. This step can generally be performed by a known method, for example, the method disclosed in Chemical Reviews, Vol. 109, p. 2551 (2009) For example, this step can be performed in the presence of a Mitsunobu reagent and a phosphine reagent in a solvent that does not adversely affect the reaction. This step is generally performed using the compound represented by Formula (IV) in an amount of generally 1 to 10 moles, preferably 1 to 5 moles, per mole of the compound represented by Formula (QQ).

Examples of Mitsunobu reagents include diethyl azodicarboxylate, diisopropyl azodicarboxylate, and the like. The amount of the Mitsunobu reagent used is generally 1 to 10 moles, preferably 1 to 5 moles, per mole of the compound represented by Formula (QQ). Examples of phosphine reagents include triphenylphosphine and tributylphosphine. The amount of the phosphine reagent used is generally 1 to 10 moles, preferably 1 to 5 moles, per mole of the compound represented by Formula (QQ)

The reaction solvent is not particularly limited, and any solvent that does not adversely affect the reaction can be used. Examples of the solvent include toluene, benzene, tetrahydrofuran, 1,4-dioxane, dimethylformamide, dimethylacetamide, N-methylpyrrolidinone, dimethylsulfoxide, and mixtures thereof.

The reaction temperature generally ranges from −78 to 200° C., preferably 0 to 50° C. The reaction time generally ranges from 5 minutes to 3 days, preferably 10 minutes to 48 hours.

The thus-obtained compound represented by Formula (WW) can be subjected to the subsequent step after, or without, isolation and purification from the reaction mixture by known separation and purification methods, such as concentration, vacuum concentration, crystallization, solvent extraction, reprecipitation, and chromatography.

Production Method 4

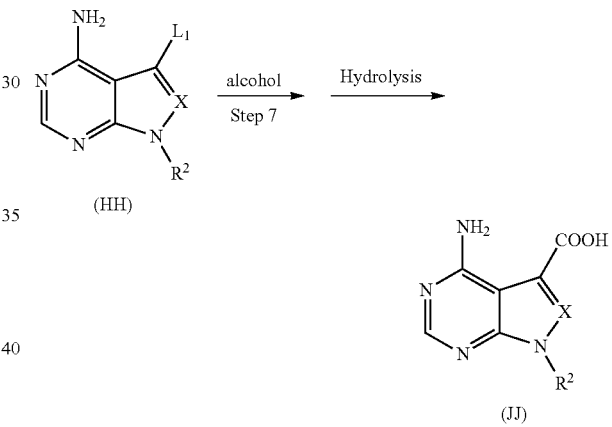

wherein $L_1$ is a leaving group, and $R^2$ and X are as defined above.

Step 7

This step produces a compound represented by Formula (JJ) by reacting a compound represented by Formula (HH) in a carbon monoxide atmosphere in the presence of an alcohol using, for example, a transition metal and optionally a base in a solvent that does not adversely affect the reaction.

The compound represented by Formula (HH) can be produced by steps 1 to 3, steps 4 and 5, or step 6 of the production method of the present application.

In this step, the pressure of carbon monoxide is generally 1 atm to 20 atms, preferably 1 atm to 10 atms.

The amount of the alcohol compound used is generally 1 to an excessive molar amount per mole of the compound represented by Formula (HH). Examples of alcohol compounds include methanol, ethanol, propanol, isopropyl alcohol, diethylaminoethanol, isobutanol, 4-(2-hydroxyethyl)morpholine, 3-morpholinopropanol, diethylaminopropanol, and the like.

Examples of transition metal catalysts usable in this step include palladium catalysts (e.g., palladium acetate, tris(benzylideneacetone)dipalladium, bis(triphenylphosphine)

palladium(II) dichloride, 1,1'-bis(diphenylphosphino)ferrocene-palladium(II) dichloride-dichloromethane complex, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (HH). The amount of the ligand used is generally 0.000 1 to 4 moles, preferably 0.01 to 2 moles, per mole of the compound represented by Formula (HH).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (HH).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., 1,2-dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time generally ranges from 0.1 to 100 hours, preferably 0.5 to 24 hours. The reaction temperature is generally 0° C. to 200° C., preferably 0 to 150° C.

An ester form corresponding to the alcohol used or a mixture of the ester form and a carboxylic acid compound (JJ) can be subjected to a hydrolysis reaction to thereby convert the ester form or the mixture into a compound represented by Formula (JJ). Hydrolysis is performed using a base. Examples of bases include organic bases, such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, potassium hydroxide, lithium hydroxide, and calcium hydroxide.

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., 1,2-dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof.

The reaction time generally ranges from 0.1 to 100 hours, preferably 0.5 to 24 hours. The reaction temperature ranges from 0° C. to the boiling temperature of the solvent, preferably 0 to 150° C.

The thus-obtained compound represented by Formula (JJ) can be subjected to the subsequent step after, or without, isolation and purification from the reaction mixture by known separation and purification methods, such as concentration, vacuum concentration, crystallization, solvent extraction, reprecipitation, and chromatography.

Production Method 5

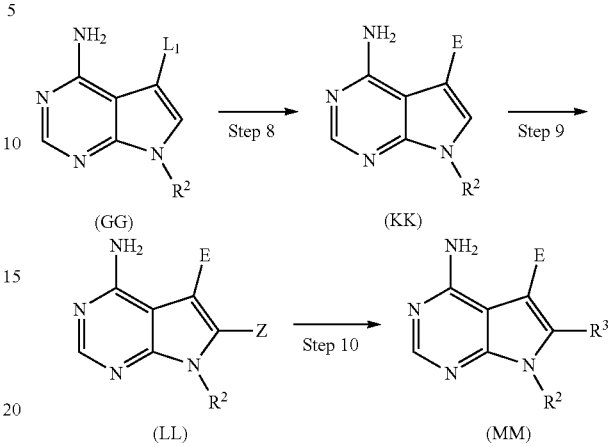

wherein $L_1$ is a leaving group; E is ester, cyano, or carboxylic acid equivalent, such as carboxamide; Z is halogen; and $R^2$ and $R^3$ are as defined above.

Step 8

This step produces an ester derivative or cyano derivative represented by Formula (KK) by reacting the compound represented by Formula (GG), in a carbon monoxide atmosphere in the presence of an alcohol, or using a cyano compound, such as copper cyanide or zinc cyanide, using, for example, a transition metal catalyst and optionally a base in a solvent that does not adversely affect the reaction.

The compound represented by Formula (GG) can be produced by steps 1 to 3 or steps 4 and 5 of the production method of the present application.

In the production of the ester derivative, the pressure of carbon monoxide is generally 1 atm to 20 atms, preferably 1 atm to 10 atms. The amount of the alcohol compound used as a reaction agent is 1 to an excessive molar amount, preferably 1 to 200 moles, per mole of the compound represented by Formula (GG). Examples of alcohol compounds include methanol, ethanol, propanol, isopropyl alcohol, diethylaminoethanol, isobutanol, 4-(2-hydroxyethyl)morpholine, 3-morpholinopropanol, diethylaminopropanol, and the like.

In the production of the cyano derivative, examples of the cyano compound used as a reaction agent include copper cyanide, zinc cyanide, tri-n-butylcyanotin, and the like. The amount of the cyano compound used as an agent is generally 1 to 100 moles, preferably 1 to 10 moles, per mole of the compound represented by Formula (GG).

Examples of transition metal catalysts usable in this step for both the production of the ester derivative and the production of the cyano derivative include palladium catalysts (e.g., palladium acetate, tetrakis triphenylphosphine palladium, tris(benzylideneacetone)dipalladium, bis(triphenylphosphine)palladium(II) dichloride, 1,1'-bis(diphenylphosphino)ferrocene-palladium(II) dichloride-dichloromethane complex, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (GG). The amount of the ligand used is generally 0.000 1 to 4 moles, preferably 0.01 to 2 moles, per mole of the compound represented by Formula (GG).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (GG).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time generally ranges from 0.1 to 100 hours, preferably 0.5 to 24 hours. The reaction temperature is 0° C. to 200° C., preferably 0 to 150° C. The thus-obtained compound represented by Formula (KK) can be subjected to the subsequent step after, or without, isolation and purification from the reaction mixture by known separation and purification means, such as concentration, vacuum concentration, crystallization, solvent extraction, reprecipitation, and chromatography.

Step 9

This step produces a halogen compound (LL) by treating the compound represented by Formula (KK) with a halogenating agent.

This step is generally performed using a halogenated reagent in an amount of generally 1 to 10 moles, preferably 1 to 5 moles, per mole of the compound represented by Formula (KK).

Examples of halogenating reagents include 1-chloromethyl-4-fluoro-1,4-diazoniabicyclo[2.2.2]octane bis(tetrafluoroborate), N-iodosuccinimide, N-bromosuccinimide, N-chlorosuccinimide, iodine, bromine, and the like. The reaction solvent is not particularly limited, and any solvent that does not adversely affect the reaction can be used. Examples of the solvent include dichloromethane, chloroform, toluene, benzene, tetrahydrofuran, 1,4-dioxane, dimethylformamide, dimethylacetamide, N-methylpyrrolidinone, dimethylsulfoxide, and mixtures thereof.

Examples of the halogen represented by Z include fluorine, chlorine, bromine, iodine, and the like.

The reaction temperature generally ranges from −78 to 200° C., preferably 0 to 50° C. The reaction time generally ranges from 5 minutes to 6 days, preferably 10 minutes to 3 days.

The thus-obtained compound represented by Formula (LL) can be subjected to the subsequent step after, or without, isolation and purification from the reaction mixture by known separation and purification means, such as concentration, vacuum concentration, crystallization, solvent extraction, reprecipitation, and chromatography.

Moreover, E can be converted to another E, as required, by a known method, such as hydrolysis or solvolysis. For example, cyano can be converted to carboxamide by hydrolysis, and cyano or carboxamide can be converted to ester by solvolysis.

Step 10

This step produces a compound represented by Formula (MM) by subjecting the compound represented by Formula (LL) to a coupling reaction with a borate derivative, boric acid derivative, tin derivative, acetylene derivative, alkali metal salt, alkaline earth metal salt, alkoxide, or thioalkoxide that has $R^3$ using, for example, a transition metal and optionally a base in a solvent that does not adversely affect the reaction.

The amount of the borate derivative, boric acid derivative, tin derivative, acetylene derivative, alkali metal salt, alkaline earth metal salt, alkoxide, or thioalkoxide that has $R^3$ used is generally 1 to 100 moles, preferably 1 to 20 moles. Examples of transition metal catalysts usable in this step include palladium catalysts (e.g., palladium acetate, tetrakis triphenylphosphine palladium, tris(benzylideneacetone)dipalladium, bis(triphenylphosphine)palladium(II) dichloride, 1,1'-bis(diphenylphosphino)ferrocene-palladium(II) dichloride-dichloromethane complex, etc.). As necessary, a ligand (e.g., triphenylphosphine, xantphos, 2-dicyclohexylphosphino-2',4',6'-triisopropylbiphenyl, 2-dicyclohexylphosphino-2',6'-dimethoxybiphenyl, tricyclohexylphosphine, tri-tert-butylphosphine, etc.) is added. Examples of copper catalysts include copper iodide, copper bromide, and copper chloride. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (LL). Transition metal catalysts can be used in combination, as necessary. The amount of the ligand used is generally 0.000 1 to 4 moles, preferably 0.01 to 2 moles, per mole of the compound represented by Formula (LL).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, potassium phosphate, sodium hydroxide, and sodium hydride. The amount of the base used is generally 0.1 to 50 moles, preferably 1 to 20 moles, per mole of the compound represented by Formula (LL).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, and ethylene glycol), aprotic polar solvents (e.g., dimethylformamide, dimethylacetamide, N-methylpyrrolidinone, dimethylsulfoxide, and hexamethylphosphoramide), water, and mixtures thereof.

The reaction time generally ranges from 0.1 to 100 hours, preferably 0.5 to 24 hours. The reaction temperature ranges from 0° C. to the boiling temperature of the solvent, preferably 0 to 160° C.

The thus-obtained compound represented by Formula (MM) can be subjected to the subsequent step after, or without, isolation and purification from the reaction mixture by known separation and purification means, such as concentration, vacuum concentration, crystallization, solvent extraction, reprecipitation, and chromatography.

Production Method 6

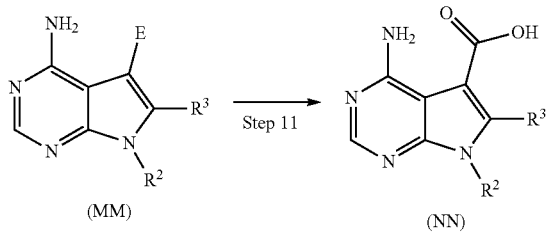

wherein E, $R^2$, and $R^3$ are as defined above.

Step 11

This step produces a carboxylic acid compound represented by Formula (NN) by hydrolyzing the compound represented by Formula (MM).

Hydrolysis is performed using a base or an acid. Examples of bases include organic bases, such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, sodium hydroxide, potassium hydroxide, lithium hydroxide, and calcium hydroxide. Examples of acids include hydrochloric acid, sulfuric acid, phosphoric acid, and the like.

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, and ethylene glycol), aprotic polar solvents (e.g., dimethylformamide, dimethylacetamide, N-methylpyrrolidinone, dimethylsulfoxide, and hexamethylphosphoramide), water, and mixtures thereof.

The reaction time generally ranges from 0.1 to 100 hours, preferably 0.5 to 24 hours. The reaction temperature ranges from 0° C. to the boiling temperature of the solvent, preferably 0 to 160° C.

The thus-obtained compound represented by Formula (NN) can be subjected to the subsequent step after, or without, isolation and purification from the reaction mixture by known separation and purification means, such as concentration, vacuum concentration, crystallization, solvent extraction, reprecipitation, and chromatography.

Production Method 7

Step 12

This step produces a compound represented by Formula (RR) by performing an amidation reaction using the compound represented by Formula (JJ) and a compound represented by Formula (VII). This step is performed in the presence of an appropriate condensing agent or activating agent as an amidation reagent, using the compound of Formula (VII) in an amount of generally 0.5 to 10 moles, preferably 1 to 3 moles, per mole of the compound represented by Formula (JJ).

The reaction solvent is not particularly limited, and any solvent that does not adversely affect the reaction can be used. Examples of the solvent include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethylsulfoxide, acetonitrile, and mixtures thereof.

The reaction temperature generally ranges from −78 to 200° C., preferably 0 to 100° C. The reaction time generally ranges from 5 minutes to 7 days, preferably 5 minutes to 3 days, more preferably 5 minutes to 10 hours.

Examples of condensing agents and activating agents include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, combination of 1-ethyl-3-(3-dimethylaminopropyl)carbodiimide and 1-hydroxybenzotriazole, 2-chloro-1,3-dimethylimidazolinium chloride, (dimethylamino)-N,N-dimethyl(3H-[1,2,3]triazolo[4,5-b]pyridin-3-yloxy)methaniminium hexafluorophosphate, 1,1-carbonyldiimidazole, N-hydroxysuccinic acid imide, and the like.

Further, a base may be added during the above reaction as necessary. Examples of bases include organic bases, such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, diazabicycloundecene, diazabicyclononene, and butyllithium; and inorganic bases, such as sodium hydrogen carbonate, sodium carbonate, potassium carbonate, cesium carbonate, sodium hydroxide, and sodium hydride. The amount of the base added is generally 1 to 100 moles, preferably 1 to 10 moles, per mole of the compound represented by Formula (JJ).

After completion of the reaction, a base, such as a sodium hydroxide solution, can be added to perform a post-treatment.

The thus-obtained compound represented by Formula (RR) can be isolated and purified by known separation and purification means, such as concentration, vacuum concentration, crystallization, solvent extraction, reprecipitation, and chromatography.

Production Method 8

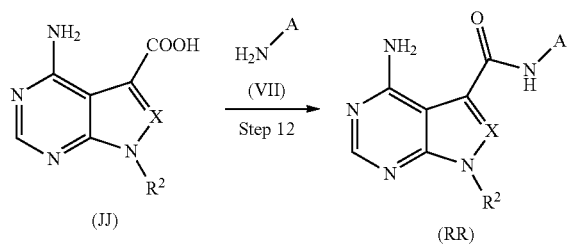

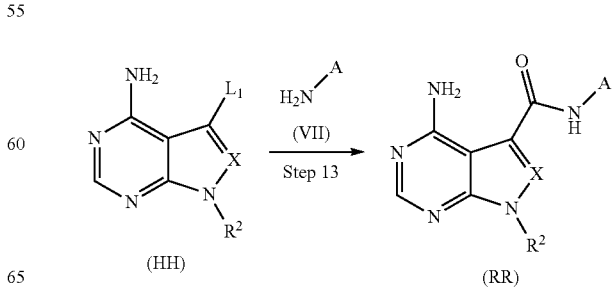

wherein A, $R^2$, and X are as defined above.

wherein $L_1$ is a leaving group, and A, $R^2$, and X are as defined above.

Step 13

This step produces a compound represented by Formula (RR) by reacting the compound represented by Formula (HH) in the presence of compound (VII) in a carbon monoxide atmosphere using, for example, a transition metal and optionally a base in a solvent that does not adversely affect the reaction.

In this step, the pressure of carbon monoxide is generally 1 atm to 20 atms, preferably 1 atm to 10 atms.

Examples of transition metal catalysts usable in this step include palladium catalysts (e.g., palladium acetate, tris(dibenzylideneacetone)dipalladium, bis(triphenylphosphine)palladium(II) dichloride, 1,1'-bis(diphenylphosphino)ferrocene-palladium(II) dichloride-dichloromethane complex, etc.). As necessary, a ligand (e.g., triphenylphosphine, xantphos, tri-tert-butylphosphine, etc.) is added. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (HH). The amount of the ligand used is generally 0.000 1 to 4 moles, preferably 0.01 to 2 moles, per mole of the compound represented by Formula (HH).

Further, a base may be added during the above reaction as necessary. Examples of bases include organic bases, such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, 1,8-diazabicyclo[5.4.0]undec-7-ene, potassium hexamethyldisilazide, and butyllithium; and inorganic bases, such as sodium hydrogen carbonate, sodium carbonate, potassium carbonate, cesium carbonate, sodium hydroxide, and sodium hydride. The amount of the base used is generally 0.1 to 50 moles, preferably 1 to 20 moles, per mole of the compound represented by Formula (HH).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethylacetamide, N-methylpyrrolidinone, dimethylsulfoxide, and hexamethylphosphoramide), water, and mixtures thereof. The reaction time generally ranges from 0.1 to 100 hours, preferably 0.5 to 24 hours. The reaction temperature ranges from 0° C. to 250° C., preferably 0 to 200° C.

The thus-obtained compound represented by Formula (RR) can be isolated and purified by known separation and purification means, such as concentration, vacuum concentration, crystallization, solvent extraction, reprecipitation, and chromatography.

Production Method 9

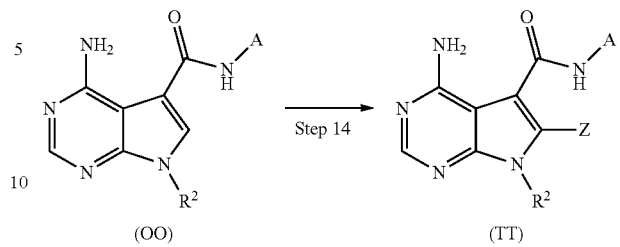

(OO)    (TT)

wherein A, Z, and $R^2$ are as defined above.

This step produces a compound represented by Formula (TT) from a compound represented by Formula (OO) using a suitable halogenated reagent.

This step is generally performed using a halogenated reagent in an amount of generally 1 to 10 moles, preferably 1 to 5 moles, per mole of the compound represented by Formula (OO).

Examples of halogenating reagents include 1-chloromethyl-4-fluoro-1,4-diazoniabicyclo[2.2.2]octane bis(tetrafluoroborate), N-iodosuccinimide, N-bromosuccinimide, N-chlorosuccinimide, iodine, bromine, and the like. The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), aprotic polar solvents (e.g., dimethylformamide, dimethylacetamide, N-methylpyrrolidinone, dimethylsulfoxide, and hexamethylphosphoramide), chloroform, dichloromethane, carbon tetrachloride, and mixtures thereof.

Examples of the halogen represented by Z include fluorine, chlorine, bromine, iodine, and the like.

The reaction temperature generally ranges from −78 to 200° C., preferably −10 to 50° C. The reaction time generally ranges from 5 minutes to 6 days, preferably 10 minutes to 3 days.

The thus-obtained compound represented by Formula (TT) can be isolated and purified by known separation and purification means, such as concentration, vacuum concentration, crystallization, solvent extraction, reprecipitation, and chromatography.

Production Method 10

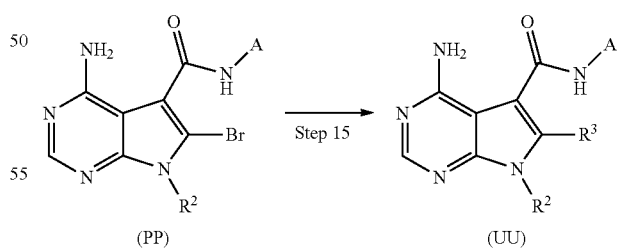

(PP)    (UU)

wherein A, $R^2$, and $R^3$ are as defined above.

This step produces a compound represented by Formula (UU) by subjecting a compound represented by Formula (PP) to a coupling reaction with a borate derivative, boric acid derivative, tin derivative, acetylene derivative, alkali metal salt, or alkaline earth metal salt that has $R^3$ using, for example, a transition metal and optionally a base in a solvent that does not adversely affect the reaction.

The amount of the borate derivative, boric acid derivative, tin derivative, acetylene derivative, alkali metal salt, alkaline earth metal salt, alkoxide, or thioalkoxide that has $R^3$ used is generally 1 to 100 moles, preferably 1 to 20 moles. Examples of transition metal catalysts usable in this step include palladium catalysts (e.g., palladium acetate, tetrakis triphenylphosphine palladium, tris(benzylideneacetone)dipalladium, bis(triphenylphosphine)palladium(II) dichloride, 1,1'-bis(diphenylphosphino)ferrocene-palladium(II) dichloride-dichloromethane complex, etc.). As necessary, a ligand (e.g., triphenylphosphine, xantphos, 2-dicyclohexylphosphino-2',4',6'-triisopropylbiphenyl, 2-dicyclohexylphosphino-2',6'-dimethoxybiphenyl, tricyclohexylphosphine, tri-tert-butylphosphine, etc.) is added. A copper catalyst can be used, as necessary. Examples of copper catalysts include copper iodide, copper bromide, and copper chloride. The amount of the transition metal catalyst varies depending on the type of catalyst. For example, the amount of the transition metal catalyst used is generally 0.0001 to 1 mole, preferably 0.001 to 0.5 moles, per mole of the compound represented by Formula (PP). Transition metal catalysts can be used, or used in combination, as necessary. The amount of the ligand used is generally 0.000 1 to 4 moles, preferably 0.01 to 2 moles, per mole of the compound represented by Formula (PP).

Further, a base may be added during the above reaction as necessary. Examples of bases include organic bases, such as triethylamine, diisopropylethylamine, diisopropylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases, such as sodium hydrogen carbonate, sodium carbonate, potassium carbonate, cesium carbonate, potassium phosphate, sodium hydroxide, and sodium hydride. The amount of the base used is generally 0.1 to 50 moles, preferably 1 to 20 moles, per mole of the compound represented by Formula (PP).

The reaction solvent is not particularly limited, and any solvent that does not adversely affect the reaction can be used. Examples of the solvent include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol, ethanol, ethylene glycol, and isopropanol), aprotic polar solvents (e.g., dimethylformamide, dimethylacetamide, N-methylpyrrolidinone, dimethylsulfoxide, and hexamethylphosphoramide), water, and mixtures thereof.

The reaction time ranges from 0.1 to 100 hours, preferably 0.5 to 48 hours. The reaction temperature ranges from 0° C. to the boiling temperature of the solvent, preferably 0 to 160° C.

The thus-obtained compound represented by Formula (UU) can be subjected to the subsequent step after, or without, isolation and purification from the reaction mixture by known separation and purification means, such as concentration, vacuum concentration, crystallization, solvent extraction, reprecipitation, and chromatography.

When the compounds of the present invention have isomers, such as optical isomers, stereoisomers, regioisomers, and rotational isomers, mixtures of any of the isomers are included within the scope of the compounds of the present invention. For example, when the compounds of the present invention have optical isomers, the optical isomer separated from a racemic mixture is also included within the scope of the compounds of the present invention. Each of such isomers can be obtained as a single compound by known synthesis and separation means (e.g., concentration, solvent extraction, column chromatography, recrystallization, etc.).

The compounds or salts thereof of the present invention may be in the form of crystals. Single crystals and polymorphic mixtures are included within the scope of the compounds or salts thereof of the present invention. Such crystals can be produced by crystallization according to a crystallization method known per se in the art. The compounds or salts thereof of the present invention may be solvates (e.g., hydrates) or non-solvates. Any of such forms are included within the scope of the compounds or salts thereof of the present invention. Compounds labeled with an isotope (e.g., $^2$H, $^3$H, $^{13}$C, $^{14}$C, $^{35}$S, $^{125}$I, etc.) are also included within the scope of the compounds or salts thereof of the present invention.

Prodrugs of the compounds or salts thereof of the present invention refer to compounds that can be converted to the compounds or salts thereof of the present invention through a reaction with an enzyme, gastric acid, or the like, under physiological conditions in vivo, i.e., compounds that can be converted to the compounds or salts thereof of the present invention by enzymatic oxidation, reduction, hydrolysis, or the like; or compounds that can be converted to the compounds or salts thereof of the present invention by hydrolysis with gastric acid or the like. Further, the prodrugs of the compounds or salts thereof of the present invention may be compounds that can be converted to the compounds or salts thereof of the present invention under physiological conditions, such as those described in "*Iyakuhin no Kaihatsu* [Development of Pharmaceuticals]," Vol. 7, Molecular Design, published in 1990 by Hirokawa Shoten Co., pp. 163-198.

The salts of the compounds of the present invention refer to common salts used in the field of organic chemistry. Examples of such salts include base addition salts to a carboxyl group when the compound has a carboxyl group, and acid addition salts to an amino or basic heterocyclic group when the compound has an amino or basic heterocyclic group.

Examples of acid addition salts include inorganic acid salts such as hydrochloride, sulfate, nitrate, phosphate, and perchlorate; organic acid salts such as acetate, formate, maleate, fumarate, tartrate, citrate, ascorbate, and trifluoroacetate; and sulfonates such as methanesulfonate, isethionate, benzenesulfonate, and p-toluenesulfonate.

In the present specification, "RET" means RET (rearranged during transfection) tyrosine kinase, and includes human RET and non-human mammal RET, preferably human RET. Further, the term "RET" includes isoforms. Moreover, it is known for RET that there are three types of proteins, i.e., RET9, RET43, and RET51, due to the difference in splicing of the carboxy terminus (Trends in Genetics, 2006, Vol. 22, pp. 627-636). In addition to these three types of proteins, "RET" includes all splicing variants that are currently known and will be known in the future, as long as they contain the ATP-binding site of RET.

Examples of human RET include a polypeptide comprising an amino acid sequence encoded by GenBank Accession number: NM_020975, and a polypeptide comprising an amino acid sequence encoded by GenBank Accession number: NM_020630.

Further, examples of the gene that encodes RET include a polynucleotide comprising the 191 to 3535th base sequence of the base sequence represented by GenBank Accession number: NM_020975, a polynucleotide comprising the 191 to 3409th base sequence of the base sequence represented by GenBank Accession number: NM_020630, and the like.

Moreover, the RET of the present invention may have translocations and mutations (including point mutations, deletion mutations, and insertion mutations), as long as it has RET kinase activity.

Translocations of RET in the present invention include a case where the whole or part of the RET protein having RET kinase activity is fused with the whole or part of another protein (e.g., KIF5B protein, CCDC6 protein, NCOA4 protein, or TRIM33 protein) to form a fused protein, and preferably CCDC6-RET and KIF5B-RET (CCDC6-RET means that part of the CCDC6 protein and part of the RET protein are fused in this order; hereinafter the same) (Drilon A, Cancer Discov., 3 (6), pp. 630-635 (2013)).

Mutations of RET in the present invention may be point mutations, deletion mutations, or insertion mutations, as long as the RET has RET kinase activity. Mutations of RET include polypeptides having RET kinase activity and comprising an amino acid sequence mutated by substitution, deletion, or addition of one or several amino acids, or by a combination thereof, in the amino acid sequence of RET, e.g., the amino acid sequence encoded by GenBank Accession number: NM_020975 or the amino acid sequence encoded by GenBank Accession number: NM_020630.

Regions to be mutated are not limited, as long as the RET has RET kinase activity. The ATP-binding region or the gatekeeper region may be mutated. The region of the residue adjacent to the hinge region to which ATP of protein kinase is bonded is called the gatekeeper region. The amino acid residue of this region greatly affects the spatial configuration of the ATP-binding pocket. The amino acid of the gatekeeper region in RET is 804th valine of the amino acid sequence encoded by GenBank accession number: NM_020975 or GenBank accession number: NM_020630. RET V804L mutation and RET V804M mutation have been clinically reported in thyroid cancer patients (Bolino A, Oncogene, 10, pp. 2415-2419, (1995), etc.).

It is also known that continuous administration of a protein kinase inhibitor often leads to spontaneous mutations in amino acid residues of the gatekeeper region (Kobayashi S, N Engl J Med., 352(8): pp. 786-792, (2005), etc.). Therefore, continuous administration of a RET inhibitor may lead to a mutation in the 804th valine in the gatekeeper region (Cranston A N, Cancer Res., 66 (20): pp. 10179-10187, (2006)). Mutations in the gatekeeper region acquire inhibitor resistance, and can therefore cause serious therapeutic problems. Actually, basic research have reported that cells obtained by introducing V804L mutation or V804M mutation into RET show resistance to Vandetanib, which is a drug having RET inhibitory activity (Carlomagno F, Oncogene, 23, pp. 6056-6063, (2004)).

These resistant mutant RETs are preferably RETs having V804L, V804M, V804E, Y806C, Y806E, Y806S, Y806H, or Y806N in which the 804th valine, which is the gatekeeper region, or its neighboring the 806th tyrosine, is substituted with another amino acid; and more preferably RET having V804L or V804M in which the 804th valine is substituted with leucine or methionine.

Moreover, the RET of the present invention may have mutations in regions other than the gatekeeper region, as long as it has RET kinase activity. Examples include, but are not limited to, RET having C618S, C620R, C630R, C634R, C634W, C634Y, C691S, E768D, A883F, A883S, E884V, S891A, S891L, or M918T (for example, C618S represents RET in which the 618th cysteine is substituted with serine; hereinafter the same) in the amino acid sequence encoded by GenBank accession number: NM_020975 or GenBank accession number: NM_020630. Preferred is C634W.

The presence of mutations of RET can be examined by analyzing the gene sequence of RET or the sequence of mRNA, which is a RET gene transcript. Examples of the sequence analysis method include the dideoxynucleotide chain termination method (Sanger et al. (1977) Proc. Natl. Acad. Sci. USA 74:5463) and the like. The sequence can also be analyzed by using a suitable DNA sequencer.

The presence of mutations of RET can also be analyzed by, for example, in situ hybridization, northern blot analysis, DNA microarray, RT-PCR, SSCP-PCR (Single-Strand Conformation Polymorphism-PCR), or the like. These methods can be performed in a standard manner (Clinical Cancer Research, 8, 457-463, 2002).

Further, the presence of mutations of RET can be analyzed by, for example, an immunochemical method (e.g., immunohistochemical technique, immunoprecipitation method, western blotting, flow cytometry, ELISA, RIA, or the like). These methods can be performed in a standard manner.

In order to analyze the presence of RET mutations by PCR, the sequence of the primer can be designed in a standard manner. The sequence of the primer can be designed by using, for example, Primer Expression (Perkin-Elmer Applied Biosystems).

Due to their excellent RET inhibitory activity, the compounds or salts thereof of the present invention are useful as pharmaceutical preparations for preventing and treating RET-related diseases. Examples of the "RET-related diseases" include diseases whose incidence can be reduced, and whose symptoms can be remitted, relieved, and/or completely cured by eliminating, suppressing, and/or inhibiting RET function. Examples of such diseases include, but are not limited to, malignant tumors, etc. Preferred examples of malignant tumors include malignant tumors with enhanced activation of RET, more preferably non-small cell lung cancer, breast cancer, colorectal cancer, or thyroid cancer with overactivated RET.

The phrase "enhanced activation of RET" indicates that the activated state of RET is enhanced due to, for example, translocations and mutations (including point mutations, deletion mutations, and insertion mutations) of the RET gene, and overexpression (including an increased copy numbers of the RET gene, overexpression of messenger RNA of RET, increased RET proteins, and constitutively activated RET proteins).

The type of cancer and tumor to be treated by the compounds or salts thereof of the present invention is not particularly limited. Examples include epithelial cancers (respiratory organ cancers, digestive organ cancers, reproductive organ cancers, secretion organ cancers, etc.), sarcomas, hematopoietic tumors, central nervous system tumors, and peripheral nerve tumors.

Specific examples of the type of cancer include head and neck cancer, thyroid cancer, esophagus cancer, gastric cancer, duodenal cancer, liver cancer, biliary tract cancer (gallbladder, cholangiocarcinoma, etc.), pancreas cancer, colorectal cancer (colon cancer, rectal cancer, etc.), lung cancer (non-small cell lung cancer, small cell lung cancer, mesothelioma, etc.), breast cancer, ovarian cancer, uterine cancer (cervical cancer, endometrial cancer, etc.), renal cancer, renal pelvis-ureteral cancer, bladder cancer, prostate cancer, testicular tumor, leukemia, malignant lymphoma, multiple myeloma, osteosarcoma, soft-tissue sarcoma, skin cancer, brain tumor, adrenal tumor, neuroblastoma, and the like. The target cancer is preferably lung cancer (non-small cell lung cancer, small cell lung cancer, mesothelioma, etc.), colorectal cancer (colon cancer, rectal cancer, etc.), thyroid cancer, breast cancer, brain tumor, and leukemia; and particularly preferably non-small cell lung cancer, breast cancer, colorectal cancer, and thyroid cancer.

When the compounds or salts thereof of the present invention are used as pharmaceutical preparations, a pharmaceutical carrier can be added, if required, thereby forming a suitable dosage form according to prevention and treatment purposes. Examples of the dosage form include oral preparations, injections, suppositories, ointments, patches, and the like; preferably oral preparations. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or coating agent in solid preparations; or as a solvent, solubilizing agent, suspending agent, isotonizing agent, pH adjuster/buffer, or soothing agent in liquid preparations. Moreover, pharmaceutical preparation additives, such as antiseptics, antioxidants, colorants, sweeteners, and stabilizers, may also be used, if required.

When a solid preparation for oral administration is prepared, optionally an excipient, a binder, a disintegrator, a lubricant, a colorant, a sweetener, and the like may be added to the compound of the present invention; and the resulting mixture may be formulated into tablets, coated tablets, granules, powders, capsules, etc., according to an ordinary method.

When an injection is prepared, a pH adjuster, a buffer, a stabilizer, an isotonizing agent, a local anesthetic, and the like may be added, as necessary, to the compound of the present invention; and the resulting mixture may be formulated into subcutaneous, intramuscular, and intravenous injections according to an ordinary method.

The amount of the compound of the present invention to be incorporated in each of such dosage unit forms depends on the condition of the patient to whom the compound is administered, the dosage form, etc. In general, in the case of an oral agent, an injection, and a suppository, the amount of the compound of the present invention is preferably 0.05 to 1000 mg, 0.01 to 500 mg, and 1 to 1000 mg, respectively, per dosage unit form.

The daily dose of the medicine in such a dosage form depends on the condition, body weight, age, gender, etc., of the patient, and cannot be generalized. For example, the daily dose of the compound of the present invention for an adult (body weight: 50 kg) may be generally 0.05 to 5000 mg, and preferably 0.1 to 1000 mg; and is preferably administered in one dose, or in two to three divided doses, per day.

The compounds or salts thereof of the present invention have excellent RET inhibitory activity, and are useful as antitumor agents. The RET mentioned herein is preferably RET in "enhanced activation," as described above. Moreover, in a preferred embodiment, the compounds or salts thereof of the present invention have high selectivity for RET, and have advantageously few side effects caused by the inhibition of off-targets, such as Src, Lck, EGFR, and Aurora B. Aurora B is a kinase involved in cell division. A clinical test of an agent having Aurora B-inhibitory activity has reported that side effects on the blood cell system, such as neutropenia, frequently occur (Non-patent literature 20). Further, inhibitors targeted for EGFR are known to mutually cause side effects, such as skin disorders or gastrointestinal disorders (Non-patent literature 21).

In a preferred embodiment, the compounds or salts thereof of the present invention also have excellent cell growth inhibitory effects on cells originally having RET-resistant mutations, on which existing RET inhibitors are less likely to work. Further, the compounds or salts thereof of the present invention have excellent cell growth inhibitory effects on cells with acquired RET-resistant mutations due to continuous administration of RET inhibitors, and allows prolonged administration.

Moreover, in a preferred embodiment, the compounds or salts thereof of the present invention have excellent stability in liver microsomes. Therefore, excellent exposure in the blood can be expected, and there is no concern about Cyp inhibition.

Furthermore, in a preferred embodiment, the compounds or salts thereof of the present invention have excellent oral absorption. Therefore, sufficient plasma concentration is observed, and the compounds or salts thereof of the present invention are useful as oral pharmaceuticals.

EXAMPLES

The following describes the present invention in more detail with reference to Examples. However, the present invention is not limited to the Examples.

Commercially available reagents were used in the Examples, unless otherwise specified. For silica gel column chromatography, the following columns were used: Purif-Pack (registered trademark) SI produced by Moritex Corp., KP-Sil (registered trademark) silica prepacked column produced by Biotage, HP-Sil (registered trademark) silica prepacked column produced by Biotage, or HP-Sphere (registered trademark) silica prepacked column produced by Biotage. For basic silica gel column chromatography, a Purif-Pack (registered trademark) NH produced by Moritex Corp. or KP-NH (registered trademark) prepacked column produced by Biotage was used. For preparative thin-layer chromatography, Kieselgel TM 60F 254, Art. 5744 produced by Merck or an $NH_2$ Silica Gel 60F254 Plate produced by Wako was used. NMR spectra were measured by using an AL400 (400 MHz; produced by JEOL), Mercury 400 (400 MHz; produced by Agilent Technologies, Inc.) model spectrometer, or Inova 400 (400 MHz; produced by Agilent Technologies, Inc.) model spectrometer equipped with an OMNMR probe (Protasis). The measurement was carried out using tetramethylsilane as an internal standard when tetramethylsilane was contained in a deuterated solvent; otherwise, an NMR solvent was used as an internal standard. All of the δ values are shown in ppm. Microwave reaction was performed using an Initiator produced by Biotage.

LCMS spectra were measured using an Acquity SQD (quadrupole) produced by Waters Corporation under the following conditions.

Column: Acquity UPLC (registered trademark) BEH C18, 2.1×50 mm, 1.7 μm (produced by Waters Corporation)

MS detection: ESI positive

UV detection: 254 and 210 nm

Column flow rate: 0.5 mL/min

Mobile phase: Water/acetonitrile (0.1% formic acid)

TABLE 1

| | Injection volume: 1 μL gradient | |
| --- | --- | --- |
| Time (min) | Water | Acetonitrile |
| 0 | 95 | 5 |
| 0.1 | 95 | 5 |
| 2.1 | 5 | 95 |
| 3.0 | STOP | |

Preparative reversed-phase HPLC purification was performed using a preparative separation system available from Gilson, Inc.

Column: CombiPrep Pro C18, 50×30 mmI.D., S-5 μm (produced by YMC)

UV detection: 254 nm

Column flow rate: 40 mL/min

Mobile phase: Water/acetonitrile (0.1% formic acid)

Injection volume: 0.1 to 1 mL

The following are the abbreviations used and the meaning of each.

s: singlet d: doublet t: triplet q: quartet dd: double doublet dt: double triplet td: triple doublet tt: triple triplet ddd: double double doublet ddt: double double triplet dtd: double triple doublet tdd: triple double doublet m: multiplet br: broad brs: broad singlet brd: broad doublet CDI: carbonyldiimidazole DMSO-$d_6$: deuterated dimethyl sulfoxide CDCl$_3$: deuterated chloroform CD$_3$OD: deuterated methanol THF: tetrahydrofuran DMF: N,N-dimethylformamide DMA: N,N-dimethylacetamide NMP: 1-methyl-2-pyrrolidinone DMSO: dimethyl sulfoxide HATU: (dimethylamino)-N,N-dimethyl(3H-[1,2,3]triazolo[4,5-b]pyridin-3-yloxy)methane iminium hexafluorophosphate DIAD: diisopropyl azodicarboxylate DIPEA: diisopropylethylamine DME: 1,2-dimethoxyethane Reference Example 1: Synthesis of 4-amino-1-cyclopentyl-1H-pyrazolo[3,4-d]pyrimidine-3-carboxylic Acid Step 1: Synthesis of 1-cyclopentyl-3-iodo-1H-pyrazolo[3,4-d]pyrimidin-4-amine

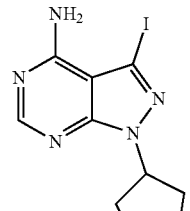

1-cyclopentyl-3-iodo-1H-pyrazolo[3,4-d]pyrimidin-4-amine

A suspension of 3.0 g of 3-iodo-1H-pyrazolo[3,4-d]pyrimidin-4-amine synthesized in accordance with the procedure described in International Publication No. WO2007/126841, 3.4 g of iodocyclopentane, and 4.8 g of potassium carbonate in 30 mL of DMF was heated to 80° C. and stirred for 18 hours. After the resulting mixture was cooled to room temperature, 200 mL of water was added thereto, followed by filtration of the precipitate. The precipitate was washed with water and dried, thereby obtaining 3.7 g of the title compound.

Physical Properties: m/z[M+H]$^+$ 330.1.

Step 2: Synthesis of 4-amino-1-cyclopentyl-1H-pyrazolo[3,4-d]pyrimidine-3-carboxylic Acid

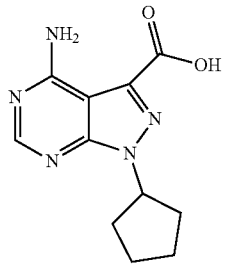

4-amino-1-cyclopentyl-1H-pyrazolo[3,4-d]pyrimidine-3-carboxylic acid 21 g of 1-cyclopentyl-3-iodo-1H-pyrazolo[3,4-d]pyrimidin-4-amine obtained in step 1, 42 ml of 2-diethylaminoethanol, and 2.24 g of Pd(PPh$_3$)$_2$Cl$_2$ were dissolved in 120 ml of NMP, and the inside of the system was replaced with carbon monoxide, followed by heating to 120° C. After stirring for 2 hours, the resulting mixture was cooled to room temperature, and 50 ml of methanol was added thereto. 19 ml of a 5N aqueous sodium hydroxide solution was further added thereto and stirred for 30 minutes. After addition of water, the aqueous layer was washed with ethyl acetate, and the washed aqueous layer was adjusted with hydrochloric acid to a pH of 3. The obtained precipitate was collected by filtration, washed with water, and dried, thereby obtaining 9.8 g of the title compound.

Physical Properties: m/z[M+H]⁺ 248.3.

Reference Example 2: Synthesis of 1-(adamantan-2-yl)-4-amino-1H-pyrazolo[3,4-d]pyrimidine-3-carboxylic Acid Step 1: Synthesis of 1-(adamantan-2-yl)-3-iodo-1H-pyrazolo[3,4-d]pyrimidin-4-amine

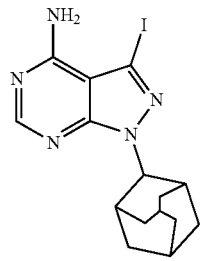

1-(adamantan-2-yl)-3-iodo-1H-pyrazolo[3,4-d]pyrimidin-4-amine 2.3 mL of diisopropyl azodicarboxylate was added to a solution of 1.5 g of 3-iodo-1H-pyrazolo[3,4-d]pyrimidin-4-amine, 2.6 g of 2-adamantanol, and 3.0 g of triphenylphosphine in 30 mL of THF at room temperature, followed by stirring overnight. After concentration, the residue was purified by silica gel chromatography (hexane→hexane/ethyl acetate=1/1), thereby obtaining 1.87 g of the title compound.

Physical Properties: m/z[M+H]⁺ 396.2.

Step 2: Synthesis of 1-(adamantan-2-yl)-4-amino-1H-pyrazolo[3,4-d]pyrimidine-3-carboxylic Acid

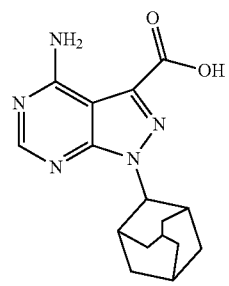

1-(adamantan-2-yl)-4-amino-1H-pyrazolo[3,4-d]pyrimidine-3-carboxylic acid 1.8 g of 1-(adamantan-2-yl)-3-iodo-1H-pyrazolo[3,4-d]pyrimidin-4-amine obtained in step 1, 3.0 mL of 2-diethylaminoethanol, and 160 mg of Pd(PPh₃)₂Cl₂ were dissolved in 5 mL of NMP, and the inside of the system was replaced with carbon monoxide, followed by heating to 120° C. After stirring for 2 hours, the resulting mixture was cooled to room temperature, and 5 mL of methanol was added thereto. 2.3 mL of a 5N aqueous sodium hydroxide solution was further added thereto, and stirred for 30 minutes. After addition of water, the aqueous layer was washed with ethyl acetate, and the washed aqueous layer was adjusted with hydrochloric acid to a pH of 3. The obtained precipitate was collected by filtration, washed with water, and dried, thereby obtaining 0.3 g of the title compound.

Physical Properties: m/z[M+H]⁺ 314.2.

Reference Example 3: Synthesis of 4-amino-1-(tert-butyl)-1H-pyrazolo[3,4-d]pyrimidine-3-carboxylic Acid Step 1: Synthesis of methyl 4-amino-1-(tert-butyl)-1H-pyrazolo[3,4-d]pyrimidine-3-carboxylate

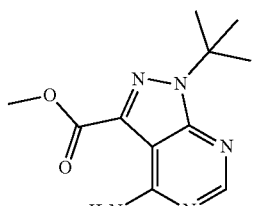

methyl 4-amino-1-(tert-butyl)-1H-pyrazolo[3,4-d]pyrimidine-3-carboxylate 3.33 g of triethylamine and 1.35 g of 1,1'-bis(diphenylphosphino)ferrocene-palladium(II) dichloride-dichloromethane complex were added to a suspension of 4.45 g of 3-bromo-(1-tert-butyl)-1H-pyrazolo[3,4-d]pyrimidin-4-amine in 45 mL of methanol. The mixture was stirred in a carbon monoxide atmosphere in an autoclave at 0.5 MPa and at 100° C. for 3 hours. After cooling, the reaction solution was concentrated, dissolved in chloroform, washed with water, and dried over anhydrous sodium sulfate. The dried mixture was then filtered and concentrated. The obtained residue was purified by silica gel column chromatography (hexane-ethyl acetate) and concentrated. The obtained precipitate was suspended and washed with hexane-ethyl acetate. After filtration, the precipitate was dried at 70° C. under reduced pressure, thereby obtaining 2.37 g of the title compound.

Physical Properties: m/z[M+H]⁺ 250.1.

Step 2: Synthesis of 4-amino-1-(tert-butyl)-1H-pyrazolo[3,4-d]pyrimidine-3-carboxylic Acid

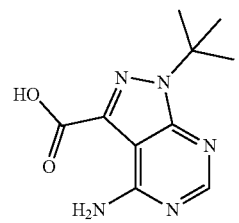

4-amino-1-(tert-butyl)-1H-pyrazolo[3,4-d]pyrimidine-3-carboxylic acid 2.23 g of methyl-4-amino-1-(tert-butyl)-1H-pyrazolo[3,4-d]pyrimidine-3-carboxylate obtained in step 1 was suspended in 33 mL of methanol, and 3.58 mL of a 5M aqueous sodium hydroxide solution was added thereto. The mixture was stirred with heating under reflux for 30 minutes. After cooling, the reaction solution was neutralized with a 5M hydrochloric acid aqueous solution, and diluted with water to collect the obtained precipitate by filtration. The obtained precipitate was dried at 60° C. under reduced pressure, thereby obtaining 2.05 g of the title compound.

Physical Properties: m/z[M+H]$^+$ 236.3.

Reference Example 4: Synthesis of 4-amino-7-isopropyl-7H-pyrrolo[2,3-d]pyrimidine-5-carboxylic Acid Step 1: Synthesis of 4-chloro-5-iodo-7-isopropyl-7H-pyrrolo[2,3-d]pyrimidine

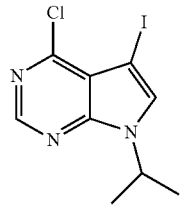

4-chloro-5-iodo-7-isopropyl-7H-pyrrolo
[2,3-d]pyrimidine 5.79 mL of diisopropyl azodicarboxylate was added to a solution of 4.0 g of 4-chloro-5-iodo-7H-pyrrolo[2,3-d]pyrimidine, 2.58 g of propan-2-ol, and 7.51 g of triphenylphosphine in 30 mL of tetrahydrofuran. The reaction solution was stirred for 18 hours. The reaction solution was concentrated, and the obtained residue was purified by silica gel chromatography (hexane→hexane/ethyl acetate=1/1), thereby obtaining 4.0 g of the title compound.

Physical Properties: m/z[M+H]$^+$ 322.0.

Step 2: Synthesis of 5-iodo-7-isopropyl-7H-pyrrolo[2,3-d]pyrimidin-4-amine

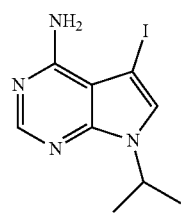

5-iodo-7-isopropyl-7H-pyrrolo
[2,3-d]pyrimidin-4-amino 30 mL of 1,2-dimethoxyethane and 30 mL of 28% ammonia water were added to 3 g of 4-chloro-5-iodo-7-isopropyl-7H-pyrrolo[2,3-d]pyrimidine obtained in step 1, and the mixture was stirred in a stainless pressure-resistant tube at 115° C. for 18 hours. 300 mL of water was added to the reaction solution, and the obtained precipitate was washed with water, thereby obtaining 2.0 g of the title compound.

Physical Properties: m/z[M+H]$^+$ 303.1.

Step 3: Synthesis of 4-amino-7-isopropyl-7H-pyrrolo[2,3-d]pyrimidine-5-carboxylic Acid

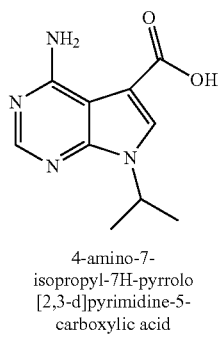

4-amino-7-isopropyl-7H-pyrrolo
[2,3-d]pyrimidine-5-carboxylic acid 3.8 g of 5-iodo-7-isopropyl-7H-pyrrolo[2,3-d]pyrimidin-4-amine obtained in step 2, 8.3 mL of 2-diethylamino ethanol, and 0.44 g of Pd(PPh$_3$)$_2$Cl$_2$ were dissolved in 10 mL of NMP, and the inside of the system was replaced with carbon monoxide, followed by heating to 120° C. After stirring for 2 hours, the reaction mixture was cooled to room temperature, and 7 mL of methanol was added thereto. 3.5 mL of a 5N aqueous sodium hydroxide solution was further added, and the mixture was stirred for 30 minutes. After addition of water, the aqueous layer was washed with ethyl acetate and adjusted with hydrochloric acid to a pH of 3, followed by filtration of the obtained precipitate. The filtered precipitate was washed with water and dried, thereby obtaining 0.670 g of the title compound.

Physical Properties: m/z[M+H]$^+$ 221.2.

Reference Example 5: Synthesis of 4-amino-7-(tert-butyl)-7H-pyrrolo[2,3-d]pyrimidine-5-carboxylic Acid Step 1: Synthesis of 7-(tert-butyl)-4-chloro-7H-pyrrolo[2,3-d]pyrimidine

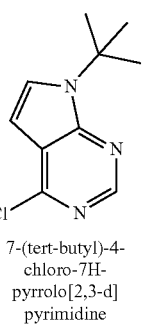

7-(tert-butyl)-4-chloro-7H-pyrrolo[2,3-d]
pyrimidine

A mixture solution of 29.3 g of 2-(4,6-dichloropyrimidin-5-yl)acetaldehyde, 13.4 g of tert-butylamine, and 29.7 g of N,N-diisopropylethylamine in 200 mL of ethanol was stirred with heating under reflux for 2 hours. After cooling, the reaction mixture was concentrated. The residue was diluted with ethyl acetate, washed with water and subsequently washed with a saturated aqueous sodium chloride solution.

The obtained organic layer was dried over anhydrous sodium sulfate, filtered, and concentrated. The obtained residue was purified by silica gel chromatography, thereby obtaining 21.5 g of the title compound.

Physical Properties: m/z[M+H]⁺ 210.0.

Step 2: Synthesis of 7-(tert-butyl)-4-chloro-5-iodo-7H-pyrrolo[2,3-d]pyrimidine

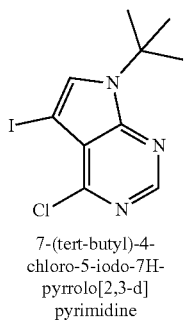

7-(tert-butyl)-4-chloro-5-iodo-7H-pyrrolo[2,3-d]pyrimidine 46.7 g of N-iodosuccinimide was added to a solution of 36 g of 7-(tert-butyl)-4-chloro-7H-pyrrolo[2,3-d]pyrimidine obtained in step 1 in 360 mL of DMF, and the mixture was stirred at room temperature for 3 days. The mixture was diluted with ethyl acetate and washed with water 3 times, followed by washing with a saturated aqueous sodium chloride solution. The obtained organic layer was dried over anhydrous sodium sulfate, filtered, and concentrated. The obtained precipitate was suspended and washed with hexane-ethyl acetate, and filtered, followed by drying under reduced pressure, thereby obtaining 45.5 g of the title compound.

Physical Properties: m/z[M+H]⁺ 335.9.

Step 3: Synthesis of 7-(tert-butyl)-5-iodo-7H-pyrrolo[2,3-d]pyrimidin-4-amine

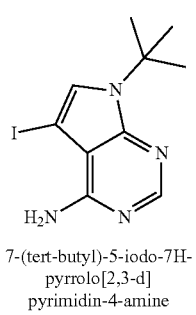

7-(tert-butyl)-5-iodo-7H-pyrrolo[2,3-d]pyrimidin-4-amine

A suspension of 52 g of 7-(tert-butyl)-4-chloro-5-iodo-7H-pyrrolo[2,3-d]pyrimidine obtained in step 2 in 180 mL of THF and 180 mL of 28% ammonia water was stirred at 120° C. for 14 hours in an autoclave. After cooling, the mixture was diluted with water to collect the obtained precipitate by filtration, followed by drying at 60° C. under reduced pressure, thereby obtaining 52 g of the title compound.

Physical Properties: m/z[M+H]⁺ 317.3.

Step 4: Synthesis of methyl 4-amino-7-(tert-butyl)-7H-pyrrolo[2,3-d]pyrimidine-5-carboxylate

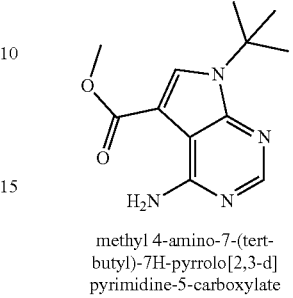

methyl 4-amino-7-(tert-butyl)-7H-pyrrolo[2,3-d]pyrimidine-5-carboxylate

A suspension of 15 g of 7-(tert-butyl)-5-iodo-7H-pyrrolo[2,3-d]pyrimidin-4-amine obtained in step 3, 1.94 g of a 1,1'-bis(diphenylphosphino)ferrocene-palladium(II) dichloride-dichloromethane complex, and 13.2 mL of triethylamine in 150 mL of methanol was stirred in a carbon monoxide atmosphere in an autoclave at 100° C. and 0.45 MPa for 1.5 hours. After cooling, the reaction solution was concentrated and purified by silica gel chromatography (hexane-ethyl acetate). After concentration, the obtained precipitate was suspended and washed with hexane-ethyl acetate, filtrated, and dried under reduced pressure, thereby obtaining 9.70 g of the title compound.

Physical Properties: m/z[M+H]⁺ 249.3.

Step 5: 4-amino-7-(tert-butyl)-7H-pyrrolo[2,3-d]pyrimidine-5-carboxylic Acid

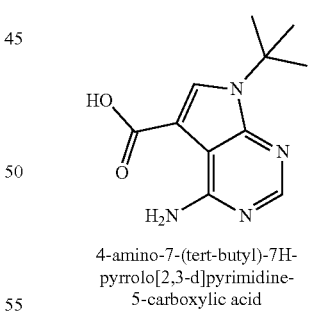

4-amino-7-(tert-butyl)-7H-pyrrolo[2,3-d]pyrimidine-5-carboxylic acid 23.4 mL of a 5M aqueous sodium hydroxide solution was added to a suspension of 9.70 g of methyl-4-amino-7-(tert-butyl)-7H-pyrrolo[2,3-d]pyrimidine-5-carboxylate obtained in step 4 in 97 mL of methanol. The mixture was stirred with heating under reflux for 2 hours. After cooling, the mixture was neutralized with a 5M hydrochloric acid aqueous solution. The thus-obtained precipitate was diluted with water, filtered, and dried at 60° C. under reduced pressure, thereby obtaining 8.0 g of the title compound.

Physical Properties: m/z[M+H]⁺ 235.2.

Reference Example 6: Synthesis of 7-(1-(fluoromethyl)cyclopropyl)-5-iodo-7H-pyrrolo[2,3-d]pyrimidin-4-amine

Step 1: Synthesis of 4-chloro-7-(1-(fluoromethyl)cyclopropyl)-7H-pyrrolo[2,3-d]pyrimidine

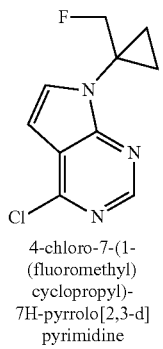

4-chloro-7-(1-(fluoromethyl)cyclopropyl)-7H-pyrrolo[2,3-d]pyrimidine

A solution of a mixture of 1.3 g of 2-(4,6-dichloropyrimidin-5-yl)acetaldehyde, 1.0 g of 1-(fluoromethyl)cyclopropanamine hydrochloride, and 4.7 mL of N,N-diisopropylethylamine in 10 mL of ethanol was stirred with heating under reflux for 2 hours. After cooling, the reaction solution was concentrated, and the obtained residue was purified by silica gel chromatography (hexane→hexane/ethyl acetate=1/1), thereby obtaining 1.1 g of the title compound.

Physical Properties: m/z[M+H]⁺ 226.0.

Step 2: Synthesis of 4-chloro-7-(1-(fluoromethyl)cyclopropyl)-5-iodo-7H-pyrrolo[2,3-d]pyrimidine

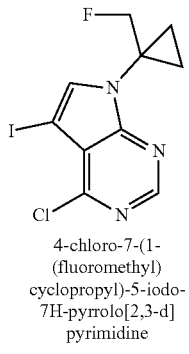

4-chloro-7-(1-(fluoromethyl)cyclopropyl)-5-iodo-7H-pyrrolo[2,3-d]pyrimidine 1.2 g of N-iodosuccinimide was added to a solution of 1.0 g of 4-chloro-7-(1-(fluoromethyl)cyclopropyl)-7H-pyrrolo[2,3-d]pyrimidine obtained in step 1 in 10 mL of DMF, and the mixture was stirred at room temperature for 18 hours. A 10% sodium thiosulfate aqueous solution was added to the reaction solution to terminate the reaction, and the reaction solution was diluted with water. The obtained precipitate was washed with water, filtered, and dried under reduced pressure, thereby obtaining 2.5 g of the title compound.

Physical Properties: m/z[M+H]⁺ 351.9.

Step 3: Synthesis of 7-(1-(fluoromethyl)cyclopropyl)-5-iodo-7H-pyrrolo[2,3-d]pyrimidin-4-amine

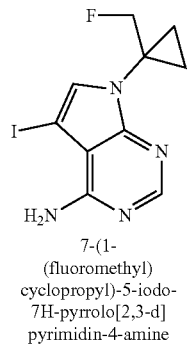

7-(1-(fluoromethyl)cyclopropyl)-5-iodo-7H-pyrrolo[2,3-d]pyrimidin-4-amine 10 mL of 1,2-dimethoxyethane and 10 mL of 28% ammonia water were added to 2.5 g of 4-chloro-7-(1-(fluoromethyl)cyclopropyl)-5-iodo-7H-pyrrolo[2,3-d]pyrimidine obtained in step 2, and the mixture was stirred in a stainless pressure-resistant tube at 115° C. for 18 hours. 200 mL of water was added to the reaction solution, and the obtained precipitate was washed with water, thereby obtaining 1.9 g of the title compound.

Physical Properties: m/z[M+H]⁺ 333.0.

Reference Example 7: Synthesis of 7-(tert-butyl)-5-iodo-6-methyl-7H-pyrrolo[2,3-d]pyrimidin-4-amine

Step 1: Synthesis of 1-(4,6-dichloropyrimidin-5-yl)propan-2-ol

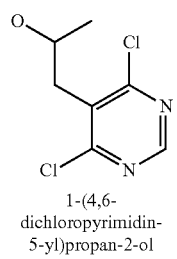

1-(4,6-dichloropyrimidin-5-yl)propan-2-ol 1 g of 2-(4,6-dichloropyrimidin-5-yl)acetaldehyde was dissolved in 20 mL of THF, and the reactor was cooled to −78° C. 4.36 mL of a methylmagnesium bromide diethyl ether solution (3 mol/L) was slowly added dropwise dropwisely thereto. At the same temperature, the mixture was stirred for 1 hour, and a saturated aqueous ammonium chloride solution was slowly added thereto to terminate the reaction. The reaction mixture was stirred at room temperature for 10 minutes and placed in a separatory funnel, followed by extraction with ethyl acetate. The organic layer was washed with a saturated aqueous sodium chloride solution, and then dried over sodium sulfate to remove the solvent. The residue was purified by basic silica gel chromatography (hexane/ethyl acetate=1/0→3/1), thereby obtaining 446 mg of the title compound.

Physical Properties: m/z[M+H]⁺ 207.0.

Step 2: Synthesis of 1-(4,6-dichloropyrimidin-5-yl)propan-2-one

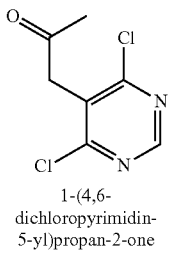

1-(4,6-dichloropyrimidin-5-yl)propan-2-one 246 mg of 1-(4,6-dichloropyrimidin-5-yl)propan-2-ol obtained in step 1 was dissolved in 2.5 mL of dichloromethane, and 1.0 g of a Dess-Martin reagent was added thereto, followed by stirring at room temperature for 1 hour. A 10% sodium thiosulfate aqueous solution and saturated sodium bicarbonate water were added to the reaction solution, and the mixture was further stirred for 30 minutes. The reaction mixture was extracted with chloroform, and the organic layer was washed with water and a saturated aqueous sodium chloride solution, followed by addition of sodium sulfate for drying. After removal of the solvent, the residue was purified by silica gel chromatography (hexane/ethyl acetate=1/0→3/1), thereby obtaining 198 mg of the title compound.

Physical Properties: m/z[M+H]$^+$ 205.0.

Step 3: Synthesis of 1-(4-(tert-butylamino)-6-chloropyrimidin-5-yl)propan-2-one

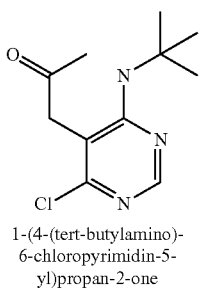 [SMILES: CC(=O)Cc1c(Cl)ncnc1NC(C)(C)C]

1-(4-(tert-butylamino)-6-chloropyrimidin-5-yl)propan-2-one 198 mg of 1-(4,6-dichloropyrimidin-5-yl)propan-2-one obtained in step 2, 122 µL of tert-butylamine, and 252 µL of diisopropylethylamine were dissolved in 2 mL of ethanol, and the solution was stirred at 90° C. overnight.

After the reaction mixture was concentrated, the residue was purified by silica gel chromatography (hexane/ethyl acetate=1/0→3/1), thereby obtaining 64 mg of the title compound.

Physical Properties: m/z[M+H]$^+$ 242.1.

Step 4: Synthesis of 7-(tert-butyl)-4-chloro-6-methyl-7H-pyrrolo[2,3-d]pyrimidine

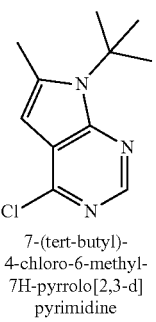

7-(tert-butyl)-4-chloro-6-methyl-7H-pyrrolo[2,3-d]pyrimidine 64 mg of 1-(4-(tert-butylamino)-6-chloropyrimidin-5-yl)propan-2-one obtained in step 3 and 42 µL of acetic acid were dissolved in 5.5 mL of ethanol, and the solution was reacted in a microwave reactor at 120° C. for 1 hour. After removal of the solvent, the residue was purified by silica gel chromatography (hexane/ethyl acetate=1/0→4/1), thereby obtaining 54 mg of the title compound.

Physical Properties: m/z[M+H]$^+$ 224.1.

Step 5: Synthesis of 7-(tert-butyl)-4-chloro-5-iodo-6-methyl-7H-pyrrolo[2,3-d]pyrimidine

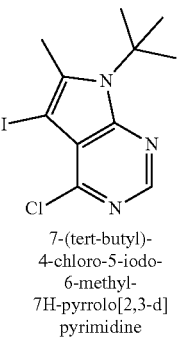 [SMILES: Cc1c(I)c2c(Cl)ncnc2n1C(C)(C)C]

7-(tert-butyl)-4-chloro-5-iodo-6-methyl-7H-pyrrolo[2,3-d]pyrimidine 7-(tert-butyl)-4-chloro-6-methyl-7H-pyrrolo[2,3-d]pyrimidine obtained in step 4 was dissolved in 1.5 mL of DMF. 64 mg of N-iodosuccinimide was added thereto, and the mixture was stirred at room temperature overnight. A 10% sodium thiosulfate aqueous solution was added to the reaction solution to terminate the reaction, followed by extraction with ethyl acetate. The organic layer was washed with water and a saturated aqueous sodium chloride solution, and dried over sodium sulfate, followed by removal of the solvent. The residue was purified by silica gel chromatography (hexane/ethyl acetate=1/0→4/1), thereby obtaining 69 mg of the title compound.

Physical Properties: m/z[M+H]$^+$ 349.9.

Step 6: 7-(tert-butyl)-5-iodo-6-methyl-7H-pyrrolo[2,3-d]pyrimidin-4-amine

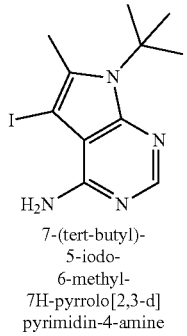 [SMILES: Cc1c(I)c2c(N)ncnc2n1C(C)(C)C]

7-(tert-butyl)-
5-iodo-
6-methyl-
7H-pyrrolo[2,3-d]
pyrimidin-4-amine 60 mg of 7-(tert-butyl)-4-chloro-5-iodo-6-methyl-7H-pyrrolo[2,3-d]pyrimidine obtained in step 5 was reacted with 600 μL of DME and 600 μL of ammonia water in a pressure-resistant tube at 115° C. for 12 hours. After air-cooling, water was added to the reaction mixture. The obtained precipitate was filtered and dried, thereby obtaining 45 mg of the title compound.

Physical Properties: m/z[M+H]$^+$ 331.0.

Reference Example 8: Synthesis of 3-fluoro-4-(methoxymethyl)aniline

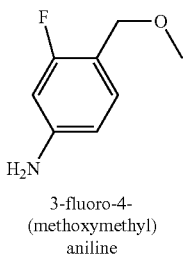

3-fluoro-4-
(methoxymethyl)
aniline 5.71 g of cesium carbonate and 3.64 mL iodomethane were added to a mixture solution of 1.0 g of (2-fluoro-4-nitrophenyl)methanol in 20 mL of THF and DMF (1:1), and the mixture was stirred for 18 hours. The resulting mixture was dissolved in ethyl acetate, washed with water, and dried over anhydrous magnesium sulfate, followed by filtration and concentration. The obtained residue was purified by silica gel column chromatography (hexane-ethyl acetate), and the reaction mixture was concentrated, thereby obtaining 0.76 g of 2-fluoro-1-(methoxymethyl)-4-nitrobenzene. Subsequently, 0.76 g of 2-fluoro-1-(methoxymethyl)-4-nitrobenzene was dissolved in 20 mL of ethanol, and 400 mg of palladium/carbon (palladium 10%) was added thereto, followed by stirring in a hydrogen atmosphere for 18 hours. The insoluble matter was filtered, and the filtrate was concentrated. The obtained residue was concentrated, thereby obtaining 567 mg of the title compound.

Physical Properties: m/z[M+H]$^+$ 156.0.

Reference Example 9: Synthesis of methyl 4-amino-6-bromo-7-(1-methylcyclopropyl)-7H-pyrrolo[2,3-d]pyrimidine-5-carboxylate

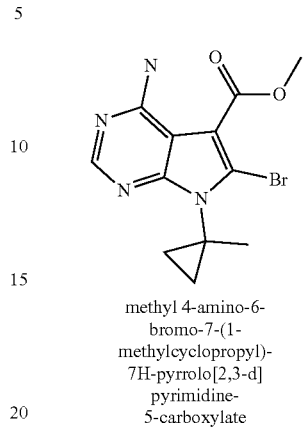

methyl 4-amino-6-
bromo-7-(1-
methylcyclopropyl)-
7H-pyrrolo[2,3-d]
pyrimidine-
5-carboxylate Step 1: Synthesis of 4-amino-7-(1-methylcyclopropyl)-7H-pyrrolo[2,3-d]pyrimidine-5-carbonitrile 2.5 mL of DMF was added to 234 mg of 5-iodo-7-(1-methylcyclopropyl)-7H-pyrrolo[2,3-d]pyrimidin-4-amine synthesized according to the procedure of steps 1 to 3 in Reference Example 5, using 1-methylcyclopropane amine hydrochloride instead of tert-butylamine, 131 mg of zinc cyanide, and 86 mg of tetrakis triphenylphosphine palladium. The mixture was reacted in a microwave reactor at 150° C. for 20 minutes. The insoluble matter was removed using Celite, and the filtrate was partitioned between toluene/ethyl acetate and water. The organic layer was washed with water and a saturated aqueous sodium chloride solution, and dried over anhydrous sodium sulfate, followed by filtration and concentration. Hexane and ethyl acetate were added to the precipitate of the residue, and the mixture was stirred at room temperature. The generated precipitate was filtered, thereby obtaining 100 mg of the title compound.

Physical Properties: m/z[M+H]$^+$ 214.2.

Step 2: Synthesis of 4-amino-6-bromo-7-(1-methylcyclopropyl)-7H-pyrrolo[2,3-d]pyrimidine-5-carbonitrile 100 mg of 4-amino-7-(1-methylcyclopropyl)-7H-pyrrolo[2,3-d]pyrimidine-5-carbonitrile obtained in step 1 was dissolved in 5 mL of DMF, and 167 mg of N-bromosuccinimide was added thereto with ice-cooling, followed by stirring for 3.5 hours. The reaction solution was partitioned between ethyl acetate and a 10% sodium thiosulfate aqueous solution. The organic layer was washed with water and a saturated aqueous sodium chloride solution, and dried over anhydrous sodium sulfate, followed by filtration and concentration. Hexane and ethyl acetate were added to the precipitate of the residue, and the mixture was stirred with ice-cooling. The generated precipitate was filtered, thereby obtaining 96 mg of the title compound.

Physical Properties: m/z[M+H]$^+$ 294.0.

Step 3: 4-amino-6-bromo-7-(1-methylcyclopropyl)-7H-pyrrolo[2,3-d]pyrimidine-5-carboxamide 96 mg of 4-amino-6-bromo-7-(1-methylcyclopropyl)-7H-pyrrolo[2,3-d]pyrimidine-5-carbonitrile obtained in step 2 was dissolved in 3 mL of DMSO, and 90 µL of a 4N NaOH aqueous solution and 41 µL of 30% hydrogen peroxide were added thereto, followed by stirring at room temperature for 1 hour. The reaction solution was partitioned between ethyl acetate and a 10% sodium thiosulfate aqueous solution. The organic layer was washed with water and a saturated aqueous sodium chloride solution, and dried over anhydrous sodium sulfate, followed by filtration and concentration, thereby obtaining 76 mg of the title compound.

Physical Properties: m/z[M+H]⁺ 312.0.

Step 4: Synthesis of methyl 4-amino-6-bromo-7-(1-methylcyclopropyl)-7H-pyrrolo[2,3-d]pyrimidine-5-carboxylate 118 mg of 4-amino-6-bromo-7-(1-methylcyclopropyl)-7H-pyrrolo[2,3-d]pyrimidine-5-carboxamide obtained in step 3 was dissolved in 2 mL of THF, and 23 mg of dimethylaminopyridine and 415 mg of di-t-butyl dicarbonate were added thereto, followed by stirring at room temperature overnight. After removal of THF, 2 mL of methanol was added thereto, and 53 mg of potassium carbonate was further added, followed by stirring at room temperature for 7 hours. The reaction solution was neutralized with 2N HCl, and partitioned between ethyl acetate and water. The organic layer was washed with water and a saturated aqueous sodium chloride solution, and dried over anhydrous sodium sulfate, followed by filtration and concentration. 2 mL of dichloromethane and 2 mL of trifluoroacetic acid were added to the residue, and the mixture was stirred at room temperature for 1 hour. After removal of trifluoroacetic acid, the residue was partitioned between ethyl acetate and a saturated aqueous sodium bicarbonate solution. The organic layer was washed with water and a saturated aqueous sodium chloride solution, and dried over anhydrous sodium sulfate, followed by filtration and concentration. The residue was purified by silica gel column (ethyl acetate/methanol=1/0→8/1), thereby obtaining 50 mg of the title compound.

Physical Properties: m/z[M+H]⁺ 327.0.

Reference Example 10: Synthesis of methyl 4-amino-1-(4,4-difluorocyclohexyl)-1H-pyrazolo[3,4-d]pyrimidine-3-carboxylate Step 1: Synthesis of 1-(4,4-difluorocyclohexyl)-3-iodo-1H-pyrazolo[3,4-d]pyrimidin-4-amine

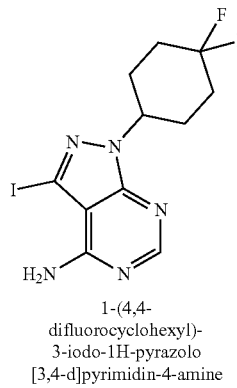

1-(4,4-difluorocyclohexyl)-3-iodo-1H-pyrazolo[3,4-d]pyrimidin-4-amine 1.6 ml of diisopropyl azodicarboxylate was added to a solution of 1.6 g of 3-iodo-1H-pyrazolo[3,4-d]pyrimidin-4-amine, 1.0 g of 4,4-difluorocyclohexanol, and 2.1 g of triphenylphosphine in 50 ml of THF at room temperature, and the mixture was stirred overnight. After concentration, the mixture was suspended and washed with methanol, followed by filtration. The obtained precipitate was dried at 60° C. under reduced pressure, thereby obtaining 1.5 g of the title compound.

Physical Properties: m/z[M+H]⁺ 380.2.

Step 2: Synthesis of methyl 4-amino-1-(4,4-difluorocyclohexyl)-1H-pyrazolo[3,4-d]pyrimidine-3-carboxylate

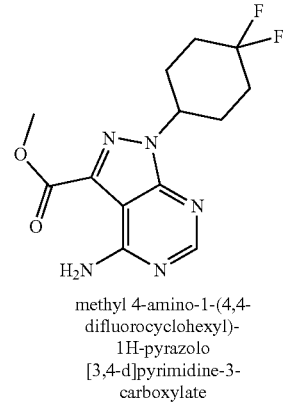 [SMILES: COC(=O)c1nn(C2CCC(F)(F)CC2)c2ncnc(N)c12]

methyl 4-amino-1-(4,4-difluorocyclohexyl)-1H-pyrazolo[3,4-d]pyrimidine-3-carboxylate A mixture solution of 1.5 g of 1-(4,4-difluorocyclohexyl)-3-iodo-1H-pyrazolo[3,4-d]pyrimidin-4-amine obtained in step 1, 330 mg of a 1,1'-bis(diphenylphosphino)ferrocene-palladium (II) dichloride-dichloromethane complex, and 3 ml of N,N-diisopropylamine in 30 ml of methanol was stirred in a carbon monoxide atmosphere in an autoclave at 0.45 MPa at 100° C. for 2 hours. After cooling, the reaction mixture was concentrated and purified by silica gel column chromatography (developing solvent: hexane-ethyl acetate). The obtained crude product was again purified by basic silica gel (developing solvent: hexane-ethyl acetate), and concentrated. The obtained precipitate was suspended and washed with hexane-ethyl acetate, filtered, and dried under reduced pressure, thereby obtaining 650 mg of the title compound.

Physical Properties: m/z[M+H]⁺ 312.1.

Reference Example 11: Synthesis of 4-amino-6-bromo-N-(3-fluoro-4-(methoxymethyl)phenyl)-7-(1-methylcyclopropyl)-7H-pyrrolo[2,3-d]pyrimidine-5-carboxamide

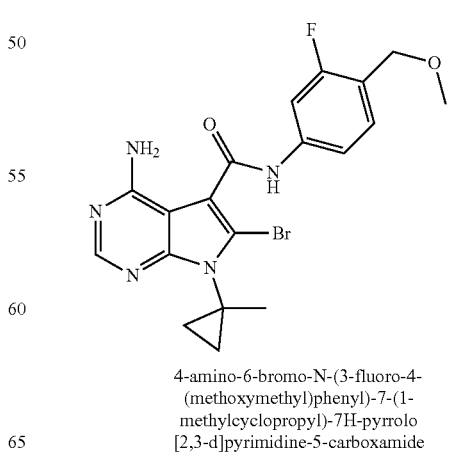

4-amino-6-bromo-N-(3-fluoro-4-(methoxymethyl)phenyl)-7-(1-methylcyclopropyl)-7H-pyrrolo[2,3-d]pyrimidine-5-carboxamide 270 mg of 4-amino-N-(3-fluoro-4-(methoxymethyl)phenyl)-7-(1-methylcyclopropyl)-7H-pyrrolo[2,3-d]pyrimidine-5-carboxamide shown in Example 48 was dissolved in 4 mL of DMF. 195 mg of N-bromosuccinimide was added thereto with ice-cooling, followed by stirring at room temperature for 15 minutes. A 10% sodium thiosulfate aqueous solution was added to the reaction solution, and the generated precipitate was filtered, followed by further washing with water, thereby obtaining 245 mg of the title compound.

Physical Properties: m/z [M+H]$^+$ 450.1.

Reference Example 12: Synthesis of 4-amino-1-phenyl-1H-pyrazolo[3,4-d]pyrimidine-3-carboxylic Acid

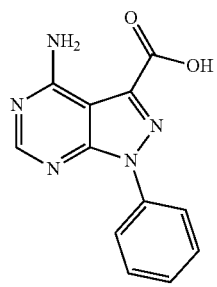

4-amino-1-phenyl-1H-pyrazolo[3,4-d]pyrimidine-3-carboxylic acid 300 mg of 1-phenyl-1H-pyrazolo[3,4-d]pyrimidin-4-amine and 453 mg of bromine were dissolved in 2 mL of water, and the solution was stirred at room temperature for 1 hour, followed by stirring at 100° C. for 1 hour. An aqueous sodium bicarbonate solution was added to the reaction solution, and the generated precipitate was collected by filtration. Further, the precipitate was washed with water, thereby obtaining 370 mg of 3-bromo-1-phenyl-1H-pyrazolo[3,4-d]pyrimidin-4-amine. A solution of 370 mg of the obtained 3-bromo-1-phenyl-1H-pyrazolo[3,4-d]pyrimidin-4-amine, 104 mg of 1,1'-bis(diphenylphosphino)ferrocene-palladium(II) dichloride-dichloromethane complex, and 500 μL of triethylamine in 5 mL of methanol was stirred in a carbon monoxide atmosphere in an autoclave at 120° C. for 4 hours. After cooling, the solvent was concentrated under reduced pressure. The obtained residue was dissolved in 5 mL of methanol, and 0.4 mL of a 5M aqueous sodium hydroxide solution was added thereto, followed by stirring at 50° C. for 2 hours. After cooling, the solvent was concentrated under reduced pressure. The residue was neutralized with a 5M aqueous hydrochloric acid solution, and the thus-obtained precipitate was diluted with water, filtered, and dried under reduced pressure, thereby obtaining the title compound.

Physical Properties: m/z [M+H]$^+$ 256.1.

Example 1: Synthesis of 4-amino-1-cyclopentyl-N-(4-(methoxymethyl)phenyl)-1H-pyrazolo[3,4-d]pyrimidine-3-carboxamide 30 mg of 4-amino-1-cyclopentyl-1H-pyrazolo[3,4-d]pyrimidine-3-carboxylic acid obtained in step 2 of Reference Example 1, 20 mg of 4-(methoxymethyl)aniline, and 55 mg of HATU were dissolved in 1 mL of DMF, and 62 μL of diisopropylethylamine was added thereto. After stirring at room temperature for 18 hours, water was added to the reaction solution, followed by extraction with ethyl acetate. The organic layer was washed with water and dried over anhydrous magnesium sulfate, followed by concentration of the organic solution under reduced pressure. The residue was purified by silica gel chromatography (chloroform-→chloroform/methanol=10/1), thereby obtaining 36 mg of the title compound.

Example 2: 4-amino-7-(tert-butyl)-N-(4-(methoxymethyl)phenyl)-7H-pyrrolo[2,3-d]pyrimidine-5-carboxamide 2.43 g of HATU was added to a solution of 1.00 g of 4-amino-7-(tert-butyl)-7H-pyrrolo[2,3-d]pyrimidine-5-carboxylic acid obtained in step 5 of Reference Example 5, 878 mg of 4-(methoxymethyl)aniline, and 2.23 mL of N,N-diisopropylethylamine in 20 mL of DMF at room temperature. The mixture was stirred at room temperature overnight, and an aqueous sodium hydroxide solution was added thereto, followed by extraction with chloroform. The obtained organic layer was dried over anhydrous sodium sulfate, filtered, concentrated, and purified by silica gel chromatography. After concentration, the obtained precipitate was suspended and washed with methanol, followed by filtration and drying under reduced pressure, thereby obtaining 1.12 g of the title compound.

Example 3: Synthesis of 4-amino-1-cyclopentyl-N-(4-((methylthio)methyl)phenyl)-1H-pyrazolo[3,4-d]pyrimidine-3-carboxamide According to the synthesis procedure of Example 1, using 4-((methylthio)methyl)aniline instead of 4-(methoxymethyl)aniline, the title compound (65%) was obtained.

Example 4: Synthesis of 4-amino-1-cyclopentyl-N-(4-(furan-2-yl)phenyl)-1H-pyrazolo[3,4-d]pyrimidine-3-carboxamide According to the synthesis procedure of Example 1, using 4-(furan-2-yl)aniline instead of 4-(methoxymethyl)aniline, the title compound (60%) was obtained.

Example 5: Synthesis of 4-amino-1-cyclopentyl-N-(4-(phenylamino)phenyl)-1H-pyrazolo[3,4-d]pyrimidine-3-carboxamide According to the synthesis procedure of Example 1, using N-phenylbenzene-1,4-diamine instead of 4-(methoxymethyl)aniline, the title compound (78%) was obtained.

Example 6: Synthesis of 4-amino-1-cyclopentyl-N-(2-methoxy-2,3-dihydro-1H-inden-5-yl)-1H-pyrazolo[3,4-d]pyrimidine-3-carboxamide According to the synthesis procedure of Example 1, using 2-methoxy-2,3-dihydro-1H-inden-5-amine instead of 4-(methoxymethyl)aniline, the title compound (88%) was obtained.

Example 7: Synthesis of 4-amino-1-cyclopentyl-N-(4-vinylphenyl)-1H-pyrazolo[3,4-d]pyrimidine-3-carboxamide According to the synthesis procedure of Example 1, using 4-vinylaniline instead of 4-(methoxymethyl)aniline, the title compound (69%) was obtained.

Example 8: Synthesis of 4-amino-N-(3-chlorophenyl)-1-cyclopentyl-1H-pyrazolo[3,4-d]pyrimidine-3-carboxamide According to the synthesis procedure of Example 1, using 3-chloroaniline instead of 4-(methoxymethyl)aniline, the title compound (61%) was obtained.

Example 9: Synthesis of (E)-4-amino-1-cyclopentyl-N-(4-(prop-1-en-1-yl)phenyl)-1H-pyrazolo[3,4-d]pyrimidine-3-carboxamide According to the synthesis procedure of Example 1, using (E)-4-(prop-1-en-1-yl)aniline instead of 4-(methoxymethyl)aniline, the title compound (82%) was obtained.

Example 10: Synthesis of 4-amino-1-(cyclopent-3-en-1-yl)-N-(4-(methoxymethyl)phenyl)-1H-pyrazolo[3,4-d]pyrimidine-3-carboxamide According to the synthesis procedures of steps 1 and 2 in Reference Example 1, using cyclopent-3-en-1-yl methanesulfonate instead of iodocyclopentane, 4-amino-1-(cyclopent-3-en-1-yl)-1H-pyrazolo[3,4-d]pyrimidine-3-carboxylic acid was obtained.

According to the procedure of Example 1, using 4-amino-1-(cyclopent-3-en-1-yl)-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (70%) was obtained.

Example 11: Synthesis of 4-amino-N-(4-(methoxymethyl)phenyl)-1-(3-methylcyclopentyl)-1H-pyrazolo[3,4-d]pyrimidine-3-carboxamide According to the synthesis procedures of steps 1 and 2 in Reference Example 1, using 3-methylcyclopentyl methanesulfonate instead of iodocyclopentane, 4-amino-1-(3-methylcyclopentyl)-1H-pyrazolo[3,4-d]pyrimidine-3-carboxylic acid was obtained.

According to the procedure of Example 1, using 4-amino-1-(3-methylcyclopentyl)-1H-pyrazolo[3,4-d]pyrimidine-3-carboxylic acid instead of 4-amino-1-cyclopentyl-1H-pyrazolo[3,4-d]pyrimidine-3-carboxylic acid, reaction was performed. The reaction solution was purified by preparative reversed-phase HPLC, and concentrated. The obtained precipitate was suspended and washed with hexane-ethyl acetate, filtered, and dried under reduced pressure, thereby obtaining the title compound (55%).

Example 12: Synthesis of 4-amino-1-cyclobutyl-N-(4-(methoxymethyl)phenyl)-1H-pyrazolo[3,4-d]pyrimidine-3-carboxamide According to the synthesis procedures of steps 1 and 2 in Reference Example 1, using bromocyclobutane instead of iodocyclopentane, 4-amino-1-cyclobutyl-1H-pyrazolo[3,4-d]pyrimidine-3-carboxylic acid was obtained.

According to the procedure of Example 1, using 4-amino-1-cyclobutyl-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (82%) was obtained.

Example 13: Synthesis of 4-amino-1-cyclobutyl-N-(4-((methylthio)methyl)phenyl)-1H-pyrazolo[3,4-d]pyrimidine-3-carboxamide According to the synthesis procedure of Example 12, using 4-((methylthio)methyl)aniline instead of 4-(methoxymethyl)aniline, the title compound (65%) was obtained.

Example 14: Synthesis of 4-amino-1-(3,3-dimethylcyclobutyl)-N-(4-(methoxymethyl)phenyl)-1H-pyrazolo[3,4-d]pyrimidine-3-carboxamide According to the synthesis procedures of steps 1 and 2 in Reference Example 1, using 3-bromo-1,1-dimethyl-cyclobutane instead of iodocyclopentane, 4-amino-1-(3,3-dimethylcyclobutyl)-1H-pyrazolo[3,4-d]pyrimidine-3-carboxylic acid was obtained.

According to the procedure of Example 1, using 4-amino-1-(3,3-dimethylcyclobutyl)-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (73%) was obtained.

Example 15: Synthesis of 4-amino-1-isopropyl-N-(4-((methylthio)methyl)phenyl)-1H-pyrazolo[3,4-d]pyrimidine-3-carboxamide According to the synthesis procedures of steps 1 and 2 in Reference Example 1, using 2-bromopropane instead of iodocyclopentane, 4-amino-1-isopropyl-1H-pyrazolo[3,4-d]pyrimidine-3-carboxylic acid was obtained.

According to the procedure of Example 1, using 4-amino-1-isopropyl-1H-pyrazolo[3,4-d]pyrimidine-3-carboxylic acid instead of 4-amino-1-cyclopentyl-1H-pyrazolo[3,4-d]pyrimidine-3-carboxylic acid, and using 4-((methylthio)methyl)aniline instead of 4-(methoxymethyl)aniline, the title compound (63%) was obtained.

Example 16: Synthesis of 4-amino-N-(4-((methylthio)methyl)phenyl)-1-(pentan-3-yl)-1H-pyrazolo[3,4-d]pyrimidine-3-carboxamide According to the synthesis procedures of steps 1 and 2 in Reference Example 1, using 3-bromopentane instead of iodocyclopentane, 4-amino-1-(pentan-3-yl)-1H-pyrazolo[3,4-d]pyrimidine-3-carboxylic acid was obtained.

According to the procedure of Example 1, using 4-amino-1-(pentan-3-yl)-1H-pyrazolo[3,4-d]pyrimidine-3-carboxylic acid instead of 4-amino-1-cyclopentyl-1H-pyrazolo[3,4-d]pyrimidine-3-carboxylic acid, and using 4-((methylthio)methyl)aniline instead of 4-(methoxymethyl)aniline, the title compound (65%) was obtained.

Example 17: 4-amino-1-cyclohexyl-N-(4-(methoxymethyl)phenyl)-1H-pyrazolo[3,4-d]pyrimidine-3-carboxamide According to the synthesis procedures of steps 1 and 2 in Reference Example 1, using bromocyclohexane instead of iodocyclopentane, 4-amino-1-cyclohexyl-1H-pyrazolo[3,4-d]pyrimidine-3-carboxylic acid was obtained.

According to the procedure of Example 1, using 4-amino-1-cyclohexyl-1H-pyrazolo[3,4-d]pyrimidine-3-carboxylic acid instead of 4-amino-1-cyclopentyl-1H-pyrazolo[3,4-d]pyrimidine-3-carboxylic acid, the title compound (16%) was obtained.

Example 18: Synthesis of 4-amino-1-cyclohexyl-N-(4-((methylthio)methyl)phenyl)-1H-pyrazolo[3,4-d]pyrimidine-3-carboxamide According to the procedure of Example 17, using 4-((methylthio)methyl)aniline instead of 4-(methoxymethyl)aniline, the title compound (85%) was obtained.

Example 19: Synthesis of 1-(adamantan-2-yl)-4-amino-N-(4-(methoxymethyl)phenyl)-1H-pyrazolo[3,4-d]pyrimidine-3-carboxamide 38 mg of 1-(adamantan-2-yl)-4-amino-1H-pyrazolo[3,4-d]pyrimidine-3-carboxylic acid obtained in step 2 of Reference Example 2, 20 mg of 4-(methoxymethyl)aniline, and 55 mg of HATU were dissolved in 1 mL of DMF, and 62 µL of diisopropylethylamine was added thereto. The mixture was stirred at room temperature for 18 hours, and water was added to the reaction solution, followed by extraction with ethyl acetate. The organic layer was washed with water, and dried over anhydrous magnesium sulfate, followed by concentration of the organic solution under reduced pressure. The residue was purified by silica gel chromatography (chloroform→chloroform/methanol=10/1), thereby obtaining 26 mg of the title compound.

Example 20: Synthesis of 4-amino-N-(4-(methoxymethyl)phenyl)-1-(trans-4-methylcyclohexyl)-1H-pyrazolo[3,4-d]pyrimidine-3-carboxamide According to the synthesis procedures of steps 1 and 2 in Reference Example 2, using cis-4-methylcyclohexanol instead of 2-adamantanol, 4-amino-1-(trans-4-methylcyclohexyl)-1H-pyrazolo[3,4-d]pyrimidine-3-carboxylic acid was obtained.

According to the procedure of Example 19, using 4-amino-1-(trans-4-methylcyclohexyl)-1H-pyrazolo[3,4-d]pyrimidine-3-carboxylic acid instead of 1-(adamantan-2-yl)-4-amino-1H-pyrazolo[3,4-d]pyrimidine-3-carboxylic acid, the title compound (82%) was obtained.

Example 21: Synthesis of 4-amino-1-(1-fluoropropan-2-yl)-N-(4-(methoxymethyl)phenyl)-1H-pyrazolo[3,4-d]pyrimidine-3-carboxamide According to the synthesis procedures of steps 1 and 2 in Reference Example 2, using 1-fluoropropan-2-ol instead of 2-adamantanol, 4-amino-1-(1-fluoropropan-2-yl)-1H-pyrazolo[3,4-d]pyrimidine-3-carboxylic acid was obtained.

According to the procedure of Example 19, using 4-amino-1-(1-fluoropropan-2-yl)-1H-pyrazolo[3,4-d]pyrimidine-3-carboxylic acid instead of 1-(adamantan-2-yl)-4-amino-1H-pyrazolo[3,4-d]pyrimidine-3-carboxylic acid, the title compound (58%) was obtained.

Example 22: Synthesis of 4-amino-1-(tert-butyl)-N-(4-(methoxymethyl)phenyl)-1H-pyrazolo[3,4-d]pyrimidine-3-carboxamide 121 mg of HATU was added to a solution of 50 mg of 4-amino-1-(tert-butyl)-1H-pyrazolo[3,4-d]pyrimidine-3-carboxylic acid obtained in step 2 of Reference Example 3, 34 mg of 4-(methoxymethyl)aniline, and 0.11 mL of N,N-diisopropylethylamine in 1 mL of DMF at room temperature. After stirring at room temperature for 1 hour, the mixture was diluted with ethyl acetate, and washed with water, followed by subsequent washing with a saturated aqueous sodium chloride solution. The obtained organic layer was dried over anhydrous sodium sulfate, followed by filtration and concentration. The obtained precipitate was suspended and washed with methanol, filtered, and dried under reduced pressure, thereby obtaining 65 mg of the title compound.

Example 23: 4-amino-1-(tert-butyl)-N-(4-((methylthio)methyl)phenyl)-1H-pyrazolo[3,4-d]pyrimidine-3-carboxamide According to the procedure of Example 22, using 4-((methylthio)methyl)aniline instead of 4-(methoxymethyl)aniline, the title compound (77%) was obtained.

Example 24: Synthesis of 4-amino-7-isopropyl-N-(4-(methoxymethyl)phenyl)-7H-pyrrolo[2,3-d]pyrimidine-5-carboxamide 67 mg of 4-amino-7-isopropyl-7H-pyrrolo[2,3-d]pyrimidine-5-carboxylic acid obtained in step 3 of Reference Example 4, 50 mg of 4-(methoxymethyl)aniline, and 138 mg of HATU were dissolved in 1 mL of DMF, and 158 µL of diisopropylethylamine was added thereto. After stirring at room temperature for 5 hours, water was added to the reaction solution, followed by extraction with chloroform. The organic layer was washed with water, and dried over anhydrous magnesium sulfate. The organic solution was concentrated under reduced pressure. The residue was purified by silica gel chromatography (chloroform→chloroform/methanol=10/1), thereby obtaining 76 mg of the title compound.

Example 25: Synthesis of 4-amino-7-cyclopentyl-N-(4-(methoxymethyl)phenyl)-7H-pyrrolo[2,3-d]pyrimidine-5-carboxamide According to the synthesis procedures of steps 1 to 3 in Reference Example 4, using cyclopentanol instead of propan-2-ol, 4-amino-7-cyclopentyl-7H-pyrrolo[2,3-d]pyrimidine-5-carboxylic acid was obtained.

According to the procedure of Example 24, using 4-amino-7-cyclopentyl-7H-pyrrolo[2,3-d]pyrimidine-5-carboxylic acid instead of 4-amino-7-isopropyl-7H-pyrrolo[2,3-d]pyrimidine-5-carboxylic acid, the title compound (69%) was obtained.

Example 26: Synthesis of 4-amino-7-(1-fluoro-2-methylpropan-2-yl)-N-(4-(methoxymethyl)phenyl)-7H-pyrrolo[2,3-d]pyrimidine-5-carboxamide According to the synthesis procedures of steps 1 to 5 in Reference Example 5, using 1-fluoro-2-methylpropan-2-amine hydrochloride instead of tert-butylamine, 4-amino-7-(1-fluoro-2-methylpropan-2-yl)-7H-pyrrolo[2,3-d]pyrimidine-5-carboxylic acid was obtained.

According to the procedure of Example 2, using 4-amino-7-(1-fluoro-2-methylpropan-2-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (67%) was obtained.

Example 27: Synthesis of 4-amino-7-(tert-butyl)-N-(4-propylphenyl)-7H-pyrrolo[2,3-d]pyrimidine-5-carboxamide According to the procedure of Example 2, using 4-propylaniline instead of 4-(methoxymethyl)aniline, the title compound (48%) was obtained.

Example 28: Synthesis of 4-amino-7-(tert-butyl)-N-(4-(pyridin-2-ylamino)phenyl)-7H-pyrrolo[2,3-d]pyrimidine-5-carboxamide According to the procedure of Example 2, using N-(2-pyridyl)benzene-1,4-diamine instead of 4-(methoxymethyl)aniline, the title compound (100%) was obtained.

Example 29: Synthesis of 4-amino-7-(tert-butyl)-N-(4-((methylthio)methyl)phenyl)-7H-pyrrolo[2,3-d]pyrimidine-5-carboxamide According to the procedure of Example 2, using 4-((methylthio)methyl)aniline instead of 4-(methoxymethyl)aniline, the title compound (29%) was obtained.

Example 30: Synthesis of 4-amino-7-(tert-butyl)-N-(3-fluoro-4-(methoxymethyl)phenyl)-7H-pyrrolo[2,3-d]pyrimidine-5-carboxamide According to the procedure of Example 2, using 3-fluoro-4-(methoxymethyl)aniline obtained in Reference Example 8 instead of 4-(methoxymethyl)aniline, the title compound (43%) was obtained.

Example 31: Synthesis of 4-amino-7-(tert-butyl)-N-(3-chloro-4-(methoxymethyl)phenyl)-7H-pyrrolo[2,3-d]pyrimidine-5-carboxamide According to the procedure of Example 2, using 3-chloro-4-(methoxymethyl)aniline instead of 4-(methoxymethyl)aniline, the title compound (27%) was obtained.

Example 32: Synthesis of 4-amino-7-(tert-butyl)-N-(4-(methoxymethyl)-3-methylphenyl)-7H-pyrrolo[2,3-d]pyrimidine-5-carboxamide According to the procedure of Example 2, using 4-(methoxymethyl)3-methyl-aniline that was obtained using (2-methyl-4-nitrophenyl)methanol instead of (2-fluoro-4-nitrophenyl)methanol in accordance with Reference Example 8, instead of 4-(methoxymethyl) aniline, the title compound (82%) was obtained.

Example 33: Synthesis of 4-amino-7-(tert-butyl)-N-(2-methoxy-4-(methoxymethyl)phenyl)-7H-pyrrolo[2,3-d]pyrimidine-5-carboxamide According to the procedure of Example 2, using 2-methoxy-4-(methoxymethyl)aniline that was obtained using (3-methoxy-4-nitrophenyl)methanol instead of (2-fluoro-4-nitrophenyl)methanol in accordance with Reference Example 8, instead of 4-(methoxymethyl)aniline, the title compound (60%) was obtained.

Example 34: Synthesis of 4-amino-7-(tert-butyl)-N-(4-ethynylphenyl)-7H-pyrrolo[2,3-d]pyrimidine-5-carboxamide According to the procedure of Example 2, using 4-(ethynylphenyl)aniline instead of 4-(methoxymethyl)aniline, the title compound (52%) was obtained.

Example 35: 4-amino-7-(tert-butyl)-N-(4-((methoxy-d3)-methyl)phenyl)-7H-pyrrolo[2,3-d]pyrimidine-5-carboxamide According to the procedure of Example 2, using 4-((methoxy-d-3)methyl)aniline that was synthesized using (4-nitrophenyl)methanol and methyl iodide (d3) in accordance with Reference Example 8, instead of 4-(methoxymethyl)aniline, the title compound (45%) was obtained.

Example 36: Synthesis of 4-amino-N-(4-(methoxymethyl)phenyl)-7-(1-methylcyclopropyl)-7H-pyrrolo[2,3-d]pyrimidine-5-carboxamide According to the synthesis procedures of steps 1 to 5 in Reference Example 5, using 1-methylcyclopropanamine hydrochloride instead of tert-butylamine, 4-amino-7-(1-methylcyclopropyl)-7H-pyrrolo[2,3-d]pyrimidine-5-carboxylic acid was obtained.

According to the procedure of Example 2, using 4-amino-7-(1-methylcyclopropyl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (8%) was obtained.

Example 37: Synthesis of 4-amino-7-(1-methylcyclopropyl)-N-(4-((methylthio)methyl)phenyl)-7H-pyrrolo[2,3-d]pyrimidine-5-carboxamide According to the procedure of Example 36, using 4-((methylthio)methyl)aniline instead of 4-(methoxymethyl)aniline, the title compound (78%) was obtained.

Example 38: Synthesis of 4-amino-N-(4-(methoxymethyl)phenyl)-7-(tert-pentyl)-7H-pyrrolo[2,3-d]pyrimidine-5-carboxamide According to the synthesis procedures of steps 1 to 5 in Reference Example 5, using 2-methylbutan-2-amine instead of tert-butylamine, 4-amino-7-(tert-pentyl)-7H-pyrrolo[2,3-d]pyrimidine-5-carboxylic acid was obtained.

According to the procedure of Example 2, using 4-amino-7-(tert-pentyl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (82%) was obtained.

Example 39: Synthesis of 4-amino-N-(4-(methoxymethyl)phenyl)-7-(1-methylcyclobutyl)-7H-pyrrolo[2,3-d]pyrimidine-5-carboxamide According to the synthesis procedures of steps 1 to 5 in Reference Example 5, using 1-methylcyclobutanamine hydrochloride instead of tert-butylamine, 4-amino-7-(1-methylcyclobutyl)-7H-pyrrolo[2,3-d]pyrimidine-5-carboxylic acid was obtained.

According to the procedure of Example 2, using 4-amino-7-(1-methylcyclobutyl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (69%) was obtained.

Example 40: Synthesis of 4-amino-7-(1-fluoro-2-methylpropan-2-yl)-N-(4-((methylthio)methyl)phenyl)-7H-pyrrolo[2,3-d]pyrimidine-5-carboxamide According to the procedure of Example 26, using 4-((methylthio)methyl)aniline instead of 4-(methoxymethyl)aniline, the title compound (55%) was obtained.

Example 41: Synthesis of 4-amino-7-(1-fluoro-2-methylpropan-2-yl)-N-(3-fluoro-4-(methoxymethyl)phenyl)-7H-pyrrolo[2,3-d]pyrimidine-5-carboxamide According to the procedure of Example 26, using 3-fluoro-4-(methoxymethyl)aniline that was obtained in Reference Example 8, instead of 4-(methoxymethyl)aniline, the title compound (50%) was obtained.

Example 42: Synthesis of 4-amino-N-(4-(methoxymethyl)phenyl)-7-(2-(thiophen-2-yl)propan-2-yl)-7H-pyrrolo[2,3-d]pyrimidine-5-carboxamide According to the synthesis procedures of steps 1 to 5 in Reference Example 5, using 2-(thiophen-2-yl)propan-2-amine instead of tert-butylamine, 4-amino-7-(2-(thiophen-2-yl)propan-2-yl)-7H-pyrrolo[2,3-d]pyrimidine-5-carboxylic acid was obtained.
According to the procedure of Example 2, using 4-amino-7-(2-(thiophen-2-yl)propan-2-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (86%) was obtained.

Example 43: Synthesis of 4-amino-7-(bicyclo[2.2.1]heptan-2-yl)-N-(4-(methoxymethyl)phenyl)-7H-pyrrolo[2,3-d]pyrimidine-5-carboxamide According to the synthesis procedures of steps 1 to 5 in Reference Example 5, using bicyclo[2.2.1]heptan-2-amine instead of tert-butylamine, 4-amino-7-(bicyclo[2.2.1]heptan-2-yl)-7H-pyrrolo[2,3-d]pyrimidine-5-carboxylic acid was obtained.
According to the procedure of Example 2, using 4-amino-7-(bicyclo[2.2.1]heptan-2-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (67%) was obtained.

Example 44: 4-amino-7-(bicyclo[1.1.1.]pentan-1-yl)-N-(4-(methoxymethyl)phenyl)-7H-pyrrolo[2,3-d]pyrimidine-5-carboxamide According to the synthesis procedures of steps 1 to 5 in Reference Example 5, using bicyclo[1.1.1]pentan-1-amine hydrochloride instead of tert-butylamine, 4-amino-7-(bicyclo[1.1.1.]pentan-1-yl)-7H-pyrrolo[2,3-d]pyrimidine-5-carboxylic acid was obtained.
According to the procedure of Example 2, using 4-amino-7-(bicyclo[1.1.1.]pentan-1-yl)-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (76%) was obtained.

Example 45: Synthesis of 4-amino-7-(1-(fluoromethyl)cyclopropyl)-N-(4-(methoxymethyl)phenyl)-7H-pyrrolo[2,3-d]pyrimidine-5-carboxamide A solution of 100 mg of 7-(1-(fluoromethyl)cyclopropyl)-5-iodo-7H-pyrrolo[2,3-d]pyrimidin-4-amine obtained in step 3 of Reference Example 6, 100 mg of 4-(methoxymethyl)aniline, 90 µL of 1,8-diazabicyclo[5.4.0]undec-7-ene, and 20 mg of 1,1'-bis(diphenylphosphino)ferrocene-palladium(II) dichloride-dichloromethane complex in 3 mL of NMP was stirred in a carbon monoxide atmosphere at 100° C. for 4 hours. The reaction solution was concentrated and purified by silica gel chromatography (hexane-ethyl acetate-methanol), thereby obtaining 86 mg of the title compound.

Example 46: Synthesis of 4-amino-7-(1-(difluoromethyl)cyclopropyl)-N-(4-(methoxymethyl)phenyl)-7H-pyrrolo[2,3-d]pyrimidine-5-carboxamide According to the synthesis procedures of steps 1 to 3 in Reference Example 6, using 1-(difluoromethyl)cyclopropanamine hydrochloride instead of 1-(fluoromethyl)cyclopropanamine hydrochloride, 7-(1-(difluoromethyl)cyclopropyl)-5-iodo-7H-pyrrolo[2,3-d]pyrimidin-4-amine was obtained.
According to the procedure of Example 45, using 7-(1-(difluoromethyl)cyclopropyl)-5-iodo-7H-pyrrolo[2,3-d]pyrimidin-4-amine instead of 7-(1-(fluoromethyl)cyclopropyl)-5-iodo-7H-pyrrolo[2,3-d]pyrimidin-4-amine, the title compound (80%) was obtained.

Example 47: Synthesis of 4-amino-7-(1-ethylcyclopropyl)-N-(4-(methoxymethyl)phenyl)-7H-pyrrolo[2,3-d]pyrimidine-5-carboxamide According to the synthesis procedures of steps 1 to 3 in Reference Example 6, using 1-ethylcyclopropanamine hydrochloride instead of 1-(fluoromethyl)cyclopropanamine hydrochloride, 7-(1-ethylcyclopropyl)-5-iodo-7H-pyrrolo[2,3-d]pyrimidin-4-amine was obtained.
According to the procedure of Example 45, using 7-(1-ethylcyclopropyl)-5-iodo-7H-pyrrolo[2,3-d]pyrimidin-4-amine instead of 7-(1-(fluoromethyl)cyclopropyl)-5-iodo-7H-pyrrolo[2,3-d]pyrimidin-4-amine, the title compound (60%) was obtained.

Example 48: Synthesis of 4-amino-N-(3-fluoro-4-(methoxymethyl)phenyl)-7-(1-methylcyclopropyl)-7H-pyrrolo[2,3-d]pyrimidine-5-carboxamide According to the synthesis procedures of steps 1 to 3 in Reference Example 6, using 1-methylcyclopropane hydrochloride instead of 1-(fluoromethyl)cyclopropanamine hydrochloride, 5-iodo-7-(1-methylcyclopropyl)-7H-pyrrolo[2,3-d]pyrimidin-4-amine was obtained.
According to the procedure of Example 45, using 5-iodo-7-(1-methylcyclopropyl)-7H-pyrrolo[2,3-d]pyrimidin-4-amine instead of 7-(1-(fluoromethyl)cyclopropyl)-5-iodo-7H-pyrrolo[2,3-d]pyrimidin-4-amine, and using 3-fluoro-4-(methoxymethyl)aniline that was obtained in Reference Example 8 instead of 4-(methoxymethyl)aniline, the title compound (80%) was obtained.

Example 49: Synthesis of 7-{[1,1-bi(cyclopropane)]-1-yl}-4-amino-N-(4-(methoxymethyl)phenyl)-7H-pyrrolo[2,3-d]pyrimidine-5-carboxamide According to the synthesis procedures of steps 1 to 3 in Reference Example 6, using 1-cyclopropylcyclopropanamine hydrochloride instead of 1-(fluoromethyl)cyclopropanamine hydrochloride, 7-([1,1-bi(cyclopropane)]-1-yl)-5-iodo-7H-pyrrolo[2,3-d]pyrimidin-4-amine was obtained.

According to the procedure of Example 45, using 7-([1,1-bi(cyclopropan)]-1-yl)-5-iodo-7H-pyrrolo[2,3-d]pyrimidin-4-amine instead of 7-(1-(fluoromethyl)cyclopropyl)-5-iodo-7H-pyrrolo[2,3-d]pyrimidin-4-amine, the title compound (50%) was obtained.

Example 50: Synthesis of 4-amino-7-(1,1-difluoro-2-methylpropan-2-yl)-N-(4-(methoxymethyl)phenyl)-7H-pyrrolo[2,3-d]pyrimidine-5-carboxamide According to the synthesis procedures of steps 1 to 3 in Reference Example 6, using 1,1-difluoro-2-methyl-propan-2-amine hydrochloride instead of 1-(fluoromethyl)cyclopropanamine hydrochloride, 7-(1,1-difluoro-2-methylpropan-2-yl)-5-iodo-7H-pyrrolo[2,3-d]pyrimidin-4-amine was obtained.

According to the procedure of Example 45, using 7-(1,1-difluoro-2-methylpropan-2-yl)-5-iodo-7H-pyrrolo[2,3-d]pyrimidin-4-amine instead of 7-(1-(fluoromethyl)cyclopropyl)-5-iodo-7H-pyrrolo[2,3-d]pyrimidin-4-amine, the title compound (32%) was obtained.

Example 51: Synthesis of 4-amino-7-(2,3-dimethylbutan-2-yl)-N-(4-(methoxymethyl)phenyl)-7H-pyrrolo[2,3-d]pyrimidine-5-carboxamide According to the synthesis procedures of steps 1 to 3 in Reference Example 6, using 2,3-dimethylbutan-2-amine hydrochloride instead of 1-(fluoromethyl)cyclopropanamine hydrochloride, 7-(2,3-dimethylbutan-2-yl)-5-iodo-7H-pyrrolo[2,3-d]pyrimidin-4-amine was obtained.

According to the procedure of Example 45, using 7-(2,3-dimethylbutan-2-yl)-5-iodo-7H-pyrrolo[2,3-d]pyrimidin-4-amine instead of 7-(1-(fluoromethyl) cyclopropyl)-5-iodo-7H-pyrrolo[2,3-d]pyrimidin-4-amine, the title compound (74%) was obtained.

Example 52: Synthesis of 4-amino-N-(4-(methoxymethyl)phenyl)-7-(2,3,3-trimethylbutan-2-yl)-7H-pyrrolo[2,3-d]pyrimidine-5-carboxamide According to the synthesis procedures of steps 1 to 3 in Reference Example 6, using 2,3,3-trimethylbutan-2-amine instead of 1-(fluoromethyl)cyclopropanamine hydrochloride, 5-iodo-7-(2,3,3-trimethylbutan-2-yl)-7H-pyrrolo[2,3-d]pyrimidin-4-amine was obtained.

According to the procedure of Example 45, using 5-iodo-7-(2,3,3-trimethylbutan-2-yl)-7H-pyrrolo[2,3-d]pyrimidin-4-amine instead of 7-(1-(fluoromethyl)cyclopropyl)-5-iodo-7H-pyrrolo[2,3-d]pyrimidin-4-amine, the title compound (80%) was obtained.

Example 53: Synthesis of 4-amino-7-(2-cyclopropylpropan-2-yl)-N-(4-(methoxymethyl)phenyl)-7H-pyrrolo[2,3-d]pyrimidine-5-carboxamide According to the synthesis procedures of steps 1 to 3 in Reference Example 6, using 2-cyclopropylpropan-2-amine hydrochloride instead of 1-(fluoromethyl)cyclopropanamine hydrochloride, 7-(2-cyclopropylpropan-2-yl)-5-iodo-7H-pyrrolo[2,3-d]pyrimidin-4-amine was obtained.

According to the procedure of Example 45, using 7-(2-cyclopropylpropan-2-yl)-5-iodo-7H-pyrrolo[2,3-d]pyrimidin-4-amine instead of 7-(1-(fluoromethyl) cyclopropyl)-5-iodo-7H-pyrrolo[2,3-d]pyrimidin-4-amine, the title compound (30%) was obtained.

Example 54: Synthesis of 4-amino-7-(2-cyclopropylpropan-2-yl)-N-(3-fluoro-4-(methoxymethyl)phenyl)-7H-pyrrolo[2,3-d]pyrimidine-5-carboxamide According to the procedure of Example 53, using 3-fluoro-4-(methoxymethyl)aniline instead of 4-(methoxymethyl)aniline, the title compound (40%) was obtained.

Example 55: 4-amino-6-bromo-N-[4-(methoxymethyl)phenyl]-7-(1-methylcyclopropyl)-7H-pyrrolo[2,3-d]pyrimidine-5-carboxamide Step 1: Synthesis of 4-amino-6-bromo-7-(1-methylcyclopropyl)-7H-pyrrolo[2,3-d]pyrimidine-5-carboxylic acid 3 mL of THF, 3 mL of methanol, and 0.62 mL of lithium hydroxide aqueous solution (4 mol/L) were added to 80 mg of methyl 4-amino-6-bromo-7-(1-methylcyclopropyl)-7H-pyrrolo[2,3-d]pyrimidine-5-carboxylate obtained in Reference Example 9. The mixture was stirred at room temperature overnight. 10 mL of water was added thereto, and the mixture was neutralized with a 2N HCl aqueous solution, thereby obtaining the precipitate. After removal of the solvent, the residue was stirred with ice-cooling for 30 minutes, and the precipitate was filtered, thereby obtaining 73 mg of the title compound.

Physical Properties: m/z[M+H]$^+$ 313.0

Step 2: Synthesis of 4-amino-6-bromo-N-[4-(methoxymethyl)phenyl]-7-(1-methylcyclopropyl) 7H-pyrrolo[2,3-d]pyrimidine-5-carboxamide 10.1 mg of 4-amino-6-bromo-7-(1-methylcyclopropyl)-7H-pyrrolo[2,3-d]pyrimidine-5-carboxylic acid obtained in step 1 was dissolved in 1 mL of DMF, and 5.3 mg of 4-(methoxymethyl)aniline, 17 μL of DIPEA, and 18.5 mg of HATU were added thereto, followed by stirring at room temperature overnight. The reaction solution was partitioned between ethyl acetate and water, and the organic layer was washed with a 1N NaOH aqueous solution, water, and a saturated aqueous sodium chloride solution, followed by drying over anhydrous sodium sulfate. After filtration, the filtrate was concentrated. The residue was purified by silica gel column (ethyl acetate/methanol=1/0→8/1), thereby obtaining 6.7 mg of the title compound.

Example 56: 4-amino-6-chloro-N-[4-(methoxymethyl)phenyl]-7-(1-methylcyclopropyl)-7H-pyrrolo[2,3-d]pyrimidine-5-carboxamide Step 1: Synthesis of methyl 4-amino-6-chloro-7-(1-methylcyclopropyl)-7H-pyrrolo[2,3-d]pyrimidine-5-carboxylate 111 mg of methyl 4-amino-7-(1-methylcyclopropyl)-7H-pyrrolo[2,3-d]pyrimidine-5-carboxylate synthesized according to the procedures of steps 1 to 4 in Reference Example 5 using 1-methylcyclopropaneamine hydrochloride instead of tert-butylamine was dissolved in 4.5 mL of DMF, and 90 mg of N-chlorosuccinimide was added thereto at room temperature, followed by stirring overnight. The reaction solution was partitioned between ethyl acetate and a 10% sodium thiosulfate aqueous solution, and the organic layer was washed with water and a saturated aqueous sodium chloride solution, followed by drying over anhydrous sodium sulfate. After filtration, the filtrate was concentrated. The residue was purified by silica gel column (ethyl acetate/methanol=1/0→8/1), thereby obtaining 45 mg of the title compound.

Physical Properties: m/z[M+H]$^+$ 281.1

Step 2: Synthesis of 4-amino-6-chloro-7-(1-methylcyclopropyl)-7H-pyrrolo[2,3-d]pyrimidine-5-carboxylic acid According to the procedure in step 1 of Example 55, from 36 mg of methyl 4-amino-6-chloro-7-(1-methylcyclopropyl)-7H-pyrrolo[2,3-d]pyrimidine-5-carboxylate obtained in step 1, the title compound (87%) was obtained.

Physical Properties: m/z[M+H]$^+$ 267.0

Step 3: Synthesis of 4-amino-6-chloro-N-[4-(methoxymethyl)phenyl]-7-(1-methylcyclopropyl)-7H-pyrrolo[2,3-d]pyrimidine-5-carboxamide According to the procedure of step 2 in Example 55, using 17.6 mg of 4-amino-6-chloro-7-(1-methylcyclopropyl)-7H-pyrrolo[2,3-d]pyrimidine-5-carboxylic acid obtained in step 2, the title compound (47%) was obtained.

Example 57: 4-amino-6-methoxy-N-[4-(methoxymethyl)phenyl]-7-(1-methylcyclopropyl)-7H-pyrrolo[2,3-d]pyrimidine-5-carboxamide Step 1: Synthesis of methyl 4-amino-6-methoxy-7-(1-methylcyclopropyl)-7H-pyrrolo[2,3-d]pyrimidine-5-carboxylate 1.66 g of 4-amino-6-bromo-7-(1-methylcyclopropyl)-7H-pyrrolo[2,3-d]pyrimidine-5-carboxamide obtained in step 3 of Reference Example 9 was dissolved in 27 mL of THF, and 327 mg of dimethylaminopyridine and 5.84 g of di-t-butyl dicarbonate were added thereto, followed by stirring at room temperature overnight. After removal of THF, 25 mL of methanol was added, and 5 mL of a solution of 5M sodium methoxide in methanol was further added thereto, followed by stirring at room temperature for 1 hour. The reaction solution was neutralized with 2N HCl, and partitioned between ethyl acetate and water. The organic layer was washed with water and a saturated aqueous sodium chloride solution, followed by drying over anhydrous sodium sulfate. After filtration, the filtrate was concentrated. 5 mL of dichloromethane and 5 mL of trifluoroacetic acid were added to the residue, and the mixture was stirred with ice-cooling for 1 hour. After the trifluoroacetic acid was removed, the residue was partitioned between ethyl acetate and an aqueous sodium bicarbonate solution. The organic layer was washed with water and a saturated aqueous sodium chloride solution, and dried over anhydrous sodium sulfate, filtered, and concentrated. The residue was purified by silica gel column (ethyl acetate/methanol=1/0→8/1), thereby obtaining 400 mg of the title compound.

Physical Properties: m/z[M+H]$^+$ 277.1

Step 2: Synthesis of 4-amino-6-methoxy-N-[4-(methoxymethyl)phenyl]-7-(1-methylcyclopropyl)-7H-pyrrolo[2,3-d]pyrimidine-5-carboxamide According to the procedures of steps 1 and 2 in Example 55, from methyl 4-amino-6-methoxy-7-(1-methylcyclopropyl)-7H-pyrrolo[2,3-d]pyrimidine-5-carboxylate obtained in step 1, the title compound (50%) was obtained.

Example 58: 4-amino-6-cyano-N-[4-(methoxymethyl)phenyl]-7-(1-methylcyclopropyl)-7H-pyrrolo[2,3-d]pyrimidine-5-carboxamide Step 1: Synthesis of methyl 4-amino-6-cyano-7-(1-methylcyclopropyl)-7H-pyrrolo[2,3-d]pyrimidine-5-carboxylate 77 mg of methyl 4-amino-6-bromo-7-(1-methylcyclopropyl)-7H-pyrrolo[2,3-d]pyrimidine-5-carboxylate obtained in Reference Example 9 was dissolved in 2.5 mL of DMF, and 53 mg of copper cyanide was added thereto, followed by stirring at 120° C. in a nitrogen atmosphere for 9 hours. The reaction solution was concentrated, and the residue was purified by silica gel chromatography (ethyl acetate/methanol=1/0→8/1), thereby obtaining 40 mg of the title compound.

Physical Properties: m/z[M+H]$^+$ 272.1

Step 2: Synthesis of 4-amino-6-cyano-N-[4-(methoxymethyl)phenyl]-7-(1-methylcyclopropyl)-7H-pyrrolo[2,3-d]pyrimidine-5-carboxamide According to the procedures of steps 1 and 2 in Example 55, from methyl 4-amino-6-cyano-7-(1-methylcyclopropyl)-7H-pyrrolo[2,3-d]pyrimidine-5-carboxylate obtained in step 1, the title compound (35%) was obtained.

Example 59: Synthesis of 4-amino-6-bromo-7-(1-methylcyclopropyl)-N-(4-((methylthio)methyl)phenyl)-7H-pyrrolo[2,3-d]pyrimidine-5-carboxamide According to the procedure of step 2 in Example 55, using 4-amino-6-bromo-7-(1-methylcyclopropyl)-7H-pyrrolo[2,3-d]pyrimidine-5-carboxylic acid obtained in step 1 of Example 55 and 4-((methylthio)methyl)aniline, the title compound (44%) was obtained.

Example 60: 4-amino-7-(tert-butyl)-N-(4-(methoxymethyl)phenyl)-6-methyl-7H-pyrrolo[2,3-d]pyrimidine-5-carboxamide Step 1: Synthesis of 4-amino-7-(tert-butyl)-6-methyl-7H-pyrrolo[2,3-d]pyrimidine-5-carboxylic acid According to the procedures of steps 4 and 5 in Reference Example 5, using 135 mg of 7-(tert-butyl)-5-iodo-6-methyl-7H-pyrrolo[2,3-d]pyrimidin-4-amine obtained in Reference Example 7, the title compound (45%) was obtained.

Physical Properties: m/z[M+H]$^+$ 249.1

Step 2: Synthesis of 4-amino-7-(tert-butyl)-N-(4-(methoxymethyl)phenyl)-6-methyl-7H-pyrrolo[2,3-d]pyrimidine-5-carboxamide According to the procedure of step 2 in Example 55, using 4-amino-7-(tert-butyl)-6-methyl-7H-pyrrolo[2,3-d]pyrimidine-5-carboxylic acid obtained in step 1, the title compound (30%) was obtained.

Example 61: 4-amino-N-(4-(methoxymethyl)phenyl)-7-(1-methylcyclopropyl)-6-(pyridin-3-yl)-7H-pyrrolo[2,3-d]pyrimidine-5-carboxamide

Step 1: Synthesis of methyl 4-amino-7-(1-methylcyclopropyl)-6-(pyridin-3-yl)-7H-pyrrolo[2,3-d]pyrimidine-5-carboxylate 50 mg of methyl 4-amino-6-bromo-7-(1-methylcyclopropyl)-7H-pyrrolo[2,3-d]pyrimidine-5-carboxylate obtained in Reference Example 9, 56 mg of 3-pyridine boronic acid, 14 mg of tris(dibenzylideneacetone)dipalladium, 14 mg of 2-(dicyclohexylphosphino)-2',4',6'-tri-isopropyl-1,1'-biphenyl, and 49 mg of sodium carbonate were reacted in a mixture of 1.5 mL of 1,4-dioxane and 500 µL of water at 120° C. for 1 hour in a microwave reactor. Chloroform was added to the reaction solution, and the insoluble matter was filtered, followed by concentration. The residue was purified by silica gel chromatography (ethyl acetate/methanol=1/0→8/1), thereby obtaining 27 mg of the title compound.

Physical Properties: m/z[M+H]$^+$ 324.1

Step 2: Synthesis of 4-amino-7-(1-methylcyclopropyl)-6-(pyridin-3-yl)-7H-pyrrolo[2,3-d]pyrimidine-5-carboxylic acid 26 mg of methyl 4-amino-7-(1-methylcyclopropyl)-6-(pyridin-3-yl)-7H-pyrrolo[2,3-d]pyrimidine-5-carboxylate obtained in step 1 was suspended in 2 mL of THF and 2 mL of methanol. 0.20 mL of a lithium hydroxide aqueous solution (4 mol/L) was added thereto, and stirred at room temperature overnight. 10 mL of water was added thereto, and the mixture was neutralized with a 2N HCl aqueous solution, followed by extraction of the aqueous layer with chloroform. The organic layer was washed with a saturated aqueous sodium chloride solution, and dried over anhydrous sodium sulfate, followed by removal of the solvent, thereby obtaining 13 mg of the title compound.

Physical Properties: m/z[M+H]$^+$ 310.1

Step 3: Synthesis of 4-amino-N-(4-(methoxymethyl)phenyl)-7-(1-methylcyclopropyl)-6-(pyridin-3-yl)-7H-pyrrolo[2,3-d]pyrimidine-5-carboxamide According to the procedure of step 2 in Example 55, using 4-amino-7-(1-methylcyclopropyl)-6-(pyridin-3-yl)-7H-pyrrolo[2,3-d]pyrimidine-5-carboxylic acid obtained in step 2, the title compound (9%) was obtained.

Example 62: 4-amino-N-(4-(methoxymethyl)phenyl)-6-methyl-7-(1-methylcyclopropyl)-7H-pyrrolo[2,3-d]pyrimidine-5-carboxamide

Step 1: Synthesis of methyl 4-amino-6-methyl-7-(1-methylcyclopropyl)-7H-pyrrolo[2,3-d]pyrimidine-5-carboxylate 30 mg of methyl 4-amino-6-bromo-7-(1-methylcyclopropyl)-7H-pyrrolo[2,3-d]pyrimidine-5-carboxylate obtained in Reference Example 9, 55 mg of methylboronic acid, 8 mg of tris(dibenzylideneacetone)dipalladium, 5 mg of tricyclohexylphosphine, and 58 mg of tripotassium phosphate were reacted in a mixture of 1.5 mL of 1,4-dioxane and 150 µL of water at 120° C. for 1 hour in a microwave reactor. Chloroform was added to the reaction solution, and the insoluble matter was filtered, followed by concentration. The residue was purified by silica gel chromatography (ethyl acetate/methanol=1/0→8/1), thereby obtaining 20 mg of the title compound.

Physical Properties: m/z[M+H]$^+$ 261.2

Step 2: Synthesis of 4-amino-N-(4-(methoxymethyl)phenyl)-6-methyl-7-(1-methylcyclopropyl)-7H-pyrrolo[2,3-d]pyrimidine-5-carboxamide According to the procedures of steps 1 and 2 in Example 55, using methyl 4-amino-6-methyl-7-(1-methylcyclopropyl)-7H-pyrrolo[2,3-d]pyrimidine-5-carboxylate obtained in step 1, the title compound (6%) was obtained.

Example 63: 4-amino-6-cyclopropyl-N-(4-(methoxymethyl)phenyl)-7-(1-methylcyclopropyl)-7H-pyrrolo[2,3-d]pyrimidine-5-carboxamide According to the procedures of steps 1 and 2 in Example 62, using methyl 4-amino-6-bromo-7-(1-methylcyclopropyl)-7H-pyrrolo[2,3-d]pyrimidine-5-carboxylate obtained in Reference Example 9 and cyclopropylboronic acid instead of methylboronic acid, the title compound (38%) was obtained.

Example 64: 6-acetyl-4-amino-N-(4-(methoxymethyl)phenyl)-7-(1-methylcyclopropyl)-7H-pyrrolo[2,3-d]pyrimidine-5-carboxamide

Step 1: Synthesis of methyl 6-acetyl-4-amino-7-(1-methylcyclopropyl)-7H-pyrrolo[2,3-d]pyrimidine-5-carboxylate 1 mL of toluene was added to 60 mg of methyl 4-amino-6-bromo-7-(1-methylcyclopropyl)-7H-pyrrolo[2,3-d]pyrimidine-5-carboxylate obtained in Reference Example 9, 75 µL of tributyl(1-ethoxy)tin, and 21 mg of tetrakis triphenylphosphine palladium, and the mixture was reacted at 130° C. for 4 hours in a microwave reactor. After the reaction solution was concentrated, the residue was purified by amino gel chromatography (hexane/ethyl acetate=10/4→0/1). After the target fraction was concentrated, 1 mL of THF and 300 µL of a hydrochloric acid solution (2 mol/L) were added thereto, followed by stirring at room temperature overnight. Thereafter, the mixture was further reacted at 50° C. for 4 hours. The reaction solution was partitioned between ethyl acetate and a saturated aqueous sodium bicarbonate solution, and the organic layer was washed with water and a saturated aqueous sodium chloride solution, followed by drying over anhydrous sodium sulfate. After filtration, the filtrate was concentrated, thereby obtaining 45 mg of the title compound.

Physical Properties: m/z[M+H]$^+$ 289.2

Step 2: Synthesis of 6-acetyl-4-amino-N-(4-(methoxymethyl)phenyl)-7-(1-methylcyclopropyl)-7H-pyrrolo[2,3-d]pyrimidine-5-carboxamide According to the procedures of steps 1 and 2 in Example 55, using methyl 6-acetyl-4-amino-7-(1-methylcyclopropyl)-7H-pyrrolo[2,3-d]pyrimidine-5-carboxylate obtained in step 1, the title compound (48%) was obtained.

Example 65: 4-amino-N-(4-(methoxymethyl)phenyl)-7-(1-methylcyclopropyl)-6-vinyl-7H-pyrrolo[2,3-d]pyrimidine-5-carboxamide Step 1: Synthesis of methyl 4-amino-7-(1-methylcyclopropyl)-6-vinyl-7H-pyrrolo[2,3-d]pyrimidine-5-carboxylate 1.5 mL of toluene was added to 90 mg of methyl 4-amino-6-bromo-7-(1-methylcyclopropyl)-7H-pyrrolo[2,3-d]pyrimidine-5-carboxylate obtained in Reference Example 9, 97 μL of tributylvinyltin, and 32 mg of tetrakis triphenylphosphine palladium, and the mixture was reacted at 130° C. for 3 hours in a microwave reactor. After the reaction solution was concentrated, the residue was purified by amino gel chromatography (hexane/ethyl acetate=4/1→3/5), thereby obtaining 67 mg of the title compound.
Physical Properties: m/z[M+H]$^+$ 273.2

Step 2: Synthesis of 4-amino-N-(4-(methoxymethyl)phenyl)-7-(1-methylcyclopropyl)-6-vinyl-7H-pyrrolo[2,3-d]pyrimidine-5-carboxamide According to the procedures of steps 1 and 2 in Example 55, using methyl 4-amino-7-(1-methylcyclopropyl)-6-vinyl-7H-pyrrolo[2,3-d]pyrimidine-5-carboxylate obtained in step 1, the title compound (27%) was obtained.

Example 66: Synthesis of 4-amino-7-cyclobutyl-N-(4-(methoxymethyl)phenyl)-7H-pyrrolo[2,3-d]pyrimidine-5-carboxamide According to the synthesis procedures of steps 1 to 5 in Reference Example 5, using cyclobutanamine instead of tert-butylamine, 4-amino-7-cyclobutyl-7H-pyrrolo[2,3-d]pyrimidine-5-carboxylic acid was obtained.
According to the procedure of Example 2, using 4-amino-7-cyclobutyl-7H-pyrrolo[2,3-d]pyrimidine-5-carboxylic acid instead of 4-amino-7-(tert-butyl)-7H-pyrrolo[2,3-d]pyrimidine-5-carboxylic acid, the title compound (86%) was obtained.

Example 67: Synthesis of 4-amino-N-(4-(methoxymethyl)phenyl)-1-(cis-2-methylcyclopentyl)-1H-pyrazolo[3,4-d]pyrimidine-3-carboxamide According to the synthesis procedures of steps 1 and 2 in Reference Example 2, using trans-2-methylcyclopentanol instead of 2-adamantanol, 4-amino-1-(cis-2-methylcyclopentyl)-1H-pyrazolo[3,4-d]pyrimidine-3-carboxylic acid was obtained.
According to the procedure of Example 19, using 4-amino-1-(cis-2-methylcyclopentyl)-1H-pyrazolo[3,4-d]pyrimidine-3-carboxylic acid instead of 1-(adamantan-2-yl)-4-amino-1H-pyrazolo[3,4-d]pyrimidine-3-carboxylic acid, the title compound (52%) was obtained.

Example 68: Synthesis of 4-amino-1-cyclopentyl-N-(4-ethynylphenyl)-1H-pyrazolo[3,4-d]pyrimidine-3-carboxamide According to the synthesis procedure of Example 1, using 4-ethynylaniline instead of 4-(methoxymethyl)aniline, the title compound (88%) was obtained.

Example 69: Synthesis of 4-amino-6-fluoro-N-(4-(methoxymethyl)phenyl)-7-(1-methylcyclopropyl)-7H-pyrrolo[2,3-d]pyrimidine-5-carboxamide 50 mg of 4-amino-N-(4-(methoxymethyl)phenyl)-7-(1-methylcyclopropyl)-7H-pyrrolo[2,3-d]pyrimidine-5-carboxamide obtained in Example 36 was dissolved in 1.5 mL of DMF, and 151 mg 1-chloromethyl-4-fluoro-1,4-diazoniabicyclo[2.2.2]octane bis(tetrafluoroborate) was added thereto with ice-cooling. The mixture was then stirred with ice-cooling, and 1 hour later, 151 mg of 1-chloromethyl-4-fluoro-1,4-diazoniabicyclo[2.2.2]octane bis(tetrafluoroborate) was added thereto. The mixture was further stirred for 1 hour, and then the reaction solution was partitioned between chloroform and water. The organic layer was washed with water and a saturated aqueous sodium chloride solution, dried over anhydrous sodium sulfate, filtered, and concentrated. The residue was purified by silica gel column (ethyl acetate/methanol=1/0→8/1), thereby obtaining 2.7 mg of the title compound.

Example 70: Synthesis of 4-amino-1-cyclopentyl-N-(4-(trifluoromethoxy)phenyl)-1H-pyrazolo[3,4-d]pyrimidine-3-carboxamide According to the synthesis procedures of Example 1, using 4-(trifluoromethoxy)aniline instead of 4-(methoxymethyl)aniline, the title compound (45%) was obtained.

Example 71: Synthesis of 4-amino-N-(3-benzylphenyl)-1-cyclopentyl-1H-pyrazolo[3,4-d]pyrimidine-3-carboxamide According to the synthesis procedures of Example 1, using 3-benzylaniline instead of 4-(methoxymethyl)aniline, the title compound (58%) was obtained.

Example 72: Synthesis of 4-amino-1-cyclopentyl-N-(4-(oxazol-2-yl)phenyl)-1H-pyrazolo[3,4-d]pyrimidine-3-carboxamide According to the synthesis procedures of Example 1, using 4-(oxazol-2-yl)aniline instead of 4-(methoxymethyl)aniline, the title compound (32%) was obtained.

Example 73: Synthesis of 4-amino-N-(4-cyanophenyl)-1-cyclopentyl-1H-pyrazolo[3,4-d]pyrimidine-3-carboxamide According to the synthesis procedure of Example 1, using 4-aminobenzonitrile instead of 4-(methoxymethyl)aniline, the title compound (69%) was obtained.

Example 74: Synthesis of 4-amino-1-cyclopentyl-N-(4-nitrophenyl)-1H-pyrazolo[3,4-d]pyrimidine-3-carboxamide According to the synthesis procedure of Example 1, using 4-nitroaniline instead of 4-(methoxymethyl)aniline, the title compound (65%) was obtained.

Example 75: Synthesis of 4-amino-N-(benzo[b]thiophen-5-yl)-1-cyclopentyl-1H-pyrazolo[3,4-d]pyrimidine-3-carboxamide According to the synthesis procedure of Example 1, using benzo[b]thiophen-5-amine instead of 4-(methoxymethyl)aniline, the title compound (33%) was obtained.

Example 76: Synthesis of 4-amino-1-cyclopentyl-N-(4-ethynyl-3-fluorophenyl)-1H-pyrazolo[3,4-d]pyrimidine-3-carboxamide According to the synthesis procedure of Example 1, using 4-ethynyl-3-fluoroaniline instead of 4-(methoxymethyl)aniline, the title compound (34%) was obtained.

Example 77: Synthesis of 4-amino-N-(4-bromo-2-methylphenyl)-1-cyclopentyl-1H-pyrazolo[3,4-d]pyrimidine-3-carboxamide According to the synthesis procedure of Example 1, using 4-bromo-2-methylaniline instead of 4-(methoxymethyl)aniline, the title compound (51%) was obtained.

Example 78: Synthesis of 4-amino-1-(3-fluoroprop-1-en-2-yl)-N-(4-(methoxymethyl)phenyl)-1H-pyrazolo[3,4-d]pyrimidine-3-carboxamide According to the synthesis procedures of steps 1 and 2 in Reference Example 2, using 1,3-difluoropropan-2-ol instead of 2-adamantanol, 4-amino-1-(3-fluoroprop-1-en-2-yl)-1H-pyrazolo[3,4-d]pyrimidine-3-carboxylic acid was obtained.
According to the procedure of Example 19, using 4-amino-1-(3-fluoroprop-1-en-2-yl)-1H-pyrazolo[3,4-d]pyrimidine-3-carboxylic acid instead of 1-(adamantan-2-yl)-4-amino-1H-pyrazolo[3,4-d]pyrimidine-3-carboxylic acid, the title compound (90%) was obtained.

Example 79: Synthesis of 4-amino-7-(1-methoxy-2-methylpropan-2-yl)-N-(4-(methoxymethyl)phenyl)-7H-pyrrolo[2,3-d]pyrimidine-5-carboxamide According to the synthesis procedures of steps 1 to 3 in Reference Example 6, using 1-methoxy-2-methylpropan-2-amine instead of 1-(fluoromethyl)cyclopropanamine hydrochloride, 5-iodo-7-(1-methoxy-2-methylpropan-2-yl)-7H-pyrrolo[2,3-d]pyrimidin-4-amine was obtained.
According to the procedure of Example 45, using 5-iodo-7-(1-methoxy-2-methylpropan-2-yl)-7H-pyrrolo[2,3-d]pyrimidin-4-amine instead of 7-(1-(fluoromethyl) cyclopropyl)-5-iodo-7H-pyrrolo[2,3-d]pyrimidin-4-amine, the title compound (70%) was obtained.

Example 80: Synthesis of N-(4-(1H-pyrazol-3-yl)phenyl)-4-amino-7-(tert-butyl)-7H-pyrrolo[2,3-d]pyrimidine-5-carboxamide According to the synthesis procedure of Example 2, using 4-(1H-pyrazol-3-yl)aniline instead of 4-(methoxymethyl)aniline, the title compound (94%) was obtained.

Example 81: Synthesis of 4-amino-7-(tert-butyl)-N-(5-(methoxymethyl)pyridine-2-yl)-7H-pyrrolo[2,3-d]pyrimidine-5-carboxamide According to the procedure of Example 45, using 7-(tert-butyl)-5-iodo-7H-pyrrolo[2,3-d]pyrimidine-4-amine obtained in step 3 of Reference Example 5 and 5-(methoxymethyl)pyridin-2-amine synthesized according to the procedure described in the international publication No. WO2010/058846 pamphlet, the title compound (64%) was obtained.

Example 82: Synthesis of 4-amino-1-(4,4-difluorocyclohexyl)-N-(4-(methoxymethyl)phenyl)-1H-pyrazolo[3,4-d]pyrimidine-3-carboxamide 33 mg of methyl-4-amino-1-(4,4-difluorocyclohexyl)-1H-pyrazolo[3,4-d]pyrimidine-3-carboxylate obtained in step 2 of Reference Example 10 was dissolved in 2 mL of methanol. 0.05 mL of a 5M aqueous sodium hydroxide solution was added thereto at room temperature, and the mixture was stirred at 60° C. for 1 hour. After cooling, 0.2 mL of a 5M aqueous hydrochloric acid solution was added, and the mixture was concentrated under reduced pressure. The obtained solid was suspended in 2 mL of DMF, and 17 mg of 4-(methoxymethyl)aniline, 60 mg of HATU, and 0.055 mL of N,N-diisopropylethylamine were added thereto at room temperature, followed by stirring at the same temperature for 1 hour. The reaction solution was diluted with ethyl acetate, and washed with water and a saturated aqueous sodium chloride solution. The obtained organic layer was dried over anhydrous sodium sulfate, filtered, and concentrated. The obtained residue was suspended in methanol, and filtered, followed by drying at 60° C. under reduced pressure, thereby obtaining 29 mg of the title compound.

Example 83: Synthesis of 4-amino-1-cyclopentyl-N-(4-(hydroxymethyl)phenyl)-1H-pyrazolo[3,4-d]pyrimidine-3-carboxamide 1 mL of trifluoroacetic acid and 50 μL of water were added to 90 mg of 4-amino-1-cyclopentyl-N-(4-(methoxymethyl)phenyl)-1H-pyrazolo[3,4-d]pyrimidine-3-carboxamide obtained in Example 1, and the mixture was stirred at 100° C. for 1 hour. After cooling, the mixture was concentrated, and an ammonia-methanol solution was added to the obtained residue, followed by stirring for 30 minutes. After concentration, the obtained residue was purified by silica gel chromatography (developing solvent: chloroform/methanol), and concentrated. The obtained precipitate was suspended and washed with methanol, and filtered, followed by drying under reduced pressure, thereby obtaining the title compound (58%).

Example 84: Synthesis of 4-amino-1-cyclopentyl-N-(isochroman-6-yl)-1H-pyrazolo[3,4-d]pyrimidine-3-carboxamide According to the synthesis procedure of Example 1, using isochroman-6-amine instead of 4-(methoxymethyl)aniline, the title compound (60%) was obtained.

Example 85: Synthesis of 4-amino-N-[4-(methoxymethyl)phenyl]-7-(1-methylcyclopropyl)-6-(3-morpholinoprop-1-yn-1-yl)-7H-pyrrolo[2,3-d]pyrimidine-5-carboxamide 5.15 g of 4-amino-6-bromo-N-[4-(methoxymethyl)phenyl]-7-(1-methylcyclopropyl)-7H-pyrrolo[2,3-d]pyrimidine-5-carboxamide shown in Example 55 was dissolved in 50 mL of DMF. 228 mg of copper iodide, 5.24 g of 4-(prop-2-yn-1-yl)morpholine, 5.0 mL of triethylamine, and 1.38 g of tetrakis triphenylphosphine palladium were added thereto, followed by degassing. Thereafter, the mixture was stirred at 100° C. for 2 hours. The solvent was removed from the reaction solution, and the residue was purified by silica gel column (chloroform/methanol=1/0→8/1). Then, the fractions containing by-products were concentrated and repurified by silica gel column (ethyl acetate/methanol=1/0→4/1), thereby obtaining 2.78 g of the title compound.

Example 86: Synthesis of 4-amino-6-(4-hydroxy-4-methylpent-1-yn-1-yl)-N-[4-(methoxymethyl)phenyl]-7-(1-methylcyclopropyl)-7H-pyrrolo[2,3-d]pyrimidine-5-carboxamide According to the procedure of Example 85, using 2-methylpen-4-tyn-2-ol instead of 4-(prop-2-yn-1-yl)morpholine, the title compound (36%) was obtained.

Example 87: Synthesis of 4-amino-N-[4-(methoxymethyl)phenyl]-7-(1-methylcyclopropyl)-6-((tetrahydro-2H-pyran-4-yl)ethynyl)-7H-pyrrolo[2,3-d]pyrimidine-5-carboxamide According to the procedure of Example 85, using 4-ethynyltetrahydro-2H-pyrane instead of 4-(prop-2-yn-1-yl)morpholine, the title compound (66%) was obtained.

Example 88: Synthesis of 4-amino-N-[4-(methoxymethyl)phenyl]-7-(1-methylcyclopropyl)-6-(3-(pyrrolidin-1-yl)prop-1-yn-1-yl)-7H-pyrrolo[2,3-d]pyrimidine-5-carboxamide According to the procedure of Example 85, using 1-(pro-2-pyn-1-yl)pyrrolidine instead of 4-(prop-2-yn-1-yl)morpholine, the title compound (46%) was obtained.

Example 89: Synthesis of (R)-4-amino-N-[4-(methoxymethyl)phenyl]-7-(1-methylcyclopropyl)-6-((tetrahydrofuran-2-yl)methoxy)-7H-pyrrolo[2,3-d]pyrimidine-5-carboxamide 721 μL of (R)-(−)-tetrahydrofurfuryl alcohol was added to a suspension of 371 mg of sodium hydride (60%) in 15 mL of DMF with stirring at ice cooling temperature. The mixture was then stirred at room temperature for 30 minutes. A solution of 800 mg of 4-amino-6-bromo-N-[4-(methoxymethyl)phenyl]-7-(1-methylcyclopropyl)-7H-pyrrolo[2,3-d]pyrimidine-5-carboxamide shown in Example 55 in 5 mL of DMF was added to the mixture, and stirred at 80° C. overnight. After cooling, the reaction mixture was partitioned between ethyl acetate and water, and the organic layer was washed with water and a saturated aqueous sodium chloride solution, followed by drying over sodium sulfate and solvent removal. The residue was purified by silica gel column (ethyl acetate/methanol=1/0→8/1), thereby obtaining 644 mg of the title compound.

Example 90: Synthesis of 4-amino-N-[4-(methoxymethyl)phenyl]-6-((1-methyl-1H-pyrazol-4-yl)ethynyl)-7-(1-methylcyclopropyl)-7H-pyrrolo[2,3-d]pyrimidine-5-carboxamide 1.2 g of 4-amino-6-bromo-N-[4-(methoxymethyl)phenyl]-7-(1-methylcyclopropyl)-7H-pyrrolo[2,3-d]pyrimidine-5-carboxamide shown in Example 55 was dissolved in 40 mL of DMF, and 53 mg of copper iodide, 890 mg of 4-ethynyl-1-methyl-pyrazole, 2.3 mL of triethylamine, and 320 mg of tetrakis triphenylphosphine palladium were added thereto, followed by degassing and stirring at 110° C. for 1.5 hours. A saturated sodium bicarbonate solution was added to the reaction solution, followed by extraction with chloroform. The organic layer was washed with water and dried over anhydrous magnesium sulfate, followed by concentration of the organic solvent under reduced pressure. The residue was purified by preparative reversed-phase HPLC, thereby obtaining 700 mg of the title compound.

Example 91: Synthesis of 4-amino-6-(imidazo[1,2-b]pyridazin-3-ylethynyl)-N-[4-(methoxymethyl)phenyl]-7-(1-methylcyclopropyl)-7H-pyrrolo[2,3-d]pyrimidine-5-carboxamide According to the procedure of Example 90, using 3-ethynylimidazo[1,2-b]pyridazine instead of 4-ethynyl-1-methyl-pyrazole, the title compound (58%) was obtained.

Example 92: Synthesis of 4-amino-N-(4-(methoxymethyl)phenyl)-6-((1-methyl-1H-pyrazol-3-yl)ethynyl)-7-(1-methylcyclopropyl)-7H-pyrrolo[2,3-d]pyrimidine-5-carboxamide According to the procedure of Example 90, using 3-ethynyl-1-methyl-pyrazole instead of 4-ethynyl-1-methyl-pyrazole, the title compound (28%) was obtained.

Example 93: Synthesis of 4-amino-N-(4-(methoxymethyl)phenyl)-6-((1-methyl-1H-imidazol-5-yl)ethynyl)-7-(1-methylcyclopropyl)-7H-pyrrolo[2,3-d]pyrimidine-5-carboxamide According to the procedure of Example 90, using 5-ethynyl-1-methyl-imidazole instead of 4-ethynyl-1-methyl-pyrazole, the title compound (37%) was obtained.

Example 94: Synthesis of 4-amino-N-[4-(methoxymethyl)phenyl]-7-(1-methylcyclopropyl)-6-(pyridin-3-ylethynyl)-7H-pyrrolo[2,3-d]pyrimidine-5-carboxamide According to the procedure of Example 90, using 3-ethynylpyridine instead of 4-ethynyl-1-methyl-pyrazole, the title compound (34%) was obtained.

Example 95: Synthesis of 4-amino-N-(4-(methoxymethyl)phenyl)-7-(1-methylcyclopropyl)-6-(prop-1-yn-1-yl)-7H-pyrrolo[2,3-d]pyrimidine-5-carboxamide 6.6 mg of copper iodide, 2.4 mL of propyne (1.0 mol/L DMF solution), 146 μL of triethylamine, and 24 mg of dichlorobistriphenylphosphine palladium were added to 150 mg of 4-amino-6-bromo-N-[4-(methoxymethyl)phenyl]-7-(1-methylcyclopropyl)-7H-pyrrolo[2,3-d]pyrimidine-5-carboxamide shown in Example 55. The mixture was stirred at 80° C. for 5 hours. The reaction solution was partitioned between chloroform and water, and filtered through a phase separator. The filtrate was concentrated, and the residue was purified by silica gel column (ethyl acetate/methanol=1/0→8/1). Then, the fractions containing by-products were concentrated and repurified by silica gel column (chloroform/methanol=1/0→8/1), thereby obtaining 107 mg of the title compound.

According to the procedure of Example 89, using the compounds shown in Table 1 instead of (R)-(−)-tetrahydrofurfuryl alcohol, compounds 96 to 102 of the Examples were obtained.

TABLE 1

| Compounds of Examples | Name of Compounds of Examples | Compounds Used | Yield |
|---|---|---|---|
| 96 | (R)-4-amino-N-(4-(methoxymethyl)phenyl)-6-(2-methoxypropoxy)-7-(1-methylcyclopropyl)-7H-pyrrolo[2,3-d]pyrimidine-5-carboxamide | (2R)-2-methoxypropan-1-ol | 66% |
| 97 | (S)-4-amino-N-(4-(methoxymethyl)phenyl)-7-(1-methylcyclopropyl)-6-((tetrahydrofuran-2-yl)methoxy)-7H-pyrrolo[2,3-d]pyrimidine-5-carboxamide | (S)-(tetrahydrofuran-2-yl)methanol | 72% |
| 98 | 4-amino-6-(2-fluoroethoxy)-N-(4-(methoxymethyl)phenyl)-7-(1-methylcyclopropyl)-7H-pyrrolo[2,3-d]pyrimidine-5-carboxamide | 2-fluoroethanol | 17% |
| 99 | 4-amino-6-isobutoxy-N-(4-(methoxymethyl)phenyl)-7-(1-methylcyclopropyl)-7H-pyrrolo[2,3-d]pyrimidine-5-carboxamide | 2-methylpropan-1-ol | 7.50% |
| 100 | 4-amino-N-(4-(methoxymethyl)phenyl)-6-(2-methoxypropoxy)-7-(1-methylcyclopropyl)-7H-pyrrolo[2,3-d]pyrimidine-5-carboxamide | 2-methoxypropan-1-ol | 52% |
| 101 | 4-amino-N-(4-(methoxymethyl)phenyl)-7-(1-methylcyclopropyl)-6-((tetrahydrofuran-3-yl)methoxy)-7H-pyrrolo[2,3-d]pyrimidine-5-carboxamide | Tetrahydro-3-furanmethanol | 64% |
| 102 | 4-amino-N-(4-(methoxymethyl)phenyl)-7-(1-methylcyclopropyl)-6-((tetrahydro-2H-pyran-2-yl)methoxy)-7H-pyrrolo[2,3-d]pyrimidine-5-carboxamide | Tetrahydropyran-2-methanol | 68% |

According to the synthesis procedure of Example 85, using the compounds shown in Table 2 instead of 4-(prop-2-yn-1-yl)morpholine, compounds 103 to 105 of the Examples were obtained.

TABLE 2

| Compounds of Examples | Name of Compounds of Examples | Compounds Used | Yield |
|---|---|---|---|
| 103 | 4-amino-6-(3-(1-hydroxycyclobutyl)prop-1-yn-1-yl)-N-(4-(methoxymethyl)phenyl)-7-(1-methylcyclopropyl)-7H-pyrrolo[2,3-d]pyrimidine-5-carboxamide | 1-(prop-2-yn-1-yl)cyclobutane-1-ol | 46% |
| 104 | 4-amino-6-(3-cyclopropyl-3-hydroxyprop-1-yn-1-yl)-N-(4-(methoxymethyl)phenyl)-7-(1-methylcyclopropyl)-7H-pyrrolo[2,3-d]pyrimidine-5-carboxamide | 1-cyclopropylprop-2-yn-1-ol | 63% |

TABLE 2-continued

| Compounds of Examples | Name of Compounds of Examples | Compounds Used | Yield |
|---|---|---|---|
| 105 | 4-amino-N-[4-(methoxymethyl)phenyl]-7-(1-methylcyclopropyl)-6-(3-(piperidin-1-yl)prop-1-yn-1-yl)-7H-pyrrolo[2,3-d]pyrimidine-5-carboxamide | 1-(prop-2-yn-1-yl)piperidine | 15% |

According to the synthesis procedure of Example 36, using the compounds shown in Table 3 instead of 4-(methoxymethyl)aniline, compounds 106 to 108 of the Examples were obtained.

TABLE 3

| Compounds of Examples | Name of Compounds of Examples | Compounds Used | Yield |
|---|---|---|---|
| 106 | 4-amino-N-(4-(furan-2-yl)phenyl)-7-(1-methylcyclopropyl)-7H-pyrrolo[2,3-d]pyrimidine-5-carboxamide | 4-(2-furyl)aniline | 68% |
| 107 | (E)-4-amino-7-(1-methylcyclopropyl)-N-(4-(prop-1-en-1-yl)phenyl)-7H-pyrrolo[2,3-d]pyrimidine-5-carboxamide | 4-[(E)-1-propenyl]aniline | 56% |
| 108 | 4-amino-N-(4-ethynylphenyl)-7-(1-methylcyclopropyl)-7H-pyrrolo[2,3-d]pyrimidine-5-carboxamide | 4-ethynylaniline | 65% |

Example 109: Synthesis of (E)-4-amino-6-(3-hydroxyprop-1-en-1-yl)-N-(4-(methoxymethyl)phenyl)-7-(1-methylcyclopropyl)-7H-pyrrolo[2,3-d]pyrimidine-5-carboxamide According to the procedures of steps 1 and 2 in Example 62, a reaction was performed using (E)-tert-buthyldimethyl ((3-(4,4,5,5-tetramethyl-1,3,2-dioxaborolan-2-yl)allyl)oxy)silane instead of methyl 4-amino-6-bromo-7-(1-methylcyclopropyl)-7H-pyrrolo[2,3-d]pyrimidine-5-carboxylate shown in Reference Example 9 and methylboronic acid, the title compound (4%) was obtained.

Example 110: Synthesis of 4-amino-6-(3-hydroxyprop-1-yn-1-yl)-N-(4-(methoxymethyl)phenyl)-7-(1-methylcyclopropyl)-7H-pyrrolo[2,3-d]pyrimidine-5-carboxamide 10 mg of 4-amino-6-(3-((tert-butyldimethylsilyl)oxy)prop-1-yn-1-yl)-N-(4-(methoxymethyl)phenyl)-7-(1-methylcyclopropyl)-7H-pyrrolo[2,3-d]pyrimidine-5-carboxamide shown in Example 180 was dissolved in 1.5 mL of THF, and 3.3 μL of acetic acid and 29 μL of tetrabutylammonium fluoride (1.0 mol/L THF solution) were added thereto, followed by stirring for 30 minutes. The reaction solution was concentrated, and the residue was purified by silica gel column (ethyl acetate/methanol=1/0→8/1), thereby obtaining 6 mg of the title compound.

According to the synthesis procedure of Example 90, using the compounds shown in Tables 4 to 7 instead of 4-ethynyl-1-methyl-pyrazole, compounds 111 to 114, 118 to 126, 128 to 132, 134, 142 to 144, 151, 152, 155 to 163, 165, 166, 168 to 170, 172 to 178, 181 to 189, 191 to 193, and 195 to 200 of the Examples were obtained.

TABLE 4

| Compounds of Examples | Name of Compounds of Examples | Compounds Used | Yield |
|---|---|---|---|
| 111 | 4-amino-6-(3-hydroxy-3-(pyridin-3-yl)but-1-yn-1-yl)-N-(4-(methoxymethyl)phenyl)-7-(1-methylcyclopropyl)-7H-pyrrolo[2,3-d]pyrimidine-5-carboxamide | 2-(pyridin-3-yl)-3-butyn-2-ol | 22% |
| 112 | 4-amino-N-(4-(methoxymethyl)phenyl)-7-(1-methylcyclopropyl)-6-((4-oxocyclohexyl)ethynyl)-7H-pyrrolo[2,3-d]pyrimidine-5-carboxamide | 4-ethynylcyclohexanone | 43% |
| 113 | 4-amino-N-(4-(methoxymethyl)phenyl)-6-((2-methoxyphenyl)ethynyl)-7-(1-methylcyclopropyl)-7H-pyrrolo[2,3-d]pyrimidine-5-carboxamide | 1-ethynyl-2-methoxy-benzene | 23% |
| 114 | 4-amino-6-((1-ethyl-1H-pyrazol-5-yl)ethynyl)-N-(4-(methoxymethyl)phenyl)-7-(1-methylcyclopropyl)-7H-pyrrolo[2,3-d]pyrimidine-5-carboxamide | 1-ethyl-5-ethynyl-pyrazole | 71% |
| 118 | 4-amino-6-((1-ethyl-1H-pyrazol-4-yl)ethynyl)-N-(4-(methoxymethyl)phenyl)-7-(1-methylcyclopropyl)-7H-pyrrolo[2,3-d]pyrimidine-5-carboxamide | 1-ethyl-4-ethynyl-pyrazole | 72% |
| 119 | 4-amino-N-(4-(methoxymethyl)phenyl)-7-(1-methylcyclopropyl)-6-(thiophen-2-ylethynyl)-7H-pyrrolo[2,3-d]pyrimidine-5-carboxamide | 2-ethynylthiophene | 28% |
| 120 | 4-amino-6-((6-chloropyridin-3-yl)ethynyl)-N-(4-(methoxymethyl)phenyl)-7-(1-methylcyclopropyl)-7H-pyrrolo[2,3-d]pyrimidine-5-carboxamide | 2-chloro-5-ethynyl-pyridine | 2.3% |
| 121 | 6-((1H-indol-3-yl)ethynyl)-4-amino-N-(4-(methoxymethyl)phenyl)-7-(1-methylcyclopropyl)-7H-pyrrolo[2,3-d]pyrimidine-5-carboxamide | 3-ethynyl-1H-indole | 36% |
| 122 | 4-amino-N-(4-(methoxymethyl)phenyl)-7-(1-methylcyclopropyl)-6-((3-((pyridin-4-ylmethyl)amino)phenyl)ethynyl)-7H-pyrrolo[2,3-d]pyrimidine-5-carboxamide | 3-ethynyl-N-(4-pyridylmethyl)aniline | 39% |
| 123 | 4-amino-6-(imidazo[1,2-a]pyridin-3-ylethynyl)-N-(4-(methoxymethyl)phenyl)-7-(1-methylcyclopropyl)-7H-pyrrolo[2,3-d]pyrimidine-5-carboxamide | 3-ethynylimidazo[1,2-a]pyridine | 55% |
| 124 | 4-amino-6-(3-hydroxybut-1-yn-1-yl)-N-(4-(methoxymethyl)phenyl)-7-(1-methylcyclopropyl)-7H-pyrrolo[2,3-d]pyrimidine-5-carboxamide | 3-butyn-2-ol | 29% |
| 125 | 4-amino-6-(3-(3-hydroxyoxetan-3-yl)prop-1-yn-1-yl)-N-(4-(methoxymethyl)phenyl)-7-(1-methylcyclopropyl)-7H-pyrrolo[2,3-d]pyrimidine-5-carboxamide | 3-prop-2-ynyloxetan-3-ol | 57% |
| 126 | 4-amino-N-(4-(methoxymethyl)phenyl)-7-(1-methylcyclopropyl)-6-((2-methylthiazol-4-yl)ethynyl)-7H-pyrrolo[2,3-d]pyrimidine-5-carboxamide | 4-ethynyl-2-methyl-thiazole | 33% |
| 128 | 6-((1H-pyrrolo[2,3-b]pyridin-5-yl)ethynyl)-4-amino-N-(4-(methoxymethyl)phenyl)-7-(1-methylcyclopropyl)-7H-pyrrolo[2,3-d]pyrimidine-5-carboxamide | 5-ethynyl-1H-pyrrolo[2,3-b]pyridine | 53% |
| 129 | 6-((1H-pyrazol-5-yl)ethynyl)-4-amino-N-(4-(methoxymethyl)phenyl)-7-(1-methylcyclopropyl)-7H-pyrrolo[2,3-d]pyrimidine-5-carboxamide | 5-ethynyl-1H-pyrazole | 43% |
| 130 | 4-amino-6-((3-fluorophenyl)ethynyl)-N-(4-(methoxymethyl)phenyl)-7-(1-methylcyclopropyl)-7H-pyrrolo[2,3-d]pyrimidine-5-carboxamide | 1-ethynyl-3-fluoro-benzene | 37% |

TABLE 5

| Compounds of Examples | Name of Compounds of Examples | Compounds Used | Yield |
|---|---|---|---|
| 131 | 4-amino-6-((1-hydroxycyclopentyl)ethynyl)-N-(4-(methoxymethyl)phenyl)-7-(1-methylcyclopropyl)-7H-pyrrolo[2,3-d]pyrimidine-5-carboxamide | 1-ethynylcyclopentanol | 41% |
| 132 | 4-amino-N-(4-(methoxymethyl)phenyl)-7-(1-methylcyclopropyl)-6-(3-(4-methylpiperazin-1-yl)prop-1-yn-1-yl)-7H-pyrrolo[2,3-d]pyrimidine-5-carboxamide | 1-methyl-4-prop-2-ynyl-piperazine | 38% |
| 134 | 4-amino-6-(3-amino-3-methylbut-1-yn-1-yl)-N-(4-(methoxymethyl)phenyl)-7-(1-methylcyclopropyl)-7H-pyrrolo[2,3-d]pyrimidine-5-carboxamide | 2-methyl-3-butyn-2-amine | 30% |
| 142 | 4-amino-N-(4-(methoxymethyl)phenyl)-6-(3-methyl-3-morpholinobut-1-yn-1-yl)-7-(1-methylcyclopropyl)-7H-pyrrolo[2,3-d]pyrimidine-5-carboxamide | 4-(1,1-dimethylprop-2-ynyl)morpholine | 20% |
| 143 | 4-amino-6-(3-(4-hydroxytetrahydro-2H-pyran-4-yl)prop-1-yn-1-yl)-N-(4-(methoxymethyl)phenyl)-7-(1-methylcyclopropyl)-7H-pyrrolo[2,3-d]pyrimidine-5-carboxamide | 4-(prop-2-yn-1-yl)oxan-4-ol | 23% |
| 144 | 4-amino-6-((1-isopropyl-1H-pyrazol-4-yl)ethynyl)-N-(4-(methoxymethyl)phenyl)-7-(1-methylcyclopropyl)-7H- | 4-ethynyl-1-isopropyl-pyrazole | 67% |

TABLE 5-continued

| | | | |
|---|---|---|---|
| 151 | 4-amino-N-(4-(methoxymethyl)phenyl)-7-(1-methylcyclopropyl)-6-(3-thiomorpholinoprop-1-yn-1-yl)-7H-pyrrolo[2,3-d]pyrimidine-5-carboxamide | 4-prop-2-ynylthiomorpholine | 51% |
| 152 | 4-amino-N-(4-(methoxymethyl)phenyl)-7-(1-methylcyclopropyl)-6-(3-(tetrahydro-2H-pyran-4-yl)prop-1-yn-1-yl)-7H-pyrrolo[2,3-d]pyrimidine-5-carboxamide | 4-prop-2-ynyltetrahydropyran | 81% |
| 155 | 4-amino-6-((6-aminopyridin-3-yl)ethynyl)-N-(4-(methoxymethyl)phenyl)-7-(1-methylcyclopropyl)-7H-pyrrolo[2,3-d]pyrimidine-5-carboxamide | 5-ethynylpyridin-2-amine | 64% |
| 156 | 4-amino-6-(3-(2,5-dioxoimidazolidin-4-yl)prop-1-yn-1-yl)-N-(4-(methoxymethyl)phenyl)-7-(1-methylcyclopropyl)-7H-pyrrolo[2,3-d]pyrimidine-5-carboxamide | 5-prop-2-ynylimidazolidine-2,4-dione | 11% |
| 157 | 4-amino-6-(4-hydroxyhex-1-yn-1-yl)-N-(4-(methoxymethyl)phenyl)-7-(1-methylcyclopropyl)-7H-pyrrolo[2,3-d]pyrimidine-5-carboxamide | 5-hexyn-3-ol | 10% |
| 158 | 4-amino-6-((3,4-dihydro-2H-benzo[b][1,4]oxazin-6-yl)ethynyl)-N-(4-(methoxymethyl)phenyl)-7-(1-methylcyclopropyl)-7H-pyrrolo[2,3-d]pyrimidine-5-carboxamide | 6-ethynyl-3,4-dihydro-2H-1,4-benzoxazine | 73% |
| 159 | 4-amino-6-(furo[3,2-b]pyridin-6-ylethynyl)-N-(4-(methoxymethyl)phenyl)-7-(1-methylcyclopropyl)-7H-pyrrolo[2,3-d]pyrimidine-5-carboxamide | 6-ethynylfuro[3,2-b]pyridine | 43% |
| 160 | 6-((1H-pyrazol-4-yl)ethynyl)-4-amino-N-(4-(methoxymethyl)phenyl)-7-(1-methylcyclopropyl)-7H-pyrrolo[2,3-d]pyrimidine-5-carboxamide | tert-butyl 4-ethynylpyrazole-1-carboxylate | 10% |
| 161 | 6-((1H-pyrrol-2-yl)ethynyl)-4-amino-N-(4-(methoxymethyl)phenyl)-7-(1-methylcyclopropyl)-7H-pyrrolo[2,3-d]pyrimidine-5-carboxamide | tert-butyl 2-ethynylpyrrole-1-carboxylate | 51% |
| 162 | 4-amino-N-(4-(methoxymethyl)phenyl)-7-(1-methylcyclopropyl)-6-(phenylethynyl)-7H-pyrrolo[2,3-d]pyrimidine-5-carboxamide | phenylacetylene | 67% |

TABLE 6

| | | | |
|---|---|---|---|
| 163 | 4-amino-N-(4-(methoxymethyl)phenyl)-6-(3-methyl-3-(1H-pyrrol-1-yl)but-1-yn-1-yl)-7-(1-methylcyclopropyl)-7H-pyrrolo[2,3-d]pyrimidine-5-carboxamide | 1-(1,1-dimethylprop-2-ynyl)pyrrole | 38% |
| 165 | 4-amino-N-(4-(methoxymethyl)phenyl)-6-((4-methoxypheny)ethynyl)-7-(1-methylcyclopropyl)-7H-pyrrolo[2,3-d]pyrimidine-5-carboxamide | 1-ethynyl-4-methoxy-benzene | 25% |
| 166 | 4-amino-6-((1-hydroxycyclopropyl)ethynyl)-N-(4-(methoxymethyl)phenyl)-7-(1-methylcyclopropyl)-7H-pyrrolo[2,3-d]pyrimidine-5-carboxamide | 1-ethynylcyclopropanol | 26% |
| 168 | 4-amino-6-(3-(3-cyclopropylureido)prop-1-yn-1-yl)-N-(4-(methoxymethyl)phenyl)-7-(1-methylcyclopropyl)-7H-pyrrolo[2,3-d]pyrimidine-5-carboxamide | 1-cyclopropyl-3-prop-2-ynyl-urea | 34% |
| 169 | 6-(3-(1H-pyrrol-1-yl)prop-1-yn-1-yl)-4-amino-N-(4-(methoxymethyl)phenyl)-7-(1-methylcyclopropyl)-7H-pyrrolo[2,3-d]pyrimidine-5-carboxamide | 1-prop-2-nylpyrrole | 2.8% |
| 170 | 4-amino-N-(4-(methoxymethyl)phenyl)-6-((1-methyl-1H-imidazol-2-yl)ethynyl)-7-(1-methylcyclopropyl)-7H-pyrrolo[2,3-d]pyrimidine-5-carboxamide | 2-ethynyl-1-methyl-imidazole | 18% |
| 172 | 4-amino-N-[4-(methoxymethyl)phenyl]-7-(1-methylcyclopropyl)-6-(pyridin-2-ylethynyl)-7H-pyrrolo[2,3-d]pyrimidine-5-carboxamide | 2-ethynylpyridine | 17% |
| 173 | 4-amino-6-(5-((2-fluoropyridin-3-yl)oxy)pent-1-yn-1-yl)-N-(4-(methoxymethyl)phenyl)-7-(1-methylcyclopropyl)-7H-pyrrolo[2,3-d]pyrimidine-5-carboxamide | 2-fluoro-3-pent-4-ny-1-yloxy-pyridine | 65% |
| 174 | 4-amino-6-(3-hydroxy-3-methylbut-1-yn-1-yl)-N-(4-(methoxymethyl)phenyl)-7-(1-methylcyclopropyl)-7H-pyrrolo[2,3-d]pyrimidine-5-carboxamide | 2-methyl-3-butyn-1-ol | 31% |
| 175 | 4-amino-6-((5-fluoropyridin-3-yl)ethynyl)-N-(4-(methoxymethyl)phenyl)-7-(1-methylcyclopropyl)-7H-pyrrolo[2,3-d]pyrimidine-5-carboxamide | 3-ethynyl-5-fluoropyridine | 31% |
| 176 | 4-amino-N-(4-(methoxymethyl)phenyl)-7-(1-methylcyclopropyl)-6-(thiophen-3-ylethynyl)-7H-pyrrolo[2,3-d]pyrimidine-5-carboxamide | 3-ethynylthiophene | 38% |
| 177 | 4-amino-6-((3-hydroxytetrahydrofuran-3-yl)ethynyl)-N-(4-(methoxymethyl)phenyl)-7-(1-methylcyclopropyl)-7H-pyrrolo[2,3-d]pyrimidine-5-carboxamide | 3-ethynyl-tetrahydrofuran-3-ol | 86% |
| 178 | 4-amino-N-(4-(methoxymethyl)phenyl)-7-(1-methylcyclopropyl)-6-(1-oxidethiomorpholino)prop-1-yn-1-yl)-7H-pyrrolo[2,3-d]pyrimidine-5-carboxamide | 4-(propy-2-nyl-1-yl)thiomorpholine 1-oxide hydrochloride | 100% |
| 181 | 4-amino-6-((1,3-dimethyl-1H-pyrazol-4-yl)ethynyl)-N-(4-(methoxymethyl)phenyl)-7-(1-methylcyclopropyl)-7H-pyrrolo[2,3-d]pyrimidine-5-carboxamide | 4-ethynyl-1,3-dimethyl-pyrazole | 79% |

TABLE 6-continued

| | | | |
|---|---|---|---|
| 182 | 4-amino-6-((1,5-dimethyl-1H-pyrazol-4-yl)ethynyl)-N-(4-(methoxymethyl)phenyl)-7-(1-methylcyclopropyl)-7H-pyrrolo[2,3-d]pyrimidine-5-carboxamide | 4-ethynyl-1,5-dimethyl-pyrazole | 65% |
| 183 | 4-amino-N-(4-(methoxymethyl)phenyl)-7-(1-methylcyclopropyl)-6-((1-methylpiperidin-4-yl)ethynyl)-7H-pyrrolo[2,3-d]pyrimidine-5-carboxamide | 4-ethynyl-1-methyl-piperidine | 30% |

TABLE 7

| | | | |
|---|---|---|---|
| 184 | 4-amino-6-((3,5-dimethylisoxazol-4-yl)ethynyl)-N-(4-(methoxymethyl)phenyl)-7-(1-methylcyclopropyl)-7H-pyrrolo[2,3-d]pyrimidine-5-carboxamide | 4-ethynyl-3,5-dimethyl-isoxazole | 20% |
| 185 | 4-amino-6-((4-hydroxytetrahydro-2H-pyran-4-yl)ethynyl)-N-(4-(methoxymethyl)phenyl)-7-(1-methylcyclopropyl)-7H-pyrrolo[2,3-d]pyrimidine-5-carboxamide | 4-ethynyltetrahydropyran-4-ol | 66% |
| 186 | 4-amino-N-[4-(methoxymethyl)phenyl]-7-(1-methylcyclopropyl)-6-(pyridin-4-ylethynyl)-7H-pyrrolo[2,3-d]pyrimidine-5-carboxamide | 4-ethynylpyridine | 7% |
| 187 | 4-amino-N-(4-(methoxymethyl)phenyl)-7-(1-methylcyclopropyl)-6-(4-morpholinobut-1-yn-1-yl)-7H-pyrrolo[2,3-d]pyrimidine-5-carboxamide | 4-(3-butyn-1-yl)morpholine | 39% |
| 188 | 4-amino-6-(4-hydroxypent-1-yn-1-yl)-N-(4-(methoxymethyl)phenyl)-7-(1-methylcyclopropyl)-7H-pyrrolo[2,3-d]pyrimidine-5-carboxamide | 4-pentyn-2-ol | 42% |
| 189 | 4-amino-N-(4-(methoxymethyl)phenyl)-6-(3-(4-methoxypiperidin-1-yl)prop-1-yn-1-yl)-7-(1-methylcyclopropyl)-7H-pyrrolo[2,3-d]pyrimidine-5-carboxamide | 4-methoxy-1-prop-2-nyl-piperidine | 63% |
| 191 | 6-((1H-imidazol-5-yl)ethynyl)-4-amino-N-(4-(methoxymethyl)phenyl)-7-(1-methylcyclopropyl)-7H-pyrrolo[2,3-d]pyrimidine-5-carboxamide | 5-ethynyl-1H-imidazole | 32% |
| 192 | 4-amino-N-(4-(methoxymethyl)phenyl)-6-((6-methoxypyridin-3-yl)ethynyl)-7-(1-methylcyclopropyl)-7H-pyrrolo[2,3-d]pyrimidine-5-carboxamide | 5-ethynyl-2-methoxy-pyridine | 18% |
| 193 | 4-amino-N-[4-(methoxymethyl)phenyl]-7-(1-methylcyclopropyl)-6-(thiazol-5-ylethynyl)-7H-pyrrolo[2,3-d]pyrimidine-5-carboxamide | 5-ethynylthiazole | 46% |
| 195 | 4-amino-6-((5-cyanopyridin-3-yl)ethynyl)-N-(4-(methoxymethyl)phenyl)-7-(1-methylcyclopropyl)-7H-pyrrolo[2,3-d]pyrimidine-5-carboxamide | 5-ethynylpyridine-3-carbonitrile | 46% |
| 196 | 4-amino-N-(4-(methoxymethyl)phenyl)-7-(1-methylcyclopropyl)-6-(pyrimidin-5-ylethynyl)-7H-pyrrolo[2,3-d]pyrimidine-5-carboxamide | 5-ethynylpyrimidine | 25% |
| 197 | 4-amino-6-(3-((2-methoxyethyl)(methyl)amino)prop-1-yn-1-yl)-N-(4-(methoxymethyl)phenyl)-7-(1-methylcyclopropyl)-7H-pyrrolo[2,3-d]pyrimidine-5-carboxamide | N-(2-methoxyethynyl)-N-methyl-prop-2-yn-1-amine | 56% |
| 198 | 4-amino-6-(3-(dimethylamino)prop-1-yn-1-yl)-N-(4-(methoxymethyl)phenyl)-7-(1-methylcyclopropyl)-7H-pyrrolo[2,3-d]pyrimidine-5-carboxamide | N,N-dimethylprop-2-yn-1-amine | 13% |
| 199 | 4-amino-6-(3-cyclohexylprop-1-yn-1-yl)-N-(4-(methoxymethyl)phenyl)-7-(1-methylcyclopropyl)-7H-pyrrolo[2,3-d]pyrimidine-5-carboxamide | propy-2-nylcyclohexane | 62% |
| 200 | 4-amino-N-(4-(methoxymethyl)phenyl)-6-(3-methoxyprop-1-yn-1-yl)-7-(1-methylcyclopropyl)-7H-pyrrolo[2,3-d]pyrimidine-5-carboxamide | 3-methoxylprop-1-yne | 44% |

According to the synthesis procedure of Example 115, using the compounds shown in Table 8 instead of 4-((methylthio)methyl)aniline, compounds 116 and 117 of the Examples were obtained.

TABLE 8

| Compounds of Examples | Name of Compounds of Examples | Compounds Used | Yield |
|---|---|---|---|
| 116 | 4-amino-6-ethoxy-N-(4-(furan-2-yl)phenyl)-7-(1-methylcyclopropyl)-7H-pyrrolo[2,3-d]pyrimidine-5-carboxamide | 4-(2-furil) aniline | 32% |
| 117 | (E)-4-amino-6-ethoxy-7-(1-methylcyclopropyl)-N-(4-(prop-1-en-1-yl)phenyl)-7H-pyrrolo[2,3-d]pyrimidine-5-carboxamide | 4-[(E)-1-propenyl] aniline | 23% |

Example 115: Synthesis of 4-amino-6-ethoxy-7-(1-methylcyclopropyl)-N-(4-((methylthio)methyl)phenyl)-7H-pyrrolo[2,3-d]pyrimidine-5-carboxamide According to the synthesis procedure of Example 59, using 4-amino-6-ethoxy-7-(1-methylcyclopropyl)-7H-pyrrolo[2,3-d]pyrimidine-5-carboxylic acid shown in step 1 of Example 127 instead of 4-amino-6-bromo-7-(1-methylcyclopropyl)-7H-pyrrolo[2,3-d]pyrimidine-5-carboxylic acid, the title compound (64%) was obtained.

Example 127: Synthesis of 4-amino-6-ethoxy-N-(4-(methoxymethyl)phenyl)-7-(1-methylcyclopropyl)-7H-pyrrolo[2,3-d]pyrimidine-5-carboxamide Step 1: Synthesis of 4-amino-6-ethoxy-7-(1-methylcyclopropyl)-7H-pyrrolo[2,3-d]pyrimidine-5-carboxylic acid 714 mg of methyl 4-amino-6-chloro-7-(1-methylcyclopropyl)-7H-pyrrolo[2,3-d]pyrimidine-5-carboxylate shown in step 1 of Example 56 was dissolved in 12 mL of THF, and 155 mg of dimethylaminopyridine and 1.66 g of tert-butyl dicarbonate were added thereto, followed by stirring at 50° C. for 1 hour.

After removal of the solvent, the residue was partitioned between ethyl acetate and water, and the organic layer was washed with water and a saturated aqueous sodium chloride solution, dried over anhydrous sodium sulfate, and concentrated. 20 mL of ethanol and 3 mL of sodium ethoxide (a 20% ethanol solution) were added to the residue, and the mixture was stirred overnight. 20 mL of ethanol and 12 mL of a 4N aqueous sodium hydroxide solution were added to the reaction solution, and the mixture was stirred at 80° C. for 6 hours. After cooling, 30 mL of water was added to the reaction solution, and ethanol was removed through an evaporator. The residue was adjusted to a pH of 4 with a 2NHCl aqueous solution, and the generated precipitate was stirred with ice-cooling for 1 hour, and filtered, thereby obtaining 400 mg of the title compound.

Step 2: Synthesis of 4-amino-6-ethoxy-N-(4-(methoxymethyl)phenyl)-7-(1-methylcyclopropyl)-7H-pyrrolo[2,3-d]pyrimidine-5-carboxamide According to the synthesis procedure in step 2 of Example 55, using 4-amino-6-ethoxy-7-(1-methylcyclopropyl)-7H-pyrrolo[2,3-d]pyrimidine-5-carboxylic acid obtained in step 1 instead of 4-amino-6-bromo-7-(1-methylcyclopropyl)-7H-pyrrolo[2,3-d]pyrimidine-5-carboxylic acid, the title compound (56%) was obtained.

Example 133: Synthesis of 4-amino-N-(4-methoxymethyl)phenyl-7-(1-methylcyclopropyl)-6-(methylthio)-7H-pyrrolo[2,3-d]pyrimidine-5-carboxamide 100 mg of 4-amino-6-bromo-N-[4-(methoxymethyl)phenyl]-7-(1-methylcyclopropyl)-7H-pyrrolo[2,3-d]pyrimidine-5-carboxamide shown in Example 55 was dissolved in 1 ml of DMF, and 330 μl of methyl mercaptan sodium salt (an about 15% aqueous solution) was added at room temperature. After stirring for 30 minutes, the mixture was diluted with water, and the obtained solid was filtered, washed with water, and dried at 60° C. under reduced pressured, thereby obtaining 87 mg of the title compound.

Example 135: Synthesis of 4-amino-N-(4-(methoxymethyl)phenyl)-7-(1-methylcyclopropyl)-6-((tetrahydrofuran-2-yl)methoxy)-7H-pyrrolo[2,3-d]pyrimidine-5-carboxamide 100 μL of tetrahydrofurfuryl alcohol was added to a suspension of 52 mg of sodium hydride (60%) in 1 mL of DMF with stirring while the mixture was cooled with ice, and then the mixture was stirred at room temperature for 30 minutes. A solution of 30 mg of 4-amino-6-chloro-N-[4-(methoxymethyl)phenyl]-7-(1-methylcyclopropyl)-7H-pyrrolo[2,3-d]pyrimidine-5-carboxamide shown in Example 56 in 1 mL of DMF was added thereto, and the mixture was stirred at 80° C. overnight. After cooling, the reaction solution was partitioned between ethyl acetate and water, and the organic layer was washed with water and a saturated aqueous sodium chloride solution, and dried over sodium sulfate, followed by removal of the solvent. The residue was purified by silica gel column (ethyl acetate/methanol=1/0→8/1) and HPLC, thereby obtaining 32.2 mg of the title compound.

According to the synthesis procedure of Example 135, using the compounds shown in Table 9 instead of tetrahydrofurfuryl alcohol, compounds 136 to 141 of the Examples were obtained.

TABLE 9

| Compounds of Examples | Name of Compounds of Examples | Compounds Used | Yield |
|---|---|---|---|
| 136 | 4-amino-N-(4-(methoxymethyl)phenyl)-7-(1-methylcyclopropyl)-6-(2-(2-oxopyrrolidin-1-yl)ethoxy)-7H-pyrrolo[2,3-d]pyrimidine-5-carboxamide | 1-(2-hydroxyethyl)pyrrolidin-2-one | 1.9% |
| 137 | 4-amino-6-(2-methoxy-2-methylpropoxy)-N-(4-(methoxymethyl)phenyl)-7-(1-methylcyclopropyl)-7H-pyrrolo[2,3-d]pyrimidine-5-carboxamide | 2-methoxy-2-propan-1-ol | 59% |
| 138 | 4-amino-6-(2-methoxyethoxy)-N-(4-(methoxymethyl)phenyl)-7-(1-methylcyclopropyl)-7H-pyrrolo[2,3-d]pyrimidine-5-carboxamide | 2-methoxyethanol | 53% |
| 139 | 4-amino-6-(3-methoxy-3-methylbutoxy)-N-(4-(methoxymethyl)phenyl)-7-(1-methylcyclopropyl)-7H-pyrrolo[2,3-d]pyrimidine-5-carboxamide | 3-methoxy-3-methylbutanol | 50% |
| 140 | 4-amino-6-(cyclopentylmethoxy)-N-(4-(methoxymethyl)phenyl)-7-(1-methylcyclopropyl)-7H-pyrrolo[2,3-d]pyrimidine-5-carboxamide | cyclopentane methanol | 57% |
| 141 | 4-amino-N-(4-(methoxymethyl)phenyl)-7-(1-methylcyclopropyl)-6-((tetrahydro-2H-pyran-4-yl)methoxy)-7H-pyrrolo[2,3-d]pyrimidine-5-carboxamide | tetrahydropyran-4-methanol | 41% |

Example 145: Synthesis of 4-amino-6-(4-(hydroxymethyl)phenyl)-N-(4-(methoxymethyl)phenyl)-7-(1-methylcyclopropyl)-7H-pyrrolo[2,3-d]pyrimidine-5-carboxamide 100 mg of 4-amino-6-bromo-N-[4-(methoxymethyl)phenyl]-7-(1-methylcyclopropyl)-7H-pyrrolo[2,3-d]pyrimidine-5-carboxamide shown in Example 55, 148 mg of potassium phosphate, 70 mg of (4-(hydroxymethyl)phenyl) boronic acid, and 13 mg of tetrakis(triphenylphosphine) palladium were stirred in a mixture solvent of 2 mL of dioxane and 0.2 mL of water at 130° C. for 1 hour in a microwave reactor. Ethyl acetate and water were added to the obtained reaction solution, and the organic layer was partitioned. The obtained organic layer was concentrated under reduced pressure, and the residue was purified by silica gel chromatography (developing solvent: chloroform-methanol). After concentration, the obtained residue was suspended in methanol, filtered, and dried under reduced pressure, thereby obtaining 57 mg of the title compound.

Example 146: Synthesis of 4-amino-6-isopropoxy-N-(4-(methoxymethyl)phenyl)-7-(1-methylcyclopropyl)-7H-pyrrolo[2,3-d]pyrimidine-5-carboxamide 50 mg of 4-amino-6-chloro-N-[4-(methoxymethyl)phenyl]-7-(1-methylcyclopropyl)-7H-pyrrolo[2,3-d]pyrimidine-5-carboxamide shown in Example 56 was dissolved in 1.5 mL of DMF, and 160 mg of sodium isopropoxide was added thereto, followed by stirring with heating at 100° C. for 8 hours. The reaction solution was partitioned between ethyl acetate and water, and the organic layer was concentrated, followed by purification of the residue by preparative reversed-phase HPLC, thereby obtaining 2.9 mg of the title compound.

According to the synthesis procedure of Example 145, using the compounds shown in Table 10 instead of [4-(hydroxymethyl)phenyl]boronic acid, compounds 147 to 150 and 203 of the Examples were obtained.

TABLE 10

| Compounds of Examples | Name of Compounds of Examples | Compounds Used | Yield |
|---|---|---|---|
| 147 | 6-(6-acetamidopyridin-3-yl)-4-amino-N-(4-(methoxymethyl)phenyl)-7-(1-methylcyclopropyl)-7H-pyrrolo[2,3-d]pyrimidine-5-carboxamide | (6-acetamido-3-pyridyl)boronic acid | 34% |
| 148 | 4-amino-6-(4-hydroxyphenyl)-N-(4-(methoxymethyl)phenyl)-7-(1-methylcyclopropyl)-7H-pyrrolo[2,3-d]pyrimidine-5-carboxamide | 4-(4,4,5,5-tetramethyl-1,3,2-dioxaborolan-2-yl)phenol | 49% |
| 149 | 4-amino-N-(4-(methoxymethyl)phenyl)-7-(1-methylcyclopropyl)-6-(prop-1-en-2-yl)-7H-pyrrolo[2,3-d]pyrimidine-5-carboxamide | 4,4,5,5-tetramethyl-2-(1-propen-2-yl)-1,3,2-dioxaborolane | 55% |
| 150 | 4-amino-N-(4-(methoxymethyl)phenyl)-6-(1-methyl-1H-pyrazol-4-yl)-7-(1-methylcyclopropyl)-7H-pyrrolo[2,3-d]pyrimidine-5-carboxamide | 1-methyl-4-(4,4,5,5-tetramethyl-1,3,2-dioxaborolan-2-yl)-1H-pyrazole | 11% |
| 203 | 4-amino-6-(3,6-dihydro-2H-pyran-4-yl)-N-(4-(methoxymethyl)phenyl)-7-(1-methylcyclopropyl)-7H-pyrrolo[2,3-d]pyrimidine-5-carboxamide | 2-(3,6-dihydro-2H-pyran-4-yl)-4,4,5,5-tetramethyl-1,3,2-dioxaborolane | 60% |

Example 153: Synthesis of 4-amino-6-(4-formylphenyl)-N-(4-(methoxymethyl)phenyl)-7-(1-methylcyclopropyl)-7H-pyrrolo[2,3-d]pyrimidine-5-carboxamide With reference to Example 145, using 4-formylphenylboronic acid instead of (4-(hydroxymethyl)phenyl)boronic acid, a reaction was performed. Ethyl acetate and water were added to the obtained reaction solution, and the organic layer was partitioned. The obtained organic layer was concentrated under reduced pressure, and the residue was purified by silica gel chromatography (developing solvent: chloroform-methanol). After concentration, the obtained residue was suspended in methanol, filtered, and dried under reduced pressure, thereby obtaining 23 mg of the title compound.

Example 154: Synthesis of 4-amino-N-(4-(methoxymethyl)phenyl)-7-(1-methylcyclopropyl)-6-phenyl-7H-pyrrolo[2,3-d]pyrimidine-5-carboxamide According to the synthesis procedure of Example 153, using phenylboronic acid instead of 4-formylphenylboronic acid, the title compound was obtained (44%).

Example 164: Synthesis of 4-amino-6-(3-(hydroxymethyl)phenyl)-N-(4-(methoxymethyl)phenyl)-7-(1-methylcyclopropyl)-7H-pyrrolo[2,3-d]pyrimidine-5-carboxamide 100 mg of 4-amino-6-bromo-N-[4-(methoxymethyl)phenyl]-7-(1-methylcyclopropyl)-7H-pyrrolo[2,3-d]pyrimidine-5-carboxamide shown in Example 55, 148 mg of potassium phosphate, 70 mg of (3-(hydroxymethyl)phenyl) boronic acid, and 13 mg of tetrakis(triphenylphosphine) palladium were stirred in a mixed solvent of 2 mL of dioxane and 0.2 mL of water at 140° C. for 1 hour in a microwave reactor. Ethyl acetate and water were added to the obtained reaction solution, and the organic layer was partitioned. The obtained organic layer was concentrated under reduced pressure, and the residue was purified by silica gel chromatography (developing solvent: chloroform-methanol). After concentration, the obtained residue was purified again by preparative reversed-phase HPLC, and basified with saturated sodium bicarbonate, followed by extraction with chloroform. The obtained organic layer was concentrated, and the residue was suspended in methanol, filtered, and dried under reduced pressure, thereby obtaining 28 mg of the title compound.

Example 167: Synthesis of 4-amino-N-(4-(methoxymethyl)phenyl)-7-(1-methylcyclopropyl)-6-(1H-pyrazol-4-yl)-7H-pyrrolo[2,3-d]pyrimidine-5-carboxamide According to the synthesis procedure of Example 164, using tert-butyl 4-(4,4,5,5-tetramethyl-1,3,2-dioxaborolan- 2-yl)pyrazole-1-carboxylate instead of [3-(hydroxymethyl) phenyl]boronic acid, 16 mg of the title compound was obtained.

Example 171: Synthesis of 4-amino-N-(4-(methoxymethyl)phenyl)-7-(1-methylcyclopropyl)-6-(4-(4-methylpiperazin-1-yl)phenyl)-7H-pyrrolo[2,3-d]pyrimidine-5-carboxamide According to the synthesis procedure of Example 145, using 1-methyl-4-[4-(4,4,5,5-tetramethyl-1,3,2-dioxaborolan-2-yl)phenyl]piperazine instead of (4-(hydroxymethyl) phenyl)boronic acid, 84 mg of the title compound was obtained.

Example 179: Synthesis of 4-amino-6-(6-(hydroxymethyl)pyridin-3-yl)-N-(4-(methoxymethyl) phenyl)-7-(1-methylcyclopropyl)-7H-pyrrolo[2,3-d] pyrimidine-5-carboxamide According to the synthesis procedure of Example 164, using (6-(hydroxymethyl)pyridin-3-yl)boronic acid instead of (4-(hydroxymethyl)phenyl)boronic acid, 47 mg of the title compound was obtained.

Example 180: Synthesis of 4-amino-6-(3-(tert-butyldimethylsilyl)oxy)prop-1-yn-1-yl-N-(4-(methoxymethyl)phenyl)-7-(1-methylcyclopropyl)-7H-pyrrolo[2,3-d]pyrimidine-5-carboxamide 50 mg of 4-amino-6-bromo-N-[4-(methoxymethyl)phenyl]-7-(1-methylcyclopropyl)-7H-pyrrolo[2,3-d]pyrimidine-5-carboxamide shown in Example 55 was dissolved in 1 mL of DMF. 2 mg of copper iodide, 65 mg of 2-propyn-1-ol, 50 µL of triethylamine, and 13 mg of tetrakis triphenylphosphine palladium were added thereto and degassed, followed by stirring at 100° C. for 1.5 hours. After completion of the reaction, the reaction solution was partitioned between chloroform and water, and the organic layer was dried over saturated sodium sulfate, filtered, and concentrated. The residue was dissolved in 2 mL of dichloromethane, and then 6 mg of imidazole and 7 mg of tert-butyldimethylsilyl chloride were added thereto, followed by stirring at room temperature for 5 hours. The reaction solution was concentrated, and the residue was purified by slica gel column (ethyl acetate/methanol=1/0→8/1), thereby obtaining 13 mg of the title compound.

Example 190: Synthesis of 4-amino-6-(6-fluoropyridin-3-yl)-N-(4-(methoxymethyl)phenyl)-7-(1-methylcyclopropyl)-7H-pyrrolo[2,3-d]pyrimidine-5-carboxamide According to the procedure of Example 164, using (6-fluoropyridin-3-yl)boronic acid instead of (4-(hydroxymethyl)phenyl)boronic acid, 47 mg of the title compound was obtained.

Example 194: Synthesis of 4-amino-N-(4-(methoxymethyl)phenyl)-7-(1-methylcyclopropyl)-6-(pyrimidin-5-yl)-7H-pyrrolo[2,3-d]pyrimidine-5-carboxamide With reference to Example 145, using 86 mg of pyrimidin-5-ylboronic acid instead of (4-(hydroxymethyl)phenyl) boronic acid, a reaction was performed. Ethyl acetate and water were added to the obtained reaction solution, and the organic layer was partitioned. The obtained organic layer was concentrated under reduced pressure, and the reside was purified by silica gel chromatography (developing solvent: chloroform-methanol). After concentration, the obtained reside was purified again by preparative reversed-phase HPLC. After concentration, the residue was purified again by silica gel chromatography (chloroform-methanol). The obtained residue was suspended in hexane-ethyl acetate, filtered, and dried under reduced pressure, thereby obtaining 10 mg of the title compound.

Example 201: Synthesis of 4-amino-6-chloro-7-(1-fluoro-2-methylpropan-2-yl)-N-(4-(methoxymethyl) phenyl)-7H-pyrrolo[2,3-d]pyrimidine-5-carboxamide Step 1: Synthesis of methyl 4-amino-6-chloro-7-(1-fluoro-2-methylpropan-2-yl)-7H-pyrrolo[2,3-d]pyrimidine-5-carboxylate With reference to the synthesis procedure of step 1 in Example 56, using methyl 4-amino-7-(1-fluoro-2-methylpropan-2-yl)-7H-pyrrolo[2,3-d]pyrimidine-5-carboxylate, which was synthesized using 1-fluoro-2-methylpropan-2-amine hydrochloride instead of tert-butylamine according to the procedures of steps 1 to 4 of Reference Example 5, instead of methyl 4-amino-7-(1-methylcyclopropyl)-7H-pyrrolo[2,3-d]pyrimidine 5-carboxylate, the title compound (12%) was obtained.

Step 2: Synthesis of 4-amino-6-chloro-7-(1-fluoro-2-methylpropan-2-yl)-7H-pyrrolo[2,3-d]pyrimidine-5-carboxylic acid According to the synthesis procedure of step 2 in Example 56, using methyl 4-amino-6-chloro-7-(1-fluoro-2-methylpropan-2-yl)-7H-pyrrolo[2,3-d]pyrimidine-5-carboxylate obtained ins step 1, the title compound (75%) was obtained.

Step 3: Synthesis of 4-amino-6-chloro-7-(1-fluoro-2-methylpropan-2-yl)-N-(4-(methoxymethyl)phenyl)-7H-pyrrolo[2,3-d]pyrimidine-5-carboxamide According to the synthesis procedure of step 3 in Example 56, using 4-amino-6-chloro-7-(1-fluoro-2-methylpropan-2-yl)-7H-pyrrolo[2,3-d]pyrimidine-5-carboxylic acid obtained ins step 2, the title compound (35%) was obtained.

Example 202: Synthesis of 4-amino-7-(tert-butyl)-6-chloro-N-(4-(methoxymethyl)phenyl)-7H-pyrrolo [2,3-d]pyrimidine-5-carboxamide Step 1: methyl 4-amino-6-chloro-7-(tert-butyl)-7H-pyrrolo[2,3-d]pyrimidine-5-carboxylate With reference to the synthesis procedure of step 1 in Example 56, using methyl 4-amino-7-(tert-butyl)-7H-pyrrolo[2,3-d]pyrimidine-5-carboxylate obtained in step 4 of Reference Example 5 instead of methyl 4-amino-7-(1-methylcyclopropyl)-7H-pyrrolo[2,3-d]pyrimidine-5-carboxylate, the title compound (11%) was obtained.

Step 2: Synthesis of 4-amino-6-chloro-7-(tert-butyl)-7H-pyrrolo[2,3-d]pyrimidine-5-carboxylic acid According to the synthesis procedure of step 2 in Example 56, using methyl 4-amino-6-chloro-7-(tert-butyl)-7H-pyrrolo[2,3-d]pyrimidine-5-carboxylate obtained in step 1, the title compound (74%) was obtained.

Step 3: Synthesis of 4-amino-7-(tert-butyl)-6-chloro-N-(4-(methoxymethyl)phenyl)-7H-pyrrolo[2,3-d]pyrimidine-5-carboxamide According to the synthesis procedure of step 3 in Example 56, using 4-amino-6-chloro-7-(tert-butyl)-7H-pyrrolo[2,3-d]pyrimidine-5-carboxylic acid obtained in step 2, the title compound (46%) was obtained.

Example 204: Synthesis of 4-amino-6-(1-hydroxyethyl)-N-(4-(methoxymethyl)phenyl)-7-(1-methylcyclopropyl)-7H-pyrrolo[2,3-d]pyrimidine-5-carboxamide 23 mg of 6-acetyl-4-amino-N-(4-(methoxymethyl)phenyl)-7-(1-methylcyclopropyl)-7H-pyrrolo[2,3-d]pyrimidine-5-carboxamide shown in Example 64 was dissolved in 2 mL of methanol. 7 mg of sodium borohydride was added thereto at room temperature, and the mixture was stirred for 2 hours. The reaction solution was partitioned between ethyl acetate and water, and the organic layer was washed with water and a saturated aqueous sodium chloride solution, dried over anhydrous sodium sulfate, filtered, and concentrated. The residue was purified by silica gel column (ethyl acetate/methanol=1/0→8/1), thereby obtaining 13.6 mg of the title compound.

Example 205: Synthesis of 4-amino-N-(3-fluoro-4-(methoxymethyl)phenyl)-7-(1-methylcyclopropyl)-6-((tetrahydro-2H-pyran-4-yl)ethynyl)-7H-pyrrolo[2,3-d]pyrimidine-5-carboxamide According to the synthesis procedure of Example 90, using 4-amino-6-bromo-N-(3-fluoro-4-(methoxymethyl)phenyl)-7-(1-methylcyclopropyl)-7H-pyrrolo[2,3-d]pyrimidine-5-carboxamide shown in Reference Example 11 instead of 4-amino-6-bromo-N-(4-(methoxymethyl)phenyl)-7-(1-methylcyclopropyl)-7H-pyrrolo[2,3-d]pyrimidine-5-carboxamide, and using 4-ethynyltetrahydropyran instead of 4-ethynyl-1-methyl-pyrazole, the title compound (53%) was obtained.

Example 206: Synthesis of 4-amino-N-(3-fluoro-4-(methoxymethyl)phenyl)-7-(1-methylcyclopropyl)-6-(3-morpholinoprop-1-yn-1-yl)-7H-pyrrolo[2,3-d]pyrimidine-5-carboxamide According to the synthesis procedure of Example 205, using 4-prop-2-ynylmorpholine instead of 4-ethynyltetrahydropyran, the title compound (42%) was obtained.

Example 207: 4-amino-6-ethyl-N-(4-(methoxymethyl)phenyl)-7-(1-methylcyclopropyl)-7H-pyrrolo[2,3-d]pyrimidine-5-carboxamide Step 1: Synthesis of methyl 4-amino-6-ethyl-7-(1-methylcyclopropyl)-7H-pyrrolo[2,3-d]pyrimidine-5-carboxylate 20 mg of methyl 4-amino-7-(1-methylcyclopropyl)-6-vinyl-7H-pyrrolo[2,3-d]pyrimidine-5-carboxylate shown in step 1 of Example 65 was dissolved in 5 mL of ethyl acetate, and 5 mg of 10% palladium-carbon was added thereto, followed by stirring in a hydrogen atmosphere for 2 hours. The insoluble matter was filtered through Celite, and the filtrate was concentrated, thereby obtaining 20 mg of the title compound.

Step 2: Synthesis of 4-amino-6-ethyl-N-(4-(methoxymethyl)phenyl)-7-(1-methylcyclopropyl)-7H-pyrrolo[2,3-d]pyrimidine-5-carboxamide According to the procedures of steps 1 and 2 of Example 55, using 4-amino-6-ethyl-7-(1-methylcyclopropyl)-7H-pyrrolo[2,3-d]pyrimidine-5-carboxylate obtained in step 1 instead of methyl 4-amino-6-bromo-7-(1-methylcyclopropyl)-7H-pyrrolo[2,3-d]pyrimidine-5-carboxylate, the title compound (26%) was obtained.

Comparative Example 1: Synthesis of 1-(tert-butyl)-3-(p-toluyl)pyrazolo[3,4-d]pyrimidin-4-amine According to the synthesis procedure of Tetrahedron Letters, 52(44), 5761-5763; 2011, the title compound (30%) was obtained.

Comparative Example 2: Synthesis of 4-amino-7-cyclopentyl-N-(4-phenoxyphenyl)-7H-pyrrolo[2,3-d]pyrimidine-5-carboxamide According to the synthesis procedures of Example 25, using 4-phenoxylaniline instead of 4-(methoxymethyl)aniline, the title compound (79%) was obtained.

Comparative Example 3: Synthesis of 4-amino-7-(tert-butyl)-N-(4-(methoxymethyl)phenyl)-N-methyl-7H-pyrrolo[2,3-d]pyrimidine-5-carboxamide Step 1: Synthesis of N-[4-(methoxymethyl)phenyl]-2-nitro-benzenesulfonamide 1.9 g of 2-nitrobenzenesulfonyl chloride was added to a solution of 1.0 g of 4-(methoxymethyl)aniline and 1.5 mL of triethylamine in 10 mL of chloroform, and the mixture was stirred overnight. After concentration, the residue was purified by silica gel chromatography (developing solvent: hexane-ethyl acetate), concentrated, and dried under reduced pressure, thereby obtaining 1.89 g of the title compound.

Step 2: Synthesis of N-[4-(methoxymethyl)phenyl]-N-methyl-2-nitro-benzenesulfonamide 0.53 mL of methyl iodide was added to a suspension of 1.84 g of N-[4-(methoxymethyl)phenyl]-2-nitro-benzenesulfonamide obtained in step 1 and 1.58 g of potassium carbonate in 20 mL of DMF, and the mixture was stirred at room temperature for 2 hours. The reaction solution was diluted with ethyl acetate and water. After extraction with ethyl acetate, the obtained organic layer was washed with water twice, and subsequently washed with a saturated aqueous sodium chloride solution, followed by drying over anhydrous sodium sulfate. The obtained solution was filtered, concentrated, and dried under reduced pressure, thereby obtaining 2.04 g of the title compound.

Step 3: Synthesis of 4-(methoxymethyl)-N-methyl-aniline 1.59 mL of 3-methylbenzenthiol was added to a suspension of 2.51 g of N-[4-(methoxymethyl)phenyl]-N-methyl- 2-nitro-benzenesulfonamide obtained in step 2 and 2.51 g of potassium carbonate in 10 mL of DMF, and the mixture was stirred at room temperature for 5 hours. The reaction solution was diluted with ethyl acetate-water, and subjected to extraction with ethyl acetate. The obtained organic layer was washed with water twice, and subsequently washed with a saturated aqueous sodium chloride solution, followed by drying over anhydrous sodium sulfate. The obtained solution was filtered and concentrated, and the resulting residue was purified by silica gel chromatography, concentrated, and dried under reduced pressure, thereby obtaining 0.81 g of the title compound.

Step 4: Synthesis of 4-amino-7-(tert-butyl)-N-(4-(methoxymethyl)phenyl)-N-methyl-7H-pyrrolo[2,3-d]pyrimidine-5-carboxamide A solution of 59 mg of 4-(methoxymethyl)-N-methylaniline, 48 µL of 1,8-diazabicyclo[5.4.0]undec-7-ene, 12 mg of 1,1'-bis(diphenylphosphino)ferrocene-palladium (II) dichloride-dichloromethane complex, and 50 mg of 7-(tert-butyl)-5-iodo-7H-pyrrolo[2,3-d]pyrimidin-4-amine shown in step 3 of Reference Example 5 in 1 mL of DMA was stirred in a carbon monoxide atmosphere at 110° C. for 1.5 hours. The reaction solution was purified by silica gel chromatography (developing solvent: chloroform-methanol), concentrated, and purified again by a preparative reversed-phase system. After concentration, the resulting residue was suspended and washed with hexane-ethyl acetate, filtered, and dried at 60° C. under reduced pressure, thereby obtaining 3.5 mg of the title compound.

Comparative Example 4: Synthesis of 7-(tert-butyl)-N-(4-(methoxymethyl)phenyl)-4-(methylamino)-7H-pyrrolo[2,3-d]pyrimidine-5-carboxamide Step 1: Synthesis of 7-(tert-butyl)-5-iodo-N-methyl-7H-pyrrolo[2,3-d]pyrimidin-4-amine 400 mg of 7-(tert-butyl)-4-chloro-5-iodo-7H-pyrrolo[2,3-d]pyrimidine shown in step 2 of Reference Example 5 was added to 10 mL of a solution of methylamine in THF, and the mixture was stirred at 120° C. for 12 hours in a microwave reactor. The obtained reaction solution was concentrated, and purified by basic silica gel chromatography (developing solvent: hexane-ethyl acetate), followed by concentration, thereby obtaining 400 mg of the title compound.

Step 2: Synthesis of 7-(tert-butyl)-N-(4-(methoxymethyl)phenyl)-4-(methylamino)-7H-pyrrolo[2,3-d]pyrimidine-5-carboxamide 7-(tert-butyl)-5-iodo-N-methyl-7H-pyrrolo[2,3-d]pyrimidin-4-amine obtained in step 1, 103 mg of 4-(methoxymethyl)aniline, 90 µl of 1,8-diazabicyclo[5.4.0]undec-7-ene, and 24 mg of 1,1'-bis(diphenylphosphino)ferrocene-palladium (II) dichloride-dichloromethane complex were added to 1 mL of DMA, and the mixture was stirred in a carbon monoxide atmosphere at 110° C. for 2 hours. The obtained reaction solution was purified by silica gel chromatography (developing solvent: hexane-ethyl acetate), concentrated, and purified again by basic silica gel chromatography, followed by concentration, thereby obtaining 52 mg of the title compound.

Comparative Example 5: Synthesis of 4-amino-N-(4-(methoxymethyl)phenyl)-1-phenyl-1H-pyrazolo[3,4-d]pyrimidine-3-carboxamide According to the synthesis procedure of Example 1, using 4-amino-1-phenyl-1H-pyrazolo[3,4-d]pyrimidine-3-carboxylic acid shown in Reference Example 12 instead of 4-amino-1-cyclopentyl-1H-pyrazolo[3,4-d]pyrimidine-3-carboxylic acid, the title compound (33%) was obtained.

Tables 11 to 34 show the structural formulae and physical properties of the compounds obtained in the Examples and Comparative Examples.

TABLE 11

| Ex. Cpd. | Structural Formula | Physical Properties |
|---|---|---|
| 1 | 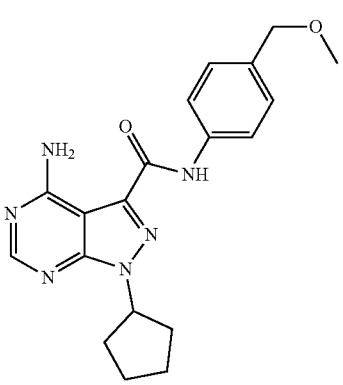 [SMILES: COCc1ccc(NC(=O)c2nn(C3CCCC3)c3ncnc(N)c23)cc1] | m/z [M + H]+ 367.1<br>1H-NMR (400 MHz, DMSO-d6) δppm: 10.36 (1H, s), 8.51 (1H, brs), 8.24 (1H, s), 8.09 (1H, brs), 7.78 (2H, d, J = 8.5 Hz), 7.32 (2H, d, J = 8.5 Hz), 5.25-5.22 (1H, m), 4.38 (2H, s), 3.28 (3H, s), 2.15-2.11 (4H, m), 1.98-1.94 (2H, m), 1.74-1.69 (2H, m). |

TABLE 11-continued

| Ex. Cpd. | Structural Formula | Physical Properties |
|---|---|---|
| 2 | | m/z [M + H]+ 354.4<br>1H-NMR (400 MHz, DMSO-d6) δppm: 10.04 (1H, s), 8.34 (1H, s), 8.11 (1H, s), 7.65 (2H, d, J = 8.3 Hz), 7.30 (2H, d, J = 8.3 Hz), 4.37 (2H, s), 3.27 (3H, s), 1.75 (9H, s). |
| 3 | | m/z [M + H]+ 383.9<br>1H-NMR (400 MHz, DMSO-d6) δppm: 10.35 (1H, s), 8.52 (1H, brs), 8.24 (1H, s), 8.09 (1H, brs), 7.75-7.72 (2H, m), 7.30 (2H, d, J = 8.5 Hz), 5.25-5.21 (1H, m), 3.68 (2H, s), 2.16-2.11 (4H, m), 1.96-1.91 (2H, m), 1.95 (3H, s), 1.71-1.67 (2H, m). |
| 4 | | m/z [M + H]+ 389.2<br>1H-NMR (400 MHz, DMSO-d6) δppm: 10.43 (1H, s), 8.50 (1H, s), 8.25 (1H, s), 8.10 (1H, s), 7.89-7.87 (2H, m), 7.73-7.69 (3H, m), 6.91 (1H, dd, J = 3.4, 0.7 Hz), 6.58 (1H, dd, J = 3.4, 1.7 Hz), 5.26-5.20 (1H, m), 2.18-2.13 (4H, m), 1.98-1.90 (2H, m), 1.74-1.69 (2H, m). |
| 5 | | m/z [M + H]+ 414.3<br>1H-NMR (400 MHz, DMSO-d6) δppm: 10.23 (1H, s), 8.61 (1H, s), 8.24 (1H, s), 8.18 (1H, s), 8.06 (1H, s), 7.65-7.61 (2H, m), 7.24-7.19 (2H, m), 7.10-704 (4H, m), 6.81-6.77 (1H, m), 5.25-5.21 (1H, m), 2.14-2.10 (4H, m), 1.96-1.93 (2H, m), 1.71-1.67 (2H, m). |

TABLE 11-continued

| Ex. Cpd. | Structural Formula | Physical Properties |
|---|---|---|
| 6 | | m/z [M + H]+ 393.2<br>1H-NMR (400 MHz, DMSO-d6) δppm: 10.24 (1H, s), 8.54 (1H, brs), 8.24 (1H, s), 8.08 (1H, brs), 7.68 (1H, s), 7.51 (1 H, dd, J = 8.0, 1.7 Hz), 7.20 (1H, d, J = 8.0 Hz), 5.25-5.21 (1H, m), 4.22-4.18 (1H, m), 3.25 (3H, s), 3.14-3.05 (2H, m), 2.86 (2H, td, J = 15.5, 3.6 Hz), 2.16-2.10 (4H, m), 1.96-1.93 (2H, m), 1.71-1.69 (2H, m). |
| 7 | | m/z [M + H]+ 349.2<br>1H-NMR (400 MHz, DMSO-d6) δppm: 10.39 (1H, s), 8.50 (1H, s), 8.24 (1H, s), 8.10 (1H, s), 7.80 (2H, d, J = 8.5 Hz), 7.48 (2H, d, J = 8.5 Hz), 6.71 (1H, dd, J = 17.6, 11.0 Hz), 5.79 (1H, d, J = 17.8 Hz), 5.25-5.20 (2H, m) 2.15-2.13 (4H, m), 1.96-1.92 (2H, m), 1.71-1.68 (2H, m). |
| 8 | | m/z [M + H]+ 357.1<br>1H-NMR (400 MHz, DMSO-d6) δppm: 10.50 (1H, s), 8.40 (1H, brs), 8.25 (1H, s), 8.11 (1H, brs), 7.98 (1H, t, J = 2.0 Hz), 7.80-7.78 (1H, m), 7.41 (1H, t, J = 8.0 Hz), 7.22 (1 H, dd, J = 7.7, 1.6 Hz), 5.26-5.22 (1H, m), 2.18-2.11 (4 H, m), 1.98-1.95 (2H, m), 1.72-1.69 (2H, m). |
| 9 | | m/z [M + H]+ 363.3<br>1H-NMR (400 MHz, DMSO-d6) δppm: 10.34 (1H, s), 8.51 (1H, s), 8.24 (1H, s), 8.09 (1H, s), 7.74 (2H, d, J = 8.5 Hz), 7.38 (2H, d, J = 8.8 Hz), 6.37 (1H, m), 6.29-6.23 (1H, m), 5.25-5.21 (1H, m), 2.15-2.11 (4H, m), 1.96-1.93 (2H, m), 1.84 (3H, dd, J = 6.6, 1.2 Hz), 1.71-1.69 (2H, m). |

TABLE 12
| | | |
|---|---|---|
| 10 | 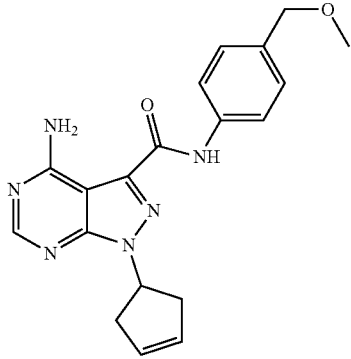 [SMILES: COCc1ccc(NC(=O)c2nn(C3CC=CC3)c3ncnc(N)c23)cc1] | m/z [M + H]+ 365.1<br>1H-NMR (400 MHz, DMSO-d6) δppm: 10.43 (1H, s), 8.51 (1H, br s), 8.25 (1H, s), 8.12 (1H, br s), 7.79-7.77 (2H, m), 7.31 (2H, d, J = 8.5 Hz), 5.82 (2H, s), 5.61-5.57 (1H, m), 4.38 (2H, s), 3.27 (3H, s), 2.99-2.86 (4H, m). |
| 11 | 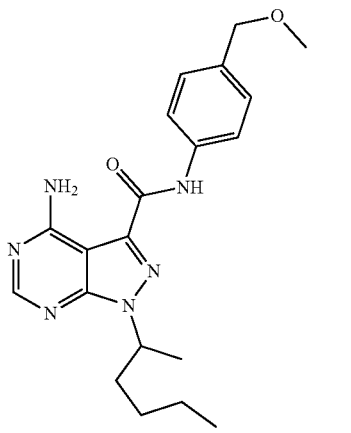 [SMILES: CCCCC(C)n1nc(C(=O)Nc2ccc(COC)cc2)c2c(N)ncnc21] | m/z [M + H]+ 381.1<br>1H-NMR (400 MHz, DMSO-d6) δppm: 10.35-10.31 (1H, m), 8.52 (1H, br s), 8.23 (1H, s), 8.10 (1H, br s), 7.78-7.73 (2H, m), 7.31 (2H, d, J = 8.4 Hz), 5.37-5.19 (1H, m), 4.37 (2H, s), 3.26 (3H, s), 2.29-1.18 (7H, m), 1.13-1.02 (3H, m). |
| 12 | 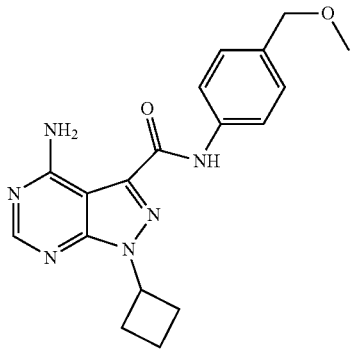 [SMILES: COCc1ccc(NC(=O)c2nn(C3CCC3)c3ncnc(N)c23)cc1] | m/z [M + H]+ 354.5<br>1H-NMR (400 MHz, DMSO-d6) δppm: 10.50 (1H, s), 8.51 (1H, br s), 8.24 (1H, s), 8.11 (1H, br s), 7.82-7.79 (2H, m), 7.33 (2H, d, J = 8.5 Hz), 5.36-5.34 (1H, m), 4.39 (2H, s), 3.28 (3H, s), 2.86-2.81 (2H, m), 2.46-2.38 (2H, m), 1.90-1.86 (2H, m). |
| 13 | 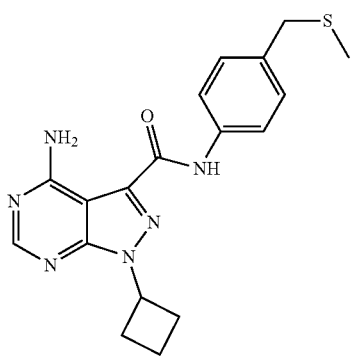 | m/z [M + H]+ 370.3<br>1H-NMR (400 MHz, DMSO-d6) δppm: 10.49 (1H, s), 8.52 (1H, br s), 8.24 (1H, s), 8.11 (1H, br s), 7.78-7.75 (2H, m), 7.31 (2H, d, J = 8.5 Hz), 5.38-5.34 (1H, m), 3.68 (2H, s), 2.86-2.79 (2H, m), 2.46-2.39 (2H, m), 1.96 (3H, s), 1.91-1.86 (2H, m). |

TABLE 12-continued

| | | |
|---|---|---|
| 14 | [structure: 4-amino-1-(3-methylcyclobutyl)-pyrazolo[3,4-d]pyrimidine-3-carboxamide with N-(4-(methoxymethyl)phenyl)] | m/z [M + H]+ 382.5<br>1H-NMR (400 MHz, DMSO-d6) δppm: 10.43 (1H, s), 8.49 (1H, br s), 8.24 (1H, s), 8.11 (1H, br s), 7.79 (2H, d, J = 8.5 Hz), 7.34 (2H, d, J = 8.3 Hz), 5.39-5.31 (1H, m), 4.39 (2H, s), 3.27 (3H, s), 2.67-2.62 (2H, m), 2.29-2.24 (2H, m), 1.28 (6H, s). |
| 15 | [structure: 4-amino-1-isopropyl-pyrazolo[3,4-d]pyrimidine-3-carboxamide with N-(4-((methylthio)methyl)phenyl)] | m/z [M + H]+ 357.8<br>1H-NMR (400 MHz, DMSO-d6) δppm: 10.40 (1H, s), 8.53 (1H, br s), 8.24 (1H, s), 8.09 (1H, brs), 7.75 (2H, d, J = 8.3 Hz), 7.30 (2H, d, J = 8.5 Hz), 5.10-5.07 (1H, m), 3.68 (2H, s), 1.95 (3H, s), 1.55 (6H, d, J = 6.6 Hz). |
| 16 | [structure: 4-amino-1-(pentan-3-yl)-pyrazolo[3,4-d]pyrimidine-3-carboxamide with N-(4-((methylthio)methyl)phenyl)] | m/z [M + H]+ 386.4<br>1H-NMR (400 MHz, DMSO-d6) δppm: 10.38 (1H, s), 8.56 (1H, brs), 8.23 (1H, s), 8.10 (1H, brs), 7.76 (2H, d, J = 8.5 Hz), 7.30 (2H, d, J = 8.5 Hz), 4.66-4.60 (1H, m), 3.68 (2H, s), 2.11-2.03 (2H, m), 1.95 (3H, s), 1.94-1.85 (2H, m), 0.67 (6H, t, J = 7.3 Hz). |
| 17 | [structure: 4-amino-1-cyclohexyl-pyrazolo[3,4-d]pyrimidine-3-carboxamide with N-(4-(methoxymethyl)phenyl)] | m/z [M + H]+ 381.1<br>1H-NMR (400 MHz, DMSO-d6) δppm: 10.38 (1H, s), 8.51 (1H, br s), 8.25 (1H, s), 8.07 (1H, br s), 7.80 (2H, d, J = 8.5 Hz), 7.32 (2H, d, J = 8.5 Hz), 4.73-4.68 (1H, m), 4.38 (2H, s), 3.29 (3H, s), 2.14-1.84 (6H, m), 1.76-1.69 (1H, m), 1.54-1.41 (2H, m), 1.33-1.22 (1H, m). |

TABLE 12-continued
| 18 | 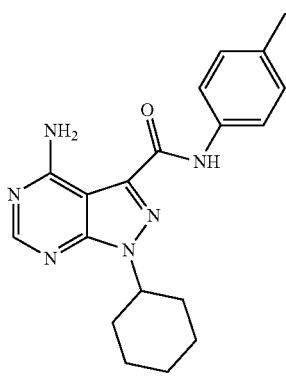 | m/z [M + H]+ 397.2<br>1H-NMR (400 MHz, DMSO-d6) δppm: 10.39 (1H, s), 8.53 (1H, brs), 8.24 (1H, s), 8.10 (1H, brs), 7.77-7.75 (2H, m), 7.30 (2H, d, J = 8.5 Hz), 4.73-4.67 (1H, m), 3.68 (2H, s), 2.09-1.86 (6H, m), 1.95 (3H, s), 1.73-1.70 (1H, m), 1.48-1.42 (2H, m), 1.28-1.22 (1H, m). |
TABLE 13
| 19 | 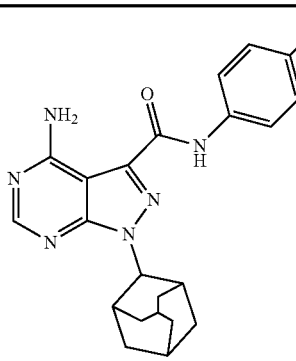 | m/z [M + H]+ 433.5<br>1H-NMR (400 MHz, DMSO-d6) δppm: 10.21 (1H, s), 8.52 (1H, brs), 8.23 (1H, s), 8.08 (1H, brs), 7.73 (2H, d, J = 8.5 Hz), 7.33 (2H, d, J = 8.5 Hz), 4.88 (1H, s), 4.39 (2H, s) 3.28 (3H, s), 2.70 (2H, m), 2.34-2.31 (2H, m), 2.00-1.90 (6H, m), 1.78 (2H, brs), 1.61-1.58 (2H, m). |
| 20 | 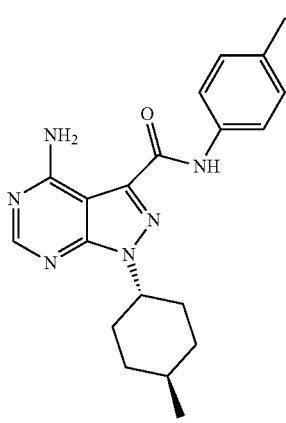 | m/z [M + H]+ 395.0<br>1H-NMR (400 MHz, DMSO-d6) δppm: 10.40 (1H, s), 8.52 (1H, brs), 8.24 (1H, s), 8.09 (1H, brs), 7.79 (2H, d, J = 8.5 Hz), 7.31 (2H, d, J = 8.3 Hz), 4.70-4.64 (1H, m), 4.38 (2H, s), 3.28 (3H, s), 2.16-2.06 (2H, m), 1.95-1.92 (2H, m), 1.84-1.81 (2H, m) 1.49-1.48 (1H, m), 1.22-1.13 (2H, m), 0.93 (3H, d, J = 6.6 Hz). |
| 21 | 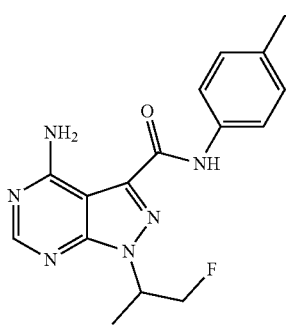 | m/z [M + H]+ 359.1<br>1H-NMR (400 MHz, DMSO-d6) δppm: 10.47 (1H, s), 8.52 (1H, brs), 8.26 (1H, s), 8.16 (1H, brs), 7.79 (2H, d, J = 8.5 Hz), 7.33 (2H, d, J = 8.5 Hz), 5.28-5.26 (1H, m), 5.05-4.73 (2H, m), 4.39 (2H, s), 3.28 (3H, s), 1.50 (3H, dd, J = 7.0, 1.3 Hz). |

TABLE 13-continued
| | | |
|---|---|---|
| 22 | 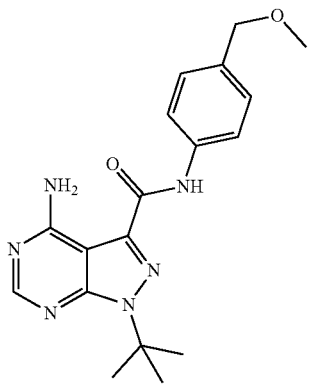 [SMILES: COCc1ccc(NC(=O)c2nn(C(C)(C)C)c3ncnc(N)c23)cc1] | m/z [M+H]+ 355.2<br>1H-NMR (400 MHz, DMSO-d6) δppm: 1H-NMR (DMSO-D6) δppm: 10.24 (1H, s), 8.52 (1H, br s), 8.22 (1H, s), 8.01 (1H, br s), 7.75 (2H, d, J = 8.4 Hz), 7.31 (2H, d, J = 8.4 Hz), 4.37 (2H, s), 3.27 (3H, s), 1.77 (9H, s). |
| 23 | 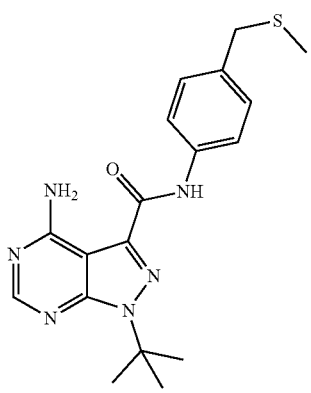 [SMILES: CSCc1ccc(NC(=O)c2nn(C(C)(C)C)c3ncnc(N)c23)cc1] | m/z [M + H]+ 371.2<br>1H-NMR (400 MHz, DMSO-d6) δppm: 10.22 (1H, s), 8.52 (1H, br s), 8.22 (1H, s), 8.00 (1H, br s), 7.70 (2H, d, J = 8.4 Hz), 7.29 (2H, d, J = 8.4 Hz), 3.66 (2H, s), 3.30 (3H, s), 1.77 (9H, s). |
| 24 | 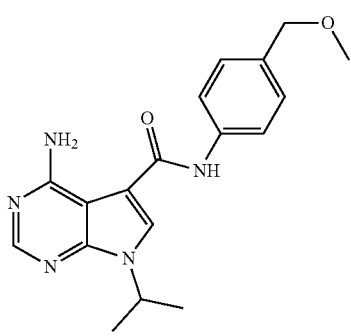 [SMILES: COCc1ccc(NC(=O)c2cn(C(C)C)c3ncnc(N)c23)cc1] | m/z [M + H]+ 341.3<br>1H-NMR (400 MHz, DMSO-d6) δppm: 10.02 (1H, s) 8.38 (1H, s), 8.12 (1H, s), 7.67 (2H, d, J = 8.4 Hz), 7.30 (2H, d, J = 8.4 Hz), 4.96-4.93 (1H, m), 4.36 (2H, s), 3.27 (3H, s), 1.48 (6H, d, J = 6.4 Hz) |
| 25 | 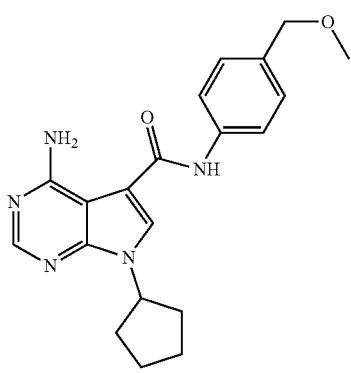 [SMILES: COCc1ccc(NC(=O)c2cn(C3CCCC3)c3ncnc(N)c23)cc1] | m/z [M + H]+ 366.3<br>1H-NMR (400 MHz, DMSO-d6) δppm: 10.01 (1H, s) 8.34 (1H, s), 8.11 (1H, s), 7.66 (2H, d, J = 8.4 Hz), 7.30 (2H, d, J = 8.8 Hz), 5.10-5.06 (1H, m), 4.37 (2H, s), 3.27 (3H, s), 2.18-2.14 (2H, m), 1.91-1.83 (4H, m), 1.73-1.71 (2H, m) |

TABLE 13-continued

| | | |
|---|---|---|
| 26 | [structure] | m/z [M + H]+ 373.5<br>1H-NMR (400 MHz, DMSO-d6) δppm: 10.10 (1H, s), 8.34 (1H, s), 8.11 (1H, s), 7.66 (2H, d, J = 8.4 Hz), 7.30 (2H, d, J = 8.8 Hz), 5.02 (2H, d, J = 47.3 Hz), 4.36 (2H, s), 3.27 (3H, s), 1.74 (6H, s) |
| 27 | [structure] | m/z [M + H]+ 352.2<br>1H-NMR (400 MHz, DMSO-d6) δppm: 9.98 (s, 1H) 8.32 (s, 1H), 8.11 (s, 1H), 7.55 (d, J = 8.5 Hz, 2H), 7.16 (d, J = 8.5 Hz, 2H), 2.53-2.49 (m, 2H), 1.74 (s, 9H), 1.59-1.53 (m, 2H), 0.87 (t, J = 7.3 Hz, 3H), |

TABLE 14

| | | |
|---|---|---|
| 28 | [structure] | m/z [M + H]+ 402.2<br>1H-NMR (400 MHz, DMSO-d6) δppm: 9.96 (1H, s), 9.01 (1H, s), 8.33 (1H, s), 8.17-8.12 (4H, m), 7.66 (2H, d, J = 9.0 Hz), 7.56-7.51 (3H, m), 6.80 (1H, d, J = 8.3 Hz), 6.70 (1H, td, J = 5.0, 2.4 Hz), 1.74 (9H, s). |
| 29 | [structure] | m/z [M + H]+ 370.3<br>1H-NMR (400 MHz, DMSO-d6) δppm: 10.05 (1H, s), 8.34 (1H, s), 8.12 (1H, s), 7.61 (2H, d, J = 8.4 Hz), 7.28 (2H, d, J = 8.5 Hz), 3.67 (2H, s), 1.95 (3H, s), 1.74 (9H, s). |

TABLE 14-continued
| 30 | 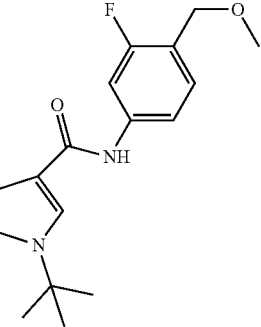 | m/z [M + H]+ 372.3<br>1H-NMR (400 MHz, DMSO-d6) δppm: 10.19 (1H, s), 8.34 (1H, s), 8.12 (1H, s), 7.65 (1H, dd, J = 12.7, 2.0 Hz), 7.46-7.37 (2H, m), 4.40 (2H, s), 3.28 (3H, s), 1.74 (9H, s). |
| --- | --- | --- |
| 31 | 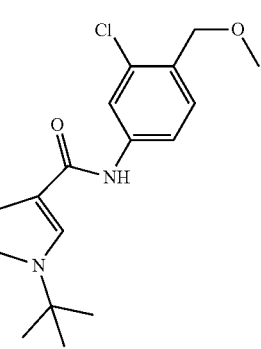 | m/z [M + H]+ 388.1<br>1H-NMR (400 MHz, DMSO-d6) δppm: 10.15 (1H, s), 8.35 (1H, s), 8.12 (1H, s), 7.86 (1H, d, J = 2.0 Hz), 7.65 (1H, dd, J = 8.4, 2.1 Hz), 7.45 (1H, d, J = 8.3 Hz), 4.44 (2H, s), 3.33 (3H, s), 1.74 (9H, s). |
| 32 | 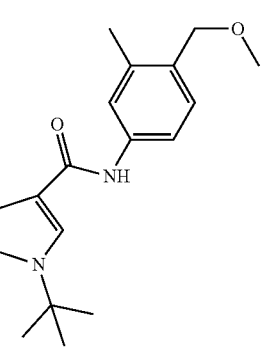 | m/z [M + H]+ 368.3<br>1H-NMR (400 MHz, DMSO-d6) δppm: 9.97 (1H, s), 8.34 (1H, s), 8.11 (1H, s), 7.50-7.49 (2H, m), 7.26-7.23 (1H, m), 4.36 (2H, s), 3.28 (3H, s), 2.27 (3H, s), 1.74 (9H, s). |
| 33 | 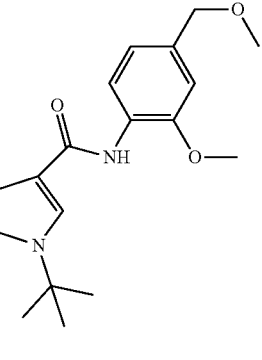 | m/z [M + H]+ 384.3<br>1H-NMR (400 MHz, DMSO-d6) δppm: 9.56 (1H, s), 8.36 (1H, s), 8.10 (1H, s), 7.44 (1H, d, J = 8.0 Hz), 7.03 (1H, d, J = 1.2 Hz), 6.90 (1H, dd, J = 8.2, 1.1 Hz), 4.40 (2H, s), 3.81 (3H, s), 3.30 (3H, s), 1.73 (9H, s). |

TABLE 14-continued
| | | |
|---|---|---|
| 34 | 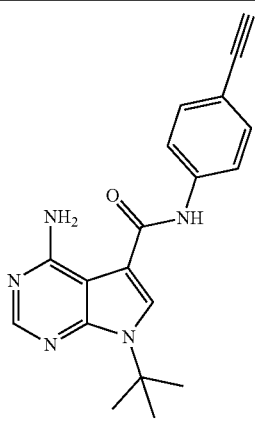 | m/z [M + H]+ 334.1<br>1H-NMR (400 MHz, DMSO-d6) δppm: 10.16 (1 H, s) 8.36 (1 H, s) 8.13 ( 1H, s) 7.82-7.67 (2 H, m) 7.53-7.43 (2 H, m) 4.13 (1 H, s) 1.76 (9 H, s) |
| 35 | 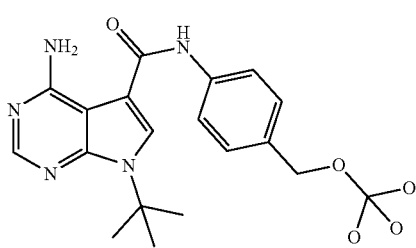 | m/z [M + H]+ 357.2<br>1H-NMR (400 MHz, DMSO-d6) δppm: 10.06 (1 H, s) 8.35 (1 H, s) 8.12 (1 H, s) 7.74-7.57 (2 H, m) 7.31 (2 H, d, J = 8.54 Hz) 4.37 (2 H, s) 1.75 (9 H, s) |
| 36 | 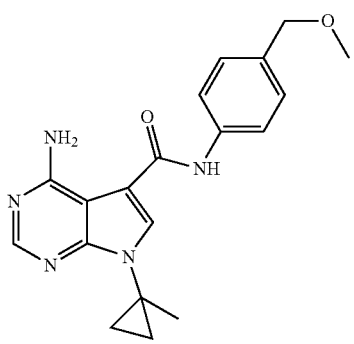 [SMILES: COCc1ccc(NC(=O)c2cn(C3(C)CC3)c3ncnc(N)c23)cc1] | m/z [M + H]+ 353.4<br>1H-NMR (400 MHz, DMSO-d6) δppm 10.01 (1H, s), 8.29 (1H, s), 8.14 (1H, s), 7.69 (2H, d, J = 8.4 Hz) 7.29 (2H, d, J = 8.8 Hz), 4.36 (2H, s), 3.27 (3H, s), 1.56 (3H, s), 1.16 (2H, m), 1.01 (2H, m) |
TABLE 15
| | | |
|---|---|---|
| 37 | 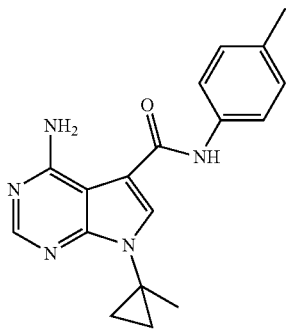 | m/z [M + H]+ 368.9<br>1H-NMR (400 MHz, DMSO-d6) δppm: 10.01 (1H, s), 8.29 (1H, s), 8.14 (1H, s), 7.62 (2H, d, J = 8.5 Hz), 7.27 (2H, d, J = 8.5 Hz), 3.66 (2H, s), 1.94 (3H, s), 1.55 (3H, s), 1.16 (2H, m), 1.01 (2H, m). |

TABLE 15-continued
| | | |
|---|---|---|
| 38 | 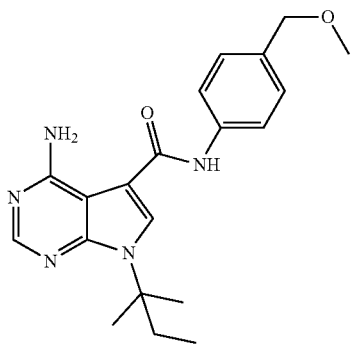 [SMILES: CCC(C)(C)n1cc(C(=O)Nc2ccc(COC)cc2)c2c(N)ncnc21] | m/z [M + H]+ 369.3<br>1H-NMR (400 MHz, DMSO-d6) δppm: 10.05 (1H, s), 8.30 (1H, s), 8.09 (1H, s), 7.65 (2H, d, J = 8.5 Hz), 7.30, (2H, d, J = 8.5 Hz), 4.36 (2H, s), 3.27 (3H, s), 2.23 (2H, q, J = 7.4 Hz), 1.70 (6H, t, J = 7.9 Hz), 0.56 (3H, t, J = 7.4 Hz). |
| 39 | 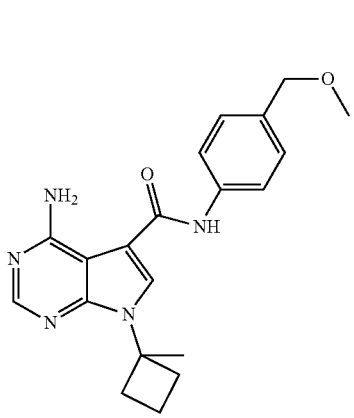 [SMILES: COCc1ccc(NC(=O)c2cn(C3(C)CCC3)c3ncnc(N)c23)cc1] | m/z [M + H]+ 367.2<br>1H-NMR (400 MHz, DMSO-d6) δppm: 10.02 (1H, s), 8.23 (1H, s), 8.08 (1H, s), 7.66 (2H, d, J = 8.5 Hz), 7.29 (2H, d, J = 8.3 Hz), 4.36 (2H, s), 3.27 (3H, s), 2.72-2.64 (2H, m), 2.40-2.35 (2H, m) 2.07-2.00 (1H, m), 1.90-1.88 (1H, m), 1.67 (3H, s). |
| 40 | 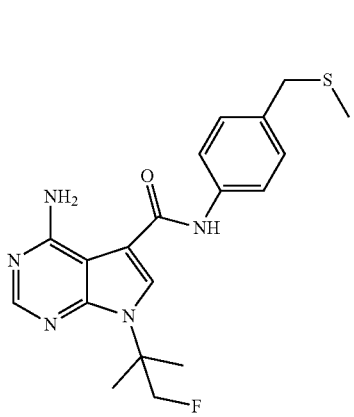 [SMILES: CSCc1ccc(NC(=O)c2cn(C(C)(C)CF)c3ncnc(N)c23)cc1] | m/z [M + H]+ 388.3<br>1H-NMR (400 MHz, DMSO-d6) δppm: 10.09 (1H, s) 8.33 (1H, s), 8.11 (1H, s), 7.63-7.61 (2H, m), 7.28 (2H, d, J = 8.4 Hz), 5.02 (2H, d, J = 47.3 Hz), 3.66 (2H, s), 1.95 (3H, s), 1.74 (6H, br s) |
| 41 | 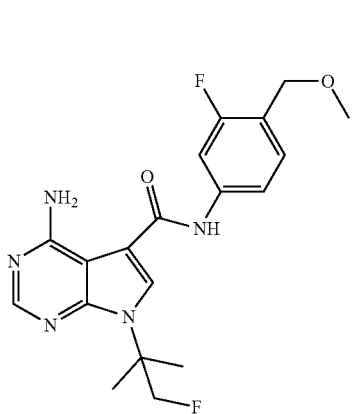 [SMILES: COCc1ccc(NC(=O)c2cn(C(C)(C)CF)c3ncnc(N)c23)cc1F] | m/z [M + H]+ 390.1<br>1H-NMR (400 MHz, DMSO-d6) δppm: 10.24 (1H, s), 8.33 (1H, s), 8.12 (1H, s), 7.67-7.64 (1H, m), 7.47-7.37 (2H, m), 5.02 (2H, d, J = 47.1 Hz), 4.40 (2H, s), 3.27 (3H, s), 1.74 (6H, s). |

TABLE 15-continued
| | | |
|---|---|---|
| 42 | 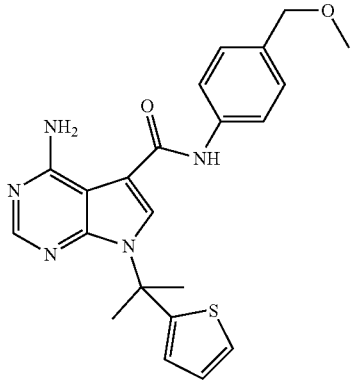 [SMILES: COCc1ccc(NC(=O)c2cn(C(C)(C)c3cccs3)c3ncnc(N)c23)cc1] | m/z [M + H]+ 422.2<br>1H-NMR (400 MHz, DMSO-d6) δppm: 10.14, (1H, s), 8.46 (1H, s), 7.98 (1H, s), 7.67-7.65 (2H, m), 7.34-7.30 (3H, m), 6.92-6.90 (2H, m), 4.37 (2H, s), 3.27 (3H, s), 2.19 (6H, s). |
| 43 | 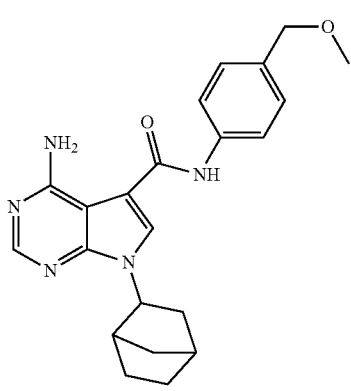 [SMILES: COCc1ccc(NC(=O)c2cn(C3CC4CCC3C4)c3ncnc(N)c23)cc1] | m/z [M + H]+ 393.5<br>1H-NMR (400 MHz, DMSO-d6) δppm: 10.01 (1H, s), 8.41 (1H, s), 8.11 (1H, s), 7.66-7.63 (2H, m), 7.30 (2H, d, J = 8.5 Hz), 4.67-4.64 (1H, m), 4.37 (2H, s), 3.27 (3H, s), 2.45 (1H, m), 2.36 (1H, m), 2.02-1.96 (1H, m), 1.86-1.83 (1H, m), 1.78-1.76 (1H, m), 1.61-1.54 (2H, m), 1.39-1.37 (1H, m), 1.30-1.28 (2H, m). |
| 44 | 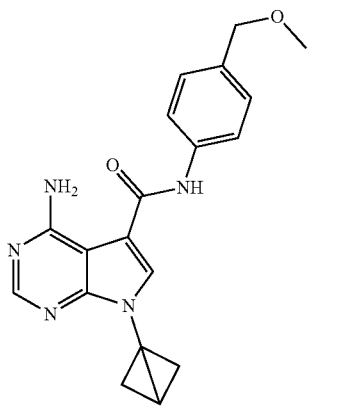 | m/z [M + H]+ 364.0<br>1H-NMR (400 MHz, DMSO-d6) δppm: 10.06 (1H, s), 8.22 (1H, s), 8.12 (1H, s), 7.66 (2H, d, J = 8.5 Hz), 7.30 (2H, d, J = 8.5 Hz), 4.37 (2H, s), 3.27 (3H, s), 2.70 (1H, s), 2.41 (6H, s). |
| 45 | 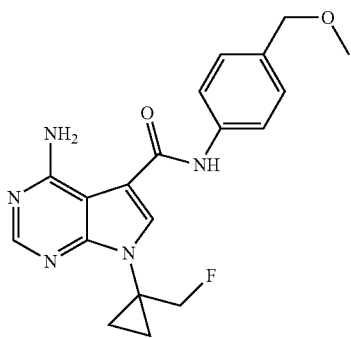 [SMILES: COCc1ccc(NC(=O)c2cn(C3(CF)CC3)c3ncnc(N)c23)cc1] | m/z [M + H]+ 370.3<br>1H-NMR (400 MHz, DMSO-d6) δppm: 10.07 (1H, s), 8.33 (1H, s), 8.15 (1H, s), 7.67 (2H, d, J = 8.3 Hz), 7.29 (2H, d, J = 8.5 Hz), 4.71-4.59 (2H, m), 4.36 (2H, s), 3.27 (3H, s), 1.32 (4H, m). |

TABLE 16

| | | |
|---|---|---|
| 46 | [structure] | m/z [M + H]+ 388.1<br>1H-NMR (400 MHz, DMSO-d6) δppm: 10.11 (1H, s), 8.34 (1H, s), 8.14 (1H, s), 7.68 (2H, d, J = 8.5 Hz), 7.30 (2H, d, J = 8.5 Hz), 6.29-6.01 (1H, m), 4.36 (2H, s), 3.27 (3H, s), 1.51-1.45 (4H, m). |
| 47 | [structure] | m/z [M + H]+ 366.3<br>1H-NMR (400 MHz, DMSO-d6) δppm: 10.01 (1H, s), 8.29 (1H, s), 8.14 (1H, s), 7.67 (2H, d, J = 8.3 Hz), 7.29 (2H, d, J = 8.5 Hz), 4.36 (2H, s), 3.27 (3H, s), 1.84-1.80 (2H, m), 1.13-1.11 (2H, m), 1.03-1.02 (2H, m), 0.78 (3H, t, J = 7.3 Hz). |
| 48 | [structure] | m/z [M + H]+ 370.1<br>1H-NMR (400 MHz, DMSO-d6) δppm: 10.16 (1H, s), 8.29 (1H, s), 8.14 (1H, s), 7.66 (1H, dd, J = 12.6, 1.8 Hz), 7.46 (1H, dd, J = 8.4, 1.8 Hz), 7.38 (1H, t, J = 8.3 Hz), 4.39 (2H, s), 3.27 (3H, s), 1.55 (3H, s), 1.18-1.16 (2H, m), 1.03-1.00 (2H, m). |
| 49 | [structure] | m/z [M + H]+ 378.2<br>1H-NMR (400 MHz, DMSO-d6) δppm: 10.00 (1H, s), 8.28 (1H, s), 8.12 (1H, s), 7.66 (2H, d, J = 8.5 Hz), 7.29 (2H, d, J = 8.5 Hz), 4.36 (2H, s), 3.26 (3H, s), 1.55 (1H, m), 1.11-1.08 (2H, m), 0.98-0.95 (2H, m), 0.40-0.37 (2H, m), 0.34-0.31 (2H, m). |

TABLE 16-continued
| 50 | 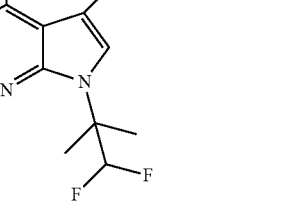 | m/z [M+ H]+ 390.2<br>1H-NMR (400 MHz, DMSO-d6) δppm: 10.12 (1H, s), 8.37 (1H, s), 8.12 (1H, s), 7.65 (2H, d, J = 8.3 Hz), 7.31 (2H, d, J = 8.3 Hz), 7.19-6.91 (1H, m), 4.37 (2H, s), 3.27 (3H, s), 1.80 (6H, s). |
| --- | --- | --- |
| 51 | 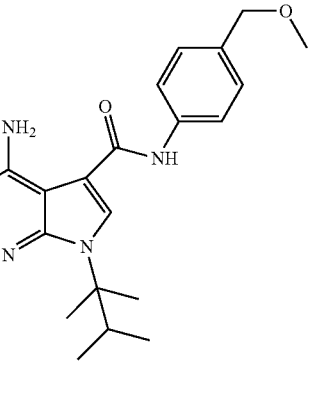 | m/z [M + H]+ 382.2<br>1H-NMR (400 MHz, DMSO-d6) δppm: 10.04 (1H, s), 8.31 (1H, s), 8.07 (1H, s), 7.65 (2H, d, J = 8.5 Hz), 7.30 (2H, d, J = 8.5 Hz), 4.36 (2H, s), 3.27 (3H, s), 3.23-3.17 (1H, m), 1.67 (6H, s), 0.70 (6H, d, J = 6.8 Hz). |
| 52 | 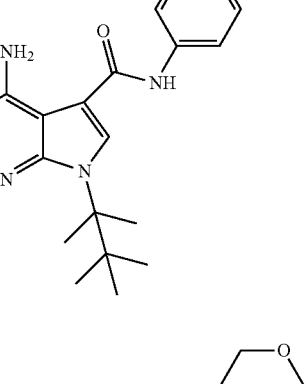 | m/z [M + H]+ 396.2<br>1H-NMR (400 MHz, DMSO-d6) δppm: 10.01 (1H, s), 8.39 (1H, s), 8.05 (1H, s), 7.64 (2H, d, J = 8.5 Hz), 7.30 (2H, d, J = 8.5 Hz), 4.36 (2H, s), 3.27 (3H, s), 1.85 (6H, s), 0.91 (9H, s). |
| 53 | 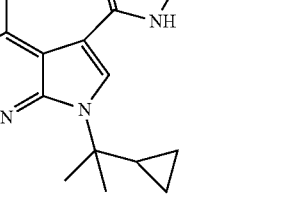 | m/z [M + H]+ 380.2<br>1H-NMR (400 MHz, DMSO-d6) δppm: 10.08 (1H, s), 8.41 (1H, s), 8.10 (1H, s), 7.64 (2H, d, J = 8.3 Hz), 7.29 (2H, d, J = 8.3 Hz), 4.36 (2H, s), 3.27 (3H, s), 1.86-1.81 (1H, m), 1.62 (6H, s), 0.56-0.47 (4H, m). |

TABLE 16-continued
| | | |
|---|---|---|
| 54 | 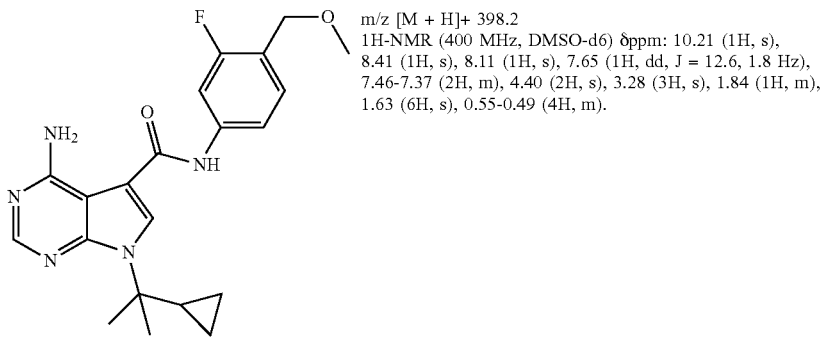 | m/z [M + H]+ 398.2<br>1H-NMR (400 MHz, DMSO-d6) δppm: 10.21 (1H, s), 8.41 (1H, s), 8.11 (1H, s), 7.65 (1H, dd, J = 12.6, 1.8 Hz), 7.46-7.37 (2H, m), 4.40 (2H, s), 3.28 (3H, s), 1.84 (1H, m), 1.63 (6H, s), 0.55-0.49 (4H, m). |
TABLE 17
| | | |
|---|---|---|
| 55 | | m/z [M + H]+ 432.0<br>1H-NMR (400 MHz, CDCl3) δppm: 8.51 (1 H, s) 8.34 (1 H, s) 7.62 (2 H, d, J = 8.29 Hz) 7.3 (2 H, d, J = 8.29 Hz) 4.47 (2 H, s) 3.40 (3 H, s) 1.61 (3 H, s) 1.38-1.10 (4 H, m) |
| | 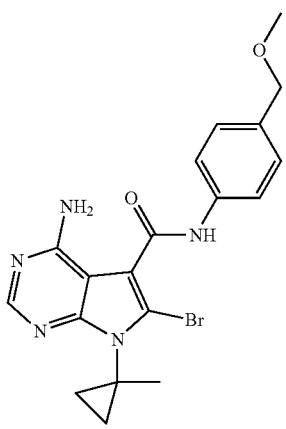 [SMILES: COCc1ccc(NC(=O)c2c(Br)n(C3(C)CC3)c3ncnc(N)c23)cc1] | |
| 56 | | m/z [M + H]+ 386.1<br>1H-NMR (400 MHz, CDCl3) δppm: 8.50 (1 H, s) 8.35 (1 H, s) 7.56-7.66 (2 H, m) 7.38 (2 H, d, J = 8.29 Hz) 4.47 (2 H, s) 3.40 (3 H, s) 1.60 (3 H, s) 1.51-1.14 (4 H, m) |
| | 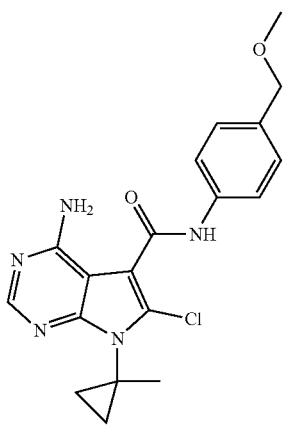 | |

TABLE 17-continued
| | | |
|---|---|---|
| 57 | 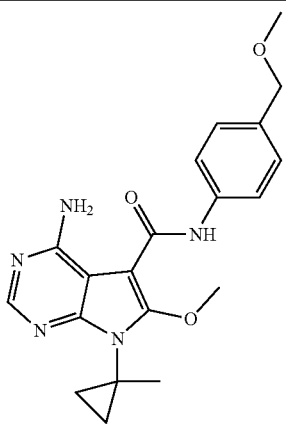 | m/z [M + H]+ 382.2<br>1H-NMR (400 MHz, DMSO-d6) δppm: 9.62 (1 H, s) 8.15 (1 H, s) 7.68 (2 H, d, J = 8.29 Hz) 7.53 (2 H, br s) 7.30 (2 H, d, J = 8.29 Hz) 4.38 (2 H, s) 4.15 (3 H, s) 3.28 (3 H, s) 1.57 (3 H, s) 1.24 -1.13 (2 H, m) 1.13-1.00 (2 H, m) |
| 58 | 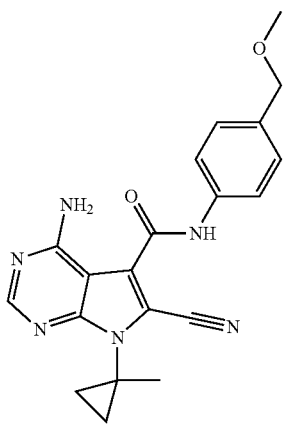 [SMILES: COCc1ccc(NC(=O)c2c(C#N)n(C3(C)CC3)c3ncnc(N)c23)cc1] | m/z [M + H]+ 377.2<br>1H-NMR (400 MHz, DMSO-d6) δppm: 10.79 (1 H, s) 8.32 (1 H, s) 7.66 (2 H, d, J = 8.54 Hz) 7.59 (2 H, br s) 7.36 (2 H, d, J = 8.54 Hz) 4.40 (2 H, s) 3.29 (3 H, s) 1.58 (3 H, s) 1.40-1.27 (2 H, m) 1.25-1.12 (2 H, m) |
| 59 | 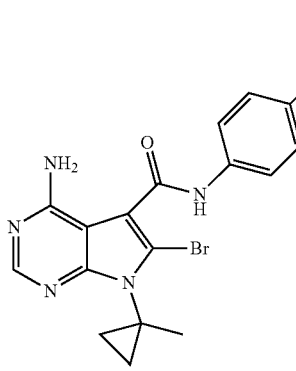 | m/z [M + H]+ 448.0<br>1H-NMR (400 MHz, CDCl3) δppm: 8.48 (1 H, s) 8.34 (1 H, s) 7.59 (2 H, d, J = 8.54 Hz) 7.35 (2 H, d, J = 8.29 Hz) 7.05 (2 H, br s) 3.69 (2 H, s) 2.02 (3 H, s) 1.60 (3 H, s) 1.38-1.12 (4 H, m) |
| 60 | 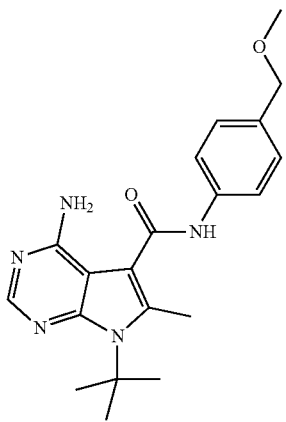 [SMILES: COCc1ccc(NC(=O)c2c(C)n(C(C)(C)C)c3ncnc(N)c23)cc1] | m/z [M + H]+ 368.2<br>1H-NMR (400 MHz, CDCl3) δppm: 8.26 (1 H, s) 7.58 (2 H, br d, J = 7.80 Hz) 7.45 (1 H, s) 7.37 (2 H, br d, J = 7.80 Hz) 6.12 (2 H, br s) 4.46 (2 H, s) 3.40 (3 H, s) 2.83 (3 H, s) 1.93 (9 H, s) |

TABLE 17-continued
| | | |
|---|---|---|
| 61 | 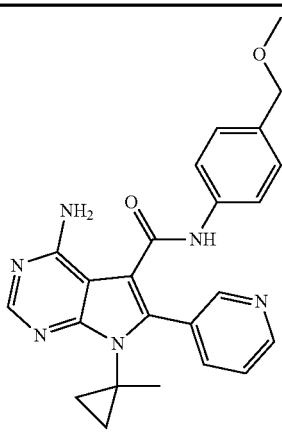 | m/z [M + H]+ 429.1<br>1H-NMR (400 MHz, DMSO-d6) δppm: 9.28 (1 H, s) 8.74-8.69 (1 H, m) 8.66-8.61 (1 H, m) 8.26 (1 H, s) 8.05-7.96 (1 H, m) 7.58-7.50 (1 H, m) 7.27-7.13 (6 H, m) 4.30 (2 H, s) 3.23 (3 H, s) 1.66 (3 H, s) 0.92-0.63 (4 H, m) |
| 62 | 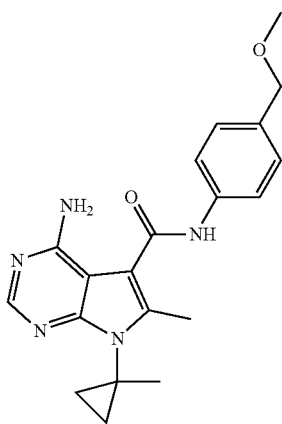 [SMILES: COCc1ccc(NC(=O)c2c(C)n(C3(C)CC3)c3ncnc(N)c23)cc1] | m/z [M + H]+ 366.2<br>1H-NMR (400 MHz, CDCl3) δppm: 8.35 (1 H, s) 7.56 (2 H, d, J = 8.54 Hz) 7.45 (1 H, br s) 7.37 (2 H, d, J = 8.29 Hz) 6.56<br>(2 H, br s) 4.46 (2 H, s) 3.40 (3 H, s) 2.84 (3 H, s) 1.56 (3 H, s) 1.33-1.12 (4 H, m) |
| 63 | 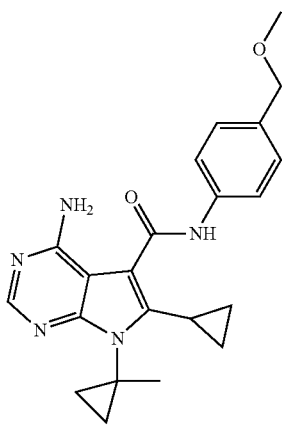 [SMILES: COCc1ccc(NC(=O)c2c(C3CC3)n(C3(C)CC3)c3ncnc(N)c23)cc1] | m/z [M + H]+ 392.3<br>1H-NMR (400 MHz, CDCl3) δppm: 8.36 (1 H, s) 8.12 (1 H, s) 7.62 (2 H, br d, J = 8.05 Hz) 7.38 (2 H, d, J = 8.54 Hz) 4.46 (2 H, s) 3.41 (3 H, s) 2.14-2.05 (1 H, m) 1.65 (3 H, s) 1.39-1.00 (8 H, m) |

TABLE 18
| | | |
|---|---|---|
| 64 | 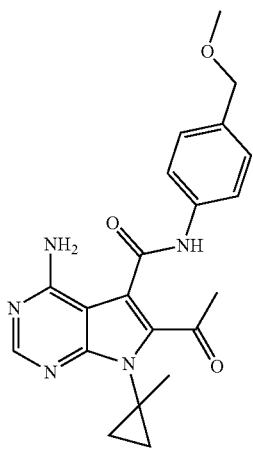 [SMILES: COCc1ccc(NC(=O)c2c(C(C)=O)n(C3(C)CC3)c3ncnc(N)c23)cc1] | m/z [M + H]+ 394.1<br>1H-NMR (400 MHz, CDCl3) δppm: 9.77 (1 H, s) 8.44 (1 H, s) 7.69-7.64 (2 H, m) 7.38-7.33 (2 H, m) 7.07-7.03 (2 H, m) 4.46 (2 H, s) 3.39 (3 H, s) 2.82 (3 H, s) 1.90 (3 H, s) 1.18-1.05 (4 H, m) |
| 65 | 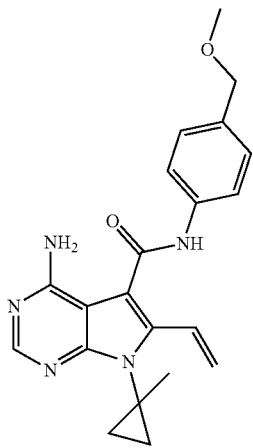 [SMILES: C=Cc1c(C(=O)Nc2ccc(COC)cc2)c2c(N)ncnc2n1C1(C)CC1] | m/z [M + H]+ 378.3<br>1H-NMR (400 MHz, CDCl3) δppm: 8.36 (1 H, s) 8.02 (1 H, s) 7.53 (2 H, d, J = 8.54 Hz) 7.38-7.33 (2 H, m) 7.19-7.08 (1 H, m) 6.00-5.89 (2 H, m) 4.45 (2 H, s) 3.40 (3 H, s) 1.59 (3 H, s) 1.32-1.08 (4 H, m) |
| 66 | 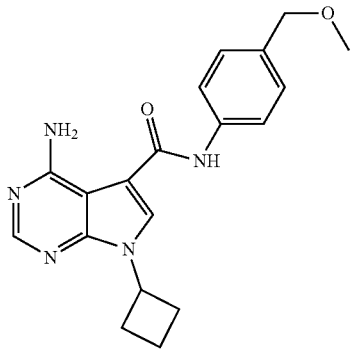 [SMILES: COCc1ccc(NC(=O)c2cn(C3CCC3)c3ncnc(N)c23)cc1] | m/z [M + H]+ 353.2<br>1H-NMR (400 MHz, DMSO-d6) δppm: 10.06 (1H, s), 8.52 (1H, s), 8.11 (1H, s), 7.68 (2H, d, J = 8.5 Hz), 7.31 (2H, d, J = 8.5 Hz), 5.18 (1H, m), 4.37 (2H, s), 3.28 (3H, s), 2.50-2.45 (4H, m), 1.90-1.86 (2H, m). |
| 67 | 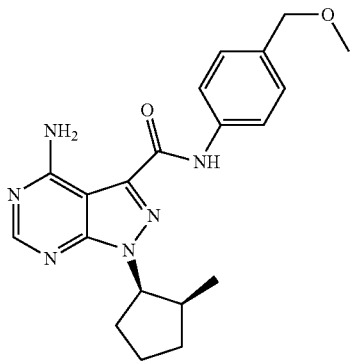 [SMILES: COCc1ccc(NC(=O)c2nn([C@@H]3CCC[C@@H]3C)c3ncnc(N)c23)cc1] | m/z [M + H]+ 381.4<br>1H-NMR (400 MHz, DMSO-d6) δppm: 10.22 (1H, s), 8.51 (1H, br s), 8.24 (1H, s), 8.07 (1H, brs), 7.76 (2H, d, J = 8.3 Hz), 7.30 (2H, m), 5.30-5.27 (1H, m), 4.39 (2H, s), 3.28 (3H, s), 2.36-1.22 (7H, m), 0.47 (2H, d, J = 6.8 Hz). |

TABLE 18-continued
| | | |
|---|---|---|
| 68 | 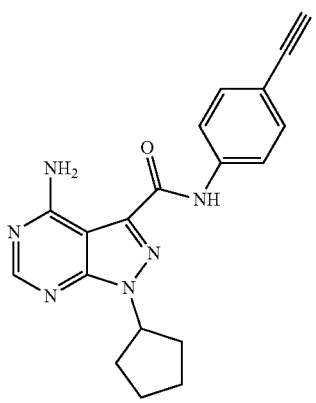 [SMILES: C#Cc1ccc(NC(=O)c2nn(C3CCCC3)c3ncnc(N)c23)cc1] | m/z [M + H]+ 347.3<br>1H-NMR (400 MHz, DMSO-d6) δppm: 10.48 (1H, s), 8.42 (1H, brs), 8.24 (1H, s), 8.08 (1H, brs), 7.86-7.83 (2H, m), 7.58 (1H, m), 7.50-7.47 (2H, m), 5.25-5.21 (1H, m), 2.14-2.07 (4H, m), 1.96-1.92 (2H, m), 1.71-1.68 (2H, m). |
| 69 | 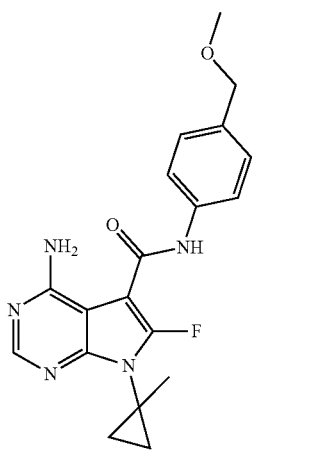 [SMILES: COCc1ccc(NC(=O)c2c(F)n(C3(C)CC3)c3ncnc(N)c23)cc1] | m/z [M + H]+ 370.3<br>1H-NMR (400 MHz, DMSO-d6) δppm: 9.94 (1 H, s) 8.19 (1 H, s) 7.71-7.53 (2 H, m) 7.44 (2 H, br s) 7.31 (2 H, d, J = 8.54 Hz) 4.38 (2 H, s) 3.28 (3 H, s) 1.52 (3 H, s) 1.31-1.13 (2 H, m) 1.12-1.03 (2 H, m) |
| 70 | 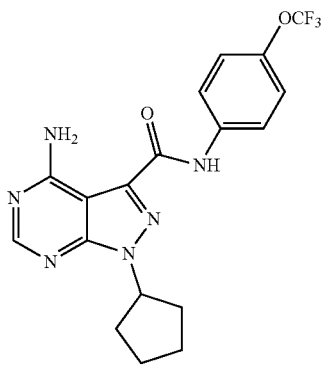 [SMILES: Nc1ncnc2c1c(C(=O)Nc1ccc(OC(F)(F)F)cc1)nn2C1CCCC1] | m/z [M + H]+ 407.4<br>1H-NMR (400 MHz, DMSO-d6) δppm: 10.54 (1H, s), 8.44 (1H, brs), 8.24 (1H, s), 8.08 (1H, brs), 7.93-7.89 (2H, m), 7.38 (2H, d, J = 8.8 Hz), 5.27-5.19 (1H, m), 2.18-2.11 (4H, m), 1.99-1.89 (2H, m), 1.74-1.68 (2H, m). |
| 71 | 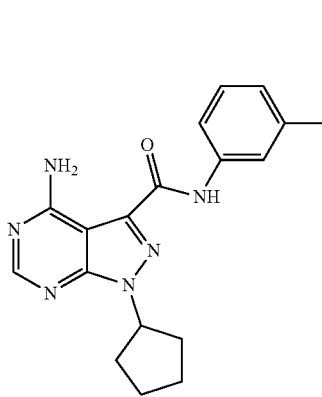 | m/z [M + H]+ 413.2<br>1H-NMR (400 MHz, DMSO-d6) δppm: 10.28 (1H, s), 8.48 (1H, brs), 8.23 (1H, s), 8.04 (1H, brs), 7.65-7.54 (3H, m), 7.31-7.23 (4H, m), 7.20-7.15 (1H, m), 7.04-7.02 (1H, m), 5.24-5.20 (1H, m), 3.94 (2H, s), 2.14-2.09 (4H, m), 1.95-1.91 (2H, m), 1.71-1.68 (2H, m). |

TABLE 18-continued

| 72 | [structure: 4-amino-N-(4-(oxazol-2-yl)phenyl)-1-cyclopentyl-1H-pyrazolo[3,4-d]pyrimidine-3-carboxamide] | m/z [M + H]+ 390.1<br>1H-NMR (400 MHz, DMSO-d6) δppm: 10.57 (1H, s), 8.42 (1H, brs), 8.25 (1H, s), 8.19 (1H, d, J = 1.0 Hz), 8.10 (1H, brs), 8.00 (4H, m), 7.36 (1H, d, J = 0.7 Hz), 5.28-5.20 (1H, m), 2.17-2.12 (4H, m), 1.99 -1. 92 (2H, m), 1.72-1.68 (2H, m). |

TABLE 19

| 73 | [structure: 4-amino-N-(4-cyanophenyl)-1-cyclopentyl-1H-pyrazolo[3,4-d]pyrimidine-3-carboxamide] | m/z [M + H]+ 348.3<br>1H-NMR (400 MHz, DMSO-d6) δppm: 10.69 (1H, s), 8.31 (1H, brs), 8.25 (1H, s), 8.11(1H, brs), 8.06-803 (2H, m), 7.86-7.83 (2H, m), 5.27-5.20 (1H, m), 2.19-2.10 (4H, m), 1.98-1.89 (2H, m), 1.75-1.69 (2H, m). |
| 74 | [structure: 4-amino-1-cyclopentyl-N-(4-nitrophenyl)-1H-pyrazolo[3,4-d]pyrimidine-3-carboxamide] | m/z [M + H]+ 368.2<br>1H-NMR (400 MHz, DMSO-d6) δppm: 10.85 (1H, s), 8.29-8.25 (4H, m), 8.18-8.13 (3H, m), 5.27-5.23 (1H, m), 2.20-2.11 (4H, m), 1.99-1.94 (2H, m), 1.73-1.69 (2H, m). |
| 75 | [structure: 4-amino-N-(benzo[b]thiophen-5-yl)-1-cyclopentyl-1H-pyrazolo[3,4-d]pyrimidine-3-carboxamide] | m/z [M + H]+ 379.2<br>1H-NMR (400 MHz, DMSO-d6) δppm: 10.46 (1H, s), 8.56 (1H, brs), 8.39 (1H, d, J = 2.0 Hz), 8.24 (1H, s), 8.07 (1H, brs), 7.99 (1H, d, J = 8.8 Hz), 7.78 (1H, d, J = 5.6 Hz), 7.75-7.72 (1H, m), 7.48-7.46 (1H, m), 5.28-5.21 (1H, m), 2.20-2.07 (4H, m), 2.00-1.91 (2H, m), 1.75-1.65 (2H, m). |

TABLE 19-continued
| 76 | 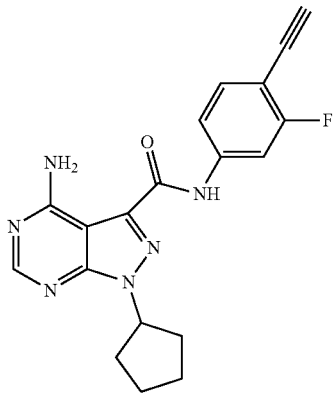 [SMILES: C#Cc1ccc(NC(=O)c2nn(C3CCCC3)c3ncnc(N)c23)cc1F] | m/z [M + H]+ 365.2<br>1H-NMR (400 MHz, DMSO-d6) δppm: 10.75 (1H, s), 8.45 (1H, brs), 8.37 (1H, s), 8.24 (1H, brs), 8.01 (1H, dd, J = 12.2, 2.0 Hz), 7.83 (1H, dd, J = 8.5, 2.2 Hz), 7.75-7.65 (1H, m), 5.39-5.32 (1H, m), 4.57 (1H, s), 2.31-2.19 (4H, m), 2.10-2.02 (2H, m), 1.87-1.77 (2H, m). |
| 77 | 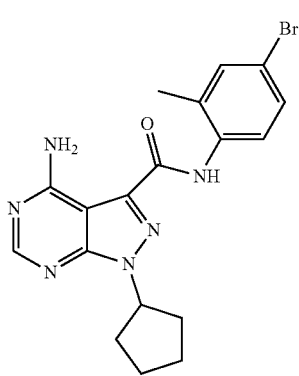 [SMILES: Cc1cc(Br)ccc1NC(=O)c1nn(C2CCCC2)c2ncnc(N)c12] | m/z [M + H]+ 417.0<br>1H-NMR (400 MHz, DMSO-d6) δppm: 10.06 (1H, s), 8.46 (1H, brs), 8.24 (1H, s), 8.05 (1H, brs), 7.53-7.41 (3H, m), 5.26-5.23 (1H, m), 2.26 (3H, s), 2.14-2.09 (4H, m), 1.95-1.93 (2H, m), 1.72-1.66 (2H, m). |
| 78 | 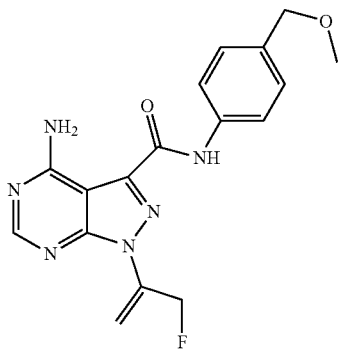 [SMILES: C=C(CF)n1nc(C(=O)Nc2ccc(COC)cc2)c2c(N)ncnc21] | m/z [M + H]+ 357.1<br>1H-NMR (400 MHz, DMSO-d6), δppm: 10.55 (1H, s), 8.62 (1H, brs), 8.34 (1H, s), 8.29 (1H, brs), 7.78 (2H, d, J = 8.5 Hz), 7.34 (2H, d, J = 8.5 Hz), 6.38 (1H, s), 5.74 (1H, s), 5.65 (1H, d, J = 2.2 Hz), 5.62 (1H, s), 4.39 (2H, s), 3.29 (3H, s). |
| 79 | 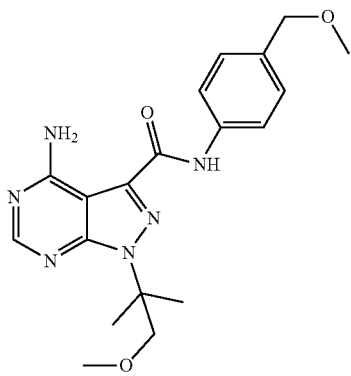 | m/z [M + H]+ 347.3<br>1H-NMR (400 MHz, DMSO-d6) δppm: 10.08 (1H, s), 8.26 (1H, s), 8.09 (1H, s), 7.65 (2H, d, J = 8.3 Hz), 7.29 (2H, d, J = 8.5 Hz), 4.36 (2H, s), 3.94 (2H, s), 3.27 (3H, s), 3.13 (3H, s), 1.70 (6H, s). |

TABLE 19-continued
| | | |
|---|---|---|
| 80 | 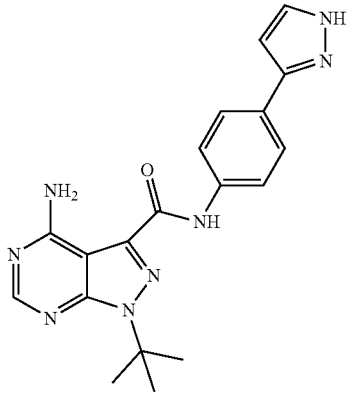 [SMILES: CC(C)(C)n1nc(C(=O)Nc2ccc(-c3cc[nH]n3)cc2)c2c(N)ncnc21] | m/z [M + H]+ 376.2<br>1H-NMR (400 MHz, DMSO-d6) δppm: 10.10 (1H, s), 8.35 (1H, s), 8.12 (1H, s), 7.93 (1H, brs), 7.78 (2H, d, J = 8.5 Hz), 7.73-7.70 (2H, m), 7.68 (1H, brs), 6.67 (1H, m), 1.75 (9H, s). |
| 81 | 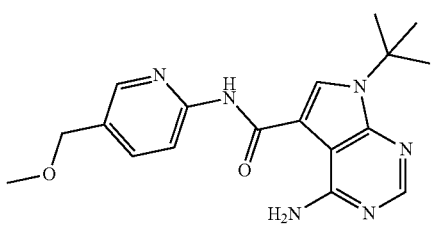 [SMILES: COCc1ccc(NC(=O)c2cn(C(C)(C)C)c3ncnc(N)c23)nc1] | m/z [M + H]+ 355.1<br>1H-NMR (400 MHz, DMSO-d6) δppm: 10.83 (1 H, s) 8.64 (1 H, s) 8.34 (1 H, d, J = 2.20 Hz) 8.14 (1 H, d, J = 8.54 Hz) 8.12 (1 H, s) 7.77 (1 H, dd, J = 8.66, 2.56 Hz) 4.41 (2 H, s) 3.30 (3 H, s) 1.73 (9 H, s) |
TABLE 20
| | | |
|---|---|---|
| 82 | 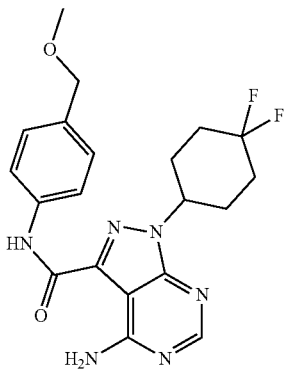 [SMILES: COCc1ccc(NC(=O)c2nn(C3CCC(F)(F)CC3)c3ncnc(N)c23)cc1] | m/z [M + H] + 417.4<br>1H-NMR (400 MHz, DMSO-d6) δppm: 10.44 (1H, s), 8.52 (1H, br s), 8.24 (1H, s), 8.11 (1H, br s), 7.76 (2H, d, J = 8.4 Hz), 7.30 (2H, d, J = 8.4 Hz), 5.01-4.91 (1H, m), 4.37 (2H, s), 3.26 (3H, s), 2.39-1.98 (8H, m). |
| 83 | 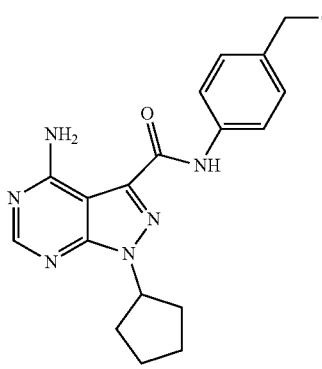 | m/z [M + H] +353.1<br>1H-NMR (400 MHz, DMSO-d6) δppm: 10.29 (1H,s) 8.52 (1H, br s), 8.24 (1H, s), 8.06 (1H, br s), 7.74 (2H, d, J = 8.5 Hz), 7.32 (2H, d, J = 8.5 Hz), 5.28-5.15 (2H, m), 4.48 (2H, d, J = 5.6 Hz), 2.18-2.09 (4H, m), 1.99-1.90 (2H, m), 1.73-1.66 (2H, m). |

| | |
|---|---|
| 84 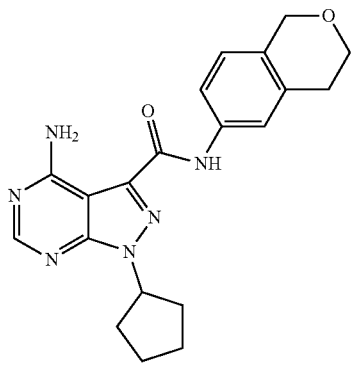 [SMILES: Nc1ncnc2c1c(C(=O)Nc1ccc3c(c1)CCOC3)nn2C1CCCC1] | m/z [M + H] +379.1<br>1H-NMR (400 MHz, DMSO-d6) δppm: 10.22 (1H, s), 8.49 (1H, br s), 8.22 (1H, s), 8.04 (1H, br s), 7.61-7.58 (1H, m), 7.57-7.53 (1H, m), 7.02 (1H, d, J = 8.1 Hz), 5.26-5.17 (1H, m), 4.64 (2H, s), 3.88-3.84 (2H, m), 2.80-2.76 (2H, m), 2.15-2.08 (4H, m), 1.98-1.89 (2H, m), 1.73-1.61 (2H, m). |
| 85 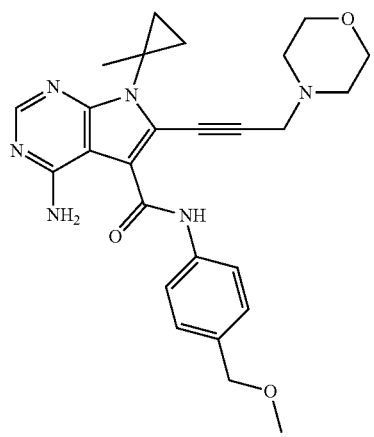 [SMILES: COCc1ccc(NC(=O)c2c(C#CCN3CCOCC3)n(C3(C)CC3)c3ncnc(N)c23)cc1] | m/z [M + H] + 475.3<br>1H-NMR (400 MHz, CDCl3) δppm: 9.28 (1H, s), 8.37 (1H, s), 7.64 (2H, d, J =8.8 Hz), 7.36 (2H, d, J = 8.4 Hz), 4.46 (2H, s), 3.78 (2H, s), 3.74-3.73 (4H, m), 3.38 (3H, s), 2.70-2.68 (4H, m), 1.62 (3H, s), 1.39-1.36 (2H, m), 1.16-1.14 (2H, m). |
| 86 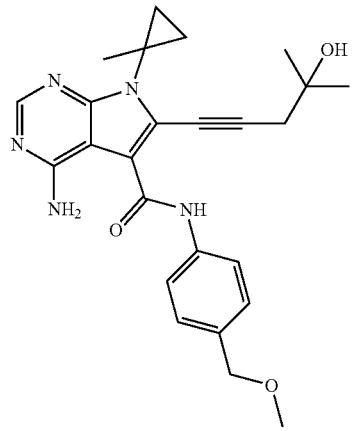 [SMILES: COCc1ccc(NC(=O)c2c(C#CCC(C)(C)O)n(C3(C)CC3)c3ncnc(N)c23)cc1] | m/z [M + H] + 448.4<br>1H-NMR (400 MHz, DMSO-d6) δppm: 9.92 (1H,s), 8.16 (1H, s), 7.66 (2H, d, J = 8.4 Hz), 7.28 (28, d, J = 8.4 Hz), 4.76 (1H, s), 4.35 (2H, s), 3.26 (3H, s), 2.72 (2H, s), 1.49 (3H, s), 1.23 (6H, s), 1.23-1.04 (4H, m). |

TABLE 20-continued
| 87 | 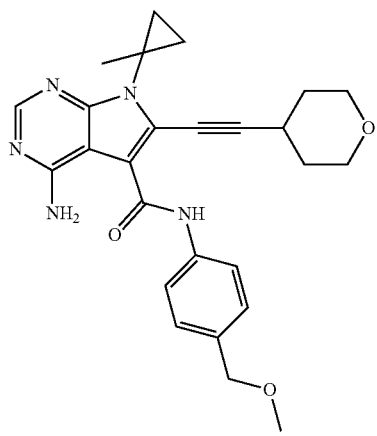 [SMILES: COCc1ccc(NC(=O)c2c(C#CC3CCOCC3)n(C3(C)CC3)c3ncnc(N)c23)cc1] | m/z [M + H] + 460.4<br>1H-NMR (400 MHz, DMSO-d6) δppm: 9.96 (1H, s), 8.17 (1H, s), 7.65 (2H, d, J = 8.4 Hz), 7.56 (2H, br s), 7.28 (2S, d, J = 8.4 Hz), 4.34 (2H, s), 3.78-3. 76 (2H, m), 3.44-3.42 (2H, m), 3.25 (3H, s), 3.12-3.08 (1H, m), 1.85-1.83 (2H, m), 1.64-1.62 (2H, m), 1.49 (3H, s), 1.24-1.22 (2H, m), 1.07-1.05 (2H, m). |
| 88 | 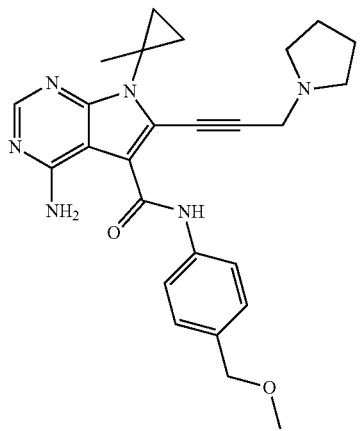 [SMILES: COCc1ccc(NC(=O)c2c(C#CCN3CCCC3)n(C3(C)CC3)c3ncnc(N)c23)cc1] | m/z [M + H] +459.2<br>1H-NMR (400 MHz, DMSO-d6) δppm:10.02 (1H, s), 8.16 (1H, s), 7.64 (2H, d, J = 8. 4 Hz), 7.53 (2H, s), 7.28 (2H, d, J = 8.4 Hz), 4.35 (2H, s), 3.80 (2H, s), 3.24 (3H, s), 2.56-2.54 (4H, m), 1.58-1.55 (4H, m), 1.49 (3H, s), 1.24-1.23 (2H, m), 1.07-1.05 (2H, m). |
| 89 | 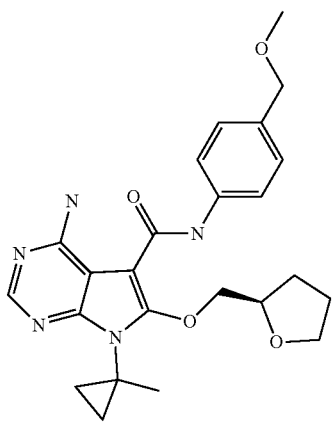 [SMILES: COCc1ccc(NC(=O)c2c(OC[C@H]3CCCO3)n(C3(C)CC3)c3ncnc(N)c23)cc1] | m/z [M + H] +452.3<br>1H-NMR (400 MHz, DMSO-d6) δppm: 9.61 (1H, s), 8.11 (1H, s), 7.62 (2H, d, J = 8. 4 Hz), 7.27 (2S, d, 3 J = 8.4 Hz), 4.51 (1H, dd, J = 9.7, 2.4 Hz), 4.34 (2H, s) , 4.30 (1H, td, 3 = 7.2, 2.4 Hz), 4.23 (1S, dd, J = 9.5, 7.7 Hz), 3.76-3.64 (2H, m), 3.25 (3H, s), 2.07-1.96 (1H, m), 1.89-1.78 (2H, m), 1.71-1.68 (1H, |

TABLE 20-continued
| 90 | 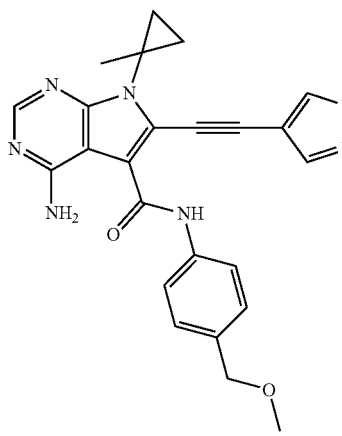 | m/z [M + H] + 456.1<br>1H-NMR (400 MHz, DMSO-d6) δppm: 10.11 (1H, s), 8.22 (1H, brs), 8.17 (1H, s), 7.72-7.63 (5H, m), 7.31 (2H, d, J = 8.5 Hz), 4.36 (2H, s), 3.88 (3H, s), 3.27 (3H, s), 1.53 (3H, s), 1.29 (2H, m), 1.13 (2H, m). |
TABLE 21
| 91 | 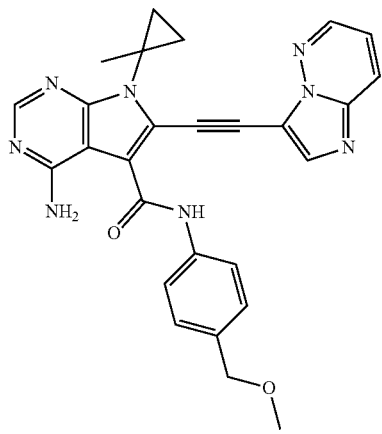 [SMILES: COCc1ccc(NC(=O)c2c(C#Cc3cnc4cccnn34)n(C3(C)CC3)c3ncnc(N)c23)cc1] | m/z [M + H] + 493.5<br>1H-NMR (400 MHz, DMSO-d6) δppm: 10.20 (1H, s), 8.47 (1H, dd, J = 4.4, 1.5 Hz), 8.28-8.26 (1H, m), 8.23 (2H, brs), 7.73 (2H, d, J = 8.8 Hz), 7.68 (2H, m), 7.39-7.36 (1H, m), 7.32 (2H, d, J = 8.8 Hz), 4.38 (2H, s), 3.27 (3H, s), 1.60 (3H, s), 1.36 (2H, m), 1.20 (2H, m). |
| 92 | 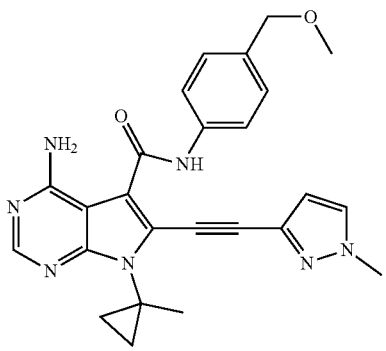 | m/z [M + H] + 493.5<br>1H-NMR (400 MHzm DMSO-d6), δppm: 10.19 (1H, s), 8.22 (1H, s), 7.83 (1H, d, J = 2.2 Hz), 7.74 (2H, d, J = 8.5 Hz), 7.64 (2H, brs), 7.30 (2H, d, J = 8.5 Hz), 6.53 (1H, d, J = 2.2 Hz), 4.36 (2H, s), 3.90 (3H, s), 3.27 (3H, s), 1.54 (3H, s), 1.31 (2H, m), 1.13 (2H, m). |
| 93 | 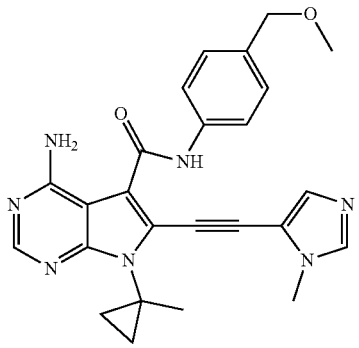 [SMILES: COCc1ccc(NC(=O)c2c(C#Cc3cncn3C)n(C3(C)CC3)c3ncnc(N)c23)cc1] | m/z [M + H] + 456.4<br>1H-NMR (400 MHz, DMSO-d6) δppm: 10.28 (1H, s), 8.22 (1H, s), 7.84 (1H, brs), 7.67 (2H, d, J = 8.5 Hz), 7.52 (2H, brs), 7.37-7.29 (3H, m), 4.36 (2H, s), 3.61 (3H, s), 3.27 (3H, s), 1.56 (3H, s), 1.31 (2H, m), 1.16 (2H, m). |

TABLE 21-continued
| 94 | 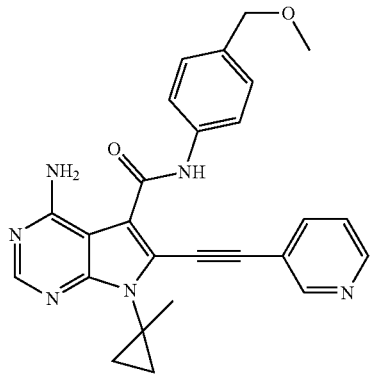 [SMILES: COCc1ccc(NC(=O)c2c(C#Cc3cccnc3)n(C3(C)CC3)c3ncnc(N)c23)cc1] | m/z [M + H] + 453.1<br>1H-NMR (400 MHz, DMSO-d6) δppm: 10.31 (1H, s), 8.95-8.62 (2H, m), 8.26 (1H, s), 7.92 (1H, d, J = 7.7 Hz), 7.71 (2H, d, J = 8.4 Hz), 7.60-7.49 (3H, m), 7.30 (2H, d, J = 8.4 Hz), 4.35 (2H, s), 3.26 (3H, s), 1.56 (3H, s), 1.33-1.31 (2H, m), 1.19-1.17 (2H, m). |
| --- | --- | --- |
| 95 | 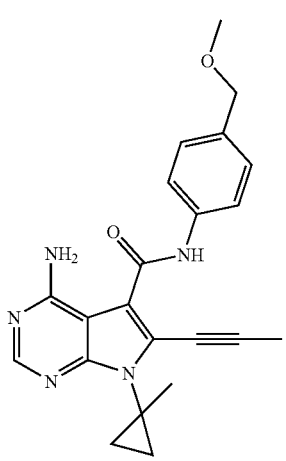 [SMILES: CC#Cc1c(C(=O)Nc2ccc(COC)cc2)c2c(N)ncnc2n1C1(C)CC1] | m/z [M + H] + 390.4<br>$^1$H NMR (400 MHz, DMSO-$d_6$) δ ppm: 9.96 (1H, s) 8.17 (1H, s) 7.67 (2H, d, J = 8.43 Hz) 7.51-7.76 (2H, m) 7.30 (2H, d, J = 8.43 Hz) 4.37 (2H, s) 3.27 (3H, s) 2.30 (3H, s) 1.49 (3H, s) 1.18-1.30 (2H, m) 1.04-1.14 (2H, m) |
| 96 | 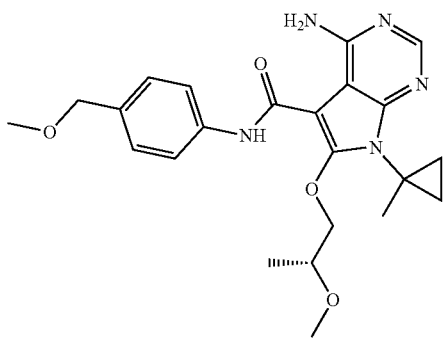 | m/z [M + H] + 440.5<br>$^1$H NMR (400 MHz, CHLOROFORM-$d_6$) δ ppm 9.35 (1H, s) 8.34 (1H, s) 7.63 (2H, d, J = 7.82 Hz) 7.33 (2H, d, J = 8.43 Hz) 4.44 (2H, s) 4.42 (1H, d, J = 2.57 Hz) 4.32-4.38 (1H, m) 3.78-3.85 (1H, m) 3.39 (3H, s) 3.30 (3H, s) 1.71 (3H, s) 1.34-1.43 (4H, m) 1.24-1.32 (1H, m) 1.05-1.17 (2H, m) |
| 97 | 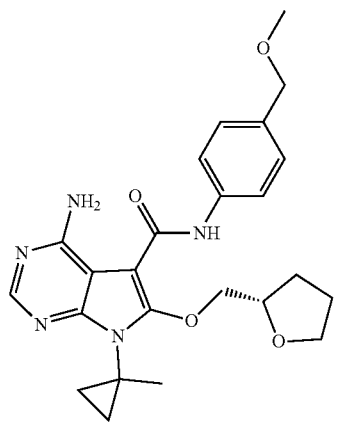 | m/z [M + H]+ 452.5<br>$^1$H NMR (400 MHz, DMSO-$d_6$) δ ppm: 9.62 (1H, s) 8.12 (1H, s) 7.63 (2H, d, J = 8.43 Hz) 7.28 (2H, d, J = 8.43 Hz) 4.52 (1H, dd, J = 9.71, 2.38 Hz) 4.35 (2H, s) 4.28-4.34 (1H, m) 4.20-4.27 (1H, m) 3.65-3.76 (2H, m) 3.26 (3H, s) 1.96-2.07 (1H, m) 1.78-1.90 (2H, m) 1.66-1.76 (1H, m) 1.59 (3H, s) 1.20-1.27 (1H, m) 1.01-1.17 (3H, m) |

TABLE 21-continued

| | | |
|---|---|---|
| 98 | 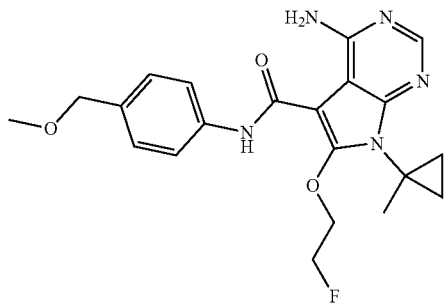 [SMILES: COCc1ccc(NC(=O)c2c(OCCF)n(C3(C)CC3)c3ncnc(N)c23)cc1] | m/z [M + H]+ 414.2<br>¹H NMR (400 MHz, DMSO-d₆) δ ppm: 9.53 (1H, s) 8.14 (1H, s) 7.62 (2H, d, J = 8.43 Hz) 7.27 (2H, d, J = 8.40 Hz) 4.89-4.93 (1H, m) 4.76-4.81 (1H, m) 4.64-4.68 (1H, m) 4.56-4.60 (1H, m) 4.35 (2H, s) 3.26 (3H, s) 1.57 (3H, s) 1.17-1.23 (2H, m) 1.01-1.08 (2H, m) |
| 99 | 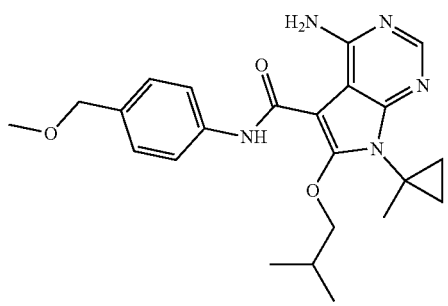 [SMILES: COCc1ccc(NC(=O)c2c(OCC(C)C)n(C3(C)CC3)c3ncnc(N)c23)cc1] | m/z [M + H]+ 424.3<br>¹H NMR (400 MHz, DMSO-d₆) δ ppm: 9.63 (1H, s) 8.13 (1H, s) 7.63 (2H, d, J = 8.43 Hz) 7.40 (2H, br s) 7.28 (2H, d, J = 8.80 Hz) 4.35 (2H, s) 4.05 (2H, d, J = 6.23 Hz) 3.26 (3H, s) 2.10 (1H, dt, J = 13.11, 6.46 Hz), 1.55 (3H, s) 1.15-1.21 (2H, m) 1.02-1.06 (2H, m) 1.00 (6H, d, J = 6.60 Hz) |

TABLE 22

| | | |
|---|---|---|
| 100 | 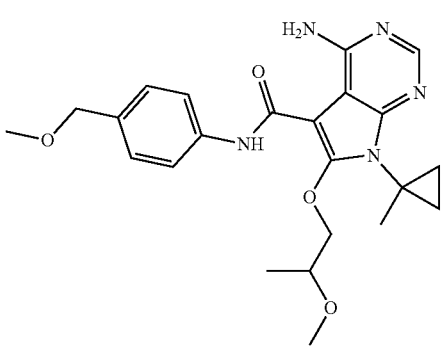 | m/z [M + H]+ 440.5<br>¹H NMR (400 MHz, CHLOROFORM-d) δ ppm: 9.35 (1H, s) 8.34 (1H, s) 7.63 (2H, d, J = 8.43 Hz) 7.33 (2H, d, J = 8.43 Hz) 4.44 (2H, s) 4.42 (1H, d, J = 2.57 Hz) 4.38 (1H, m) 3.78-3.85 (1H, m) 3.39 (3H, s) 3.30 (3H, s) 1.70 (3H, s) 1.34-1.43 (4H, m) 1.22-1.33 (1H, m) 1.05-1.17 (2H, m) |
| 101 | 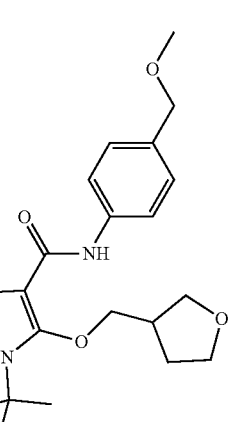 | m/z [M + H]+ 452.4<br>¹H NMR (400 MHz, CHLOROFORM-d) δ ppm: 8.75 (1H, s) 8.34 (1H, s) 7.57 (2H, d, J = 8.43 Hz) 7.35 (2H, d, J = 8.43 Hz) 4.44 (2H, s) 4.26-4.37 (2H, m) 3.91-3.97 (2H, m) 3.76-3.85 (2H, m) 3.39 (3H, s) 2.81-2.91 (1H, m) 2.14-2.24 (1H, m) 1.72-1.83 (1H, m) 1.69 (3H, s) 1.27-1.36 (2H, m) 1.10-1.17 (2H, m) |

| | | |
|---|---|---|
| 102 | 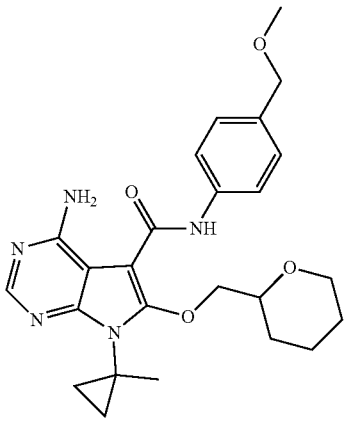 [SMILES: COCc1ccc(NC(=O)c2c(OCC3CCCCO3)n(C3(C)CC3)c3ncnc(N)c23)cc1] | m/z [M + H]+ 466.5<br>¹H NMR (400 MHz, CHLOROFORM-d) δ ppm: 9.41 (1H, s) 8.33 (1H, s) 7.61 (2H, d, J = 8.43 Hz) 7.29-7.35 (2H, m) 4.42-4.46 (3H, m) 4.30 (1H, dd, J = 9.90, 7.33 Hz) 3.88 (1H, dd, J = 11.36, 2.93 Hz) 3.76-3.83 (1H, m) 3.39-3.47 (1H, m) 3.39 (3H, s) 1.70 (3H, s) 1.51-1.61 (6H, m) 1.24-1.38 (2H, m) 1.06-1.13 (2H, m) |
| 103 | 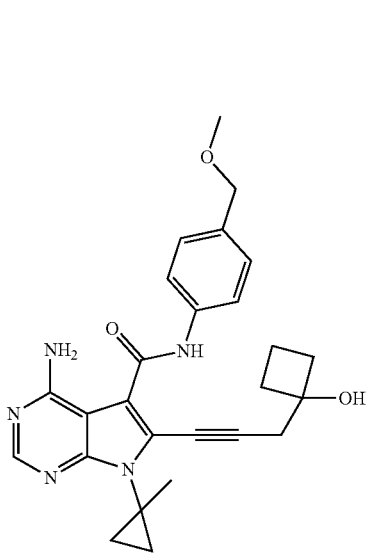 [SMILES: COCc1ccc(NC(=O)c2c(C#CCC3(O)CCC3)n(C3(C)CC3)c3ncnc(N)c23)cc1] | m/z [M + H]+ 460.4<br>¹H NMR (400 MHz, DMSO-d₆) δ ppm 9.89 (1H, s) 8.17 (1H, s) 7.68 (2H, d, J = 8.43 Hz) 7.29 (2H, d, J = 8.43 Hz) 5.40 (1H, s) 4.36 (2H, s) 3.26 (3H, s) 2.89 (2H, s) 1.98-2.13 (4H, m) 1.52-1.69 (2H, m) 1.49 (3H, s) 1.22-1.27 (2H, m) 1.05-1.11 (2H, m) |
| 104 | 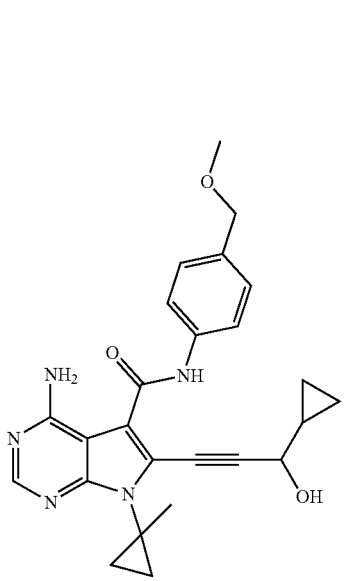 [SMILES: COCc1ccc(NC(=O)c2c(C#CC(O)C3CC3)n(C3(C)CC3)c3ncnc(N)c23)cc1] | m/z [M + H]+ 446.4<br>¹H NMR (400 MHz, DMSO-d₆) δ ppm 9.90 (1H, s) 8.19 (1H, br s) 7.67-7.72 (2H, m) 7.29 (2H, d, J = 8.43 Hz) 5.78 (1 H, d, J = 6.23 Hz) 4.36 (2H, s) 4.28-4.34 (1H, m) 3.26 (3H, s) 1.50 (3H, s) 1.20-1.29 (3H, m) 1.01-1.17 (2H, m) 0.28-0.50 (4H, m) |

TABLE 22-continued

| 105 | 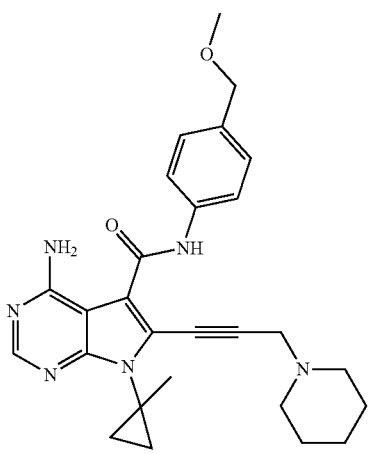 [SMILES: COCc1ccc(NC(=O)c2c(C#CCN3CCCCC3)n(C3(C)CC3)c3ncnc(N)c23)cc1] | m/z [M + H]+ 473.4<br>1H NMR (400 MHz, DMSO-d6) δ ppm 10.09 (1H, br s) 8.20 (1H, s) 7.68 (2H, d, J = 8.54 Hz) 7.55 (2H, br s) 7.31 (2H, d, J = 8.54 Hz) 4.37 (2H, s) 3.68 (2H, s) 3.26 (3H, s) 2.45-2.48 (4H, m) 1.53 (3H, s) 1.36-1.46 (4H, m) 1.20-1.29 (4H, m) 1.06-1.13 (2H, m) |
|---|---|---|
| 106 | 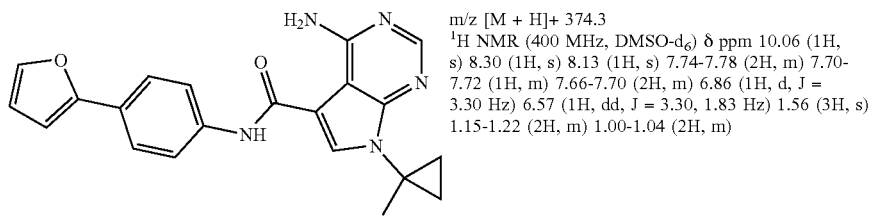 | m/z [M + H]+ 374.3<br>$^1$H NMR (400 MHz, DMSO-$d_6$) δ ppm 10.06 (1H, s) 8.30 (1H, s) 8.13 (1H, s) 7.74-7.78 (2H, m) 7.70-7.72 (1H, m) 7.66-7.70 (2H, m) 6.86 (1H, d, J = 3.30 Hz) 6.57 (1H, dd, J = 3.30, 1.83 Hz) 1.56 (3H, s) 1.15-1.22 (2H, m) 1.00-1.04 (2H, m) |
| 107 | 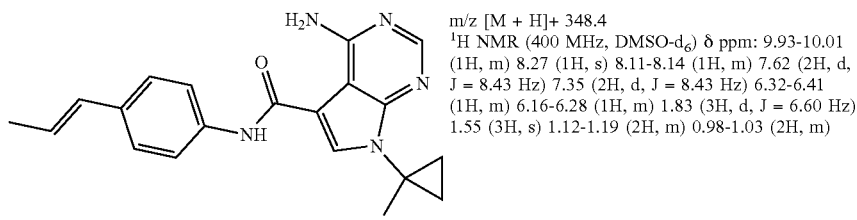 | m/z [M + H]+ 348.4<br>$^1$H NMR (400 MHz, DMSO-$d_6$) δ ppm: 9.93-10.01 (1H, m) 8.27 (1H, s) 8.11-8.14 (1H, m) 7.62 (2H, d, J = 8.43 Hz) 7.35 (2H, d, J = 8.43 Hz) 6.32-6.41 (1H, m) 6.16-6.28 (1H, m) 1.83 (3H, d, J = 6.60 Hz) 1.55 (3H, s) 1.12-1.19 (2H, m) 0.98-1.03 (2H, m) |
| 108 | 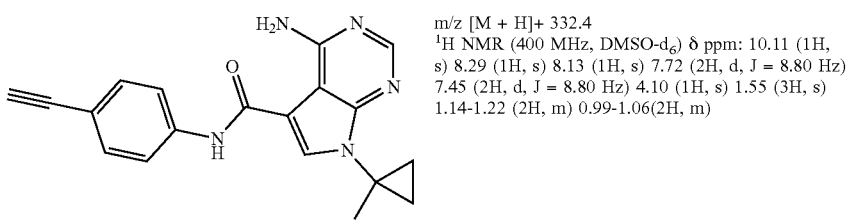 | m/z [M + H]+ 332.4<br>$^1$H NMR (400 MHz, DMSO-$d_6$) δ ppm: 10.11 (1H, s) 8.29 (1H, s) 8.13 (1H, s) 7.72 (2H, d, J = 8.80 Hz) 7.45 (2H, d, J = 8.80 Hz) 4.10 (1H, s) 1.55 (3H, s) 1.14-1.22 (2H, m) 0.99-1.06 (2H, m) |

TABLE 23

| 109 | 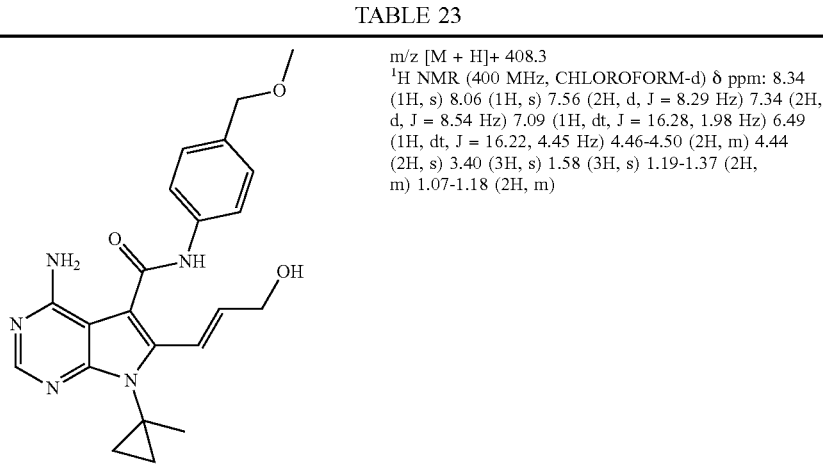 | m/z [M + H]+ 408.3<br>$^1$H NMR (400 MHz, CHLOROFORM-d) δ ppm: 8.34 (1H, s) 8.06 (1H, s) 7.56 (2H, d, J = 8.29 Hz) 7.34 (2H, d, J = 8.54 Hz) 7.09 (1H, dt, J = 16.28, 1.98 Hz) 6.49 (1H, dt, J = 16.22, 4.45 Hz) 4.46-4.50 (2H, m) 4.44 (2H, s) 3.40 (3H, s) 1.58 (3H, s) 1.19-1.37 (2H, m) 1.07-1.18 (2H, m) |
|---|---|---|

TABLE 23-continued
| | | |
|---|---|---|
| 110 | 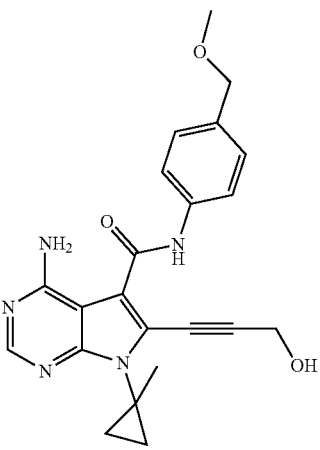 [SMILES: COCc1ccc(NC(=O)c2c(C#CCO)n(C3(C)CC3)c3ncnc(N)c23)cc1] | m/z [M + H]+ 406.1<br>1H NMR (400 MHz, DMSO-d6) δ ppm: 9.94 (1H, s) 8.18 (1H, s) 7.70 (2H, d, J = 8.43 Hz) 7.30 (2H, d, J = 8.43 Hz) 5.61 (1H, t, J = 5.87 Hz) 4.51 (2H, d, J = 5.87 Hz) 4.36 (2H, s) 3.26 (3H, s) 1.50 (3H, s) 1.17-1.29 (2H, m) 1.06-1.16 (2H, m) |
| 111 | 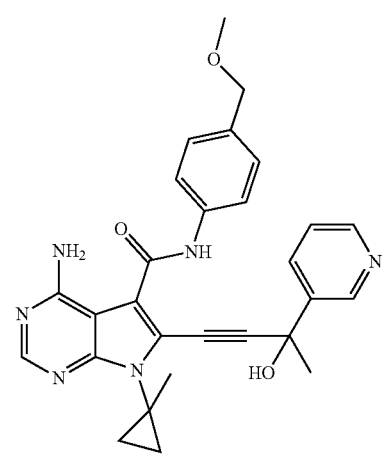 [SMILES: COCc1ccc(NC(=O)c2c(C#CC(C)(O)c3cccnc3)n(C3(C)CC3)c3ncnc(N)c23)cc1] | m/z [M + H]+ 497.2<br>$^1$H NMR (400 MHz, DMSO-d$_6$) δ ppm: 10.02 (1H, s) 8.89 (1H, d, J = 2.20 Hz) 8.39-8.51 (2H, m) 8.19 (1H, s) 8.00 (1H, dt, J = 7.97, 1.88 Hz) 7.54-7.68 (4H, m) 7.21-7.31 (3H, m) 4.35 (2H, s) 3.26 (3H, s) 1.81 (3H, s) 1.47(3H, s) 1.16-1.29 (2H, m) 0.95-1.06 (2H, m) |
| 112 | 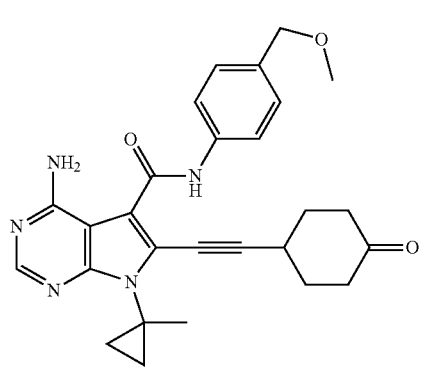 [SMILES: COCc1ccc(NC(=O)c2c(C#CC3CCC(=O)CC3)n(C3(C)CC3)c3ncnc(N)c23)cc1] | m/z [M + H]+ 472.2<br>1H-NMR (DMSO-d$_6$) δ ppm: 10.06 (1H, s), 8.18 (1H, brs), 8.13 (1H, brs), 8.13 (1H, brs), 7.66 (2H, d, J = 8.5 Hz), 7.54 (2H, s), 7.29 (2H, d, J = 8.5 Hz), 4.36 (2H, s), 3.26 (3H, s), 2.45-2.42 (2H, m), 2.34-2.30 (2H, m), 2.13-2.10 (2H, m), 1.98-1.95 (2H, m), 1.51 (3H, s), 1.25 (2H, m), 1.08 (2H, m). |
| 113 | 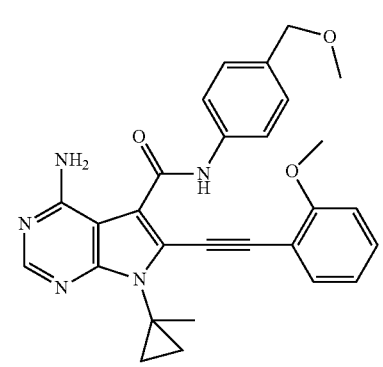 [SMILES: COCc1ccc(NC(=O)c2c(C#Cc3ccccc3OC)n(C3(C)CC3)c3ncnc(N)c23)cc1] | m/z [M + H]+ 482.5<br>1H-NMR (DMSO-D6)δ ppm: 10.09 (1H, s), 8.21 (1H, s), 7.68 (2H, d, J = 8.5 Hz), 7.63-7.42 (2H, m), 7.33 (2H, d, J = 8.4 Hz), 7.10 (1H, d, J = 8.5 Hz), 7.01 (1H, t, J = 7.4 Hz), 4.38 (2H, s), 3.55 (3H, s), 3.27 (3H, s), 1.57 (3H, s), 1.33 (2H, t, J = 6.0 Hz), 1.16 (2H, t, J = 6.3 Hz). |

TABLE 23-continued

| 114 | 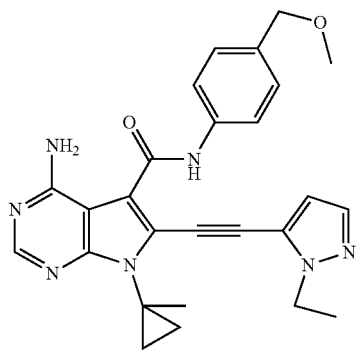 [SMILES: CCn1nccc1C#Cc1c(C(=O)Nc2ccc(COC)cc2)c2c(N)ncnc2n1C1(C)CC1] | m/z [M + H]+ 470.5<br>1H-NMR (DMSO-D6)δ ppm: 10.42 (1H, s), 8.24 (1H, s), 7.67 (2H, d, J = 8.5 Hz), 7.56 (1H, d, J = 2.0 Hz), 7.50 (2H, brs), 7.31 (2H, d,J = 8.5 Hz), 6.61 (1H, d,J = 2.0 Hz), 4.37 (2H, s), 4.17 (2H, q, J = 7.2 Hz), 3.26 (3H, s), 1.57 (3H, s), 1.32-1.31 (2H, m), 1.18-1.15 (5H, m). |
| --- | --- | --- |
| 115 | 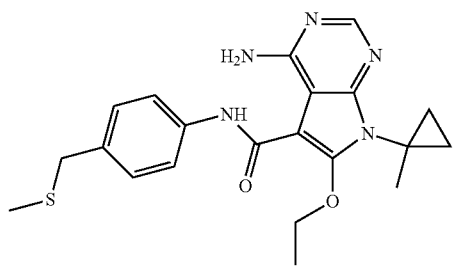 [SMILES: CCOc1c(C(=O)Nc2ccc(CSC)cc2)c2c(N)ncnc2n1C1(C)CC1] | m/z [M + H]+ 412.3<br>$^1$H NMR (400 MHz, DMSO-d$_6$) δ ppm:9.59 (1H, s) 8.13 (1H, s) 7.61 (2H, d, J = 8.43 Hz) 7.48-7.59 (2H, m) 7.27 (2H, d, J = 8.43 Hz) 4.38 (2H, q, J = 6.97 Hz) 3.65 (2H, s) 1.89-2.01 (3H, m) 1.55 (3H, s) 1.43 (3H, t, J = 6.96 Hz) 1.14-1.22 (2H, m) 1.02-1.10 (2H, m) |
| 116 | 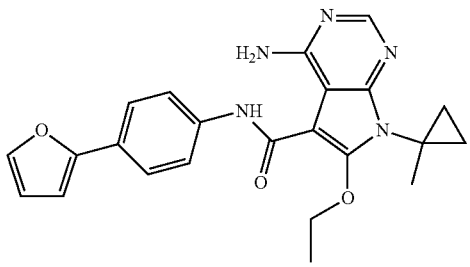 [SMILES: CCOc1c(C(=O)Nc2ccc(-c3ccco3)cc2)c2c(N)ncnc2n1C1(C)CC1] | m/z [M + H]+ 418.4<br>$^1$H NMR (400 MHz, DMSO-d$_6$) δppm: 9.70 (1H, s) 8.13 (1H, s) 7.72-7.76 (2H, m) 7.70-7.72 (1H, m) 7.65-7.69 (2H, m) 7.51 (2H, br s) 6.86 (1H, d, J = 3.65 Hz) 6.57 (1H, dd, J = 3.30, 1.83 Hz) 4.39 (2H, q, J = 7.21 Hz) 1.55 (3H, s) 1.44 (3H, t, J = 6.96 Hz) 1.16-1.21 (2H, m) 0.99-1.10 (2H, m) |
| 117 | 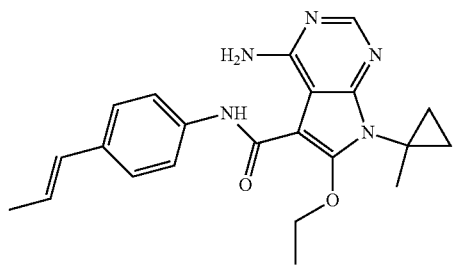 [SMILES: C/C=C/c1ccc(NC(=O)c2c(OCC)n(C3(C)CC3)c3ncnc(N)c23)cc1] | m/z [M + H]+ 392.2<br>$^1$H NMR (400 MHz, DMSO-d$_6$) δ ppm: 9.59 (1H, s) 8.13 (1H, s) 7.61 (2H, d, J = 8.80 Hz) 7.34 (2H, d, J = 8.80 Hz) 6.37 (1H, dd, J = 15.76, 1.47 Hz) 6.21 (1H, dq, J = 15.72, 6.37 Hz) 4.37 (2H, q, J = 6.96 Hz) 1.82 (3H, dd, J = 6.42, 1.28 Hz) 1.55 (3H, s) 1.43 (3H, t, J = 6.96 Hz) 1.15-1.20 (2H, m) 1.02-1.08 (2H, m) |

TABLE 24

| 118 | 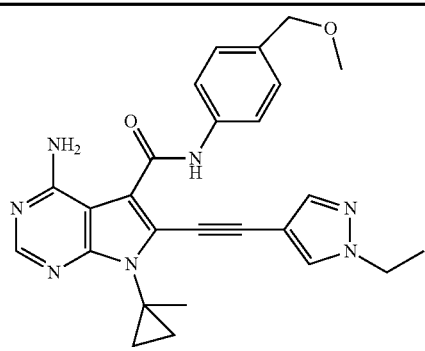 | m/z [M + H]+ 470.5<br>1H-NMR (DMSO-D6) δ ppm: 10.11 (1H, s), 8.21-8.20 (2H, m), 7.72 (1H, d, J = 0.5 Hz), 7.69-7.67 (2H, m), 7.63-7.62 (2H, m), 7.31 (2H, d, J = 8.5 Hz), 4.36 (2H, s), 4.17 (2H, q, J = 7.2 Hz), 3.27 (3H, s), 1.53 (3H, s), 1.37 (3H, t, J = 7.3 Hz), 1.31-1.28 (2H, m), 1.14-1.12 (2H, m). |
| --- | --- | --- |

TABLE 24-continued
| | | |
|---|---|---|
| 119 | 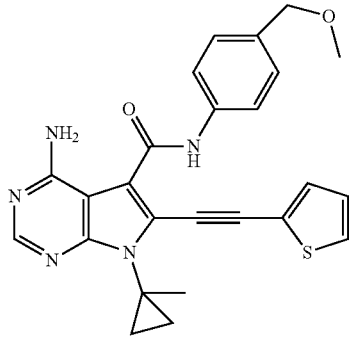 [SMILES: COCc1ccc(NC(=O)c2c(C#Cc3cccs3)n(C3(C)CC3)c3ncnc(N)c23)cc1] | m/z [M + H]+ 458.1<br>1H-NMR (DMSO-D6) δ ppm: 10.26 (1H, s), 8.22 (1H, s), 7.77 (1H, dd, J = 5.1, 1.2 Hz), 7.73 (2H, dd, J = 6.7, 1.8 Hz), 7.46 (1H, dd, J = 3.7, 1.0 Hz), 7.31 (2H, d, J = 8.8 Hz), 7.17 (1H, dd, J = 5.1, 3.7 Hz), 4.37 (2H, s), 3.27 (3H, s), 1.55 (3H, s), 1.31-1.30 (2H, m), 1.16-1.13 (2H, m). |
| 120 | 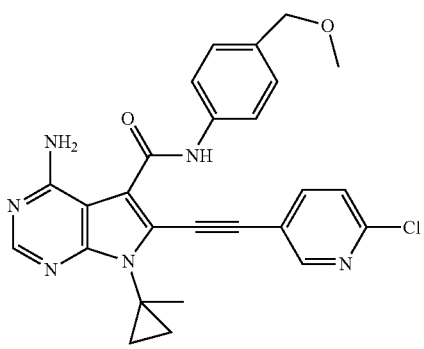 [SMILES: COCc1ccc(NC(=O)c2c(C#Cc3ccc(Cl)nc3)n(C3(C)CC3)c3ncnc(N)c23)cc1] | m/z [M + H]+ 487.1<br>1H-NMR (DMSO-D6)δ ppm: 10.31 (1H, s), 8.54 (1H, d, J = 2.2 Hz), 8.23 (1H, s), 7.98 (1H, t, J = 4.1 Hz), 7.72 (2H, d, J = 6.8 Hz), 7.66-7.55 (1H, m), 7.32 (2H, d, J = 8.3 Hz), 4.37 (2H, s), 3.28 (3H, s), 1.57 (3H, s), 1.32 (2H,m), 1.20 (2H, m). |
| 121 | 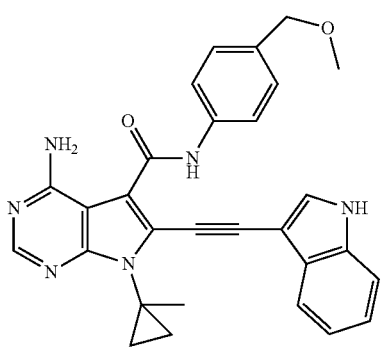 [SMILES: COCc1ccc(NC(=O)c2c(C#Cc3c[nH]c4ccccc34)n(C3(C)CC3)c3ncnc(N)c23)cc1] | m/z [M + H]+ 491.2<br>1H-NMR (DMSO-D6)δ ppm: 11.81 (1H, s), 10.24 (1H, s), 8.21 (1H, s), 7.84 (1H, d, J = 2.7 Hz), 7.71 (2H, d, J = 8.5 Hz), 7.64-7.47 (4H, m), 7.30 (2H, d, J = 8.5 Hz), 7.18 (1H, dt, J = 10.4, 3.8 Hz), 7.00 (1H, dt, J = 10.3, 3.8 Hz), 4.37 (2H, s), 3.27 (3H, s), 1.61 (3H, s), 1.38-1.35 (2H, m), 1.21-1.17 (2H, m). |
| 122 | 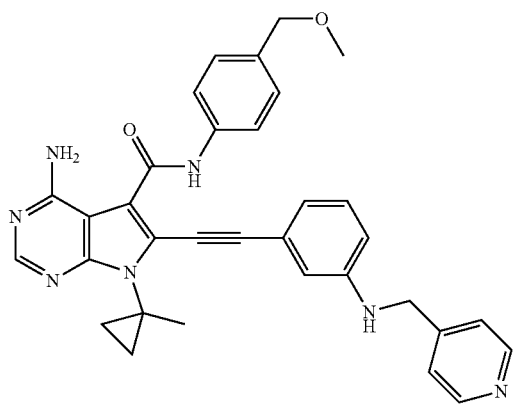 [SMILES: COCc1ccc(NC(=O)c2c(C#Cc3cccc(NCc4ccncc4)c3)n(C3(C)CC3)c3ncnc(N)c23)cc1] | m/z [M + H]+ 558.4<br>1H-NMR (DMSO-D6)δ ppm: 10.17 (1H, s), 8.47 (1H, m), 8.21 (1H, s), 7.72-7.70 (2H, m), 7.60-7.54 (2H, brs), 7.32-7.25 (3H, m), 7.15-7.11 (2H, m), 6.73-6.67 (3H, m), 6.62 (1H, brs), 4.36 (2H, s), 4.25-4.24 (2H, m), 3.27 (3H, s), 1.52 (3H, s), 1.30-1.27 (2H, m), 1.10-1.07 (2H, m). |

| | | |
|---|---|---|
| 123 | 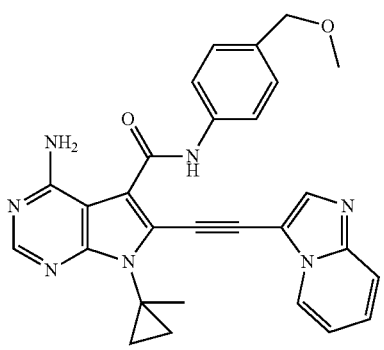 [SMILES: COCc1ccc(NC(=O)c2c(C#Cc3cnc4ccccn34)n(C3(C)CC3)c3ncnc(N)c23)cc1] | m/z [M + H]+ 492.3<br>1H-NMR (DMSO-D6)δ ppm: 10.45 (1H, s), 8.42 (1H, m), 8.25 (2H, m), 7.75-7.74 (1H, m), 7.67 (2H, m), 7.52 (2H, brs), 7.42 (1H, t, J = 6.7 Hz), 7.30 (2H, d, J = 8.5 Hz), 6.90 (1H, t, J = 6.7 Hz), 4.36 (2H, s), 3.26 (3H, s), 1.60 (3H, s), 1.38-1.35 (2H, m), 1.21-1.18 (2H, m). |
| 124 | 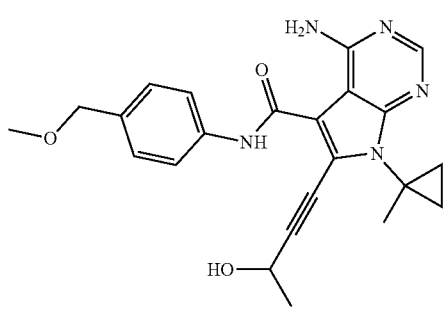 [SMILES: COCc1ccc(NC(=O)c2c(C#CC(C)O)n(C3(C)CC3)c3ncnc(N)c23)cc1] | m/z [M + H]+ 420.3<br>$^1$H NMR (400 MHz, DMSO-$d_6$) δ ppm: 9.92 (1H, s) 8.18 (1H, s) 7.70 (3H, d, J = 8.43 Hz) 7.29 (2H, d, J = 8.43 Hz) 4.78(1 H, q, J = 6.60 Hz) 4.36 (2H, s) 3.26 (3H, s) 1.50 (3H, s) 1.43 (3H, d, J = 6.60 Hz) 1.19-1.29 (2H, m) 1.06-1.11 (2H, m) |
| 125 | 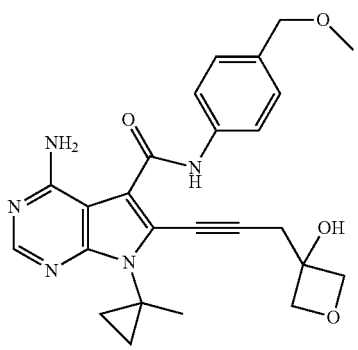 [SMILES: COCc1ccc(NC(=O)c2c(C#CCC3(O)COC3)n(C3(C)CC3)c3ncnc(N)c23)cc1] | m/z [M + H]+ 462.4<br>1H-NMR (DMSO-D6)δ ppm: 9.90 (1H, s), 8.18 (1H, s), 7.69-7.66 (2H, m), 7.30 (2H, d, J = 8.5 Hz), 4.48 (4H, q, J = 6.8 Hz), 4.37 (2H, s), 3.27 (3H, s), 3.11 (2H, s), 1.49 (3H, s), 1.23 (2H, m), 1.08 (2H, m). |
| 126 | 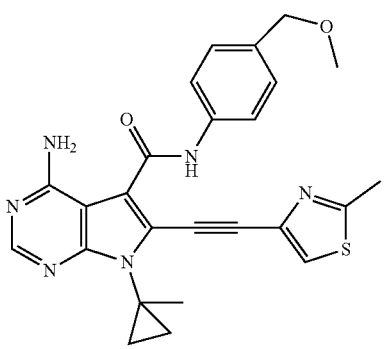 [SMILES: COCc1ccc(NC(=O)c2c(C#Cc3csc(C)n3)n(C3(C)CC3)c3ncnc(N)c23)cc1] | m/z [M + H]+ 473.2<br>1H-NMR (DMSO-D6)δ ppm: 10.22 (1H, s), 8.24 (1H, brs), 7.99 (1H, s), 7.76 (2H, d, J = 8.5 Hz), 7.30 (2H, d, J = 8.5 Hz), 4.36 (2H, s), 3.27 (3H, s), 2.70 (3H, s), 1.55 (3H, s), 1.33-1.300 (2H, m), 1.17-1.13 (2H, m). |

TABLE 25
| | | |
|---|---|---|
| 127 | 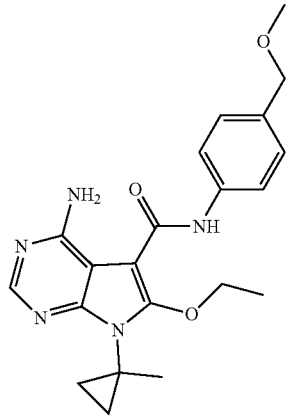 [SMILES: CCOc1c(C(=O)Nc2ccc(COC)cc2)c2c(N)ncnc2n1C1(C)CC1] | m/z [M + H]+ 396.2<br>¹H NMR (400 MHz, DMSO-d₆) δ ppm: 9.61 (1H, s) 8.12 (1H, s) 7.64 (2H, d, J = 8.43 Hz) 7.52 (2H, br s) 7.26-7.31 (2H, m) 4.34-4.41 (4H, m) 3.25-3.27 (3H, m) 1.55 (3H, s) 1.43 (3H, t, J = 6.96 Hz) 1.15-1.21 (2H, m) 1.03-1.10 (2H, m) |
| 128 | 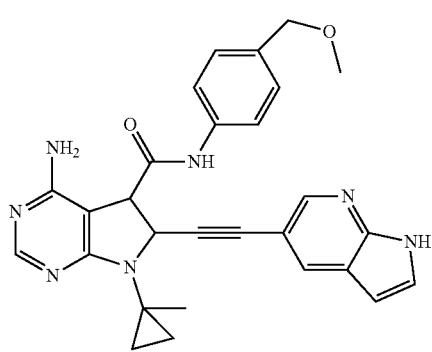 [SMILES: COCc1ccc(NC(=O)C2c3c(N)ncnc3N(C3(C)CC3)C2C#Cc2cnc3[nH]ccc3c2)cc1] | m/z [M + H]+ 492.3<br>1H-NMR (DMSO-D6)δ ppm: 12.02 (1H, s), 10.27 (1H, s), 8.37 (1H, brs), 8.23 (1H, m), 8.16 (1H, m), 7.75 (2H, d, J = 8.5 Hz), 7.61-7.56 (3H, m), 7.32 (2H, d, J = 8.3 Hz), 6.53-6.50 (1H, m), 4.37 (2H, d, J = 5.1 Hz), 3.28 (3H, s), 1.59 (3H, s), 1.35 (2H, m), 1.23-1.20 (2H, m). |
| 129 | 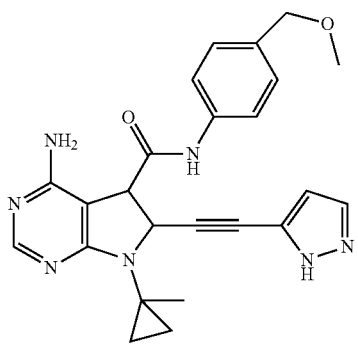 [SMILES: COCc1ccc(NC(=O)C2c3c(N)ncnc3N(C3(C)CC3)C2C#Cc2ccn[nH]2)cc1] | m/z [M + H]+ 442.4<br>1H-NMR (DMSO-D6)δ ppm: 13.41 (1H, s), 10.19 (1H, s), 8.22 (1H, s), 7.89 (1H, brs), 7.73 (2H, d, J = 8.0 Hz), 7.68-7.64 (2H, m), 7.29 (2H, d, J = 8.3 Hz), 6.57 (1H, d, J = 1.7 Hz), 4.36 (2H, s), 3.27 (3H, s), 1.55 (3H, s), 1.33-1.30 (2H, m), 1.14 (2H, m). |
| 130 | 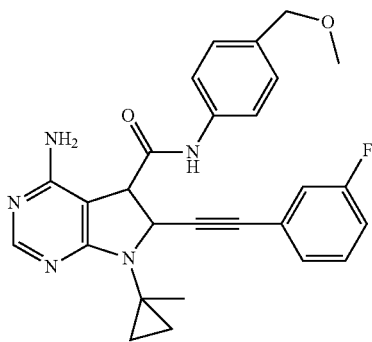 [SMILES: COCc1ccc(NC(=O)C2c3c(N)ncnc3N(C3(C)CC3)C2C#Cc2cccc(F)c2)cc1] | m/z [M + H]+ 470.2<br>1H-NMR (DMSO-D6)δ ppm: 10.33 (1H, s), 8.24 (1H, brs), 7.73 (2H, d, J = 8.5 Hz), 7.58 (2H, brs), 7.54-7.48 (1H, m), 7.38-7.31 (5H, m), 4.37 (2H, s), 3.27 (3H, s), 1.57 (3H, s), 1.34-1.31 (2H, m), 1.21-1.18 (2H, m). |

TABLE 25-continued

| | | |
|---|---|---|
| 131 | 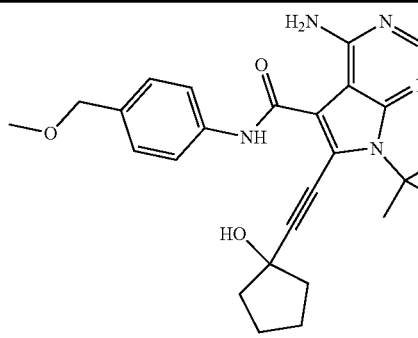 | m/z [M + H]+ 460.3<br>$^1$H NMR (400 MHz, DMSO-d$_6$) δ ppm 9.89 (1H, s) 8.18 (1H, s) 7.71 (2H, d, J = 8.43 Hz) 7.30 (2H, d, J = 8.43 Hz) 4.36(2H, s) 3.26(3H, s) 1.89-2.03 (4H, m) 1.63-1.80(4H, m) 1.49 (3H, s) 1.19-1.30(2H, m) 1.05-1.13 (2H, m) |
| 132 | 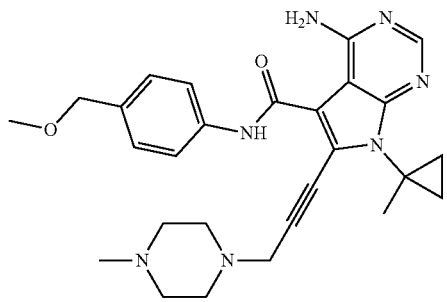 [SMILES: COCc1ccc(NC(=O)c2c(C#CCN3CCN(C)CC3)n(C3(C)CC3)c3ncnc(N)c23)cc1] | m/z [M + H]+ 488.3<br>$^1$H NMR (400 MHz, CHLOROFORM-d) δ ppm 9.31 (1H, s) 8.36 (1H, s) 7.64 (2H, m, J = 8.43 Hz) 7.35 (2H, d, m, J = 8.43 Hz) 4.45 (2H, s) 3.76 (2H, s) 3.39 (3H, s) 2.65-2.79 (4H, m) 2.37-2.57 (4H, m) 2.28 (3H, s) 1.60 (3H, s) 1.33-1.40(2H, m) 1.10-1.17(2H, m) |
| 133 | 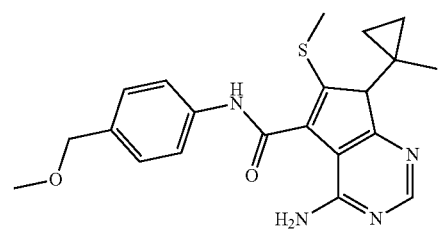 | m/z [M + H]+ 398.6<br>1H-NMR (DMSO-D6)δ ppm: 10.44 (1H, s), 8.17 (1H, s), 7.69 (2H, J = 8.3 Hz, d), 7.41-7.31 (4H, m), 4.37 (2H, s), 3.28 (3H, s), 2.43 (3H, s), 1.52 (3H, s), 1.24-1.12 (4H, m). |
| 134 | 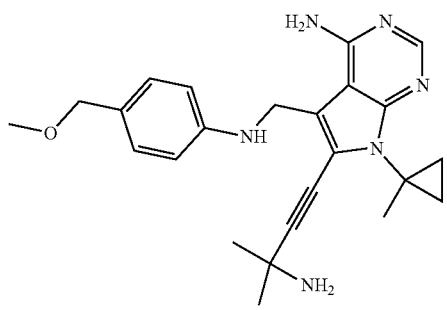 | m/z [M + H]+ 433.2<br>$^1$H NMR (400 MHz, DMSO-d$_6$) δ ppm: 9.85 (1H, s) 8.17 (1H, s) 7.72 (2H, d, J = 8.80 Hz) 7.30 (2H, d, J = 8.43 Hz) 4.36 (2H, s) 3.26 (3H, s) 1.49 (3H, s) 1.43 (6H, s) 1.21-1.33 (2H, m) 1.06-1.18 (2H, m) |
| 135 | 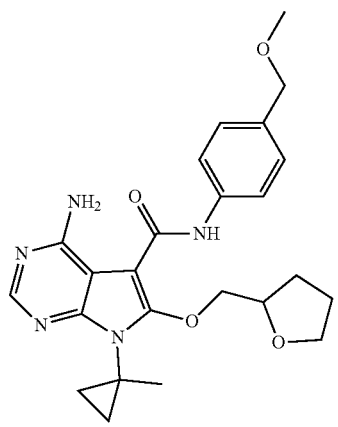 [SMILES: COCc1ccc(NC(=O)c2c(OCC3CCCO3)n(C3(C)CC3)c3ncnc(N)c23)cc1] | m/z [M + H]+ 452.4<br>$^1$H NMR (400 MHz, DMSO-d$_6$) δ ppm: 9.62 (1H, s) 8.12 (1H, s) 7.63 (2H, d, J = 8.43 Hz) 7.28 (2H, d, J = 8.43 Hz) 4.53 (1H, dd, J = 9.71, 2.38 Hz) 4.35 (2H, s) 4.28-4.34 (1H, m) 4.20-4.27 (1H, m) 3.65-3.76 (2H, m) 3.26 (3H, s) 1.95-2.08 (1H, m) 1.79-1.90 (2H, m) 1.66-1.77 (1H, m) 1.59 (3H, s) 1.21-1.28 (1H, m) 1.03-1.19 (3H, m) |

TABLE 26
| | | |
|---|---|---|
| 136 | 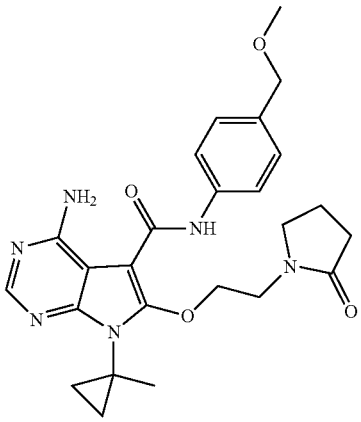 [SMILES: COCc1ccc(NC(=O)c2c(OCCN3CCCC3=O)n(C3(C)CC3)c3ncnc(N)c23)cc1] | m/z [M + H]+ 479.1<br>¹H NMR (400 MHz, DMSO-d₆) δ ppm: 9.61 (1H, s) 8.12 (1H, s) 7.67 (2H, d, J = 8.43 Hz) 7.47 (2H, br s) 7.28 (2 H, d, J = 8.43 Hz) 4.39 (2 H, t, J = 5.13 Hz) 4.36 (2H, s) 3.63 (2H, t, J = 5.13 Hz) 3.47 (2H, t, J = 6.96 Hz) 3.25 (3H, s) 2.09-2.19 (2H, m) 1.80-1.91 (2H, m) 1.55 (3H, s) 1.13-1.23 (2H, m) 1.02-1.11 (2H, m) |
| 137 | 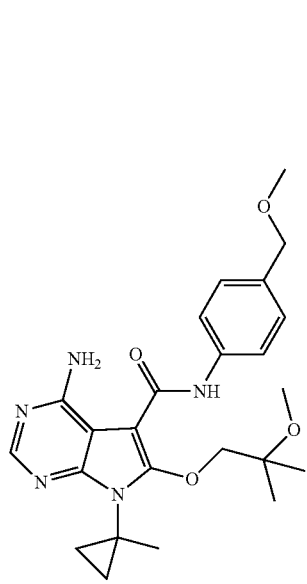 [SMILES: COCc1ccc(NC(=O)c2c(OCC(C)(C)OC)n(C3(C)CC3)c3ncnc(N)c23)cc1] | m/z [M + H]+ 454.4<br>¹H NMR (400 MHz, CHLOROFORM-d) δ ppm: 9.46 (1H, s) 8.34 (1H, s) 7.61 (2H, d, J = 8.43 Hz) 7.33 (2H, d, J = 8.43 Hz) 4.45 (2H, s) 4.25 (2H, s) 3.39 (3H, s) 3.16 (3H, s) 1.72 (3H, s) 1.40 (6H, s) 1.30-1.35 (2H, m) 1.08-1.13 (2H, m) |
| 138 | 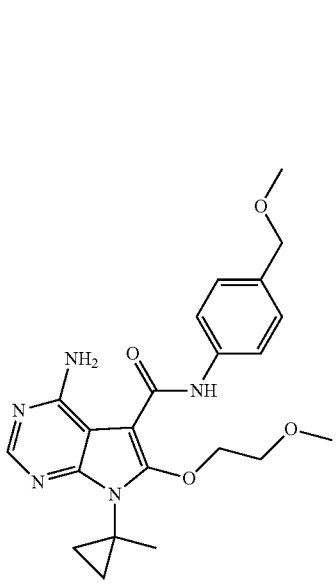 [SMILES: COCCOc1c(C(=O)Nc2ccc(COC)cc2)c2c(N)ncnc2n1C1(C)CC1] | m/z [M + H]+ 426.2<br>¹H NMR (400 MHz, CHLOROFORM-d) δ ppm: 9.28 (1H, s) 8.33-8.37 (1H, m) 7.62 (2H, d, J = 7.83 Hz) 7.33 (2H, d, J = 8.43 Hz) 4.54-4.58 (2H, m) 4.45 (2H, s) 3.82-3.86 (2H, m) 3.39 (3H, s) 3.36 (3H, s) 1.70-1.72 (3H, m) 1.31-1.37(2H, m) 1.08-1.13 (2H, m) |

TABLE 26-continued

| 139 | 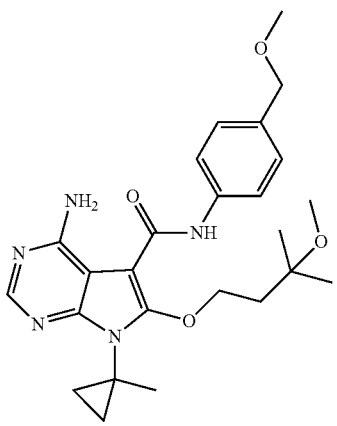 [SMILES: COCc1ccc(NC(=O)c2c(OCCC(C)(C)OC)n(C3(C)CC3)c3ncnc(N)c23)cc1] | m/z [M + H]+ 468.2<br>$^1$H NMR (400 MHz, DMSO-d$_6$) δ ppm: 9.64 (1H, s) 8.12 (1H, s) 7.64 (2H, d, J = 8.43 Hz) 7.47 (2H, br s) 7.28 (2H, d, J = 8.43 Hz) 4.31-4.39 (4H, m) 3.25 (3H, s) 2.99 (3H, s) 2.04 (2H, t, J = 7.51 Hz) 1.54 (3H, s) 1.14-1.21 (2H, m) 1.09 (6H, s) 1.01-1.07 (2H, m) |
| 140 | 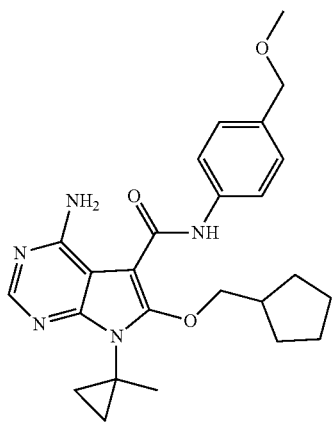 [SMILES: COCc1ccc(NC(=O)c2c(OCC3CCCC3)n(C3(C)CC3)c3ncnc(N)c23)cc1] | m/z [M + H]+ 450.6<br>$^1$H NMR (400 MHz, DMSO-d$_6$) δ ppm 9.64-9.66 (1H, m) 8.13 (1H, s) 7.63 (2H, d, J = 7.67 Hz) 7.42 (2H, br s) 7.28 (2H, d, J = 8.43 Hz) 4.35 (2H, s) 4.16 (2H, d, J = 6.97 Hz) 3.26 (3H, s) 2.29-2.46 (1H, m) 1.68-1.80 (2H, m) 1.54-1.57(4H, m) 1.55 (3H, s) 1.34-1.44 (2H, m) 1.12-1.25 (2H, m) 1.02-1.07(2H, m) |
| 141 | 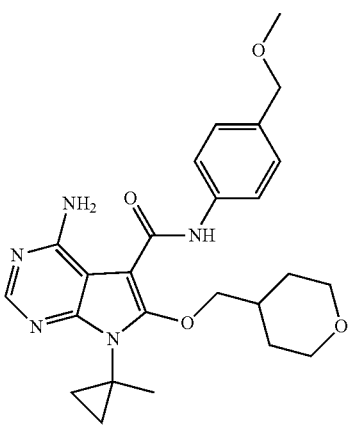 [SMILES: COCc1ccc(NC(=O)c2c(OCC3CCOCC3)n(C3(C)CC3)c3ncnc(N)c23)cc1] | m/z [M + H]+ 466.2<br>$^1$H-NMR (400 MHz, DMSO-d$_6$) δ ppm 9.68 (1H, s) 8.14 (1H, s) 7.63 (2H, d, J = 8.43 Hz) 7.37 (2H, br s) 7.28 (2 H, d, J = 8.43 Hz) 4.31-4.39 (2H, m) 4.10 (2H, d, J = 5.87 Hz) 3.81 (2H, br dd, J = 11.36, 2.93 Hz) 3.21-3.30 (5H, m) 2.00-2.22 (1H, m) 1.66 (2H, br d, J = 12.46 Hz) 1.54 (3H, s) 1.32-1.49 (2H, m) 1.10-1.25 (2H, m) 1.02-1.07 (2H, m) |
| 142 | 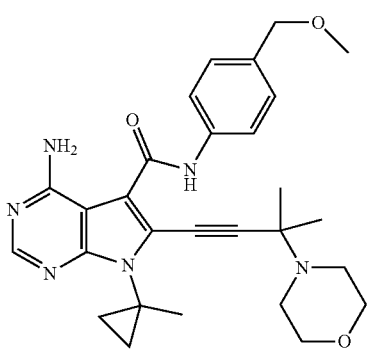 [SMILES: COCc1ccc(NC(=O)c2c(C#CC(C)(C)N3CCOCC3)n(C3(C)CC3)c3ncnc(N)c23)cc1] | m/z [M + H]+ 503.3<br>1H-NMR (DMSO-D6)δ ppm: 10.02 (1H, s), 8.19 (1H, s), 7.68-7.66 (2H, m), 7.47 (2H, brs), 7.29 (2H, d, J = 8.5 Hz), 4.36 (2H, s), 3.50-3.48 (4H, m), 3.26 (3H, s), 2.58 (4H, t, J = 4.5 Hz), 1.53 (3H, s), 1.39 (6H, s), 1.26 (2H, m), 1.11 (2H, m). |

TABLE 26-continued

| | | |
|---|---|---|
| 143 | *[structure]* | m/z [M + H]+ 490.4<br>¹H NMR (400 MHz, DMSO-d₆) δ ppm: 9.95 (1H, s) 8.19 (1H, br s) 7.65-7.71 (2H, m) 7.67 (2H, d, J = 8.43 Hz) 7.29 (2H, d, J = 8.43 Hz) 4.81 (1H, s) 4.36 (2H, s) 3.49-3.61 (4H, m) 3.26 (3H, s) 2.78 (2H, s) 1.61-1.84 (2H, m) 1.44-1.56 (2H, m) 1.50 (3H, s) 1.19-1.30 (2H, m) 1.06-1.16 (2H, m) |
| 144 | *[structure]* | m/z [M + H]+ 484.5<br>1H-NMR (DMSO-D6)δ ppm: 10.11 (1H, s), 8.21-8.20 (2H, m), 7.71 (1H, m), 7.70-7.68 (2H, m), 7.31 (2H, d, J = 8.5 Hz), 4.55 (1H, m), 4.36 (2H, s), 3.27 (3H, s), 1.53 (3H, s), 1.41 (6H, d, J = 6.8 Hz), 1.31-1.24 (2H, m), 1.16-1.13 (2H, m). |

TABLE 27

| | | |
|---|---|---|
| 145 | *[structure]* | m/z [M + H]+ 458.4<br>1H-NMR (DMSO-S6)δ ppm: 8.61 (1H, s), 8.22 (1H, s), 7.57 (2H, J = 8.3 Hz, d), 7.47 (2H, J = 8.3 Hz, d), 7.30 (2H, s), 7.17-7.12 (4H, m), 5.35 (1H, J = 5.6 Hz, t), 4.59 (2H, J = 5.6 Hz, d), 4.28 (2H, s), 3.22 (3H, s), 1.59 (3H, s), 0.85-0.65 (4H, m). |
| 146 | *[structure]* | m/z [M + H]+ 410.3<br>¹H NMR (400 MHz, DMSO-d₆) δ ppm 9.51 (1H, s) 8.13 (1H, s) 7.63 (2H, d, J = 8.43 Hz) 7.29 (2H, d, J = 8.43 Hz) 4.80 (1H, quin, J = 6.14 Hz) 4.35 (2H, s) 3.26 (3H, s) 1.58 (3H, s) 1.37 (6H, d, J = 6.23 Hz) 1.16-1.22 (2H, m) 1.03-1.08 (2H, m) |

| | | |
|---|---|---|
| 147 | 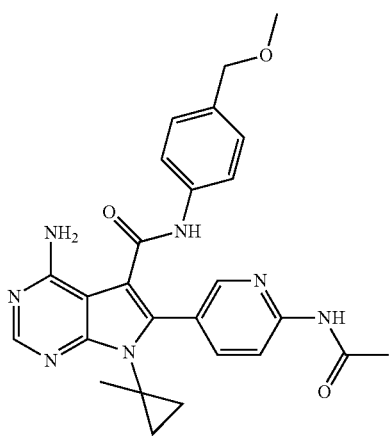 [SMILES: COCc1ccc(NC(=O)c2c(-c3ccc(NC(C)=O)nc3)n(C3(C)CC3)c3ncnc(N)c23)cc1] | m/z [M + H]+ 486.1<br>¹H NMR (400 MHz, DMSO-d₆) δ ppm 10.66(1H, s) 9.31(1H, s) 8.38(1H, d, J = 1.71 Hz) 8.25 (1H, s) 8.20 (1H, s) 7.97-8.05 (1H, m) 7.26-7.31 (2H, m) 7.17-7.21 (2H, m) 7.13-7.17 (2H, m) 4.31 (2H, s) 3,25 (3H, s) 2.11 (3H, s) 1.66 (3H, s) 0.71-0.90 (4H, m) |
| 148 | 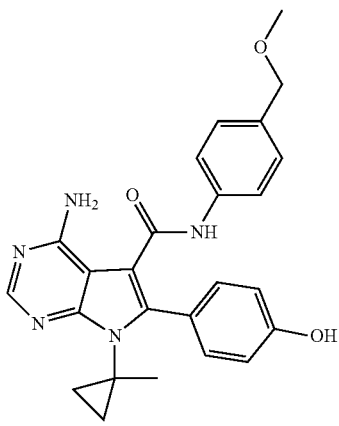 [SMILES: COCc1ccc(NC(=O)c2c(-c3ccc(O)cc3)n(C3(C)CC3)c3ncnc(N)c23)cc1] | m/z [M + H]+ 444.3<br>¹H NMR (400 MHz, DMSO-d₆) δ ppm 10.05 (1H, s) 8,47 (1H, s) 8.39 (1H, s) 7.42-7.47 (2H, m) 7.09-7.25 (4H, m) 6.94-6.99 (2H, m) 4.31 (2H, s) 3.24(5H, s) 1.58 (3H, s) 0.72-0.91 (4H, m) |
| 149 | 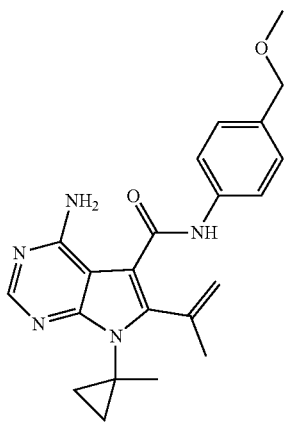 [SMILES: C=C(C)c1c(C(=O)Nc2ccc(COC)cc2)c2c(N)ncnc2n1C1(C)CC1] | m/z [M + H]+ 392.1<br>¹H NMR (400 MHz, DMSO-d₆) δ ppm 9.51 (1H, s) 8.19 (1H, s) 7.56 (2 H, d, J = 8.30 Hz) 7.29 (2H, d, J = 8.54 Hz) 7.08 (2H, s) 5.64 (1H, s) 5.38 (1H, s) 4.36 (2H, s) 3.27 (3H, s) 2.21 (3H, s) 1.61 (3H, s) 1.22-1.29 (2H, m) 0.98-1.04 (2H, m) |
| 150 | 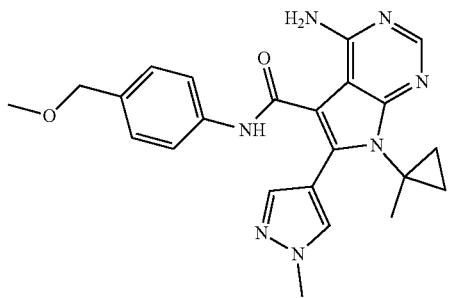 [SMILES: COCc1ccc(NC(=O)c2c(-c3cnn(C)c3)n(C3(C)CC3)c3ncnc(N)c23)cc1] | m/z [M + H]+ 432.3<br>¹H NMR (400 MHz, DM50-d₆) δ ppm 9.39 (1H, s) 8.18 (1H, s) 7.61 (2H, d, J = 8.54 Hz) 7.30 (2H, d, J = 8.54 Hz) 7.23 (2H, s) 4.37 (2H, s) 3.25-3.30 (3H, m) 2.27(3H, s) 1.58 (3H, s) 0.97-1.09 (4H, m) |

TABLE 27-continued
| | | |
|---|---|---|
| 151 | 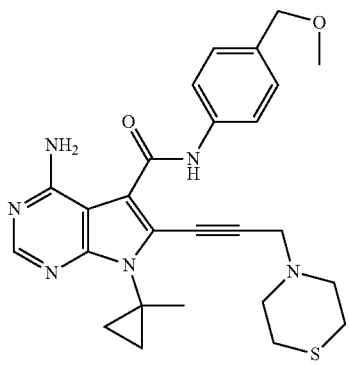 [SMILES: COCc1ccc(NC(=O)c2c(C#CCN3CCSCC3)n(C3(C)CC3)c3ncnc(N)c23)cc1] | m/z [M + H]+ 491.3<br>1H-NMR (DMSO-D6)δ ppm: 10.09 (1H, s), 8.20 (1H, s), 7.68-7.66 (2H, m), 7.55 (2H, brs), 7.30 (2H, d, J = 8.5 Hz), 4.36 (2H, s), 3.72 (2H, s), 3.26 (3H, s), 2.79-2,77 (4H, m), 2.53 (4H, m), 1.52 (3H, s), 1.28-1.25 (2H, m), 1.13-1.09 (2H, m). |
| 152 | 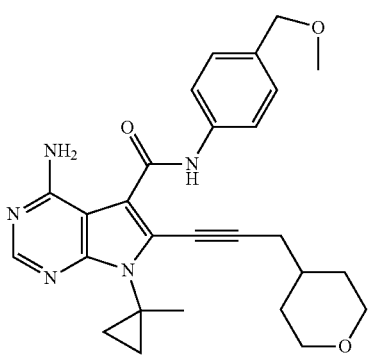 [SMILES: COCc1ccc(NC(=O)c2c(C#CCC3CCOCC3)n(C3(C)CC3)c3ncnc(N)c23)cc1] | m/z [M + H]+ 474.5<br>1H-NMR (DMSO-D6)δ ppm: 9.99 (1H, s), 8.18 (1H, s), 7.66-7.64 (2H, m), 7.32-7.29 (2H, d,J = 8.5 Hz), 4.37 (2H, s), 3.73 (2H, dt, J = 10.2, 1.8 Hz), 3.26 (3H, s), 3.14 (2H, td, 3 = 11.7, 2.0 Hz), 2.61 (2H, d, 3 = 6.6 Hz), 1.78 (1H, m), 1.65 (2H, dd, J = 12,9, 2.0 Hz), 1.50 (3H, s), 1.32-1.31 (2H, m), 1.25 (2H, m), 1.09-1.06 (2H, m). |
| 153 | 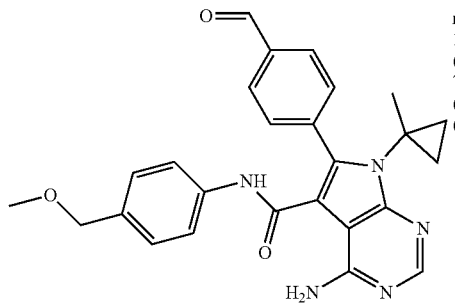 | m/z [M + H]+ 456.4<br>1H-NMR (DMSO-D6)δ ppm: 10.05 (1H, s), 9.20 (1H, s), 8.26 (1H, s), 8.01 (2H, J = 8.3 Hz, d), 7.79 (2H, 3 J = 8.3 Hz, d), 7.21-7.14 (6H, m), 4.28 (2H, s), 3.22 (3H, s), 1.68 (3H, s), 0.84-0.62 (4H, m). |
TABLE 28
| | | |
|---|---|---|
| 154 | 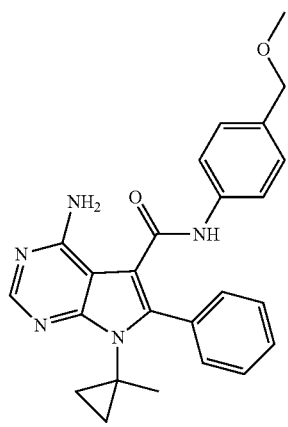 [SMILES: COCc1ccc(NC(=O)c2c(-c3ccccc3)n(C3(C)CC3)c3ncnc(N)c23)cc1] | m/z [M + H]+ 428.2<br>$^1$H NMR (400 MHz, DMSO-$d_6$) δ ppm: 8.62 (1H, s) 8.25 (1H, s) 7.60-7.65 (2H, m) 7.52-7.59 (3H, m) 7.31 (2H, s) 7.05-7.25 (4H, m) 4.29 (2H, s) 3.23 (3H, s) 1.60 (3H, s) 0.64-0.90 (4H, m) |

| | | |
|---|---|---|
| 155 | 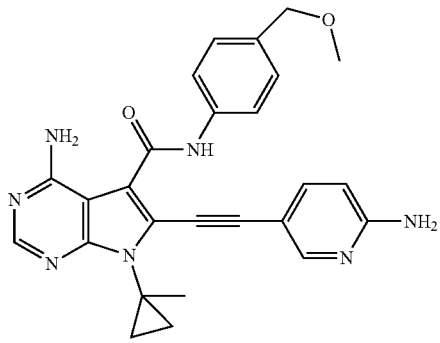 [SMILES: COCc1ccc(NC(=O)c2c(C#Cc3ccc(N)nc3)n(C3(C)CC3)c3ncnc(N)c23)cc1] | m/z [M + H]+ 468.2<br>1H-NMR (DMSO-D6)δ ppm: 10.15 (1H, s), 8.20 (1H, s), 8.11 (1H, d, J = 2.2 Hz), 7.72-7.70 (2H, m), 7.48 (1H, dd, J = 8.7, 2.3 Hz), 7.31 (2H, d, J = 8.5 Hz), 6.66 (2H, s), 6.49-6.46 (1H, m), 4.37 (2H, s), 3.27 (3H, s), 1.54 (3H, s), 1.31-1.28 (2H, m), 1.17-1.13 (2H, m). |
| 156 | 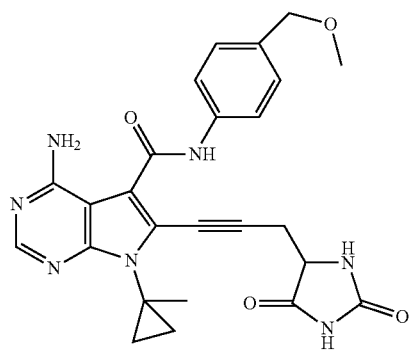 [SMILES: COCc1ccc(NC(=O)c2c(C#CCC3NC(=O)NC3=O)n(C3(C)CC3)c3ncnc(N)c23)cc1] | m/z [M + H]+ 488.3<br>1H-NMR (DMSO-D6)δ ppm: 10.85 (1H, s), 9.87 (1H, s), 8.18 (1H, brs), 8.12 (1H, brs), 7.67 (2H, d, J = 8.5 Hz), 7.31 (2H, d, J = 8.5 Hz), 4.37 (2H, d, J = 5.1 Hz), 4.36-4.33 (1H, m), 3.27 (3H, s), 3.10-3.07 (2H, m), 1.45 (3H, s), 1.18-1.17 (2H, m), 1.09-1.08 (2H, m). |
| 157 | 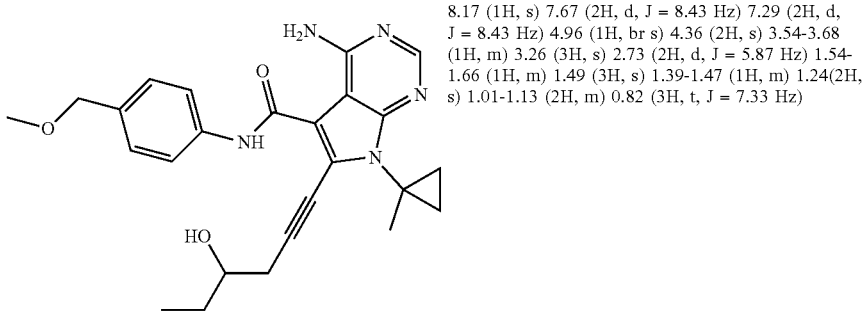 | m/z [M + H]+ 448.3<br>$^{1}$H NMR (400 MHz, DMSO-d$_{6}$) δ ppm 9.92 (1H, s) 8.17 (1H, s) 7.67 (2H, d, J = 8.43 Hz) 7.29 (2H, d, J = 8.43 Hz) 4.96 (1H, br s) 4.36 (2H, s) 3.54-3.68 (1H, m) 3.26 (3H, s) 2.73 (2H, d, J = 5.87 Hz) 1.54-1.66 (1H, m) 1.49 (3H, s) 1.39-1.47 (1H, m) 1.24(2H, s) 1.01-1.13 (2H, m) 0.82 (3H, t, J = 7.33 Hz) |
| 158 | 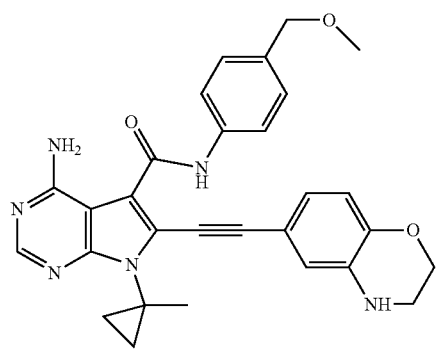 [SMILES: COCc1ccc(NC(=O)c2c(C#Cc3ccc4c(c3)NCCO4)n(C3(C)CC3)c3ncnc(N)c23)cc1] | m/z [M + H]+ 509.3<br>1H-NMR (DMSO-D6)δ ppm: 10.12 (1H, s), 8.20 (1H, s), 7.73-7.69 (2H, m), 7.32 (2H, d, J = 8.5 Hz), 6.79 (1H, t, J = 1.0 Hz), 6.70 (2H, d, J = 1.5 Hz), 6.06 (1H, brs), 4.37 (2H, s), 4.15 (2H, m), 3.30-3.26 (2H, m), 3.27 (3H, s), 1.55 (3H, s), 1.32 (2H, m), 1.14 (2H, m). |

TABLE 28-continued
| | | |
|---|---|---|
| 159 | 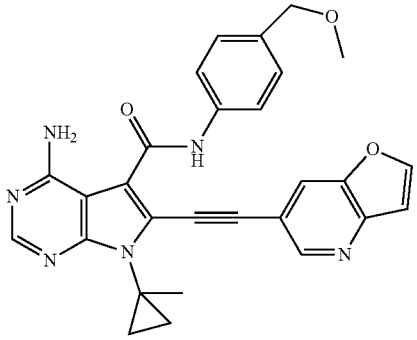 [SMILES: COCc1ccc(NC(=O)c2c(C#Cc3cnc4ccoc4c3)n(C3(C)CC3)c3ncnc(N)c23)cc1] | m/z [M + H]+ 493.3<br>1H-NMR (DMSO-D6)δ ppm: 10.36 (1H, s), 8.64 (1H, d, J = 1.7 Hz), 8.47 (1H, d, J = 2.4 Hz), 8.24 (1H, s),<br>8.21 (1H, m), 7.75 (2H, d, J = 8.5 Hz), 7.59 (2H, brs), 7.32 (2H, d,J = 8.5 Hz), 7.24 (1H, dd, J = 2.3, 0.9 Hz), 4.37 (2H, s), 3.27 (3H, s), 1.59 (3H, s), 1.36-1.33 (2H, m), 1.25-1.22 (2H, m). |
| 160 | 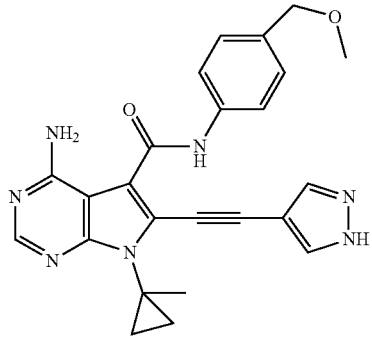 [SMILES: COCc1ccc(NC(=O)c2c(C#Cc3cn[nH]c3)n(C3(C)CC3)c3ncnc(N)c23)cc1] | m/z [M + H]+ 442.1<br>1H-NMR (DMSO-D6)δ ppm: 13.41 (1H, brs), 10.11 (1H, s), 8.20 (2H, s), 7.76 (1H, brs), 7.69 (2H, d, J = 8.3 Hz), 7.62 (2H, brs), 7.30 (2H, d, J = 8.5 Hz), 4.36 (2H, s), 3.27 (3H, s), 1.53 (3H, s), 1.31-1.28 (2H, m), 1.16-1.13 (2H, t, J = 6.5 Hz). |
| 161 | 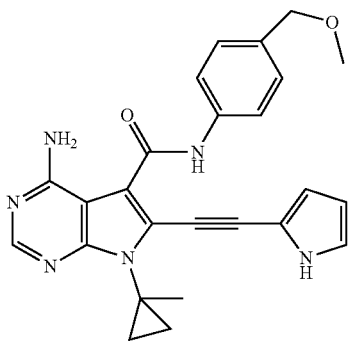 [SMILES: COCc1ccc(NC(=O)c2c(C#Cc3ccc[nH]3)n(C3(C)CC3)c3ncnc(N)c23)cc1] | m/z [M + H]+ 441.5<br>1H-NMR (DMSO-D6)δ ppm: 11.72 (1H, s), 10.06 (1H, s), 8.20 (1H, s), 7.68 (2H, d, J = 8.5 Hz), 7.29 (2H, d,<br>J = 8.5 Hz), 7.00-6.99 (1H, m), 6.53-6.51 (1H, m), 6.18-6.16 (1H, m), 4.36 (2H, s), 3.26 (3H, s), 1.54 (3H, s), 1.29-1.28 (2H, m), 1.18-1.14 (2H, m). |
| 162 | 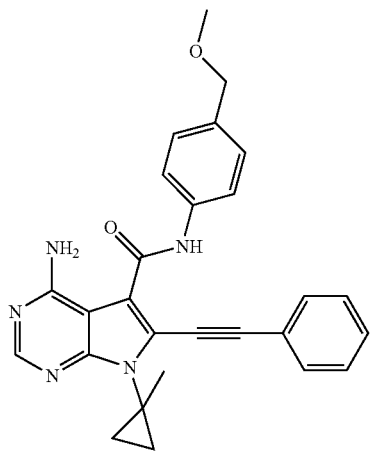 [SMILES: COCc1ccc(NC(=O)c2c(C#Cc3ccccc3)n(C3(C)CC3)c3ncnc(N)c23)cc1] | m/z [M + H]+ 452.4<br>$^1$H NMR (400 MHz, DMSO-$d_6$) δ ppm 10.29 (1H, s) 8.23 (1H, s) 7.74 (2H, d, J = 8.54 Hz) 7.53-7.62 (4H, m) 7.45-7.52 (3H, m) 7.33 (2H, d, J = 8.78 Hz) 4.39 (2H, s) 3.29 (3H, s) 1.58 (3H, s) 1.28-1.43 (2H, m) 1.12-1.27 (2H, m) |

TABLE 29
163 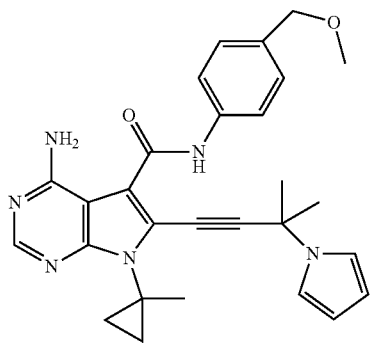 [SMILES: COCc1ccc(NC(=O)c2c(C#CC(C)(C)n3cccc3)n(C3(C)CC3)c3ncnc(N)c23)cc1]
m/z [M + H]+ 483.4
1H-NMR (DMSO-D6)δ ppm: 10.17 (1H, s), 8.21 (1H, s), 7.63 (2H, d, J = 8.5 Hz), 7.50 (2H, brs), 7.28 (2H, d, J = 8.5 Hz), 7.07 (2H, t, J = 2.2 Hz), 5.98 (2H, t, J = 2.2 Hz), 4.36 (2H, s), 3.26 (3H, s), 1.83 (6H, s), 1.50 (3H, s), 1.25-1.23 (2H, m), 1.09-1.06 (2H, m).
164 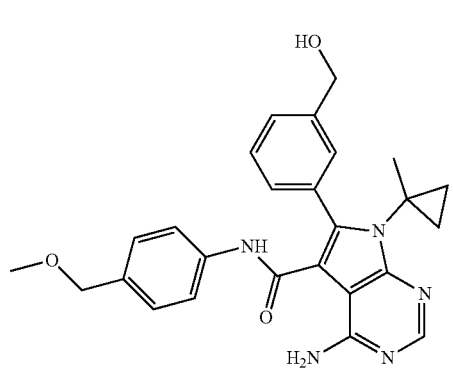 [SMILES: COCc1ccc(NC(=O)c2c(-c3cccc(CO)c3)n(C3(C)CC3)c3ncnc(N)c23)cc1]
m/z [M + H]+ 458.5
1H-NMR (DMSO-D6)δ ppm: 8.54 (1H, s), 8.23 (1H, s), 7.55-7.49 (4H, m), 7.34 (2H, s), 7.17-7.09 (4H, m), 5.32 (1H, br s), 4.55 (2H, s), 4.28 (2H, s), 3.22 (3H, s), 1.58 (3H, s), 0.84-0.65 (4H, m).
165 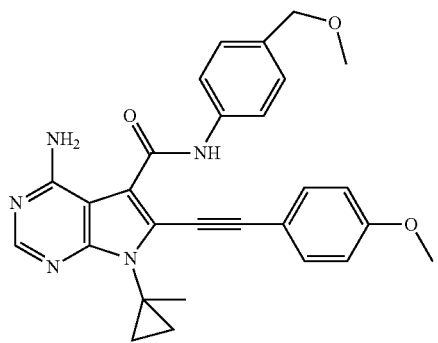 [SMILES: COCc1ccc(NC(=O)c2c(C#Cc3ccc(OC)cc3)n(C3(C)CC3)c3ncnc(N)c23)cc1]
m/z [M + H]+ 482.1
1H-NMR (DMSO-D6)δ ppm: 10.22 (1H, s), 8.21 (1H, s), 7.72 (2H, d, J = 8.3 Hz), 7.59 (2H, brs), 7.49 (2H, d, J = 8.8 Hz), 7.31 (2H, d, J = 8.3 Hz), 7.03 (2H, d, J = 8.8 Hz), 4.37 (2H, s), 3.79 (3H, s), 3.27 (3H, s), 1.56 (3H, s), 1.33-1.30 (2H, m), 1.18-1.15 (2H, m).
166 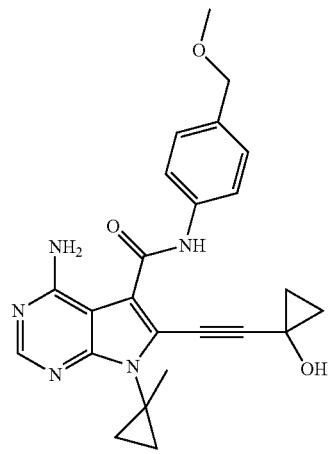 [SMILES: COCc1ccc(NC(=O)c2c(C#CC3(O)CC3)n(C3(C)CC3)c3ncnc(N)c23)cc1]
m/z [M + H]+ 432.4
$^1$H NMR (400 MHz, CHLOROFORM-d) δ ppm: 9.32 (1H, s) 8.42 (1H, s) 7.67 (2H, d, J = 8.43 Hz) 7.36 (2H, d, J = 8.06 Hz) 4.45 (2H, s) 3.40 (3H, s) 1.57 (3H, s) 1.39-1.43 (2H, m) 1.30-1.36 (2H, m) 1.24-1.29 (2H, m) 1.06-1.13 (2H, m)

| | | |
|---|---|---|
| 167 | 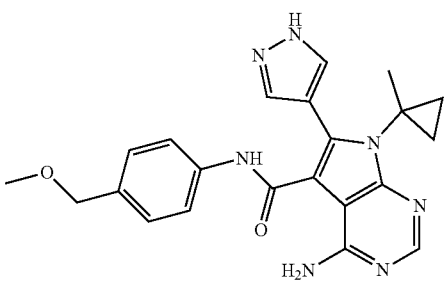 [SMILES: COCc1ccc(NC(=O)c2c(-c3cn[nH]c3)n(C3(C)CC3)c3ncnc(N)c23)cc1] | m/z [M + H]+ 418.3<br>1H-NMR (DMSO-D6)δ ppm: 13.28 (1H, s), 8.96 (1H, s), 8.16 (1H, s), 8.09 (1H, br s), 7.76 (1H, br s), 7.30-7.23 (4H, m), 7.19 (2H, J = 8.4 Hz, d), 4.30 (2H, s), 3.22 (3H, s), 1.51 (3H, s), 0.90-0.78 (4H, m). |
| 168 | 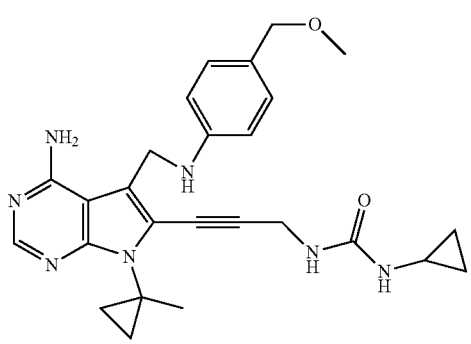 | m/z [M + H]+ 488.4<br>1H-NMR (DMSO-D6)δ ppm: 9.86 (1H, s), 8.18 (1H, s), 7.69 (2H, m), 7.30 (2H, d, J =8.5 Hz), 6.43 (2H, d, J = 2.4 Hz), 4.37 (2H, s), 4.27-4.26 (2H, m), 3.27 (3H, s), 2.35 (1H, m), 1.49 (3H, s), 1.22 (2H, m), 1.08 (2H, m), 0.56-0.53 (2H, m), 0.30 (2H, m). |
| 169 | 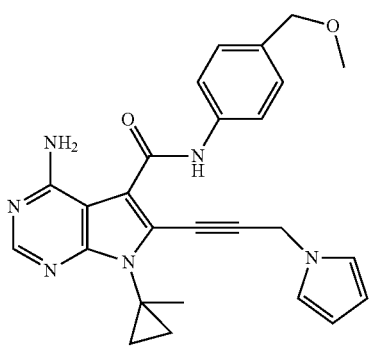 [SMILES: COCc1ccc(NC(=O)c2c(C#CCn3cccc3)n(C3(C)CC3)c3ncnc(N)c23)cc1] | m/z [M + H]+ 455.3<br>1H-NMR (DMSO-D6)δ ppm: 10.02 (1H, s), 8.19 (1H, s), 7.60 (2H, d, J = 8.3 Hz), 7.56 (2H, brs), 7.29 (2H, d, J = 8.5 Hz), 6.88 (2H, m), 6.02 (2H, m), 5.28 (2H, s), 4.38 (2H, s), 3.28 (3H, s), 1.46 (3H, s), 1.21 (2H,m), 1.00 (2H, m). |
| 170 | 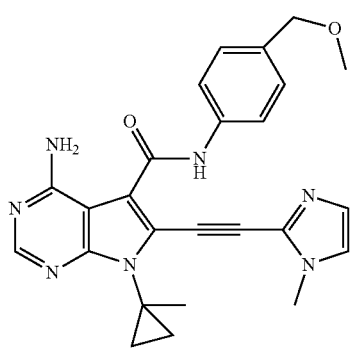 [SMILES: COCc1ccc(NC(=O)c2c(C#Cc3nccn3C)n(C3(C)CC3)c3ncnc(N)c23)cc1] | m/z [M + H]+ 456.2<br>1H-NMR (DMSO-D6)δ ppm: 10.32 (1H, s), 8.25 (1H, brs), 7.72 (2H, d,J = 8.5 Hz), 7.58 (2H, brs), 7.39 (1H, brs), 7.30 (2H, d, J = 8.0 Hz), 7.09 (1H, brs), 4.36 (2H, s), 3.65 (3H, s), 3.27 (3H, s), 1.58 (3H, s), 1.35-1.32 (2H, m), 1.17-1.14 (2H, m). |

TABLE 29-continued
| | | |
|---|---|---|
| 171 | 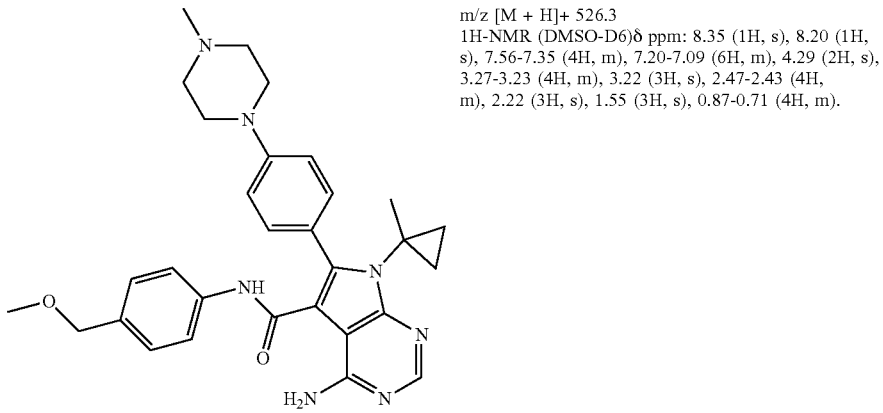 | m/z [M + H]+ 526.3<br>1H-NMR (DMSO-D6)δ ppm: 8.35 (1H, s), 8.20 (1H, s), 7.56-7.35 (4H, m), 7.20-7.09 (6H, m), 4.29 (2H, s), 3.27-3.23 (4H, m), 3.22 (3H, s), 2.47-2.43 (4H, m), 2.22 (3H, s), 1.55 (3H, s), 0.87-0.71 (4H, m). |
TABLE 30
| | | |
|---|---|---|
| 172 | 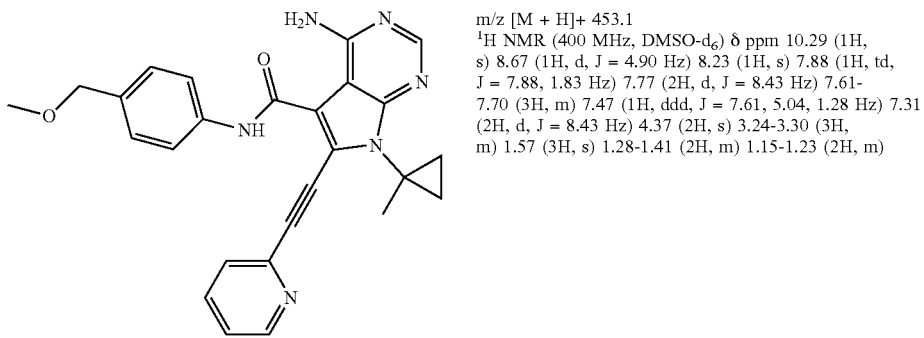 | m/z [M + H]+ 453.1<br>$^1$H NMR (400 MHz, DMSO-$d_6$) δ ppm 10.29 (1H, s) 8.67 (1H, d, J = 4.90 Hz) 8.23 (1H, s) 7.88 (1H, td, J = 7.88, 1.83 Hz) 7.77 (2H, d, J = 8.43 Hz) 7.61-7.70 (3H, m) 7.47 (1H, ddd, J = 7.61, 5.04, 1.28 Hz) 7.31 (2H, d, J = 8.43 Hz) 4.37 (2H, s) 3.24-3.30 (3H, m) 1.57 (3H, s) 1.28-1.41 (2H, m) 1.15-1.23 (2H, m) |
| 173 | 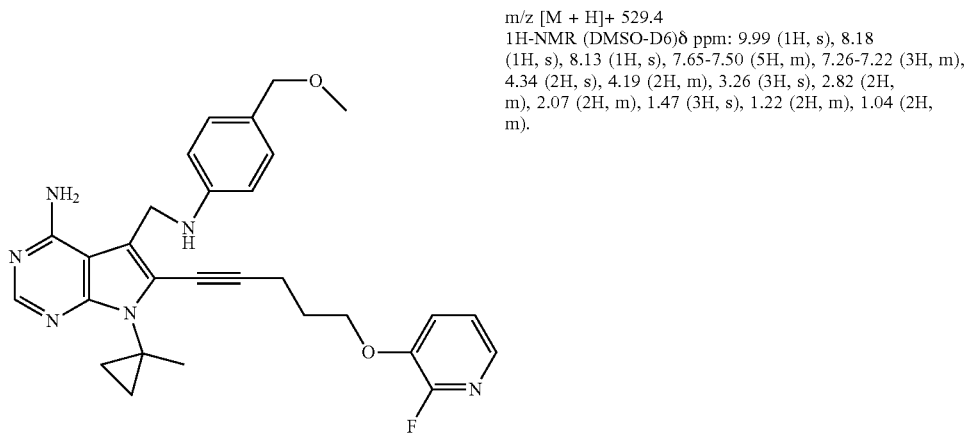 | m/z [M + H]+ 529.4<br>1H-NMR (DMSO-D6)δ ppm: 9.99 (1H, s), 8.18 (1H, s), 8.13 (1H, s), 7.65-7.50 (5H, m), 7.26-7.22 (3H, m), 4.34 (2H, s), 4.19 (2H, m), 3.26 (3H, s), 2.82 (2H, m), 2.07 (2H, m), 1.47 (3H, s), 1.22 (2H, m), 1.04 (2H, m). |
| 174 | 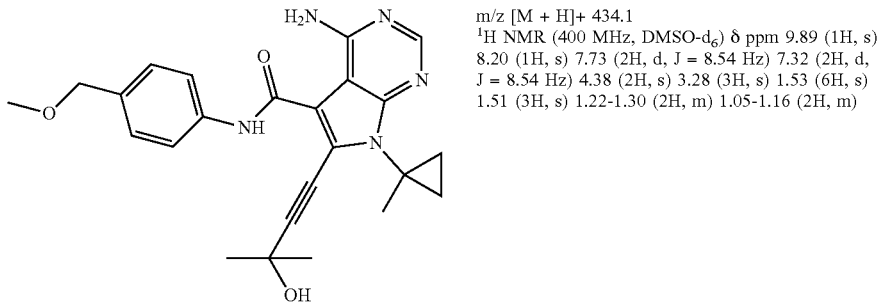 | m/z [M + H]+ 434.1<br>$^1$H NMR (400 MHz, DMSO-$d_6$) δ ppm 9.89 (1H, s) 8.20 (1H, s) 7.73 (2H, d, J = 8.54 Hz) 7.32 (2H, d, J = 8.54 Hz) 4.38 (2H, s) 3.28 (3H, s) 1.53 (6H, s) 1.51 (3H, s) 1.22-1.30 (2H, m) 1.05-1.16 (2H, m) |

TABLE 30-continued
| 175 | 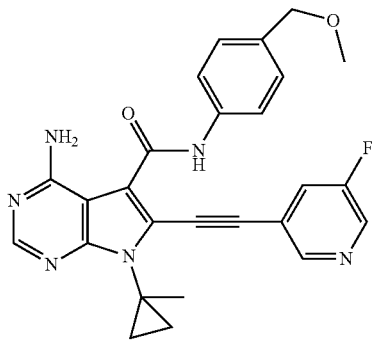 [SMILES: COCc1ccc(NC(=O)c2c(C#Cc3cncc(F)c3)n(C3(C)CC3)c3ncnc(N)c23)cc1] | m/z [M + H]+ 471.1<br>1H-NMR (DMSO-D6)δ ppm: 10.37 (1H, s), 8.68 (1H, s), 8.55 (1H, s), 8.25 (1H, brs), 7.90-7.87 (1H, m), 7.73 (2H, d, J = 8.5 Hz), 7.58 (2H, brs), 7.32 (2H, d, J = 8.5 Hz), 4.37 (2H, s), 3.27 (3H, s), 1.57 (3H, s), 1.32 (2H, m), 1.22 (2H, m). |
|---|---|---|
| 176 | 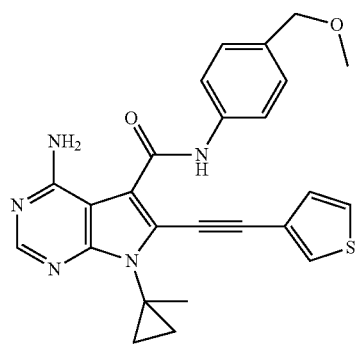 [SMILES: COCc1ccc(NC(=O)c2c(C#Cc3ccsc3)n(C3(C)CC3)c3ncnc(N)c23)cc1] | m/z [M + H]+ 458.1<br>1H-NMR (DMSO-D6)δ ppm: 10.21 (1H, s), 8.22 (1H, s), 7.97 (1H, dd, J = 2.9, 1.2 Hz), 7.72-7.70 (3H, m), 7.31 (2H, d, J = 8.5 Hz), 7.22 (1H, dd, J = 4.9, 1.2 Hz), 4.37 (2H, s), 3.27 (3H, s), 1.55 (3H, s), 1.31 (2H, m), 1.17 (2H, m). |
| 177 | 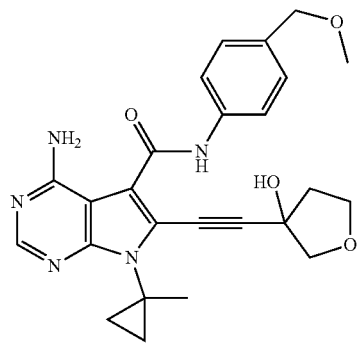 [SMILES: COCc1ccc(NC(=O)c2c(C#CC3(O)CCOC3)n(C3(C)CC3)c3ncnc(N)c23)cc1] | m/z [M + H]+ 462.3<br>1H-NMR (DMSO-D6)δ ppm: 9.97 (1H, s), 8.20 (1H, s), 7.72-7.69 (2H, m), 7.31 (2H, d,J = 8.8 Hz), 4.37 (2H, s), 3.91-3.81 (4H, m), 3.25 (3H, s), 2.33-2.24 (2H, m),1.50 (3H, s), 1.25-1.23 (2H, m), 1.11-1.08 (2H, m). |
| 178 | 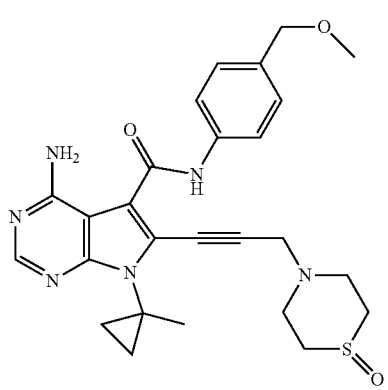 [SMILES: COCc1ccc(NC(=O)c2c(C#CCN3CCS(=O)CC3)n(C3(C)CC3)c3ncnc(N)c23)cc1] | m/z [M + H]+ 507.3<br>1H-NMR (DMSO-D6)δ ppm: 10.06 (1H, s), 8.20 (1H, s), 7.67 (2H, d, J = 8.5 Hz), 7.56 (2H, brs), 7.31 (2H, d, J = 8.3 Hz), 4.37 (2H, s), 3.80 (2H, s), 3.27 (3H, s), 3.13-2.69 (8H, m), 1.52 (3H, s), 1.26-1.24 (2H, m), 1.17-1.14 (2H, m). |

TABLE 30-continued
| 179 | 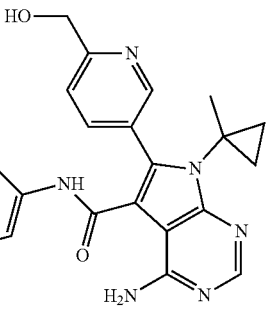 | m/z [M + H]+ 459.4<br>1H-NMR (DMSO-D6)δ ppm: 9.27 (1H, s), 8.61 (1H, J = 2.0 Hz, d), 8.24 (1H, s), 8.00 (1H, J = 8.0, 2.2 Hz, dd), 7.58 (1H, J = 8.0 Hz, d), 7.24 (2H, J = 8.5 Hz, d), 7.19-7.11 (4H, m), 5.53 (1H, J = 5.9 Hz, t), 4.60 (2H, J = 5.9 Hz, d), 4.29 (2H, s), 3.23 (3H, s), 1.65 (3H, s), 0.85-14.65 (4H, m). |
| --- | --- | --- |
| 180 | 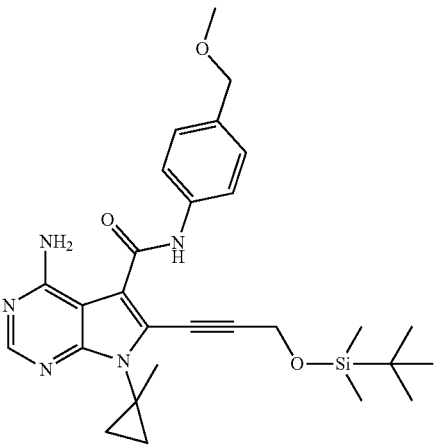 [SMILES: COCc1ccc(NC(=O)c2c(C#CCO[Si](C)(C)C(C)(C)C)n(C3(C)CC3)c3ncnc(N)c23)cc1] | m/z [M + H]+ 520.2<br>$^1$H NMR (400 MHz, DMSO-d$_6$) δ ppm 9.96 (1H, s) 8.13 (1H, s) 7.61 (2H, d, J = 8.80 Hz) 7.54 (2H, br s) 7.22 (2H, d, J = 8.43 Hz) 4.67 (2H, s) 4.30 (2H, s) 3.19 (3H, s) 1.44 (3H, s) 1.16-1.21 (2H, m) 0.97-1.08 (2H, m) 0.77 (9H, s) 0.00 (6H, s) |
TABLE 31
| 181 | 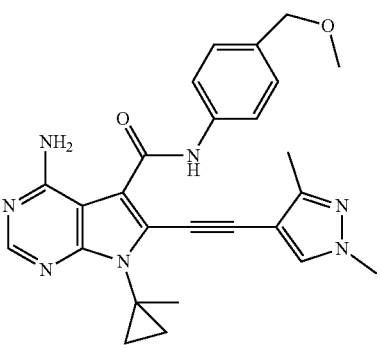 [SMILES: COCc1ccc(NC(=O)c2c(C#Cc3cn(C)nc3C)n(C3(C)CC3)c3ncnc(N)c23)cc1] | m/z [M + H]+ 470.3<br>1H-NMR (DMSO-D6)δ ppm: 10.13 (1H, s), 8.20 (1H, s), 8.02 (1H, s), 7.66 (2H, d, J = 8.3 Hz), 7.57 (2H, brs), 7.29 (2H, d, J = 8.4 Hz), 4.36 (2H, s), 3.78 (3H, s), 3.27 (3H, s), 2.12 (3H, s), 1.54 (3H, s), 1.31-1.28 (2H, m), 1.43-1.11 (2H, m). |
| --- | --- | --- |
| 182 | 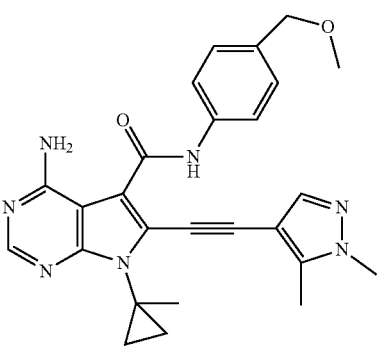 [SMILES: COCc1ccc(NC(=O)c2c(C#Cc3cnn(C)c3C)n(C3(C)CC3)c3ncnc(N)c23)cc1] | m/z [M + H]+ 470.4<br>1H-NMR (DMSO-D6)δ ppm: 10.12 (1H, s), 8.20 (1H, s), 7.67 (2H, d, J = 8.5 Hz), 7.58 (1H, s), 7.30 (2H, d, J = 8.5 Hz), 4.36 (2H, s), 3.75 (3H, s), 3.27 (3H, s), 2.27 (3H, s), 1.55 (3H, s), 1.30 (2H, m), 1.14-1.13 (2H, m). |

| | | |
|---|---|---|
| 183 | 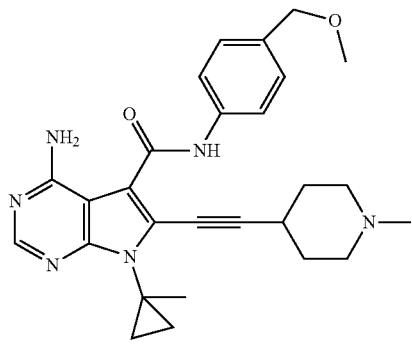 [SMILES: COCc1ccc(NC(=O)c2c(C#CC3CCN(C)CC3)n(C3(C)CC3)c3ncnc(N)c23)cc1] | m/z [M + H]+ 473.4<br>1H-NMR (DMSO-D6)δ ppm: 9.97 (1H, s), 8.18 (1H, s), 7.66 (2H, d, J =8.3 Hz), 7.62-7.57 (2H, m), 7.30 (2H, d, J = 8.3 Hz), 4.36 (2H, s), 3.27 (3H, s), 2.87-2.85 (1H, m), 2.63-2.60 (2H, m), 2.17-2.16 (2H, m), 2.14 (3H, s), 1.89-1.85 (2H, m), 1.72-1.65 (2H, m), 1.50 (3H, s), 1.26-1.23 (2H, m), 1.09-1.06 (2H, m). |
| 184 | 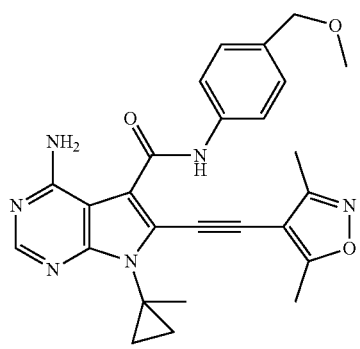 [SMILES: COCc1ccc(NC(=O)c2c(C#Cc3c(C)noc3C)n(C3(C)CC3)c3ncnc(N)c23)cc1] | m/z [M + H]+ 471.4<br>1H-NMR (DMSO-D6)δ ppm: 10.33 (1H, s), 8.23 (1H, s), 7.66-7.52 (2H, m), 7.46 (2H, brs), 7.30 (2H, d, J = 8.5 Hz), 4.36 (2H, s), 3.26 (3H, s), 2.36 (3H, s), 2.15 (3H, s), 1.57 (3H, s), 1.31 (2H, m), 1.14 (2H, m). |
| 185 | 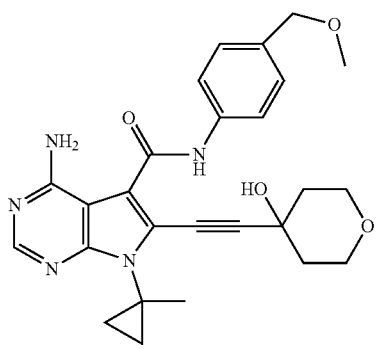 [SMILES: COCc1ccc(NC(=O)c2c(C#CC3(O)CCOCC3)n(C3(C)CC3)c3ncnc(N)c23)cc1] | m/z [M + H]+ 476.3<br>1H-NMR (DMSO-D6)δ ppm: 9.97 (1H, s), 8.20 (1H, s), 7.69 (2H, d,J = 8.5 Hz), 7.30 (2H, d, J = 8.5 Hz), 6.00 (1H, s), 4.36 (2H, s), 3.76-3.72 (2H, m), 3.64-3.58 (2H, m), 3.26 (3H, s), 1.95-1.92 (2H, m), 1.77-1.71 (2H, m), 1.52 (3H, s), 1.28-1.25 (2H, m), 1.11-1.07 (2H, m). |
| 186 | 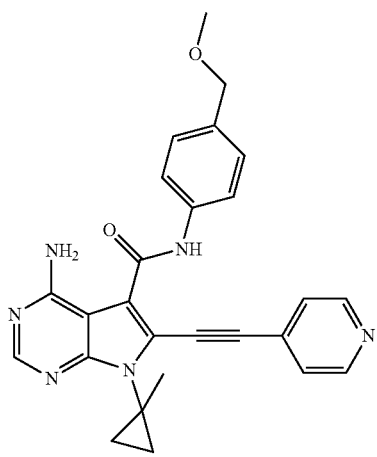 [SMILES: COCc1ccc(NC(=O)c2c(C#Cc3ccncc3)n(C3(C)CC3)c3ncnc(N)c23)cc1] | m/z [M + H]+ 453.1<br>¹H NMR (400 MHz, DMSO-d6) δ ppm: 10.37 (1H, s) 8.65 (2H, d, J = 5.87 Hz) 8.24 (1H, s) 7.73 (2H, d, J = 8.43 Hz) 7.57 (2H, s) 7.44 (2H, d, J = 4.70 Hz) 7.32 (2H, m, J = 8.43 Hz) 4.37 (2H, s) 3.28 (3H, s) 1.57 (3H, s) 1.27-1.39 (2H, m) 1.18-1.26 (2H, m) |

TABLE 31-continued
| 187 | 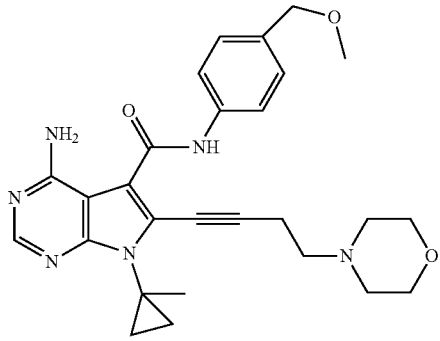 [SMILES: COCc1ccc(NC(=O)c2c(C#CCCN3CCOCC3)n(C3(C)CC3)c3ncnc(N)c23)cc1] | m/z [M + H]+ 489.2<br>1H-NMR (DMSO-D6)δ ppm: 9.96 (1H, s), 8.18 (1H, s), 7.68-7.66 (4H, m), 7.30 (2H, d, J = 8.5 Hz), 4.37 (2H, s), 3.49 (4H, m), 3.26 (3H, s), 2.82 (2H, t, J = 7.0 Hz), 2.57 (2H, t, J = 7.1 Hz), 2.36 (4H, m), 1.50 (3H, s), 1.23 (2H, m), 1.09 (2H, m). |
|---|---|---|
| 188 | 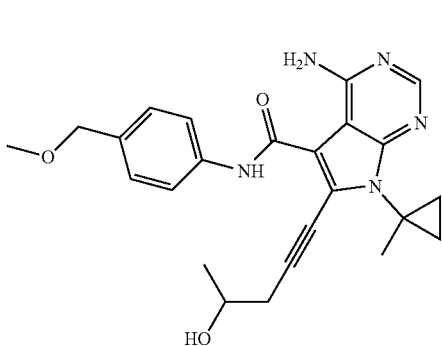 [SMILES: COCc1ccc(NC(=O)c2c(C#CCC(C)O)n(C3(C)CC3)c3ncnc(N)c23)cc1] | m/z [M + H]+ 434.2<br>$^1$H NMR (400 MHz, DMSO-$d_6$) δ ppm 9.92 (1H, s) 8.25 (1H, br s) 7.67 (2H, br d, J = 8.06 Hz) 7.29 (2H, br d, J = 8.06 Hz) 4.99 (1H, br s) 4.36 (2H, s) 3.82-3.98 (1H, m) 3.26 (3H, s) 2.63-2.79 (2H, m) 1.49 (3H, s) 1.21-1.27(2H, m) 1.18 (3H, br d, J = 5.87 Hz) 1.03-1.10 (2H, m) |
| 189 | 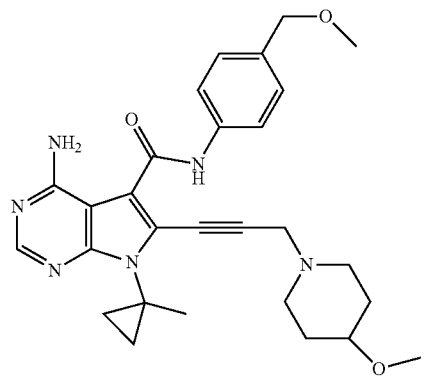 [SMILES: COCc1ccc(NC(=O)c2c(C#CCN3CCC(OC)CC3)n(C3(C)CC3)c3ncnc(N)c23)cc1] | m/z [M + H]+ 503.2<br>1H-NMR (DMSO-D6)δ ppm: 10.05 (1H, s), 8.19 (1H, s), 7.66 (2H, d, J = 8.5 Hz), 7.54-7.52 (2H, m), 7.30 (2H, d, J = 8.5 Hz), 4.36 (2H, s), 3.70 (2H, s), 3.27 (3H, s), 3.14 (3H, s), 2.98 (1H, m), 2.73-2.69 (2H, m), 2.34-2.28 (2H, m), 1.72-1.68 (2H, m), 1.51 (3H, s), 1.36-1.32 (2H, m), 1.27-1.24 (2H, m), 1.11-1.08 (2H, m). |
TABLE 32
| 190 | 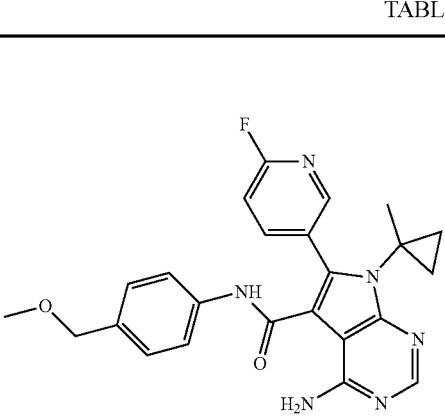 | m/z [M + H]+ 447.5<br>1H-NMR (DMSO-D6)δ ppm: 9.39 (1H, s), 8.39-8.37 (1H, m), 8.25 (1H, s), 8.21-8.15 (1H, m), 7.34 (1H, J = 8.5, 2.7 Hz, dd), 7.26 (2H, J = 8.5 Hz, d), 7.19 (2H, J = 8.5 Hz, d), 7.14 (2H, br s), 4.30 (2H, s), 3.23 (3H, s), 1.64 (3H, s), 0.83-0.69 (4H, m). |
|---|---|---|

TABLE 32-continued

| 191 | 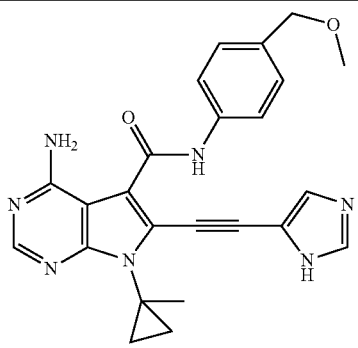 | m/z [M + H]+ 442.4<br>1H-NMR (DMSO-D6)δ ppm: 10.11 (1H, s), 8.21 (1H, s), 7.84 (1H, brs), 7.75 (2H, d, J = 8.5 Hz), 7.65 (1H, brs), 7.29 (2H, d, J = 8.5 Hz), 4.36 (2H, s), 3.26 (3H, s), 1.54 (3H, s), 1.32-1.29 (2H, m), 1.15-1.12 (2H, m). |
|---|---|---|
| 192 | 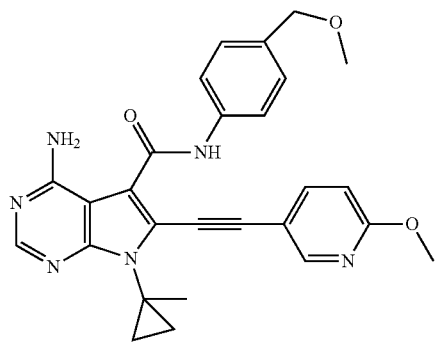 | m/z [M + H]+ 483.1<br>1H-NMR (DMSO-D6)δ ppm: 10.27 (1H, s), 8.38 (1H, m), 8.21 (1H, brs), 7.83 (1H, dt, J = 8.5, 1.1 Hz), 7.72 (2H, d, J = 8.3 Hz), 7.31 (2H, d, J = 8.3 Hz), 6.95 (1H, d, J = 8.8 Hz), 4.37 (2H, s), 3.89 (3H, s), 3.27 (3H, d, J = 0.7 Hz), 1.56 (3H, s), 1.32 (2H, m), 1.19 (2H, m). |
| 193 | 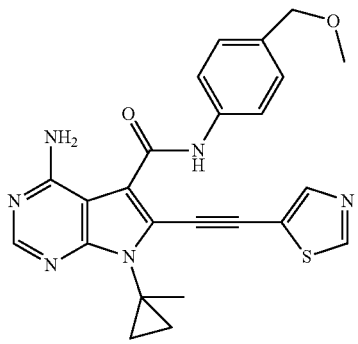 [SMILES: COCc1ccc(NC(=O)c2c(C#Cc3cncs3)n(C3(C)CC3)c3ncnc(N)c23)cc1] | m/z [M + H]+ 459.2<br>1H-NMR (DMSO-D6)δ ppm: 10.31 (1H, s), 9.23 (1H, s), 8.26 (1H, s), 8.23 (1H, s), 7.72 (2H, d, J = 8.5 Hz), 7.58 (2H, brs), 7.31 (2H, d, J = 8.5 Hz), 4.37 (2H, s), 3.27 (3H, s), 1.55 (3H, s), 1.31 (2H, m), 1.16 (2H, m). |
| 194 | 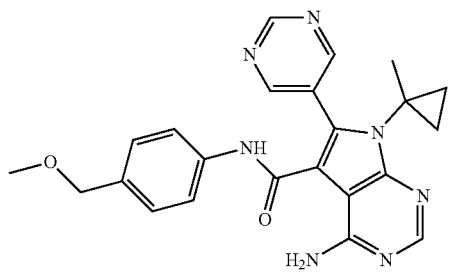 [SMILES: COCc1ccc(NC(=O)c2c(-c3cncnc3)n(C3(C)CC3)c3ncnc(N)c23)cc1] | m/z [M + H]+ 430.7<br>1H-NMR (CDCl3)δ ppm: 9.42 (1H, s), 9.01 (2H, br s), 8.45 (1H, s), 7.24 (2H, J = 8.3 Hz, d), 7.12-7.08 (2H, br m), 6.86-6.71 (3H, br m), 4.39 (2H, s), 3.38 (3H, s), 1.71 (3H, s), 0.97-0.81 (4H, m). |
| 195 | 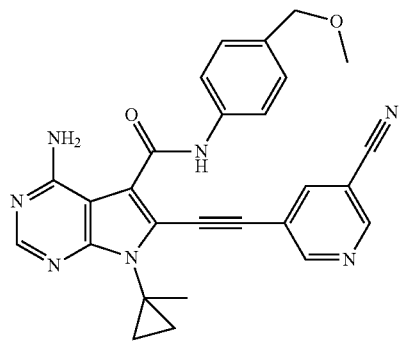 [SMILES: COCc1ccc(NC(=O)c2c(C#Cc3cncc(C#N)c3)n(C3(C)CC3)c3ncnc(N)c23)cc1] | m/z [M + H]+ 478.4<br>1H-NMR (DMSO-D6)δ ppm: 10.38 (1H, s), 9.06 (1H, d, J = 2.0 Hz), 8.88 (1H, d, J = 2.0 Hz), 8.49 (1H, t, J = 2.1 Hz), 8.25 (1H, s), 7.73 (2H, d, J = 8.5 Hz), 7.58 (2H, brs), 7.32 (2H, d, J = 8.5 Hz), 4.37 (2H, s), 3.27 (3H, s), 1.57 (3H, s), 1.31-1.30 (2H, m), 1.25-1.22 (2H, m). |

TABLE 32-continued
| | | |
|---|---|---|
| 196 | 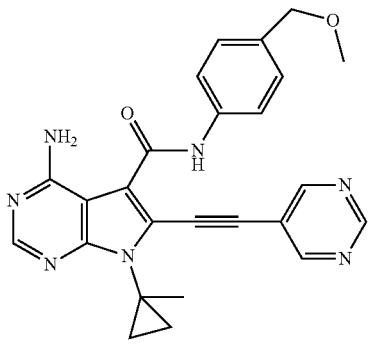 [SMILES: COCc1ccc(NC(=O)c2c(C#Cc3cncnc3)n(C3(C)CC3)c3ncnc(N)c23)cc1] | m/z [M + H]+ 454.3<br>1H-NMR (DMSO-D6)δ ppm: 10.36 (1H, s), 9.24 (1H, s), 8.94 (2H, s), 8.25 (1H, brs), 7.73 (2H, d, J = 8.5 Hz), 7.59 (2H, brs), 7.32 (2H, d, J = 8.5 Hz), 4.37 (2H, s), 3.27 (3H, s), 1.57 (3H, s), 1.34-1.31 (2H, m), 1.23-1.20 (2H, m). |
| 197 | 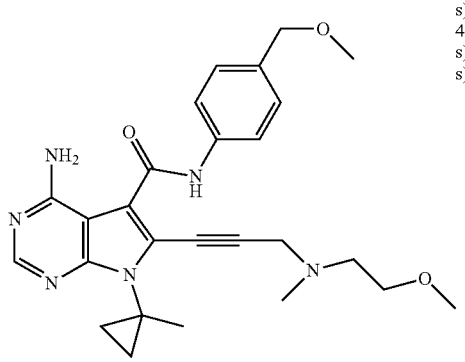 | m/z [M + H]+ 477.4<br>1H-NMR (DMSO-D6)δ ppm: 10.01 (1H, s), 8.19 (1H, s), 7.66 (2H, d, J = 8.3 Hz), 7.30 (2H, d, J = 8.5 Hz), 4.37 (2H, s), 3.77 (2H, s), 3.30-3.27 (2H, m), 3.27 (3H, s), 3.16 (3H, s), 2.61 (2H, t, J = 5.7 Hz), 2.29 (3H, s), 1.52 (3H, s), 1.26 (2H, m), 1.09 (2H, m). |
| 198 | 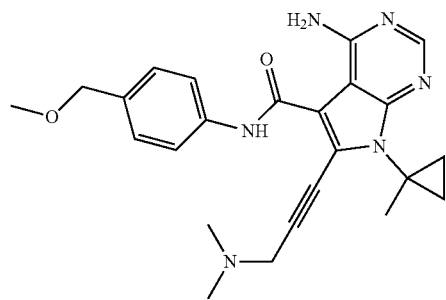 [SMILES: COCc1ccc(NC(=O)c2c(C#CCN(C)C)n(C3(C)CC3)c3ncnc(N)c23)cc1] | m/z [M + H]+ 433.2<br>$^1$H NMR (400 MHz, CHLOROFORM-d) δ ppm 9.33 (1H, s) 8.36 (1H, s) 7.61 (2H, d, J = 7.53 Hz) 7.36 (2H, d, J = 8.80 Hz) 4.45 (2H, s) 3.76 (2H, s) 3.40 (3H, s) 2.44 (6H, s) 1.63 (3H, s) 1.35-1.41 (2H, m) 1.13-1.18 (2H, m) |
TABLE 33
| | | |
|---|---|---|
| 199 | 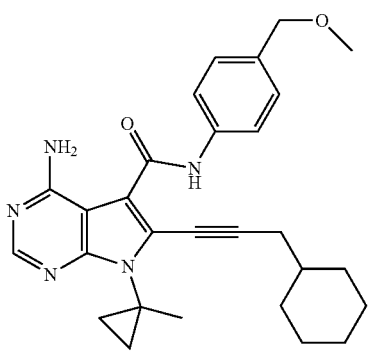 [SMILES: COCc1ccc(NC(=O)c2c(C#CCC3CCCCC3)n(C3(C)CC3)c3ncnc(N)c23)cc1] | m/z [M + H]+ 472.5<br>1H-NMR (DMSO-D6)δ ppm: 9.97 (1H, s), 8.18 (1H, s), 7.66-7.63 (2H, m), 7.30 (2H, d, J = 8.5 Hz), 4.37 (2H, s), 3.26 (3H, s), 2.55 (2H, d, J = 6.3 Hz), 1.79-1.76 (2H, m), 1.60-1.53 (4H, m), 1.50 (3H, s), 1.25-1.23 (2H,m), 1.11-1.03 (7H, m). |

TABLE 33-continued
| | | |
|---|---|---|
| 200 | 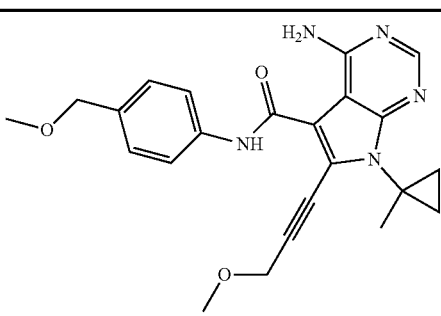 | m/z [M + H]+ 420.3<br>$^1$H NMR (400 MHz, DMSO-d$_6$) δ ppm: 10.09 (1H, s) 8.24 (1H, s) 7.67 (2H, d, J = 8.80 Hz) 7.57 (2H, br s) 7.29 (2 H, d, J = 8.43 Hz) 4.50 (2H, s) 4.36 (2H, s) 3.32 (3H, s) 3.26 (3H, s) 1.51 (3H, s) 1.23-1.29 (2H, m) 1.06-1.12 (2H, m) |
| 201 | 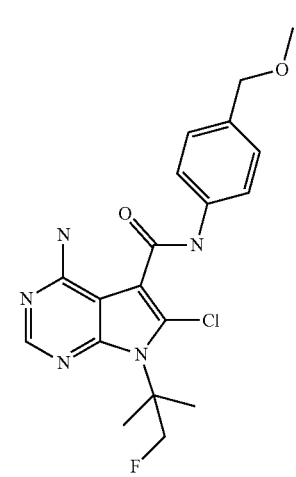 [SMILES: COCc1ccc(NC(=O)c2c(Cl)n(C(C)(C)CF)c3ncnc(N)c23)cc1] | m/z [M + H]+ 406.3<br>$^1$H NMR (400 MHz, DMSO-d$_6$) δ ppm 10.47 (1H, s) 8.16 (1H, s) 7.69 (2H, d, J = 8.54 Hz) 7.31 (2H, d, J = 8.54 Hz) 7.05 (2H, br s) 5.20 (2H, d, J = 47.07 Hz) 4.37 (2H, s) 3.27 (3H, s) 1.92 (6H, s) |
| 202 | 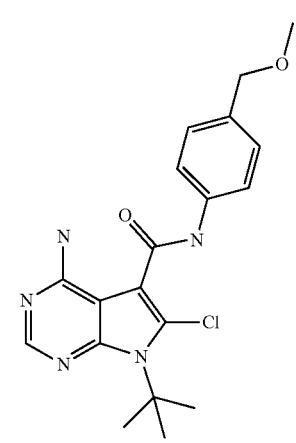 [SMILES: COCc1ccc(NC(=O)c2c(Cl)n(C(C)(C)C)c3ncnc(N)c23)cc1] | m/z [M + H]+ 388.1<br>1H NMR (400 MHz, DMSO-d$_6$) δ ppm: 10.42 (1H, s) 8.16 (1H, s) 7.69 (2H, d, J = 8.29 Hz) 7.31 (2H, d, J = 8.29 Hz) 6.99 (2H, br s) 4.38 (2H, s) 3.28 (3H, s) 1.95 (9H, s) |
| 203 | 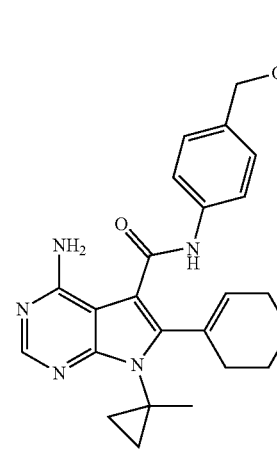 | m/z [M + H]+ 434.3<br>$^1$H NMR (400 MHz, CHLOROFORM-d) δ ppm: 8.39 (1H, s) 8.37 (1H, s) 7.58 (2H, d, J = 8.54 Hz) 7.36 (2H, d, J = 8.54 Hz) 7.01 (2H, br s) 6.33-6.46 (1H, m) 4.49-4.53 (2H, m) 4.45 (2H, s) 4.00 (2H, t, J = 5.37 Hz) 3.40(3H, s) 2.45-2.61 (2H, m) 1.64(3H, s) 1.17-1.23 (2H, m) 1.07-1.13 (2H, m) |

| | | |
|---|---|---|
| 204 | 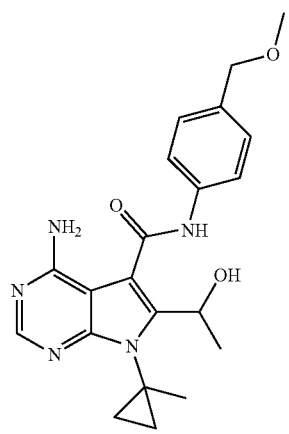 [SMILES: COCc1ccc(NC(=O)c2c(C(C)O)n(C3(C)CC3)c3ncnc(N)c23)cc1] | m/z [M + H]+ 396.4<br>¹H NMR (400 MHz, DMSO-d₆) δ ppm 11.62-11.88 (1H, m) 8.10-8.18 (1H, m) 7.66 (2H, d, J = 8.29 Hz) 7.34 (2H, d, J = 8.54 Hz) 5.71-5.86 (1H, m) 4.38 (2H, s) 3.28 (3H, s) 3.17 (1H, d, J = 5.12 Hz) 1.42-1.64 (6H, m) 0.93-1.40 (4H, m) |
| 205 | 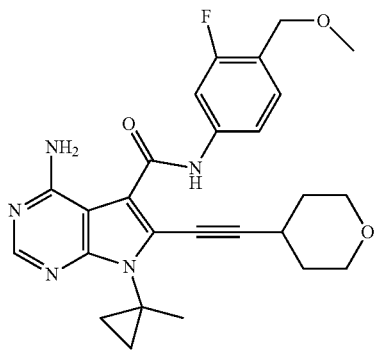 [SMILES: COCc1ccc(NC(=O)c2c(C#CC3CCOCC3)n(C3(C)CC3)c3ncnc(N)c23)cc1F] | m/z [M + H]+ 478.3<br>1H-NMR (DMSO-D6)δ ppm: 10.18 (1H, s), 8.19 (1H, s), 7.68-7.37 (3H, m), 4.40 (2H, s), 3.81-3.76 (2H, m), 3.48-3.42 (2H, m), 3.28 (3H, s), 3.11-3.10 (1H, m), 1.88-1.84 (2H, m), 1.68-1.63 (2H, m), 1.51 (3H, s), 1.25-1.24 (2H, m), 1.10-1.07 (2H, m). |
| 206 | 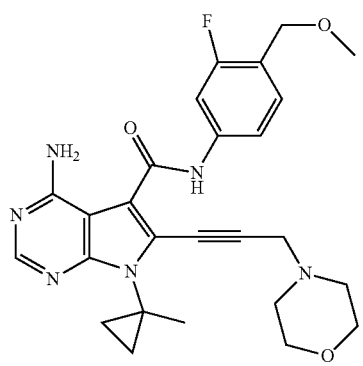 [SMILES: COCc1ccc(NC(=O)c2c(C#CCN3CCOCC3)n(C3(C)CC3)c3ncnc(N)c23)cc1F] | m/z [M + H]+ 493.4<br>1H-NMR (DMSO-D6)δ ppm: 10.28 (1H, s), 8.20 (1H, s), 7.65 (1H, d, J = 12.4 Hz), 7.46-7.37 (4H, m), 4.40 (2H, s), 3.69 (2H, s), 3.49 (4H, m), 3.27 (3H, s), 2.53-2.50 (4H, m), 1.51 (3H, s), 1.27-1.24 (2H, m), 1.11-1.08 (2H, m). |
| 207 | 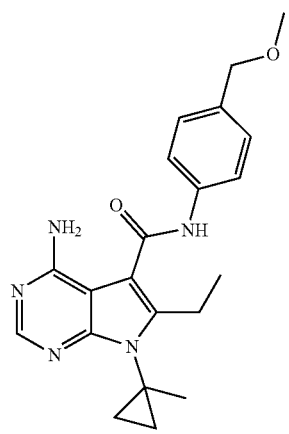 [SMILES: CCc1c(C(=O)Nc2ccc(COC)cc2)c2c(N)ncnc2n1C1(C)CC1] | m/z [M + H]+ 380.3<br>¹H NMR (400 MHz, CHLOROFORM-d) δ ppm: 8.37 (1H, s) 7.57 (2H, d, J = 8.54 Hz) 7.38 (2H, d, J = 8.54 Hz) 4.47 (2H, s) 3.41 (3H, s) 3.21-3.37 (2H, m) 1.59 (3H, s) 1.46 (3H, t, J = 7.56 Hz) 1.03-1.36 (4H, m) |

TABLE 34

| | | |
|---|---|---|
| Compound 1 of Comparative Examples | (structure) | m/z [M + H] + 282.3<br>1H-NMR (400 MHz, CDCl3) δppm: 8.36 (s, 1H) , 7.58 (d, J = 7.8 Hz, 2H), 7.33 (d, J = 7. 8 Hz, 2H) , 5.35 (br s. 2H), 2.43 (s, 3H), 1.84 (s, 9H) |
| Compound 2 of Comparative Examples | (structure) | m/z [M+ H] + 414.2<br>1H-NMR (400 MHz, DMSO-d6) δppm: 10.04 (s, 1H), 8.32 (s, 1H), 8.11 (s, 1H) , 7.66 - 7.70 (m, 2H) , 7.36-7.40 (m, 2H), 7.09-7.13 (m, 1H) 6.98-7.05 (m, 4H) , 5.04-5.12 (m, 1H), 2.14-2.18 (m, 2H), 1.81-1.92 (m, 4H), 1.71-1.73 (m, 2H) |
| Compound 3 of Comparative Examples | (structure) | m/z [M + H]+ 368.3<br>1H-NMR (CDCl3)δ ppm: 8.23 (1H, s), 7.38 (2H, J = 8.3 Hz, d), 7.24 (2H, J = 8.3 Hz, d), 6.18 (1H, s), 4.48 (2H, s), 3.47 (3H, s), 3.42 (3H, s), 1.43 (9H, s). |
| Compound 4 of Comparative Examples | (structure) | m/z [M + H]+ 368.3<br>1H-NMR (DMSO-D6)δ ppm: 10.06 (1H, s), 9.29-9.22 (1H, m), 8.34 (1H, s), 8.20 (1H, s), 7.64 (2H, J = 8.5 Hz, d), 7.31 (2H, J = 8.5 Hz, d), 4.37 (2H, s), 3.28 (3H, s), 2.99 (3H, J = 4.6 Hz, d), 1.75 (9H, s). |
| Compound 5 of Comparative Examples | (structure) | m/z [M + H]+ 375.2<br>1H-NMR (DMSO-D6)δ ppm: 10.32 (1H, s), 8.43-8.41 (3H, m), 8.35 (1H, s), 8.13 (2H, d, J = 8.8 Hz), 7.76 (2H, d, J = 8.5 Hz), 7.30 (2H, d, J = 8.5 Hz), 4.37 (2H, s), 3.27 (3H, s). |

Test Example 1: Measurement of Inhibitory Activity Against RET (In Vitro)

Regarding the conditions for measurement of in vitro inhibitory activity of compounds against RET kinase activity, the website of AnaSpec states that Srctide (GEEPLYWSFPAKKK) corresponds to the substrate peptide for reaction to measure RET kinase activity. Thus, the amino acid sequence was partly modified and biotinylated to prepare biotinylated peptides (biotin-EEPLYWSFPAKKK). The purified recombinant human RET protein used in the test was purchased from Carna Biosciences, Inc.

To measure the inhibitory activity, first, the compounds of the present invention were individually diluted with dimethyl sulfoxide (DMSO) stepwise. Subsequently, RET protein, the substrate peptide (the final concentration: 250 nM), magnesium chloride (the final concentration: 10 mM), ATP (the final concentration: 10 μM), and a solution of the compound of the present invention in DMSO (the final concentration of DMSO: 2.5%) were added to a buffer for kinase reaction (13.5 mM Tris, pH of 7.5, 2 mM dithiothreitol, 0.009% Tween-20). Each of the mixtures was incubated at 25° C. for 100 minutes to perform a kinase reaction. EDTA was then added thereto to give a final concentration of 24 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under the excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as the $IC_{50}$ value (nM).

Tables 35 and 36 show $IC_{50}$ (nM) of the RET inhibitory activity of Vandetanib, the compounds of the Examples, and compounds 2 to 5 of the Comparative Examples.

Vandetanib is known to have a high inhibitory activity against RET (Carlomagno F. Cancer Res. 2002 Dec. 15; 62(24): 7284-90). The compounds of the present invention or salts thereof represented by the compounds of the Examples were found to exhibit in vitro RET inhibitory activity at a level equivalent to or higher than that of Vandetanib. In contrast, compounds 2 to 5 of the Comparative Examples exhibited a significantly lower inhibitory activity against RET.

TABLE 35

| Comound of Examples | RET IC50 (nM) |
| --- | --- |
| 1 | 2.6 |
| 2 | 1.1 |
| 3 | 0.5 |
| 4 | 6.3 |
| 5 | 8.5 |
| 6 | 4.7 |
| 7 | 10.2 |
| 8 | 9.2 |
| 9 | 6.8 |
| 10 | 10.3 |
| 11 | 3.8 |
| 12 | 3.4 |
| 13 | 0.7 |
| 14 | 4.4 |
| 15 | 0.6 |
| 16 | 9.2 |
| 17 | 7.2 |
| 18 | 1.3 |
| 19 | 5.8 |
| 20 | 7.2 |
| 21 | 6.6 |
| 22 | 1.1 |
| 23 | 0.3 |
| 24 | 3.2 |
| 25 | 1.7 |
| 26 | 1.1 |
| 27 | 5.7 |
| 28 | 7.9 |
| 29 | 0.6 |
| 30 | 0.8 |
| 31 | 2.1 |
| 32 | 4.1 |
| 33 | 7.0 |
| 34 | 5.6 |
| 35 | 2.9 |
| 36 | 0.9 |
| 37 | 0.2 |
| 38 | 3.6 |

TABLE 35-continued

| Comound of Examples | RET IC50 (nM) |
| --- | --- |
| 39 | 1.5 |
| 40 | 0.4 |
| 41 | 0.6 |
| 42 | 4.9 |
| 43 | 1.3 |
| 44 | 1.6 |
| 45 | 4.4 |
| 46 | 2.7 |
| 47 | 3.9 |
| 48 | 0.8 |
| 49 | 2.3 |
| 50 | 1.9 |
| 51 | 4.7 |
| 52 | 10.2 |
| 53 | 0.9 |
| 54 | 0.5 |
| 55 | 0.3 |
| 56 | 0.4 |
| 57 | 1.2 |
| 58 | 2.7 |
| 59 | 0.1 |
| 60 | 1.8 |
| 61 | 3.8 |
| 62 | 1.4 |
| 63 | 3.2 |
| 64 | 7.7 |
| 65 | 1.0 |
| 66 | 2.8 |
| 67 | 9.2 |
| 68 | 6.7 |
| 69 | 1.9 |
| 85 | 0.2 |
| 86 | 0.2 |
| 87 | 0.2 |
| 88 | 0.2 |
| 89 | 0.4 |
| 90 | 0.3 |
| 91 | 0.1 |
| 92 | 0.4 |
| 93 | 0.3 |
| 94 | 0.3 |
| 95 | 0.2 |
| 96 | 2.2 |
| 97 | 3.5 |
| 98 | 0.9 |
| 99 | 1.7 |
| 100 | 1.9 |
| 101 | 3.0 |
| 102 | 4.6 |
| 103 | 0.2 |
| 104 | 0.2 |
| 105 | 0.2 |
| 106 | 3.8 |
| 107 | 3.8 |
| 108 | 3.3 |
| 109 | 2.5 |
| 110 | 0.3 |
| 111 | 0.5 |

TABLE 36

| Comound of Examples | RET IC50 (nM) |
| --- | --- |
| 112 | 0.2 |
| 113 | 9.0 |
| 114 | 0.5 |
| 115 | 0.4 |
| 116 | 2.0 |
| 117 | 1.9 |
| 118 | 0.6 |
| 119 | 0.5 |
| 120 | 0.5 |
| 121 | 4.2 |

TABLE 36-continued

| Comound of Examples | RET IC50 (nM) |
|---|---|
| 122 | 4.4 |
| 123 | 0.4 |
| 124 | 0.4 |
| 125 | 0.2 |
| 126 | 0.5 |
| 127 | 0.5 |
| 128 | 0.5 |
| 129 | 0.4 |
| 130 | 1.6 |
| 131 | 0.1 |
| 132 | 1.3 |
| 133 | 0.7 |
| 134 | 1.6 |
| 135 | 0.7 |
| 136 | 6.8 |
| 137 | 2.2 |
| 138 | 1.7 |
| 139 | 1.6 |
| 140 | 1.4 |
| 141 | 5.6 |
| 142 | 1.3 |
| 143 | 0.2 |
| 144 | 2.4 |
| 145 | 1.0 |
| 146 | 1.1 |
| 147 | 1.9 |
| 148 | 1.2 |
| 149 | 1.2 |
| 150 | 1.7 |
| 151 | 0.2 |
| 152 | 0.2 |
| 153 | 1.3 |
| 154 | 1.3 |
| 155 | 0.2 |
| 156 | 0.2 |
| 157 | 0.1 |
| 158 | 2.6 |
| 159 | 0.2 |
| 160 | 0.2 |
| 161 | 2.4 |
| 162 | 1.2 |
| 163 | 0.3 |
| 164 | 1.7 |
| 165 | 2.9 |
| 166 | 0.6 |
| 167 | 1.8 |
| 168 | 1.8 |
| 169 | 0.2 |
| 170 | 0.9 |
| 171 | 2.0 |
| 172 | 0.3 |
| 173 | 0.7 |
| 174 | 0.4 |
| 175 | 0.4 |
| 176 | 1.1 |
| 177 | 0.8 |
| 178 | 0.8 |
| 179 | 2.8 |
| 180 | 2.8 |
| 181 | 0.4 |
| 182 | 0.3 |
| 183 | 0.3 |
| 184 | 1.0 |
| 185 | 0.3 |
| 186 | 0.2 |
| 187 | 0.8 |
| 188 | 0.2 |
| 189 | 1.0 |
| 190 | 4.6 |
| 191 | 0.3 |
| 192 | 0.9 |
| 193 | 0.3 |
| 194 | 5.6 |
| 195 | 0.3 |
| 196 | 0.4 |
| 197 | 0.6 |
| 198 | 0.3 |
| 199 | 0.6 |
| 200 | 0.7 |
| 203 | 4.8 |
| 204 | 8.6 |
| 205 | 0.2 |
| 206 | 0.3 |
| 207 | 6.1 |
| Vandetanib | 9.2 |
| Comound 2 of Comparative Examples | 196 |
| Comound 3 of Comparative Examples | 435 |
| Comound 4 of Comparative Examples | >5000 |
| Comound 5 of Comparative Examples | >5000 |

Test Example 2: Selectivity for RET Over Other Kinases (In Vitro)

Since multikinase inhibitors inhibit not only RET but also various signaling pathways to suppress cell growth and other functions, the inhibitors raise concerns about possible various side effects, which may require dose reduction or drug holidays, leading to insufficient RET inhibitory activity. The following discusses selectivity for RET over other kinases of the compounds of the present invention or salts thereof.

1) RET Inhibitory Activity Measurement

Inhibitory activity against RET was measured in the same manner as in Test Example 1.

2) SRC Inhibitory Activity Measurement

Regarding the conditions for measurement of in vitro inhibitory activity of compounds against SRC kinase activity, the price list of LabChip-series consumable reagents of PerkinElmer shows that FL-Peptide 4 corresponds to the substrate peptide for measurement of SRC kinase activity. Thus, FL-Peptide 4 was used as a substrate. The purified recombinant human SRC protein used in the test was purchased from Carna Biosciences, Inc.

To measure the inhibitory activity, first, the test compounds were individually diluted with dimethyl sulfoxide (DMSO) stepwise. Subsequently, SRC protein, FL-Peptide 4 (the final concentration: 1.5 μM), magnesium chloride (the final concentration: 10 mM), ATP (the final concentration: 15 μM), and a solution of a test compound in DMSO (the final concentration of DMSO: 5%) were added to a reaction buffer (100 mM HEPES, pH of 7.0, 1 mM dithiothreitol, 0.003% Brij35, 0.04% Tween-20) containing a phosphatase inhibitor cocktail (PhosSTOP, Roche) and a protease inhibitor cocktail (cOmplete Mini, EDTA-free, Roche) at recommended concentrations. Each mixture was incubated at 30° C. for 90 minutes to perform a kinase reaction. EDTA diluted with a separation buffer available from PerkinElmer (the final concentration: 30 mM) was then added thereto to terminate the kinase reaction. Finally, non-phosphorylated substrate peptides (S) and phosphorylated peptides (P) were separated and detected by microchannel capillary electrophoresis using a LabChip EZ Reader II (PerkinElmer). The phosphorylation level was calculated from the height of the peaks of S and P, and the compound concentration at which phosphorylation was inhibited by 50% was defined as the $IC_{50}$ value (nM)

3) LCK Inhibitory Activity Measurement

Regarding the conditions for measurement of in vitro inhibitory activity of compounds against LCK kinase activity, the website of AnaSpec states that Srctide (GEEPLY-WSFPAKKK) corresponds to the substrate peptide for reaction to measure LCK kinase activity. Thus, the amino acid sequence was partly modified and biotinylated to prepare biotinylated peptides (biotin-EEPLYWSFPAKKK). The purified recombinant human LCK protein used in the test was purchased from Carna Biosciences, Inc.

To measure the inhibitory activity, first, the test compounds were individually diluted with dimethyl sulfoxide (DMSO) stepwise. Subsequently, LCK protein, the substrate peptides (the final concentration: 250 nM), magnesium chloride (the final concentration: 10 mM), ATP (the final concentration: 50 μM), and a solution of a test compound in DMSO (the final concentration of DMSO: 5%) were added to a buffer for kinase reaction (13.5 mM Tris, pH of 7.5, 2 mM dithiothreitol, 0.009% Tween-20). Each mixture was incubated at 25° C. for 60 minutes to perform a kinase reaction. EDTA was then added thereto to give a final concentration of 40 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as the $IC_{50}$ value (nM).

4) AURB (Aurora B) Inhibitory Activity Measurement

The in vitro inhibitory activity of the compounds against AURB kinase was measured with reference to the procedure described in JP2008-81492A. The purified recombinant human AURB protein used in the test was purchased from Carna Biosciences, Inc.

To measure the inhibitory activity, first, the test compounds were individually diluted with dimethyl sulfoxide (DMSO) stepwise. Subsequently, AURB protein, FL-Peptide 21 (caliper Life Sciences, the final concentration: 100 nM), magnesium chloride (the final concentration: 1 mM), ATP (the final concentration: 40 μM), and a solution of a test compound in DMSO (the final concentration of DMSO: 5%) were added to a buffer solution for kinase reaction (20 mM HEPES, pH of 7.4, 2 mM dithiothreitol, 0.01% Tween-20), and each mixture was incubated at 25° C. for 60 minutes to perform a kinase reaction. An IMAP Progressive Binding Reagent diluted with IMAP Progressive Binding Buffer A (1:500 dilution, Molecular Devices, LLC.) was added thereto to terminate the kinase reaction. The reaction solution was allowed to stand in a dark place at room temperature for 120 minutes, and the phosphorylation level was calculated from the fluorescence polarization degree measured with PHERAstar (BMG LABTECH, the excitation wavelength: 485 nm, the detection wavelength: 520 nm). The compound concentration at which phosphorylation was inhibited by 50% was defined as the $IC_{50}$ value (nM).

5) Measurement of Inhibitory Activity Against EGFR

Regarding the conditions for measurement of in vitro inhibitory activity of compounds against EGFR kinase activity, the price list of LabChip (trademark) series consumable reagents of PerkinElmer shows that FL-Peptide 22 corresponds to the substrate peptide for measurement of EGFR kinase activity. Thus, with reference to the amino acid sequence, a biotinylated peptide (biotin-EEPLYWSF-PAKKK) was prepared. The purified recombinant human EGFR protein used in the test was purchased from Carna Biosciences, Inc.

To measure the inhibitory activity, first, the test compounds were individually diluted with dimethyl sulfoxide (DMSO) stepwise. Subsequently, EGFR protein, the substrate peptide (the final concentration: 250 nM), magnesium chloride (the final concentration: 10 mM), manganese chloride (the final concentration: 10 mM), ATP (the final concentration: 1.5 μM), and a solution of a test compound in DMSO (the final concentration of DMSO: 2.5%) were added to a buffer solution for kinase reaction (Carna Biosciences, Inc.). Each mixture was incubated at 25° C. for 120 minutes to perform a kinase reaction. EDTA was then added thereto to give a final concentration of 24 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as the $IC_{50}$ value (nM).

6) Selectivity for RET Inhibition

From the values obtained in sections 1) to 5) above, SRC inhibitory activity $IC_{50}$ (nM)/RET inhibitory activity $IC_{50}$ (nM), LCK inhibitory activity $IC_{50}$ (nM)/RET inhibitory activity $IC_{50}$ (nM), AURB inhibitory activity $IC_{50}$ (nM)/RET inhibitory activity $IC_{50}$ (nM), and EGFR inhibitory activity $IC_{50}$ (nM)/RET inhibitory activity $IC_{50}$ (nM) were calculated, and the selectivity for RET inhibition of the test compounds was examined.

Tables 37 to 44 show the results. Tables 37 to 44 reveal that the compounds of the present invention or salts thereof represented by the compounds of the Examples exhibited higher selectivity for RET inhibition over SRC, LCK, Aurora B, and EGFR, as compared with compound 1 of the Comparative Examples. The compounds of the present invention or salts thereof also exhibited excellent selectivity for RET inhibition over other kinases (PI3K, TrkB). Thus, the results suggest that the compounds of the present invention or salts thereof have a low potential for causing side effects attributed to inhibition of kinases other than RET.

TABLE 37

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
|---|---|---|---|---|
| 1 | >1000 | >1000 | | >1000 |
| 2 | >5000 | >5000 | >1000 | >1000 |
| 3 | >10000 | >5000 | >1000 | >1000 |
| 4 | >1000 | >1000 | | |
| 5 | >1000 | | | |
| 6 | >1000 | | | |
| 8 | >1000 | >1000 | >1000 | |
| 9 | >1000 | >1000 | | |
| 11 | >1000 | >1000 | | |
| 12 | >1000 | >1000 | | >1000 |
| 13 | >10000 | >1000 | | >5000 |
| 14 | >1000 | >1000 | | |
| 15 | >10000 | >1000 | | >5000 |
| 16 | >1000 | >1000 | >1000 | |
| 17 | >1000 | | | |
| 18 | >5000 | >1000 | >1000 | |
| 19 | >1000 | >1000 | >1000 | |
| 20 | >1000 | | >1000 | |
| 21 | >1000 | >1000 | | |
| 22 | >5000 | >1000 | >1000 | >1000 |
| 23 | >10000 | >10000 | >5000 | >10000 |
| 24 | >1000 | >1000 | | >1000 |
| 25 | >5000 | >1000 | | |
| 26 | >5000 | >1000 | >1000 | >1000 |

TABLE 38

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
|---|---|---|---|---|
| 27 | >1000 | | | |
| 28 | >1000 | | | |
| 29 | >10000 | >1000 | >1000 | |
| 30 | >10000 | >1000 | >1000 | >1000 |
| 31 | >1000 | >1000 | | |
| 32 | >1000 | >1000 | | |
| 33 | >1000 | >1000 | >1000 | |
| 34 | >1000 | | | |
| 35 | >1000 | >1000 | >1000 | |
| 36 | >10000 | >1000 | >1000 | >1000 |
| 37 | >10000 | >5000 | >1000 | >1000 |
| 38 | >1000 | >1000 | >1000 | >1000 |
| 39 | >5000 | >1000 | >1000 | >1000 |
| 40 | >10000 | >1000 | >1000 | >1000 |
| 41 | >10000 | >5000 | >1000 | >1000 |
| 42 | >1000 | >1000 | >1000 | |
| 43 | >5000 | >1000 | >1000 | |
| 44 | >5000 | >1000 | >1000 | >1000 |
| 45 | >1000 | >1000 | | >1000 |
| 46 | >1000 | >1000 | | >1000 |
| 47 | >1000 | >1000 | >1000 | |
| 48 | >10000 | >1000 | >1000 | >1000 |
| 49 | >1000 | >1000 | | >1000 |
| 50 | >5000 | >1000 | >1000 | |

TABLE 39

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
|---|---|---|---|---|
| 51 | >1000 | >1000 | >1000 | |
| 53 | >10000 | >1000 | >1000 | >1000 |
| 54 | >1000 | >1000 | >1000 | >1000 |
| 55 | >10000 | >10000 | >10000 | >10000 |
| 56 | >10000 | >10000 | >5000 | >10000 |
| 57 | >5000 | >5000 | >1000 | >1000 |
| 58 | >1000 | >1000 | >1000 | >1000 |
| 59 | >10000 | >10000 | >5000 | >5000 |
| 60 | >5000 | >5000 | >1000 | >1000 |
| 61 | >1000 | >1000 | >1000 | |
| 62 | >5000 | >5000 | >5000 | >1000 |
| 63 | >1000 | >1000 | >1000 | >1000 |
| 64 | >1000 | >1000 | | |
| 65 | >10000 | >10000 | >10000 | >5000 |
| 66 | >1000 | >1000 | | >1000 |
| 67 | >1000 | >1000 | | |
| 68 | >1000 | >1000 | | |
| 69 | >5000 | >5000 | >1000 | >1000 |
| 85 | >10000 | >10000 | >10000 | >1000 |
| 86 | >10000 | >10000 | >5000 | >10000 |
| 87 | >10000 | >10000 | >10000 | >10000 |
| 88 | >10000 | >10000 | >10000 | >10000 |
| 89 | >10000 | >10000 | >5000 | >5000 |
| 90 | >10000 | >10000 | >10000 | >5000 |

TABLE 40

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
|---|---|---|---|---|
| 91 | >10000 | >10000 | >10000 | >10000 |
| 92 | >10000 | >10000 | >10000 | >10000 |
| 93 | >10000 | >10000 | >5000 | >5000 |
| 94 | >10000 | >10000 | >10000 | >5000 |
| 95 | >10000 | >10000 | >10000 | >1000 |
| 96 | >1000 | >1000 | >1000 | >1000 |
| 97 | >1000 | >1000 | | >1000 |
| 98 | >10000 | >1000 | >1000 | >1000 |
| 99 | >5000 | >1000 | >1000 | >1000 |
| 100 | >5000 | >1000 | >1000 | >1000 |
| 101 | >1000 | >1000 | >1000 | >1000 |
| 102 | >1000 | >1000 | | |
| 103 | >10000 | >1000 | >5000 | >5000 |
| 104 | >10000 | >5000 | >1000 | >10000 |
| 105 | >10000 | >10000 | >10000 | >10000 |
| 106 | >1000 | | | |

TABLE 40-continued

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 107 | >1000 | | | |
| 108 | >1000 | | | |
| 109 | >1000 | >1000 | >1000 | >1000 |
| 110 | >10000 | >5000 | >1000 | >1000 |
| 111 | >10000 | >5000 | >5000 | >10000 |
| 112 | >10000 | >10000 | >1000 | >10000 |
| 113 | >1000 | >1000 | >1000 | |
| 114 | >10000 | >10000 | >10000 | >5000 |

TABLE 41

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 115 | >10000 | >1000 | >1000 | |
| 116 | >1000 | >1000 | | |
| 117 | >5000 | | | |
| 118 | >10000 | >10000 | >5000 | >5000 |
| 119 | >10000 | >10000 | >10000 | >5000 |
| 120 | >10000 | >10000 | >10000 | >1000 |
| 121 | >1000 | >1000 | >1000 | >1000 |
| 122 | >1000 | >1000 | >1000 | |
| 123 | >10000 | >10000 | >10000 | >1000 |
| 124 | >10000 | >5000 | >1000 | >5000 |
| 125 | >10000 | >10000 | >10000 | >10000 |
| 126 | >10000 | >10000 | >10000 | >5000 |
| 127 | >10000 | >10000 | >5000 | >5000 |
| 128 | >10000 | >5000 | >5000 | |
| 129 | >10000 | >10000 | >5000 | >5000 |
| 130 | >5000 | >5000 | >5000 | >1000 |
| 131 | >10000 | >10000 | >5000 | >10000 |
| 132 | >5000 | >5000 | | >1000 |
| 133 | >10000 | >1000 | >1000 | >5000 |
| 134 | >5000 | >5000 | >1000 | >1000 |
| 135 | >10000 | >10000 | >1000 | >5000 |
| 136 | >1000 | | | |
| 137 | >1000 | >1000 | >1000 | >1000 |
| 138 | >5000 | >1000 | >1000 | >1000 |

TABLE 42

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 139 | >5000 | >5000 | >1000 | >1000 |
| 140 | >5000 | >1000 | | >1000 |
| 141 | >1000 | >1000 | >1000 | |
| 142 | >5000 | >5000 | >1000 | >1000 |
| 143 | >10000 | >10000 | >10000 | >5000 |
| 144 | >1000 | >1000 | >1000 | >1000 |
| 145 | >5000 | >5000 | >5000 | >1000 |
| 146 | >5000 | >1000 | >1000 | >1000 |
| 147 | >5000 | >5000 | >5000 | >1000 |
| 148 | >5000 | >5000 | >5000 | >1000 |
| 149 | >5000 | >5000 | >5000 | >1000 |
| 150 | >5000 | >5000 | >1000 | >1000 |
| 151 | >10000 | >10000 | >10000 | >10000 |
| 152 | >10000 | >10000 | >10000 | >1000 |
| 153 | >5000 | >5000 | >5000 | >1000 |
| 154 | >5000 | >5000 | >5000 | >1000 |
| 155 | >10000 | >10000 | >10000 | >10000 |
| 156 | >10000 | >10000 | >1000 | >10000 |
| 157 | >10000 | >10000 | >10000 | >10000 |
| 158 | >1000 | >1000 | >1000 | >1000 |
| 159 | >10000 | >10000 | >10000 | >10000 |
| 160 | >10000 | >10000 | >10000 | >10000 |

TABLE 42-continued

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 161 | >1000 | >1000 | >1000 | |
| 162 | >5000 | >5000 | >5000 | >1000 |

TABLE 43

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 163 | >10000 | >10000 | >5000 | >5000 |
| 164 | >5000 | >5000 | >1000 | >1000 |
| 165 | >1000 | >1000 | >1000 | >1000 |
| 166 | >10000 | >1000 | >1000 | >5000 |
| 167 | >5000 | >5000 | >1000 | >1000 |
| 168 | >5000 | >1000 | | >1000 |
| 169 | >10000 | >5000 | >5000 | >5000 |
| 170 | >10000 | >1000 | >1000 | >5000 |
| 171 | >5000 | >5000 | >5000 | >1000 |
| 172 | >10000 | >10000 | >10000 | >10000 |
| 173 | >10000 | >10000 | >10000 | >5000 |
| 174 | >10000 | >10000 | >1000 | >10000 |
| 175 | >10000 | >10000 | >5000 | >5000 |
| 176 | >5000 | >1000 | >5000 | |
| 177 | >10000 | >10000 | >1000 | >5000 |
| 178 | >10000 | >10000 | >10000 | >5000 |
| 179 | >1000 | >1000 | >1000 | >1000 |
| 180 | >1000 | >1000 | >1000 | >1000 |
| 181 | >10000 | >10000 | >10000 | >10000 |
| 182 | >10000 | >10000 | >10000 | >5000 |
| 183 | >10000 | >10000 | >5000 | >10000 |
| 184 | >10000 | >10000 | >1000 | >1000 |
| 185 | >10000 | >10000 | >5000 | >10000 |
| 186 | >10000 | >10000 | >10000 | >10000 |

TABLE 44

| Compound of Examples | SRC IC50 (nM)/ RET IC50 (nM) | LCK IC50 (nM)/ RET IC50 (nM) | AURB IC50 (nM)/ RET IC50 (nM) | EGFR IC50 (nM)/ RET IC50 (nM) |
| --- | --- | --- | --- | --- |
| 187 | >10000 | >10000 | >10000 | >5000 |
| 188 | >10000 | >10000 | >5000 | >5000 |
| 189 | >10000 | >10000 | >10000 | >5000 |
| 190 | >1000 | >1000 | | >1000 |
| 191 | >10000 | >5000 | >5000 | >5000 |
| 192 | >10000 | >10000 | >10000 | >5000 |
| 193 | >10000 | >10000 | >10000 | >10000 |
| 194 | >1000 | >1000 | >1000 | |
| 195 | >10000 | >10000 | >10000 | >10000 |
| 196 | >10000 | >10000 | >10000 | >10000 |
| 197 | >10000 | >10000 | >10000 | >5000 |
| 198 | >10000 | >10000 | >10000 | >10000 |
| 199 | >10000 | >10000 | >10000 | >5000 |
| 200 | >10000 | >10000 | >1000 | >5000 |
| 203 | >1000 | >1000 | >1000 | >1000 |
| 204 | >1000 | | | |
| 205 | >10000 | >10000 | >5000 | >10000 |
| 206 | >10000 | >10000 | >10000 | >10000 |
| 207 | >1000 | >1000 | >1000 | |
| Compound 1 of Comparative Examples | 10 | 12 | | |

Test Example 3: Inhibitory Activity Against Resistance Mutation of RET (In Vitro)

1) Measurement of Inhibitory Activity Against RET (V804L)

Regarding the conditions for measurement of in vitro inhibitory activity of compounds against RET (V804L) (i.e., RET with V804L mutation) kinase activity, the website of AnaSpec states that Srctide (GEEPLYWSFPAKKK) corresponds to the substrate peptide for reaction to measure RET kinase activity. Thus, the amino acid sequence was partly modified and biotinylated to prepare biotinylated peptides (biotin-EEPLYWSFPAKKK). The purified recombinant human RET (V804L) protein used in the test was purchased from Eurofins.

To measure the inhibitory activity, first, the test compounds were individually diluted with dimethyl sulfoxide (DMSO) stepwise. Subsequently, RET (V804L) protein, the substrate peptides (the final concentration: 250 nM), magnesium chloride (the final concentration: 10 mM), ATP (the final concentration: 10 µM), and a solution of a test compound in DMSO (the final concentration of DMSO: 5%) were added to a buffer for kinase reaction (13.5 mM Tris, pH of 7.5, 2 mM dithiothreitol, 0.009% Tween-20). Each of the mixtures was incubated at 25° C. for 120 minutes to perform a kinase reaction. EDTA was then added thereto to give a final concentration of 40 mM so that the reaction was terminated. A detection solution containing Eu-labeled antiphosphotyrosine antibody PT66 (PerkinElmer) and SureLight APC-SA (PerkinElmer) was added thereto, and each mixture was allowed to stand at room temperature for 2 hours or more. Finally, the intensity of fluorescence under excitation light with a wavelength of 337 nm was measured with a PHERAstar FS (BMG Labtech) at the two wavelengths of 620 nm and 665 nm. The phosphorylation level was calculated from the ratio of the fluorescence intensity at the two wavelengths, and the compound concentration at which phosphorylation was inhibited by 50% was defined as the $IC_{50}$ value (nM).

2) Measurement of Inhibitory Activity Against RET (V804M)

RET (V804M) (i.e., RET with V804M mutation) kinase activity was measured using purified recombinant human RET (V804M) protein purchased from Eurofins with the final concentration of ATP being 13 µM in the kinase reaction system, following procedure 1) for the other part.

Tables 45 to 48 show the $IC_{50}$ (nM) of the inhibitory activity against RET with resistance mutantation of the compounds of the Examples, Vandetanib, and compounds 1 to 4 of the Comparative Examples.

Vandetanib is known to have a high inhibitory activity against RET (Carlomagno F. Cancer Res. 2002 Dec. 15; 62(24): 7284-90). However, Vandetanib exhibited a significantly low inhibitory activity against RET (V804L) and RET (V804M)

Compounds 1 to 4 of the Comparative Examples also exhibited a significantly low inhibitory activity against RET (V804L) and RET (V804M).

Alectinib is reported to exhibit an inhibitory effect on RET (V804L), and has an $IC_{50}$ (nM) of 32 in vitro (Mol Cancer Ther. 2014 December; 13 (12): 2910-8). The compounds of the present invention or salts thereof represented by the compounds of the Examples exhibited an excellent inhibitory activity against RET (V804L) at a level equivalent to or higher than that of Alectinib. The compounds of the present invention or salts thereof represented by the compounds of the Examples also exhibited a high inhibitory activity against RET (V804M) The results suggest that the compounds of the present invention or salts thereof have an antitumor effect on cancers and tumors expressing RET with mutation in its gatekeeper site (e.g., V804L and V804M).

TABLE 45

| Compound of Examples | RET (V804L) IC50 (nM) | RET (V804M) IC50 (nM) |
|---|---|---|
| 1 | 3.8 | 13.9 |
| 2 | 2.1 | 8.9 |
| 3 | 0.9 | 2.8 |
| 4 | 6.8 | |
| 5 | 10.1 | |
| 6 | 3.0 | 17.6 |
| 7 | 13.2 | |
| 8 | 22.0 | |
| 9 | 4.9 | |
| 10 | 16.4 | |
| 11 | 6.6 | |
| 12 | 6.0 | |
| 13 | 1.4 | 4.3 |
| 14 | 7.6 | |
| 15 | 1.5 | 5.2 |
| 16 | 27.7 | |
| 17 | 9.4 | |
| 18 | 2.3 | 8.3 |
| 19 | 6.4 | |
| 20 | 8.0 | |
| 21 | 12.6 | |
| 22 | 3.7 | 14.6 |
| 23 | 0.7 | 2.1 |
| 24 | 6.4 | |
| 25 | 3.8 | 14.9 |
| 26 | 4.1 | 16.3 |
| 27 | 25.7 | |
| 28 | 14.4 | |
| 29 | 1.0 | 3.8 |
| 30 | 2.6 | 16.0 |
| 31 | 7.4 | |
| 32 | 9.0 | |
| 33 | 16.6 | |
| 34 | 6.0 | 19.9 |
| 35 | 4.6 | 14.9 |
| 36 | 2.8 | 11.5 |
| 37 | 0.9 | 1.9 |
| 38 | 10.4 | |
| 39 | 3.8 | 15.0 |
| 40 | 0.7 | 2.2 |
| 41 | 1.9 | 17.5 |
| 42 | 16.0 | |
| 43 | 2.6 | 8.4 |
| 44 | 3.0 | 13.4 |
| 45 | 9.7 | |
| 46 | 6.6 | |
| 47 | 10.4 | |
| 48 | 4.0 | |
| 49 | 5.6 | 19.4 |
| 50 | 4.7 | |

TABLE 46

| Compound of Examples | RET (V804L) IC50 (nM) | RET (V804M) IC50 (nM) |
|---|---|---|
| 51 | 8.1 | |
| 52 | 19.2 | |
| 53 | 1.9 | 7.7 |
| 54 | 1.6 | 13.5 |
| 55 | 1.1 | 3.7 |
| 56 | 1.2 | 5.8 |
| 57 | 2.3 | 10.7 |
| 58 | 8.3 | |
| 59 | 0.3 | 0.8 |
| 60 | 10.6 | |
| 61 | 16.6 | |
| 62 | 5.5 | 14.6 |

TABLE 46-continued

| Compound of Examples | RET (V804L) IC50 (nM) | RET (V804M) IC50 (nM) |
| --- | --- | --- |
| 63 | 12.1 | |
| 65 | 4.2 | 13.6 |
| 66 | 6.0 | |
| 67 | 22.7 | |
| 68 | 9.8 | |
| 69 | 5.5 | 20.2 |
| 73 | 23.6 | |
| 79 | 25.5 | |
| 80 | 30.6 | |
| 81 | 23.2 | |
| 85 | 0.7 | 1.8 |
| 86 | 0.3 | 1.0 |
| 87 | 0.6 | 2.0 |
| 88 | 0.4 | 0.9 |
| 89 | 0.6 | 2.4 |
| 90 | 0.9 | 3.2 |
| 91 | 0.3 | 1.0 |
| 92 | 1.4 | 5.1 |
| 93 | 0.9 | 2.9 |
| 94 | 0.8 | 3.1 |
| 95 | 0.3 | 1.3 |
| 96 | 4.6 | |
| 97 | 8.1 | |
| 98 | 1.9 | 6.6 |
| 99 | 3.5 | 13.6 |
| 100 | 3.9 | 15.3 |
| 101 | 11.5 | |
| 102 | 9.5 | |
| 103 | 0.3 | 1.0 |
| 104 | 0.4 | 1.1 |
| 105 | 0.4 | 1.0 |
| 106 | 5.3 | 17.9 |
| 107 | 3.5 | 10.3 |
| 108 | 3.6 | 18.3 |
| 109 | 12.8 | |
| 110 | 0.8 | 2.9 |
| 111 | 1.8 | 4.3 |
| 112 | 0.5 | 1.2 |

TABLE 47

| Compound of Examples | RET (V804L) IC50 (nM) | RET (V804M) IC50 (nM) |
| --- | --- | --- |
| 113 | 20.6 | |
| 114 | 1.6 | 5.0 |
| 115 | 1.0 | 2.5 |
| 116 | 4.3 | 18.1 |
| 117 | 2.7 | 10.3 |
| 118 | 1.9 | 5.7 |
| 119 | 1.7 | 6.2 |
| 120 | 1.2 | 3.6 |
| 121 | 6.4 | |
| 122 | 12.4 | |
| 123 | 1.8 | 5.8 |
| 124 | 1.4 | 3.7 |
| 125 | 0.6 | 2.5 |
| 126 | 2.0 | 5.9 |
| 127 | 1.3 | 7.5 |
| 128 | 0.9 | 2.9 |
| 129 | 1.2 | 3.8 |
| 130 | 4.1 | 13.5 |
| 131 | 0.5 | 1.4 |
| 132 | 3.7 | 14.2 |
| 133 | 2.3 | 8.4 |
| 134 | 6.0 | 18.2 |
| 135 | 1.9 | 7.1 |
| 136 | 13.2 | |
| 137 | 4.3 | |
| 138 | 3.3 | 19.7 |
| 139 | 7.2 | |
| 140 | 2.2 | 11.0 |
| 141 | 15.3 | |
| 142 | 6.1 | 20.1 |

TABLE 47-continued

| Compound of Examples | RET (V804L) IC50 (nM) | RET (V804M) IC50 (nM) |
| --- | --- | --- |
| 143 | 0.6 | 1.6 |
| 144 | 8.7 | |
| 145 | 4.7 | 16.3 |
| 146 | 3.0 | 12.8 |
| 147 | 11.7 | |
| 148 | 6.1 | 15.6 |
| 149 | 4.8 | |
| 150 | 7.5 | |
| 151 | 0.3 | 0.3 |
| 152 | 0.3 | 0.6 |
| 153 | 6.7 | 19.5 |
| 154 | 6.1 | |
| 155 | 0.5 | 1.8 |
| 156 | 0.5 | 1.6 |
| 157 | 0.3 | 1.0 |
| 158 | 6.8 | 19.1 |
| 159 | 0.5 | 1.6 |
| 160 | 0.6 | 1.4 |

TABLE 48

| Compound of Examples | RET (V804L) IC50 (nM) | RET (V804M) IC50 (nM) |
| --- | --- | --- |
| 161 | 5.1 | 16.0 |
| 162 | 2.8 | 11.8 |
| 163 | 0.7 | 1.5 |
| 164 | 8.6 | |
| 165 | 7.3 | |
| 166 | 1.5 | 5.7 |
| 167 | 7.9 | 17.9 |
| 168 | 5.2 | 15.6 |
| 169 | 0.3 | 0.8 |
| 170 | 1.8 | 8.0 |
| 171 | 12.1 | |
| 172 | 1.2 | 4.4 |
| 173 | 1.5 | 5.0 |
| 174 | 1.1 | 4.1 |
| 175 | 0.4 | 3.4 |
| 176 | 2.3 | 9.4 |
| 177 | 1.8 | 7.0 |
| 178 | 1.9 | 5.6 |
| 179 | 14.4 | |
| 180 | 4.5 | 10.2 |
| 181 | 1.3 | 3.5 |
| 182 | 1.0 | 3.3 |
| 183 | 1.1 | 2.8 |
| 184 | 3.7 | 12.5 |
| 185 | 1.0 | 3.4 |
| 186 | 0.7 | 1.8 |
| 187 | 2.7 | 8.4 |
| 188 | 0.7 | 2.2 |
| 189 | 3.7 | 11.9 |
| 190 | 24.2 | |
| 191 | 1.1 | 3.3 |
| 192 | 2.7 | 10.6 |
| 193 | 0.6 | 2.0 |
| 195 | 1.1 | 3.8 |
| 196 | 1.1 | 3.1 |
| 197 | 1.5 | 5.3 |
| 198 | 0.8 | 2.6 |
| 199 | 0.8 | 1.3 |
| 200 | 1.8 | 5.9 |
| 203 | 23.3 | |
| 205 | 0.7 | 6.6 |
| 206 | 1.1 | 5.2 |
| Vandetanib | 4748 | 4330 |
| Compound 1 of Comparative Examples | 3288 | 3434 |
| Compound 2 of Comparative Examples | 561 | 774 |

TABLE 48-continued

| Compound of Examples | RET (V804L) IC50 (nM) | RET (V804M) IC50 (nM) |
|---|---|---|
| Compound 3 of Comparative Examples | 1410 | 3785 |
| Compound 4 of Comparative Examples | >10000 | >10000 |

Test Example 4: Evaluation of Stability in Liver Microsome

Solutions of the test compounds in DMSO/acetonitrile (the final concentration of each test compound was 1 μM, the final concentration of DMSO was 0.01%, and the final concentration of acetonitrile was 1%) were individually added to a liver microsome mixture solution (mouse liver microsome with a final concentration of 0.25 mg/mL, a potassium phosphate buffer with a final concentration of 100 mM, and magnesium chloride with a final concentration of 3 mM), and each mixture was pre-incubated at 37° C. for 5 minutes. A NADPH-generating system (glucose-6-phosphate with a final concentration of 10 mM, oxidized nicotinamide adenine dinucleotide phosphate with a final concentration of 1 mM, and glucose-6-phosphate dehydrogenase with a final concentration of 1 unit/mL) was added to a portion of each mixture solution, and a metabolic reaction was started. After incubation at 37° C. for 30 minutes, a double amount of ethanol was added thereto to terminate the reaction, thereby obtaining post-reaction samples. A double amount of ethanol was added to each of the remaining mixture solutions, and a NADPH-generating system was further added thereto, thereby obtaining pre-reaction samples. The pre-reaction samples and post-reaction samples were centrifuged at 2000×g, and their supernatant was filtered through a glass filter. Each filtrate was then introduced into LC-MS/MS, and MS/MS peaks of the test compounds were detected. From the ratio of the post-reaction MS/MS peak to the pre-reaction MS/MS peak of the test compounds, the percentage of the remaining test compounds (remaining %) was calculated.

Table 49 shows the results. Whereas compounds 1 and 2 of the Comparative Examples had a remaining percentage of 0% in either case, the compounds of the present invention or salts thereof represented by the compounds of the Examples had a high remaining percentage. This indicates that the compounds of the present invention or salts thereof are significantly more stable in mouse liver microsome than the compounds of the Comparative Examples.

TABLE 49

| Compound of Examples | Remaining (%) |
|---|---|
| 2 | 64 |
| 26 | 60 |
| 30 | 54 |
| 33 | 57 |
| 35 | 58 |
| 36 | 73 |
| 41 | 56 |
| 45 | 66 |
| 46 | 65 |
| 48 | 58 |
| 49 | 67 |

TABLE 49-continued

| Compound of Examples | Remaining (%) |
|---|---|
| 50 | 53 |
| 55 | 56 |
| 56 | 62 |
| 57 | 86 |
| 58 | 76 |
| 60 | 81 |
| 61 | 81 |
| 64 | 89 |
| 65 | 79 |
| 69 | 69 |
| 80 | 50 |
| 85 | 79 |
| 86 | 66 |
| 87 | 63 |
| 88 | 59 |
| 89 | 69 |
| 90 | 67 |
| 91 | 65 |
| 92 | 67 |
| 93 | 53 |
| 94 | 60 |
| 96 | 71 |
| 97 | 70 |
| 99 | 51 |
| 100 | 76 |
| 101 | 68 |
| 102 | 60 |
| 103 | 60 |
| 104 | 52 |
| 105 | 52 |
| 107 | 63 |
| 108 | 60 |
| 109 | 68 |
| 113 | 79 |
| 114 | 55 |
| 116 | 55 |
| 117 | 53 |
| 118 | 73 |
| 119 | 70 |
| 120 | 72 |
| 121 | 74 |
| 122 | 62 |
| 125 | 74 |
| 126 | 69 |
| 127 | 70 |
| 128 | 82 |
| 129 | 54 |
| 130 | 84 |
| 131 | 55 |
| 132 | 77 |
| 133 | 70 |
| 134 | 79 |
| 135 | 67 |
| 136 | 78 |
| 137 | 53 |
| 138 | 68 |
| 140 | 52 |
| 141 | 68 |
| 143 | 68 |
| 144 | 79 |
| 145 | 72 |
| 147 | 68 |
| 148 | 61 |
| 149 | 62 |
| 150 | 78 |
| 152 | 57 |
| 154 | 50 |
| 155 | 64 |
| 156 | 67 |
| 157 | 59 |
| 158 | 85 |
| 159 | 78 |
| 161 | 68 |
| 162 | 76 |
| 165 | 90 |
| 167 | 80 |
| 171 | 77 |

TABLE 49-continued

| Compound of Examples | Remaining (%) |
|---|---|
| 172 | 61 |
| 174 | 72 |
| 175 | 66 |
| 176 | 70 |
| 177 | 72 |
| 178 | 88 |
| 179 | 85 |
| 181 | 62 |
| 182 | 61 |
| 183 | 77 |
| 184 | 58 |
| 185 | 80 |
| 187 | 68 |
| 188 | 68 |
| 190 | 58 |
| 191 | 53 |
| 192 | 79 |
| 193 | 51 |
| 194 | 67 |
| 195 | 70 |
| 196 | 53 |
| 197 | 52 |
| 198 | 57 |
| 199 | 80 |
| 203 | 68 |
| 204 | 83 |
| 205 | 58 |
| 206 | 77 |
| 207 | 72 |
| Compound 1 of Comparative Examples | 0 |
| Compound 2 of Comparative Examples | 0 |

Test Example 5: Evaluation of Oral Absorption

The compounds of the present invention were suspended or dissolved in 0.5% HPMC and 0.1N hydrochloric acid, and orally administered to BALB/cA mice. At a time point of 0.5, 1, 2, 4, and 6 hours after the oral administration, the blood of the mice was collected from their ocular fundus to obtain plasma. The concentration of the compounds in the obtained plasma was measured by LC-MS/MS, and oral absorption was evaluated.

The results reveal that the concentration of the compounds of the present invention in plasma was sufficient, indicating excellent oral absorption.

Test Example 6: Evaluation of Cell Growth Inhibitory Effect (1)

An in vitro cytotoxicity test was performed on TT cells (a human thyroid cancer cell line with RET activating mutation (C634W)).

A TT cell suspension prepared with Ham's F12K (kaighn's) medium (Life Technologies Japan) containing 10% FBS was inoculated into each well of a 96-well flat-bottomed microplate in an amount of $5 \times 10^3$ cells/well (0.15 mL), and cultured in an incubator containing 5% carbon dioxide at 37° C. overnight (day 0). The compounds of the present invention were individually dissolved in dimethyl sulfoxide to give a concentration of 10 mM, and further diluted with a 10% FBS-containing RPMI1640 medium (produced by Wako Pure Chemical Industries, Ltd.) so that the compounds of the present invention respectively had a final concentration of 40, 12, 4, 1.2, 0.4, 0.12, 0.04, and 0.012 µM. The compounds of different concentrations were individually added to wells of the TT cell-containing culture plate described above in an amount of 0.05 mL/well (day 1), and cultured in an incubator containing 5% carbon dioxide at 37° C. for 7 days. After culture (day 8), 0.1 mL of the medium was removed from each well, and 0.1 mL of a CellTiter Glo 2.0 reagent (Promega Corporation), which is an intracellular ATP luminescence detection reagent, was added thereto, followed by shaking for 1 minute. After shaking, each culture was allowed to stand at room temperature for 15 minutes, and the chemiluminescence was measured with a luminometer to use it as an index of the number of viable cells. The growth rate from day 1 at different concentrations of the compounds was calculated from the following equations, depending on the value of $T_{day\ 8}$ and $C_{day\ 1}$, to determine the concentration ($GI_{50}$ (nM)) of the test compounds capable of suppressing cell growth by 50%.

$$T_{day\ 8} \geq C_{day\ 1} \quad \text{1)}$$

Growth Rate (%)=$(T_{day\ 8}-C_{day\ 1})/(C_{day\ 8}-C_{day\ 1}) \times 100$ $$T_{day\ 8} < C_{day\ 1} \quad \text{2)}$$

Growth Rate (%)=$(T_{day\ 8}-C_{day\ 1})/(C_{day\ 1}) \times 100$

T: The absorbance of the well to which a test compound was added.
C: The absorbance of the well to which a test compound was not added.
Day 1: The day on which a test compound was added.
Day 8: The day on which evaluation was performed.

Table 50 shows the results. The compounds of the present invention exhibited a high growth inhibitory effect against TT cells.

TABLE 50

| Example No. | TT Cell GI50 (nM) |
|---|---|
| 59 | 11 |
| 85 | 10 |
| 86 | 5 |
| 87 | 8 |
| 88 | <3 |
| 90 | 20 |
| 91 | 6 |
| 93 | 16 |
| 94 | 13 |
| 95 | 12 |
| 103 | 5 |
| 104 | 6 |
| 105 | <3 |
| 111 | 15 |
| 114 | 20 |
| 125 | 12 |
| 131 | 6 |
| 143 | 7 |
| 152 | <3 |
| 155 | 10 |
| 157 | 5 |
| 160 | 6 |
| 163 | 17 |
| 169 | 4 |
| 174 | 19 |
| 183 | 4 |
| 186 | 9 |
| 188 | 13 |
| 191 | 13 |
| 193 | 20 |
| 197 | 18 |
| 198 | 7 |

TABLE 50-continued

| Example No. | TT Cell GI50 (nM) |
|---|---|
| 199 | 20 |
| 205 | 4 |
| 206 | 4 |

Test Example 7: Evaluation of Cell Growth Inhibitory Effect (2)

An in vitro cytotoxicity test was performed on LC-2/ad cells (a human lung adenocarcinoma cell line with CCDC6-RET fusion gene).

A suspension of LC-2/ad cells prepared with a 10% FBS-containing RPMI1640 medium was inoculated into each well of a 96-well flat-bottomed microplate in an amount of $5\times10^3$ cells/well (0.15 mL), and cultured in an incubator containing 5% carbon dioxide at 37° C. overnight (day 0). The compounds of the present invention were individually dissolved in dimethyl sulfoxide to give a concentration of 10 mM, and further diluted with a 10% FBS-containing RPMI1640 medium such that the compounds of the present invention respectively had a final concentration of 40, 12, 4, 1.2, 0.4, 0.12, 0.04, and 0.012 µM. The compounds of different concentrations were individually added to each well of the LC-2/ad cell-containing culture plate described above in an amount of 0.05 mL/well (day 1), and cultured in an incubator containing 5% carbon dioxide at 37° C. for 7 days. After culture (day 8), 0.1 mL of the medium was removed from each well, and 0.1 mL of a CellTiter Glo 2.0 reagent (Promega Corporation), which is an intracellular ATP luminescence detection reagent, was added thereto, followed by shaking for 5 minutes. After shaking, each culture was allowed to stand at room temperature for 15 minutes, and the chemiluminescence was measured with a luminometer to use it as an index of the number of viable cells. The concentration ($GI_{50}$ (nM)) was determined in the same manner as in Test Example 6, depending on the value of $T_{day\ 8}$ and $C_{day\ 1}$.

Table 51 shows the results. The compounds of the present invention exhibited a high growth inhibitory effect.

TABLE 51

| Example No. | LC-2/ad Cell GI50 (nM) |
|---|---|
| 85 | 17.7 |
| 87 | 55.4 |
| 88 | 44.6 |
| 89 | 59.5 |
| 90 | 90.6 |
| 91 | 30.9 |

Test Example 8: Evaluation of Cell Growth Inhibitory Effect (3)

An in vitro cytotoxicity test was performed on Ba/F3_TEL-RET V804L cells (a Ba/F3 cell to which a TEL-RET fusion gene with gatekeeper mutation V804L was introduced).

Ba/F3_TEL-RET V804L cells were obtained by introducing plasmid DNA that was prepared introducing V804L mutation into the RET gene of a TEL-RET fusion gene into Ba/F3 cells with an standard technique. A suspension of Ba/F3_TEL-RET V804L cells prepared with a 10% FBS-containing RPMI1640 medium was inoculated into each well of a 96-well flat-bottomed microplate in an amount of $1\times10^3$ cells/well (0.075 mL). The compounds of the present invention were individually dissolved in dimethyl sulfoxide to give a concentration of 10 mM, and further diluted with a 10% FBS-containing RPMI1640 medium such that the compounds of the present invention respectively had a final concentration of 40, 12, 4, 1.2, 0.4, 0.12, 0.04, and 0.012 µM. The compounds of different concentrations were individually added to each well of the Ba/F3_TEL-RET V804L cell-containing culture plate described above in an amount of 0.025 mL/well (day 1), and cultured in an incubator containing 5% carbon dioxide at 37° C. for 4 days. After culture (day 4), 0.1 mL of a CellTiter Glo 2.0 reagent (Promega Corporation), which is an intracellular ATP luminescence detection reagent, was added thereto, followed by shaking for 5 minutes. After shaking, each culture was allowed to stand at room temperature for 15 minutes, and the chemiluminescence was measured with a luminometer to use it as an index of the number of viable cells. Evaluation was performed on day 4, and the concentration ($GI_{50}$ (nM)) was determined in the same manner as in Test Example 6, depending on the value of $T_{day\ 8}$ and $C_{day\ 1}$.

Table 52 shows the results. The $GI_{50}$ of Alectinib, known for its inhibitory effect against RET V804L mutation, was 206 (nM). In comparison, the compounds of the present invention exhibited a far superior growth inhibitory effect against the Ba/F3_TEL-RET V804L cells.

TABLE 52

| Example No. | Ba/F3_TEL-RET V804L GI50(nM) |
|---|---|
| 85 | 8 |
| 86 | 5 |
| 87 | 5 |
| 88 | <3 |
| 89 | 14 |
| 92 | 16 |
| 93 | 12 |
| 94 | 12 |
| 103 | 9 |
| 104 | 3 |
| 105 | 4 |
| 110 | 13 |
| 112 | 20 |
| 124 | 19 |
| 127 | 15 |
| 131 | 5 |
| 143 | 8 |
| 152 | 8 |
| 155 | 7 |
| 157 | <3 |
| 163 | 9 |
| 166 | 9 |
| 169 | <3 |
| 174 | 15 |
| 185 | 11 |
| 188 | 6 |
| 200 | 16 |

Test Example 9: Evaluation of Cell Growth Inhibitory Effect (4)

An in vitro cell growth inhibitory test was performed on Ba/F3_BCR-RET V804M cells (a Ba/F3 cell to which a BCR-RET fusion gene with gatekeeper mutation V804M was introduced).

A suspension of Ba/F3_BCR-RET V804M cells prepared with a RPMI1640 medium containing 10% FCS and 2 ng/mL IL3 (Interleukin3) was inoculated into each well of a 384-well plate in an amount of $5 \times 10^3$ cells/well (0.05 mL). The compounds of the present invention were individually dissolved in dimethyl sulfoxide to give a concentration of 10 mM, and further diluted with a medium such that the compounds of the present invention respectively had a final concentration of 1000, 300, 100, 30, 10, 3, 1, and 0.3 µM. The compounds of different concentrations were individually added to each well of the Ba/F3_BCR-RET V804M cell-containing culture plate described above in an amount of 50 nL/well (day 1), and cultured in an incubator containing 5% carbon dioxide at 37° C. for 2 days. After culture (day 3), 0.015 mL of a CellTiter Glo (Promega Corporation), which is an intracellular ATP luminescence detection reagent, was added thereto, and the chemiluminescence was measured with a luminometer to use it as an index of the number of viable cells. The compound concentration ($IC_{50}$ (nM)) at which the cell viability on day 3 was inhibited by 50% was determined from the following equation.

Survival rate (%)=$(T_{day\ 3})/(C_{day\ 3}) \times 100$

T: The absorbance of the well to which a test compound was added.
C: The absorbance of the well to which a test compound was not added.
Day 1: The day on which a test compound was added.
Day 3: The day on which evaluation was performed.

Table 53 shows the results. The compounds of the present invention exhibited a high growth inhibitory effect on Ba/F3_BCR-RET V804M cells.

TABLE 53

| Example No. | Ba/F3_BCR-RET V804M IC50(nM) |
|---|---|
| 85 | 6.5 |
| 86 | 5.7 |
| 87 | 9.7 |
| 88 | 3.1 |
| 90 | 17.1 |
| 91 | 5.3 |
| 93 | 10.1 |
| 94 | 12.0 |
| 103 | 6.9 |
| 105 | 3.9 |
| 111 | 8.3 |
| 112 | 8.4 |
| 131 | 8.9 |
| 143 | 4.6 |
| 152 | 4.4 |
| 155 | 6.7 |
| 157 | 4.5 |
| 159 | 12.6 |
| 160 | 7.8 |
| 169 | 4.7 |
| 174 | 11.6 |
| 181 | 12.4 |
| 182 | 11.3 |
| 183 | 7.9 |
| 185 | 11.1 |
| 186 | 8.6 |
| 193 | 7.9 |
| 198 | 7.2 |
| 206 | 10.6 |

Test Example 10: Evaluation of In Vivo Antitumor Effect Using Mice Model Subcutaneously Implanted TT Cells (Human Thyroid Cancer Cell Line with RET Activating Mutation)

Human thyroid cancer cell lines (TT) were subcutaneously implanted into the right frank of 6- to 7-week-old BALB/cA Jcl-nu/nu male mice. After about 2 to 3 weeks from the cell implantation, the length (mm) and the width (mm) of tumors found in mouse bodies were measured. After their tumor volume (tumor volume: TV) was calculated, the mice were divided into groups (n=5 or 6) so that the groups had a substantially equal mean TV. The day on which the mice were divided into groups was determined to be the "grouping day" (day 0 or 1).

Test solutions containing the compounds of the present invention were prepared at a dose of 50, 100, or 150 mg/kg/day, and orally administered to the mice for consecutive 14 days (the first administration day is day 1). A control group was administered a solvent (0.5% HPMC/0.1N HCl).

Figure 2:
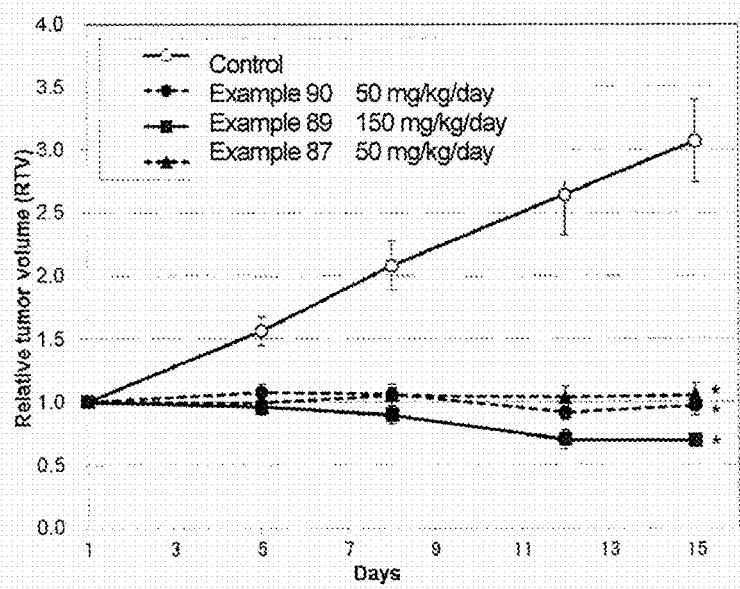
FIG. 2 illustrates relative tumor volume changes observed over time in Test Example 10.

To determine the index of the antitumor effect, TV of each drug-administrated group was measured on day 15, and the tumor volume on day 15 relative to the tumor volume on the grouping day (day 0 or 1) (relative tumor volume: RTV) and T/C (%) were calculated from the following equations, and the antitumor effect was evaluated. When a group administered any of the compounds of the present invention (test compound treatment group) exhibited a statistically significantly smaller mean RTV (Dunnett's test, p<0.05) than the mean RTV of the control group, an antitumor effect was determined to be present. FIGS. 1 and 2 and Tables 54 and 55 show the results. In the figures, the symbol "*" indicates a statistically significant difference.

Figure 3:
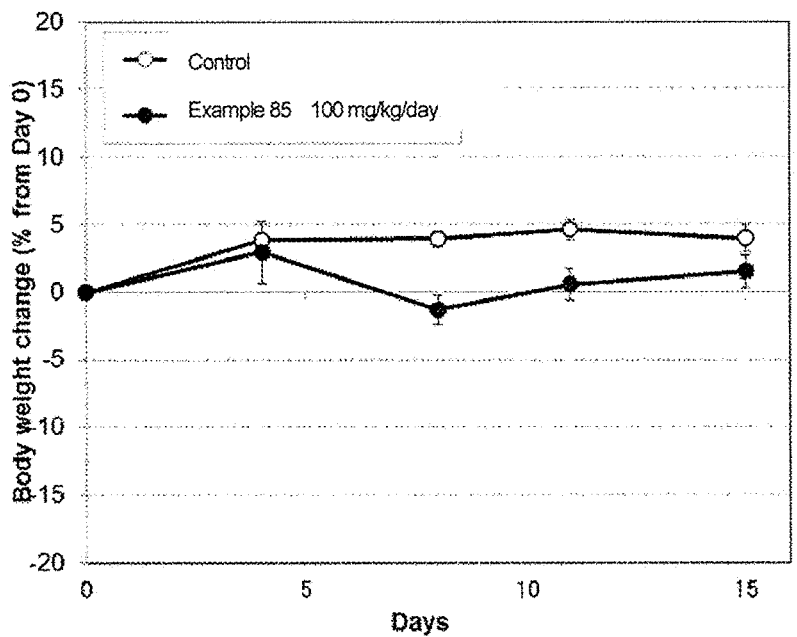
FIG. 3 illustrates average body weight changes observed over time in Test Example 10.
Figure 4:
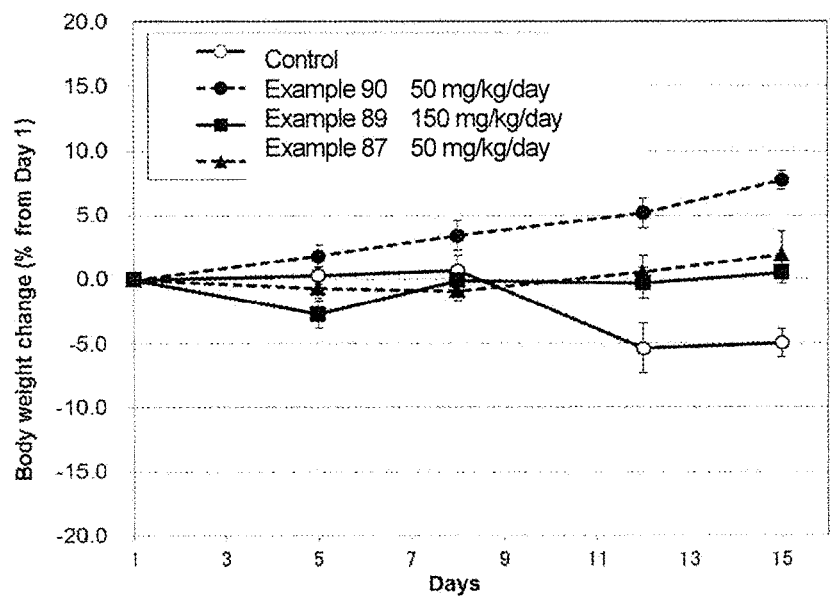
FIG. 4 illustrates average body weight changes observed over time in Test Example 10.

$TV\ (mm^3)=(length \times width^2)/2$ $RTV=(TV\ on\ day\ 15)/(TV\ on\ day\ 0\ or\ day\ 1)$ $T/C(\%)=$(the mean $RTV$ of a test compound treatment group)/(the mean $RTV$ of the control group)$\times 100$ To determine the index of the toxicity, the body weight (body weight: BW (g)) of the mice was measured over time, and the mean body weight change (body weight change: BWC (%)) from the grouping day (day 0 or day 1) to day 15 was calculated from the following equation (n: the day on which the body weight was measured at 2 times/week, and the final measurement day was day 15 on which the final evaluation was performed). FIGS. 3 and 4 show the results.

$BWC\ (\%)=[(BW\ on\ day\ n)-(BW\ on\ day\ 0\ or\ day\ 1)]/(BW\ on\ day\ 0\ or\ day\ 1) \times 100$ The compounds of the present invention exhibited a remarkable antitumor effect on the human thyroid cancer line TT with RET-activating mutation, which was subcutaneously implanted into nude mice. Toxicity, such as weight loss, was not observed.

TABLE 54

| Compound Name | Dose (mg/kg/day) | Number of Animals | TV (mm³) Day 0 Mean ± SE | TV (mm³) Day 15 Mean ± SE | RTV Day 15 Mean ± SE | T/C (%) |
|---|---|---|---|---|---|---|
| Control | — | 5 | 168.64 ± 17.09 | 604.38 ± 55.15 | 3.70 ± 0.43 | 100 |
| Example 85 | 100 | 5 | 169.45 ± 16.73 | 139.42 ± 10.17 | 0.87 ± 0.13 | 23 |

TABLE 55

| Compound Name | Dose (mg/kg/day) | Number of Animals | TV (mm³) Day 1 Mean ± SE | TV (mm³) Day 15 Mean ± SE | RTV Day 15 Mean ± SE | T/C (%) |
|---|---|---|---|---|---|---|
| Control | — | 6 | 133.53 ± 9.05 | 401.04 ± 32.06 | 3.07 ± 0.33 | 100 |
| Example 90 | 50 | 6 | 131.00 ± 7.73 | 128.26 ± 14.57 | 0.97 ± 0.07 | 32 |
| Example 89 | 150 | 6 | 128.61 ± 7.79 | 90.24 ± 9.95 | 0.69 ± 0.05 | 23 |
| Example 87 | 50 | 6 | 129.35 ± 8.52 | 137.42 ± 17.76 | 1.05 ± 0.09 | 34 |

The invention claimed is:

1. A method for treating a malignant tumor comprising administering a compound represented by Formula (I) below or a salt thereof to a mammal:

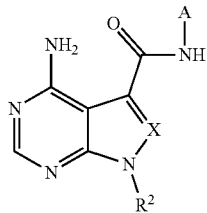

(I)

wherein in Formula (I), A is

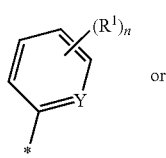

A1

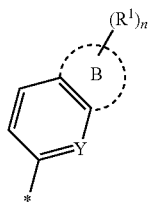

A2 wherein $R^1$ is selected from the group consisting of
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, and
a substituted or unsubstituted 4- to 10-membered monocyclic or polycyclic unsaturated heterocyclic group containing 1 to 3 identical or different heteroatoms selected from nitrogen, oxygen, and sulfur,
Y is N or CH, and
n is an integer of 0 to 2,
wherein when n is 2, the two $R^1$ may be identical or different from each other;
in Formula A2, the group:

B forms, together with phenyl or pyridinyl to which this group is bonded, polycyclic C8-C14 aromatic hydrocarbon or an 8- to 14-membered polycyclic unsaturated heterocyclic group containing 1 to 3 identical or different heteroatoms selected from nitrogen, oxygen, and sulfur;
$R^2$ is selected from the group consisting of
substituted or unsubstituted C3-C10 alkyl,
substituted or unsubstituted C3-C7 cycloalkyl,
substituted or unsubstituted C4-C12 bridged cycloalkyl,
substituted or unsubstituted C2-C6 alkenyl,
substituted or unsubstituted C3-C7 cycloalkenyl, and
a substituted or unsubstituted 4- to 10-membered monocyclic or polycyclic saturated heterocyclic group containing 1 to 3 identical or different heteroatoms selected from nitrogen, oxygen, and sulfur,
provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and X is
  N or
  CR³, wherein R³ is selected from the group consisting of
    hydrogen,
    halogen,
    cyano,
    nitro,
    substituted or unsubstituted C1-C6 alkyl,
    substituted or unsubstituted C1-C6 alkoxy,
    substituted or unsubstituted C1-C6 alkylthio,
    substituted or unsubstituted C3-C7 cycloalkyl,
    substituted or unsubstituted C2-C6 alkenyl,
    substituted or unsubstituted C2-C6 alkynyl,
    substituted or unsubstituted amino,
    substituted or unsubstituted carbamoyl,
    substituted or unsubstituted C6-C14 aromatic hydrocarbon, and
    a substituted or unsubstituted 4- to 10-membered monocyclic or polycyclic saturated or unsaturated heterocyclic group containing 1 to 3 identical or different heteroatoms selected from nitrogen, oxygen, and sulfur.

2. The method according to claim 1, wherein when A is A1, A1 is

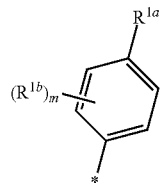

wherein R$^{1a}$ is selected from the group consisting of
  C1-C6 alkyl that is unsubstituted or substituted with C1-C6 alkoxy or C1-C6 alkylthio, wherein hydrogen contained in the alkoxy may be replaced by 1 or more deuterium atoms,
  C2-C6 alkenyl,
  C2-C6 alkynyl,
  amino that may be substituted with one or more 4- to 10-membered monocyclic or polycyclic unsaturated heterocyclic groups containing 1 to 3 identical or different heteroatoms selected from nitrogen, oxygen, and sulfur, or C6-C14 aromatic hydrocarbon, and
  a 4- to 10-membered monocyclic or polycyclic unsaturated heterocyclic group containing 1 to 3 identical or different heteroatoms selected from nitrogen, oxygen, and sulfur;
R$^{1b}$ is halogen, C1-C6 alkyl, or C1-C6 alkoxy; and
m is an integer of 0 or 1.

3. The method according to claim 1, wherein R² is selected from the group consisting of:
  C3-C10 alkyl that may be substituted with halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,
  C3-C7 cycloalkyl that may be substituted with C1-C6 alkyl, C3-C7 cycloalkyl, or halogeno C1-C6 alkyl,
  C4-C12 bridged cycloalkyl, and
  C3-C7 cycloalkenyl.

4. The method according to claim 1, wherein when X is CR³, R³ is selected from the group consisting of:
  hydrogen,
  halogen,
  cyano,
  C1-C4 alkyl that may be substituted with hydroxy or oxo,
  C1-C6 alkoxy that may be substituted with halogen, C1-C6 alkoxy, C3-C7 cycloalkyl, or one or more 4- to 10-membered monocyclic saturated heterocyclic groups that may be substituted with oxo and contain 1 to 3 identical or different heteroatoms selected from nitrogen, oxygen, and sulfur,
  C1-C4 alkylthio,
  C3-C5 cycloalkyl,
  C2-C6 alkenyl that may be substituted with hydroxy,
  C2-C6 alkynyl that is unsubstituted or substituted with a substitutent selected from the group consisting of:
    hydroxy,
    C1-C6 alkoxy,
    amino that may be substituted with R⁴, wherein R⁴ is C1-C6 alkyl, C1-C4 alkoxy C1-C6 alkyl, or carbamoyl that may be substituted with C3-C7 cycloalkyl,
    C1-C6 alkylsilyloxy,
    C3-C7 cycloalkyl that may be substituted with hydroxy or oxo,
    C6-C14 aromatic hydrocarbon that may be substituted with R⁵, wherein R⁵ is halogen, C1-C4 alkylamino that may be substituted with one or more 4- to 10-membered monocyclic unsaturated heterocyclic groups containing 1 to 3 identical or different heteroatoms selected from nitrogen, oxygen, and sulfur, or C1-C6 alkoxy,
    one or more 4- to 10-membered monocyclic saturated heterocyclic groups that may be substituted with R⁶ and contain 1 to 3 identical or different heteroatoms selected from nitrogen, oxygen, and sulfur, wherein R⁶ is hydroxy, C1-C6 alkyl, C1-C6 alkoxy, or oxo,
    one or more 4- to 10-membered monocyclic or polycyclic unsaturated heterocyclic groups that may be substituted with R⁷ and contain 1 to 3 identical or different heteroatoms selected from nitrogen, oxygen, and sulfur, wherein R⁷ is halogen, cyano, C1-C6 alkyl, C1-C6 alkoxy, or amino, and
    unsaturated heterocyclic oxy that may be substituted with halogen, wherein the unsaturated heterocyclic ring is a 4- to 10-membered monocyclic or polycyclic unsaturated heterocyclic ring containing 1 to 3 identical or different heteroatoms selected from nitrogen, oxygen, and sulfur,
    wherein the position of the triple bond of the C2-C6 alkynyl is disposed between the carbon atom bonded to the 7H-pyrrolo[2,3-d]pyrimidine skeleton and a carbon atom adjacent to the carbon atom,
  C6-C14 aromatic hydrocarbon that is unsubstituted or substituted with one or more substituents selected from the group consisting of
    hydroxy,
    C1-C6 alkyl that may be substituted with hydroxy,
    formyl, and
    one or more 4- to 10-membered monocyclic saturated heterocyclic groups that may be substituted with C1-C6 alkyl and contain 1 to 3 identical or different heteroatoms selected from nitrogen, oxygen, and sulfur, and
  a 4- to 6-membered monocyclic unsaturated heterocyclic group that may be substituted with one or more substituents selected from the group consisting of halogen,
C1-C6 alkyl that may be substituted with hydroxy, and
amino that may be substituted with C1-C6 alkyl(carbonyl),
wherein said 4- to 6-membered monocyclic unsaturated heterocyclic group contains 1 to 3 identical or different heteroatoms selected from nitrogen, oxygen, and sulfur.

5. The method according to claim 1, wherein A is

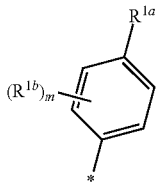

wherein $R^{1a}$ is selected from the group consisting of:
C1-C6 alkyl that is unsubstituted or substituted with C1-C6 alkoxy or C1-C6 alkylthio, wherein hydrogen contained in the alkoxy may be replaced by 1 or more deuterium atoms,
C2-C6 alkenyl,
C2-C6 alkynyl,
amino that may be substituted with one or more 4- to 6-membered monocyclic unsaturated heterocyclic groups containing 1 to 3 identical or different heteroatoms selected from nitrogen, oxygen, and sulfur, or C6-C10 aromatic hydrocarbon, and
a 4- to 6-membered monocyclic unsaturated heterocyclic group containing 1 to 3 identical or different heteroatoms selected from nitrogen, oxygen, and sulfur;
$R^{1b}$ is halogen, C1-C6 alkyl, or C1-C6 alkoxy;
m is an integer of 0 or 1;
$R^2$ is selected from the group consisting of:
C3-C10 alkyl that may be substituted with halogen, C3-C7 cycloalkyl, or one or more 4- to 10-membered monocyclic or polycyclic unsaturated heterocyclic groups containing 1 to 3 identical or different heteroatoms selected from nitrogen, oxygen, and sulfur,
C3-C7 cycloalkyl that may be substituted with C1-C6 alkyl, C3-C7 cycloalkyl, or halogeno C1-C6 alkyl, and
C4-C12 bridged cycloalkyl; and
X is selected from the group consisting of:
N and
$CR^3$, wherein $R^3$ is
hydrogen,
halogen,
cyano,
C1-C4 alkyl,
C1-C6 alkoxy that may be substituted with one or more substituents selected from the group consisting of:
halogen,
C1-C6 alkoxy,
C3-C7 cycloalkyl, and
one or more 4- to 10-membered monocyclic saturated heterocyclic groups that may be substituted with oxo and contain 1 to 3 identical or different heteroatoms selected from nitrogen, oxygen, and sulfur,
C1-C4 alkylthio,
C3-C5 cycloalkyl,
C2-C4 alkenyl that may be substituted with hydroxy,
C2-C6 alkynyl that may be substituted with one or more substituents selected from the group consisting of:
hydroxy,
C1-C4 alkoxy,
amino that may be substituted with $R^4$, wherein $R^4$ is C1-C4 alkyl, C1-C4 alkoxy C1-C4 alkyl, or carbamoyl that may be substituted with C3-C5 cycloalkyl,
tri-C1-C6 alkylsilyloxy,
C3-C7 cycloalkyl that may be substituted with hydroxy or oxo,
phenyl that may be substituted with $R^5$, wherein $R^5$ is halogen, methylamino that may be substituted with one or more 4- to 6-membered monocyclic unsaturated heterocyclic groups containing 1 to 3 identical or different heteroatoms selected from nitrogen, oxygen, and sulfur, or C1-C4 alkoxy,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, C1-C4 alkoxy, or oxo,
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino, and
unsaturated heterocyclic oxy that may be substituted with halogen, wherein the unsaturated heterocyclic ring is a 4- to 6-membered monocyclic unsaturated heterocyclic ring containing 1 to 3 identical or different heteroatoms selected from nitrogen, oxygen, and sulfur,
wherein the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with one or more substituents selected from the group consisting of:
hydroxy,
C1-C4 alkyl that may be substituted with hydroxy,
formyl, and
one or more 4- to 6-membered monocyclic saturated heterocyclic groups that may be substituted with C1-C4 alkyl and contain 1 to 3 identical or different heteroatoms selected from nitrogen, oxygen, and sulfur, and
a 4- to 6-membered monocyclic unsaturated heterocyclic group that may be substituted with one or more substituents selected from the group consisting of:
halogen,
C1-C4 alkyl that may be substituted with hydroxy, and
amino that may be substituted with C1-C4 alkyl (carbonyl),
wherein said 4- to 6-membered monocyclic unsaturated heterocyclic group contains 1 to 3 identical or different heteroatoms selected from nitrogen, oxygen, and sulfur.

6. The method according to claim 1, wherein A is

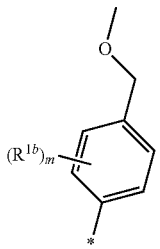

wherein $R^{1b}$ is halogen;
m is an integer of 0 or 1;
$R^2$ is selected from the group consisting of branched C3-C6 alkyl that may be substituted with halogen, and C3-C7 cycloalkyl that may be substituted with C1-C4 alkyl or C3-C5 cycloalkyl; and
X is $CR^3$, wherein $R^3$ is selected from the group consisting of
hydrogen,
halogen,
C1-C4 alkoxy that may be substituted with one or more substituents selected from the group consisting of:
C1-C4 alkoxy,
C3-C7 cycloalkyl, and
one or more 4- to 6-membered monocyclic saturated heterocyclic groups containing one oxygen atom,
C1-C4 alkylthio,
C2-C4 alkenyl,
C2-C6 alkynyl that may be substituted with one or more substituents selected from the group consisting of:
hydroxy,
amino that may be substituted with $R^4$, wherein $R^4$ is C1-C4 alkyl or C1-C4 alkoxy C1-C4 alkyl,
C3-C7 cycloalkyl that may be substituted with hydroxy,
phenyl that may be substituted with $R^5$, wherein $R^5$ is halogen,
one or more 4- to 6-membered monocyclic saturated heterocyclic groups that may be substituted with $R^6$ and contain 1 to 3 identical or different heteroatoms selected from nitrogen, oxygen, and sulfur, wherein $R^6$ is hydroxy, C1-C4 alkyl, or oxo, and
one or more 4- to 10-membered monocyclic or bicyclic unsaturated heterocyclic groups that may be substituted with $R^7$ and contain 1 to 3 identical or different heteroatoms selected from nitrogen, oxygen, and sulfur, wherein $R^7$ is halogen, cyano, C1-C4 alkyl, C1-C4 alkoxy, or amino,
wherein the position of the triple bond of the C2-C6 alkynyl is disposed between the carbon atom bonded to the 7H-pyrrolo[2,3-d]pyrimidine skeleton and a carbon atom adjacent to the carbon atom,
phenyl that may be substituted with hydroxy or C1-C4 alkyl that may be substituted with hydroxy, and
a 4- to 6-membered monocyclic unsaturated heterocyclic group containing 1 or 2 nitrogen atoms.

7. The method according to claim 1, comprising administering to a mammal in need of such treatment, a composition comprising a compound or a salt thereof according to Formula (I') as an active ingredient

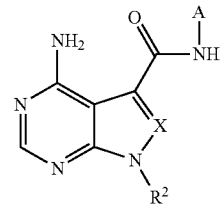

(I')

wherein in Formula (I'), A is

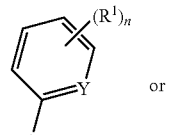

A1 or

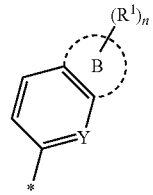

A2 wherein $R^1$ is selected from the group consisting of
halogen,
cyano,
nitro,
substituted or unsubstituted C1-C6 alkyl,
substituted or unsubstituted C1-C6 alkoxy,
substituted or unsubstituted C2-C6 alkenyl,
substituted or unsubstituted C2-C6 alkynyl,
substituted or unsubstituted amino, and
a substituted or unsubstituted 4- to 10-membered monocyclic or polycyclic unsaturated heterocyclic group containing 1 to 3 identical or different heteroatoms selected from nitrogen, oxygen, and sulfur,
Y is N or CH, and
n is an integer of 0 to 2,
wherein when n is 2, the two $R^1$ may be identical or different from each other;
in Formula A2, the group:

forms, together with phenyl or pyridinyl to which this group is bonded, polycyclic C8-C14 aromatic hydrocarbon or an 8- to 14-membered polycyclic unsaturated heterocyclic group containing 1 to 3 identical or different heteroatoms selected from nitrogen, oxygen, and sulfur;
$R^2$ is selected from the group consisting of
substituted or unsubstituted C3-C10 alkyl,
substituted or unsubstituted C3-C4 cycloalkyl,
substituted or unsubstituted C4-C12 bridged cycloalkyl,
substituted or unsubstituted C2-C6 alkenyl,
substituted or unsubstituted C3-C4 cycloalkenyl, and
a substituted or unsubstituted 4- to 10-membered monocyclic or polycyclic saturated heterocyclic group containing 1 to 3 identical or different heteroatoms selected from nitrogen, oxygen, and sulfur, provided that when each group represented by $R^2$ has a substituent, the substituent must not be a substituted or unsubstituted saturated heterocyclic group that may have at least one identical or different heteroatom selected from oxygen and sulfur, and has at least one nitrogen atom; and X is

- N or
- $CR^3$, wherein $R^3$ is selected from the group consisting of
- hydrogen,
- halogen,
- cyano,
- nitro,
- substituted or unsubstituted C1-C6 alkyl,
- substituted or unsubstituted C1-C6 alkoxy,
- substituted or unsubstituted C1-C6 alkylthio,
- substituted or unsubstituted C3-C7 cycloalkyl,
- substituted or unsubstituted C2-C6 alkenyl,
- substituted or unsubstituted C2-C6 alkynyl,
- substituted or unsubstituted amino,
- substituted or unsubstituted carbamoyl,
- substituted or unsubstituted C6-C14 aromatic hydrocarbon, and
- a substituted or unsubstituted 4- to 10-membered monocyclic or polycyclic saturated or unsaturated heterocyclic group containing 1 to 3 identical or different heteroatoms selected from nitrogen, oxygen, and sulfur.

* * * * *